US012157883B2

(12) United States Patent
Hay et al.

(10) Patent No.: US 12,157,883 B2
(45) Date of Patent: *Dec. 3, 2024

(54) DNA SEQUENCE MODIFICATION-BASED GENE DRIVE

(71) Applicant: California Institute of Technology, Pasadena, CA (US)

(72) Inventors: Bruce A Hay, Pasadena, CA (US); Georg Oberhofer, Pasadena, CA (US); Tobin William Ivy, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,728

(22) Filed: May 3, 2018

(65) Prior Publication Data

US 2018/0320164 A1 Nov. 8, 2018

Related U.S. Application Data

(60) Provisional application No. 62/502,338, filed on May 5, 2017.

(51) Int. Cl.
| | |
|---|---|
| *C12N 15/10* | (2006.01) |
| *C12N 5/14* | (2006.01) |
| *C12N 5/16* | (2006.01) |
| *C12N 15/90* | (2006.01) |
| *C12N 15/74* | (2006.01) |
| *C12N 15/80* | (2006.01) |
| *C12N 15/82* | (2006.01) |

(52) U.S. Cl.
CPC ............ *C12N 15/102* (2013.01); *C12N 5/14* (2013.01); *C12N 5/16* (2013.01); *C12N 15/905* (2013.01); *C12N 15/907* (2013.01); *C12N 15/74* (2013.01); *C12N 15/80* (2013.01); *C12N 15/8273* (2013.01); *C12N 15/8274* (2013.01); *C12N 15/8281* (2013.01); *C12N 15/8283* (2013.01); *C12N 15/8286* (2013.01); *C12N 2310/20* (2017.05)

(58) Field of Classification Search
None
See application file for complete search history.

(56) References Cited

U.S. PATENT DOCUMENTS

| 5,753,434 A | 5/1998 | Ryner |
| 10,570,200 B2 | 2/2020 | Hay et al. |
| 2003/0213005 A1 | 11/2003 | Alphey |
| 2007/0056051 A1 | 3/2007 | Alphey |
| 2009/0183269 A1 | 7/2009 | Alphey |
| 2013/0298266 A1 | 11/2013 | Alphey |
| 2014/0223591 A1 | 8/2014 | Hay |
| 2014/0283155 A1 | 9/2014 | Akbari |
| 2015/0159175 A1* | 6/2015 | Frendewey ........ A01K 67/0278 435/462 |
| 2015/0237838 A1 | 8/2015 | Hay |
| 2016/0060358 A1 | 3/2016 | Hay |
| 2016/0345556 A1 | 12/2016 | Hay |
| 2019/0241879 A1* | 8/2019 | Esvelt ................ A01K 67/0275 |
| 2020/0140885 A1 | 5/2020 | Hay et al. |
| 2020/0404892 A1 | 12/2020 | Hay et al. |

FOREIGN PATENT DOCUMENTS

| JP | 2544120 B2 | 10/1996 | |
| KR | 10-2017-0041640 A | 4/2017 | |
| WO | WO 1999/065520 A1 | 12/1999 | |
| WO | WO 2008/009960 A2 | 1/2008 | |
| WO | WO 2010/049777 A1 | 5/2010 | |
| WO | WO 2012/143401 A1 | 10/2012 | |
| WO | WO-2013176772 A1 * | 11/2013 | ............ C12N 15/70 |
| WO | WO-2014096428 A1 * | 6/2014 | ............... A01H 1/00 |
| WO | WO 2014/120975 A1 | 8/2014 | |
| WO | WO 2016/049230 A1 | 3/2016 | |
| WO | WO 2018/204722 A1 | 11/2018 | |

OTHER PUBLICATIONS

Noble et al Sci. Adv. ;Apr. 15, 3: e1601964 , 1-7 (Year: 2017).*
Oberhofer et al PNAS, 115, 40, E9343-E9352 (Year: 2018).*
Greisman et al. 1 Science 275:657-661 (Year: 1997).*
Tan et al. PNAS, pp. 11997-12002 (Year: 2003).*
Akbari et al ACS Synth Biol. Dec. 19; 3(12): 915-928 (Year: 2014).*
Hamaza et al Genetics, 201, 1263-1274 (Year: 2015).*
Gloor et al Science 253: 1110-1117 (Year: 1991).*
Tham et al. / DNA Repair 38 75-83 (Year: 2016).*
Guilinger et al Nature Biotechnology, 32(6), 577-583 (Year: 2014).*
Esvelt et al, eLife 3: e03401, 1-21 (Year: 2014).*
Oberhofer et al PNAS, 6250-6259 (Year: 2019).*
Jinek et al Science 343, 1215, 1247997-1-1247997-11 (Year: 2014).*
Nishimasu H., et al Cell 156(5), 935-949 (Year: 2014).*
Sternberg et al Nature 507(7490), 62-67 (Year: 2014).*
Knott et al., Sciencevol. 361: 866-869 (Year: 2018).*
Buchman et al., PNAS, vol. 115(18): 4725-4730 (Year: 2018).*
Hammond et al.,PLOS Genetics,, vol. 13(10), pp. 1-16 (Year: 2017).*
Burt A, Trivers R Genes in Conflict: The Biology of Selfish Genetic Elements Belknap Press, Cambridge, MA, 1st Ed. pp. 1-602, only p. 43 (Year: 2008).*
Advisory Action Dated Dec. 31, 2015 in U.S. Appl. No. 14/206,011.
Advisory Action Dated Nov. 21, 2016 in U.S. Appl. No. 14/206,011.
Akbari, O.S. et al., A synthetic gene drive system for local, reversible modification and suppression of insect populations, Curr. Biol., vol. 23 No. 8, pp. 671-677. 2013.
Akbari, O.S. et al., Novel synthetic Medea selfish genetic elements drive population replacement in *Drosophila*; a theoretical exploration of Medea-dependent population suppression, ACS Synth Biol. vol. 3 No. 12, pp. 915-928; 2014.
Alphey, L. et al., Malaria Control with Genetically Manipulated Insect, Nature vol. 415, 702; 2002.

(Continued)

*Primary Examiner* — Anoop K Singh
(74) *Attorney, Agent, or Firm* — Knobbe, Martens, Olson & Bear, LLP

(57) ABSTRACT

Described herein are embodiments relating to manipulation of populations and sex ratio in populations through DNA sequence modifications.

8 Claims, 33 Drawing Sheets

Specification includes a Sequence Listing.

(56) References Cited

OTHER PUBLICATIONS

Alphey, L. Genetic Control of Mosquitoes. Annu. Rev. Entomol, vol. 59, pp. 205-224, (2014).
Altrock, P. M. et al., Stability properties of underdominance in finite subdivided populations, PLOS Comput. Biol., vol. 7 No. 11, e1002260; 2011.
Altrock, P. M. et al., Using underdominance to bi-stably transform local populations, J Theor Biol, vol. 267 No. 1, pp. 62-75; 2010.
Amin et al., "Organization of the *Drosophila melanogaster* hsp70 heat shock regulation unit," Molecular and Cellular Biology 7:1055-1062 (1987).
Ant et al., "Control of the olive fruit fly using genetics-enhanced sterile insect technique," BMC Biology 10:51 (2012).
Arndt, K. M. et al., Helix-stabilized Fv (hsFv) antibody fragments: substituting the constant domains of a Fab fragment for a heterodimeric coiled-coil domain, J Mol Biol, vol. 312 No. 1, pp. 221-228.; 2001.
Asman, S. M. et al., Field studies of genetic control systems for mosquitoes, Annu Rev Entomol., vol. 26 No. 1, pp. 289-318; 1981.
Baker, R.H., Chromosome Rearrangements in the Control of Mosquitos, Prev Vet Med 2, pp. 529-540; 1984.
Baker et al., "Genetic sexing for a mosquito sterile-male release", The Journal of Heredity, vol. 7, No. 2, pp. 216-218, 1981.
Beaghton, A., et al., Gene Drive through a Landscape: Reaction-Diffusion Models of Population Suppression and Elimination by a Sex Ratio Distorter, Theoretical Population Biology, vol. 108, pp. 51-69, (2016).
Beaghton, A., et al., Requirements for Driving Antipathogen Effector Genes into Populations of Disease Vectors by Homing, Genetics, vol. 205 (4), pp. 1587-1596, (2017).
Ben-David, E. et al., A Maternal-Effect Selfish Genetic Element in Caenorhabditis Elegans, Science 356 (6342), pp. 1051-1055, (2017).
Bergmann, A. et al., The Drosophila gene hid is a direct molecular target of Ras-dependent survival signaling, Cell, vol. 95 No. 3, pp. 331-341; 1998.
Beumer, K. J. et al., "Induced chromosomal exchange directs the segregation of recombinant chromatids in mitosis of *Drosophila*. Genetics," Genetics, vol. 150 No. 1, pp. 173-188; (1998).
Bier V.M.G.A.E. et al., The mutagenic chain reaction: A method for converting heterozygous to homozygous mutations, Science, vol. 348 No. 6233, pp. 442-444; 2015.
Billeter, J. C. et al., Specialized cells tag sexual and species identity in *Drosophila melanogaster*, Nature, vol. 461 No. 7266, pp. 987-991; 2009.
Bischof, J. et al., An Optimized Transgenesis System for *Drosophila* Using Germ-Line-Specific phiC31 Integrases., Proceedings of the National Academy of Sciences of the United States of America 104 (9): 3312-17, (2007).
Boerjan et al., "Lignin biosynthesis," Annu Rev Plant Biol 54:519-546 (2003).
Boete C. et al., A theoretical approach to predicting the success of genetic manipulation of malaria mosquitoes in malaria control, Malar J, vol. 1 No. 3; 2002.
Boete C. et al., Evolutionary ideas about genetically manipulated mosquitoes and malaria control, Trends Parasitol, vol. 19 No. 1, pp. 32-38; 2003.
Bohannon J., Food aid. Zambia rejects GM corn on scientists' advice, Science, vol. 298 No. 5596, pp. 1153-1154; 2002.
Borycz J. et al., ABC transporter mutants white, brown and scarlet have altered contents and distribution of biogenic amines in the brain, J Exp Biol, vol. 211 No. 21, pp. 3454-3466; 2008.
Bossin et al., "Somatic transformation efficiencies and expression patterns using the JcDNV and piggyBac transposon gene factors in insects," Insect Mol. Biol. 16:37-47 (2007).
Braig, H. R. et al., The spread of genetic constructs in natural insect populations. In D. K. Letourneau & B. E. Burrows (Eds.) Genetically Engineered Organisms: Assessing Environmental and Human Health Effects (pp. 251-314). Cleveland, OH/Boca Raton, FL: CRC Press; 2002.
Brelesfoard, C. et al., Wolbachia-based strategies to control insect pests and disease vectors. Asia Pac J Mol Biol Biotechnol vol. 17, pp. 55-63 (2009).
Brunel et al., "Cloning and sequencing of pseudomonas genes encoding vanillate demethylase," J. Bacteriol. 170:4924-4930 (1988).
Buchman, A., et al., Engineered Reciprocal Chromosome Translocations Drive High Threshold, Reversible Population Replacement in *Drosophila*, ACS Synthetic Biology, (2018).
Burt, A. et al., Homing endonuclease genes: the rise and fall and rise again of a selfish element. Curr. Opin. Genet. Dev. vol. 14, pp. 609-615 (2004).
Burt, A. et al Genetic Conflicts in Genomic Imprinting. Proceedings. Biological Sciences / the Royal Society 265 (1413): pp. 2393-2397, (1998).
Burt, A.., Site-Specific Selfish Genes as Tools for the Control and Genetic Engineering of Natural Populations, Proceedings. Biological Sciences / the Royal Society 270 (1518): pp. 921-928. (2003).
Bushland et al., "Eradication of Screw-Worms through Release of Sterilized Males", Science, vol. 122, No. 3163, pp. 287-288, 1955.
Carvalho D.O. et al., Two step male release strategy using transgenic mosquito lines to control transmission of vector-borne diseases, Acta Trop 132S, S170-S177; 2014.
Carvalho et al., "Mass Production of Genetically Modified Aedes aegypti for Field Releases in Brazil", Journal of Visualized Experiments vol. 83, e3579, pp. 1-10, 2014.
Castillo, J. et al., Complex interaction between dengue virus replication and expression of miRNA-133a., BMC Infect. Dis. 16, (2016).
Champer, J. et al., Novel CRISPR/Cas9 Gene Drive Constructs Reveal Insights into Mechanisms of Resistance Allele Formation and Drive Efficiency in Genetically Diverse Populations., PLoS Genetics, (2017).
Chan, Y. et al. Optimising Homing Endonuclease Gene Drive Performance in a Semi-Refractory Species: The *Drosophila melanogaster* Experience, (2013).
Chan, Yuk-Sang, Daniel A. Naujoks, David S. Huen, and Steven Russell. 2011. "Insect Population Control by Homing Endonuclease-Based Gene Drive: An Evaluation in *Drosophila melanogaster*." Genetics 188 (1): 33-44.
Chen C.H. et al., A synthetic maternal-effect selfish genetic element drives population replacement in *Drosophila*, Science, vol. 316 No. 5824, pp. 597-600; 2007.
Cheriyan, M. et al., Faster protein splicing with the Nostoc punctiforme DnaE intein using non-native extein residues, J Biol Chem, vol. 288 No. 9, pp. 6202-6211; 2013.
Clark, A. et al., "Evolution of Genes and Genomes on the *Drosophila* Phylogeny." Nature 450 (7167), pp. 203-218. (2007).
Collins et al., "Effects of irradiation dose rate on quality and sterility of Queensland fruit flies, *Bactrocera tryoni* (Froggatt)," J. Appl. Entomol. 132:398-405 (2008).
Condon et al., "Genetic sexing through the use of Y-linked transgenes", Insect Biochemistry and Molecular Biology, vol. 37, pp. 1168-1176, 2007.
Cook, R. K. et al., The generation of chromosomal deletions to provide extensive coverage and subdivision of the *Drosophila melanogaster* genome, Genome Biol, vol. 13 No. 3, R21; 2012.
Corby-Harris, V. et al., Activation of Akt signaling reduces the prevalence and intensity of malaria parasite infection and lifespan in *Anopheles stephensi* mosquitoes, PLoS Pathog, vol. 6 No. 7, e1001003; 2010.
Crompton, P. D. et al., Malaria immunity in man and mosquito: insights into unsolved mysteries of a deadly infectious disease, Annu Rev of Immunol, vol. 32 No. 1, pp. 157-187; 2014.
Curtis et al., "Genetic sex separation in Anopheles arabiensis and the production of sterile hybrids", Bulletin in the World of Health Organization, vol. 56, No. 3, pp. 453-454, 1978.
Curtis et al., "Genetic Sexing System in *Anopheles gambiae* Species A", Mosquito News, vol. 36, No. 4, pp. 492-498, 1976.
Curtis C.F. et al., "Computer simulation of the use of double translocations for pest control," Genetics, vol. 69 No. 1, 97-113; 1971.

(56) References Cited

OTHER PUBLICATIONS

Curtis, C. F., Possible use of translocations to fix desirable genes in insect pest populations, Nature, vol. 218 No. 5139, pp. 368-369; 1968.

Daborn et al., "Evaluating the insecticide resistance potential of eight *Drosophila melanogaster* cytochrome P450 genes by transgenic over-expression", Insect Biochemistry and Molecular Biology, vol. 37, pp. 512-519, 2007.

Dang, Y. et al. Optimizing sgRNA Structure to Improve CRISPR-Cas9 Knockout Efficiency. Genome Biology 16 (December): 280, (2015).

Dantuma N.P. et al., Short-lived green fluorescent proteins for quantifying ubiquitin/proteasome-dependent proteolysis in living cells, Nat Biotechnol., vol. 18 No. 5, pp. 538-543; 2000.

Davis S. et al., Engineered underdominance allows efficient and economical introgression of traits into pest populations, J Theor Biol., vol. 212 No. 1, pp. 83-98; 2010.

De Jesus C. et al., Use of genetic modified mosquitoes to fight dengue in Brazil, International Journal of Research in Pharmaceutical and Nano Sciences, vol. 2 No. 6, pp. 811-816; 2000.

De La Rocque S. et al., A review of trends in the distribution of vector-borne diseases: is international trade contributing to their spread? Rev Sci Tech, vol. 30 No. 1, pp. 119-130; 2011.

De Lara Capurro M. et al., Virus-expressed, recombinant single-chain antibody blocks sporozoite infection of salivary glands in Plasmodium gallinaceum-infected Aedes aegypti, Am J Trop Med Hyg., vol. 62 No. 4, pp. 427-433; 2000.

De N. et al., Highly complementary target RNAs promote release of guide RNAs from human Argonaute2, Mol Cell, vol. 50 No. 3, pp. 344-355; 2013.

Deredec A et al., The population genetics of using homing endonuclease genes in vector and pest management, Genetics, vol. 179 No. 4, pp. 2013-2026; 2008.

Dhar T. et al., Modification of transmembrane and GPI-anchored proteins on living cells by efficient protein trans-splicing using the Npu DnaE intein, Chem Commun (Camb), vol. 47 No. 11, pp. 3063-3065; 2011.

Dicarlo, J. E. et al., "Safeguarding CRISPR-Cas9 gene drives in yeast", Nature Biotechnology, vol. 33, No. 12, pp. 1250-1255, (2015).

Doench, J.G. et al., Optimized sgRNA Design to Maximize Activity and Minimize off-Target Effects of CRISPR-Cas9, Nature Biotechnology, vol. 34, No. 2, pp. 184-191, 2016.

Egli D et al., An efficient method to generate chromosomal rearrangements by targeted DNA double-strand breaks in *Drosophila melanogaster*, Genome Res., vol. 14 No. 7, pp. 1382-1393; 2004.

Enayati A. et al., Malaria management: past, present, and future, Annu Rev Entomol., vol. 55, pp. 569-591; 2010.

Engler, C. et al., A one pot, one step, precision cloning method with high throughput capability, PLoS one, vol. 3 No. 11, e3647; 2008.

Engler, C. et al., Golden gate shuffling: a one-pot DNA shuffling method based on type IIs restriction enzymes, PLoS one, vol. 4 No. 5, e5553; 2009.

Eppstein, M. J., Payne, J. L., & Goodnight, C. J. (2009). Underdominance, multiscale interactions, and self-organizing barriers to gene flow. Journal of Artificial Evolution and Applications 5, 1-13.

Esvelt, K.M. et al., Concerning RNA-guided gene drives for the alteration of wild populations, Elife, e03401; 2014.

Feng, et al. "Vanillic acid derivatives from the green algae Cladophora socialis as potent protein tyrosine phosphatase 1B inhibitors." Journal of natural products 70.11 (2007): 1790-1792.

Fields, S. et al., A novel genetic system to detect protein-protein interactions, Nature, vol. 340 No. 6230, pp. 245-246; 1989.

Filipowicz, W. et al., Post-transcriptional gene silencing by siRNAs and miRNAs, Curr Opin Struct Biol., vol. 15 No. 3, pp. 331-341; 2005.

Focks et al., "An improved separator for the developmental stages, sexes, and species of mosquitoes (*Diptera culicidae*)", Journal of Medical Entomology, vol. 17, No. 6, pp. 567-568, 1980.

Forster, A. et al., Chromosomal translocation engineering to recapitulate primary events of human cancer, Cold Spring Harb Symp Quant Biol, vol. 70, pp. 275-282; 2005.

Foster, G.et al., Chromosome rearrangements for the control of insect pests, Science, vol. 176 No. 4037, pp. 875-880; 1972.

Franz, A. W. et al., Engineering RNA interference-based resistance to dengue virus type 2 in genetically modified Aedes aegypti, Proc Natl Acad Sci U S A, vol. 103 No. 11, pp. 4198-4203; 2006.

Fu et al., "Female-specific flightless phenotype for mosquito control," Proc. Natl. Acad. Sci. USA 107:4550-4554 (2010).

Gallup, J.L. et al., The economic burden of malaria, Am J Trop Med Hyg, vol. 64 No. 1-2 Suppl, pp. 85-96; 2001.

Galizi, R. et al., A synthetic sex ratio distortion system for the control of the human malaria mosquito. Nat. Commun. vol. 5, (2014).

Galizi, R., A. Hammond, K. Kyrou, C. Taxiarchi, F. Bernardini, S. M. O'Loughlin, P. A. Papathanos, T. Nolan, N. Windbichler, and A. Crisanti. 2016. "A CRISPR-Cas9 Sex-Ratio Distortion System for Genetic Control." Scientific Reports 6: 31139.

Gantz, V. M. et al., Highly efficient Cas9-mediated gene drive for population modification of the malaria vector mosquito *Anopheles stephensi*, PNAS, vol. 112, No. 49, pp. E6736-E6743, (2015).

Gantz, V. M., N. Jasinskiene, O. Tatarenkova, A. Fazekas, V. M. Macias, E. Bier, and A. A. James. 2015. "Highly Efficient Cas9-Mediated Gene Drive for Population Modification of the Malaria Vector Mosquito *Anopheles stephensi*." Proceedings of the National Academy of Sciences of the United States of America 112 (49): E6736-43.

Gdula, D.A. et al., Genetic and molecular analysis of the gypsy chromatin insulator of *Drosophila*, Proc Natl Acad Sci USA, vol. 93 No. 18, pp. 9378-9383; 1996.

Gibson, D. G. et al., Enzymatic assembly of DNA molecules up to several hundred kilobases, Nat Methods, vol. 6 No. 5, pp. 343-345; 2009.

Gimble, F. Invasion of a multitude of genetic niches by mobile endonuclease genes. FEMS Microbiol. Lett. vol. 185, pp. 99-107 (2000).

Githeko, A. K. et al., Climate change and vector-borne diseases: a regional analysis, Bulletin of the World Health Organization, vol. 78, No. 9, pp. 1136-1147, 2000.

Gitzinger et al., "The food additive vanillic acid controls transgene expression in mammalian cells and mice," Nucleic Acids Research 40 (2012).

Godfray, H. C. J., A. North, and A. Burt. 2017. "How Driving Endonuclease Genes Can Be Used to Combat Pests and Disease Vectors." BMC Biology 15 (1): 81.

Gokhale, Chaitanya S., Richard Guy Reeves, and Floyd A. Reed. 2014. "Dynamics of a Combined Medea-Underdominant Population Transformation System." BMC Evolutionary Biology 14: 98.

Gong et al., "A dominant lethal genetic system for autocidal control of the Mediterranean fruit fly," Nat. Biotechnol. 23:453-456 (2005).

Gong, W. J. et al., Ends-out, or replacement, gene targeting in *Drosophila*, Proceedings of the National Academy of Sciences, vol. 100, No. 5, pp. 2556-2561, 2003.

Gossen et al., "Tight control of gene expression in mammalian cells by tetracycline-responsive promoters," Proc Natl Acad Sci USA 89:5547-5551 (1992).

Gould, F. et al., Population genetics of autocidal control and strain replacement, Annu Rev Entomol, vol. 49, pp. 193-217, 2004.

Gould, F. et al., A Killer-Rescue system for selflimiting gene drive of anti-pathogen constructs, Proceedings of the Royal Society B: Biological Sciences, vol. 275, No. 1653, pp. 2823-2829, 2008.

Gould, F. et al., Genetic strategies for controlling mosquitoborne diseases: engineered genes that block the transmission of malaria and dengue can hitch a ride on selfish DNA and spread into wild populations, American scientist, pp. 238-246, 2006.

Groth, A. C. et al., Construction of transgenic *Drosophila* by using the site-specific integrase from phage PC31, Genetics, vol. 166, No. 4, pp. 1775-1782, 2004.

Gubler, D. J. et al., Climate variability and change in the United States: potential impacts on vector- and rodent-borne diseases, Environmental health perspectives, vol. 109, Suppl 2, pp. 223, 2001.

(56) References Cited

OTHER PUBLICATIONS

Gubler, D. J., Resurgent vector-borne diseases as a global health problem, Emerging infectious diseases, vol. 4, No. 3, pp. 442, 1998.
Gutierrez, E. et al., Specialized hepatocytelike cells regulate *Drosophila* lipid metabolism, Nature, vol. 445, No. 7125, pp. 275-280, 2007.
Hagmann et al., "The VP16 paradox: Herpes simplex virus VP16 contains a long-range activation domain but within the natural multiprotein complex activates only from promoter-proximal positions," J Virol 71:5952-5962 (1997).
Hammond, A., R. Galizi, K. Kyrou, A. Simoni, C. Siniscalchi, D. Katsanos, M. Gribble, et al. 2016. "A CRISPR-Cas9 Gene Drive System Targeting Female Reproduction in the Malaria Mosquito Vector Anopheles Gambiae." Nature Biotechnology 34 (1): 78-83.
Han, Z. et al., Hand is a direct target of Tinman and GATA factors during *Drosophila cardiogenesis* and hematopoiesis, Development, vol. 132, No. 15, pp. 3525-3536, 2005.
Handler et al., "Use of the piggyBac transposon for germ-line transformation of insects", Insect Biochemistry and Molecular Biology, vol. 32, pp. 1211-1220, 2002.
Harris, A. F. et al., Field performance of engineered male mosquitoes, Nature biotechnology, vol. 29, No. 11, pp. 1034-1037, 2011.
Harris et al., "Successful suppression of a field mosquito population by sustained release of engineered male mosquitoes", Nature Biotechnology, vol. 30, No. 9, pp. 828-830, 2012.
Hartl, D.L. et al., Principles of Population Genetics, Sunderland, MA: Sinauer Associates, Inc., 1997.
Harwood et al., "The beta-ketoadipate pathway and the biology of self-identity," Ann Rev Microbiol 50:553-590 (1996).
Hay, B. A. et al., Engineering the genomes of wild insect populations: challenges, and opportunities provided by synthetic Medea selfish genetic elements, J Insect Physiol, vol. 56, No. 10, pp. 1402-1413, 2010.
Heravi, et al. "Transcriptional regulation of the vanillate utilization genes (vanABK operon) of Corynebacterium glutamicum by VanR, a PadR-like repressor", Journal of Bacteriology, JB.02431-14, pp. 1-60., (2014).
Hendrichs et al., "Medfly area wide sterile insect technique programmes for preventions, suppression or eradication: The importance of mating behavior studies," Fla Entomol 85:1-13 (2002).
Hoffmann, A. A. et al., Successful establishment of Wolbachia in Aedes populations to suppress dengue transmission, Nature, vol. 476, No. 7361, pp. 454-457, 2011.
Hollingdale, M., et al., Nussenzweig, R. S. Inhibition of entry of Plasmodium falciparum and P. vivax sporozoites into cultured cells; an in vitro assay of protective antibodies. J. Immunol. 132, pp. 909-913, (1984).
Hongenboom, Melissa, "Genetically modified flies 'could save crops'", BBC News, Science and Environment, Aug. 12, 2014. 3 pages.
Huang, Y. et al. Introducing Desirable Transgnes into Insect Populations Using Y-Linked Meiotic Drive? A Tehoretical Assesement, Evolution vol. 61, pp. 717-726.
International Search Report and Written Opinion Mailed Apr. 25, 2014 in International Application No. PCT/US2014/013943.
International Search Report and Written Opinion Mailed Aug. 31, 2018 in International Application No. PCT/US2018/030990.
Issacs, A., et al. Engineered Resistance to Plasmodium falciparum Development in Transgenic Anopheles stephensi. PLoS Pathog. 7, e1002017 (2011).
Ito, J. et al. Transgenic anopheline mosquitoes impaired in transmission of a malaria parasite, Nature, vol. 417, No. 6887, pp. 452-455, 2002.
Iwaki et al., "Rapid selection of Drosophila S2 cells with the puromycin resistance gene", Biotechniques, vol. 35, pp. 482-486, 2003.
Jacobs-Lorena, M. Genetic approached for malaria control. In Bogers, R.J. (ed.), Bridging Laboratory and Field Research for Genetic Control of Disease Vectors, pp. 52-65, Retrieved from http://library.wur.nl/frontis/, 2004.

James, A. A, Gene drive systems in mosquitoes: rules of the road, Trends Parasitol, vol. 21, No. 2, pp. 64-67, 2005.
Jansen V.A. et al., Stochastic spread of Wolbachia, Proc Biol Sci, vol. 275 No. 1652, pp. 2769-2776; 2008.
Kaiser, P.E. et al., Radiation induced reciprocal translocations and inversions in Anopheles albimanus, Can J Genet Cytol, vol. 24 No. 2, pp. 177-188; 1982.
Kakkar, et al., "A review on protocatechuic acid and its pharmacological potential." ISRN pharmacology 2014 (2014).
Kerremans et al., "Use of a Temperature-Sensitive Lethal Mutation Strain of Medfly (*Ceratitis capitata*) for the Suppression of Pest Populations", Theoretical and Applied Genetics, vol. 90, pp. 511-518, 1995.
Kim et al., "A genetic sexing strain of Anopheles quadrimaculatus, species A", Journal of the American Mosquito Control Association, vol. 3, No. 1, pp. 50-53, 1987.
Kim, W. et al., Ectopic expression of a cecropin transgene in the human malaria vector mosquito *Anopheles gambiae* (Diptera: Culicidae): effects on susceptibility to Plasmodium, Journal of medical entomology, vol. 41, No. 3, pp. 447-455, 2004.
Kim, et al., "Vanillic acid glycoside and quinic acid derivatives from Gardeniae Fructus." Journal of natural products 69.4 (2006): 600-603.
Koonin, E., et al., Diversity, classification and evolution of CRISPR-Cas systems. Curr. Opin. Microbiol. 37, pp. 67-78, (2017).
Koonin, E., et al. Evolutionary Genomics of Defense Systems in Archaea and Bacteria. Annu. Rev. Microbiol. 71, 233-261 (2017).
Knols, B. G. et al., Transgenic mosquitoes and the fight against malaria: managing technology push in a turbulent GMO world, Am J Trop Med Hyg., vol. 77, 6 Suppl, pp. 232-242, 2007.
Krafsur et al., "Screwworm eradication is what it seems," Nature 323:495-496 (1986).
Krafsur et al., "Screwworm eradication in North and Central America," Parasitology Today 3:131:137 (1987).
Krafsur, E. S. et al., Sterile insect technique for suppressing and eradicating insect populations: 55 years and counting, J. Agr. Entomol., vol. 15, 303-317, 1998.
Krstic, D. et al., Influence of the White Locus on the Courtship Behavior of *Drosophila* Males, PLoS one, vol. 8, No. 10, e77904, 2013.
Kuhlman, et al. Combinatorial transcriptional control of the lactose operon of *Escherichia coli*, Procedings of the National Academy of Sciences, USA, 104(14): 6043-48., (2007).
Kwit, C. et al., Transgene introgression in crop relatives: molecular evidence and mitigation strategies. Trends Biotechnol, vol. 29, No. 6, pp. 284-293, 2011.
Kyrchanova, O., et al., Orientation-dependent interaction between *Drosophila* insulators is a property of this class of regulatory elements, Nucleic acids research, vol. 36, No. 22, pp. 7019-7028, 2008.
Labbe et al., "Female-specific flightless (fsRIDL) phenotype for control of Aedes albopictus," PLoS Negl Trop Dis 6, e1724 (2012).
Lambrechts, L. et al., Can transgenic mosquitoes afford the fitness cost? Trends Parasitol, vol. 24 No. 1, pp. 4-7; 2008.
Leftwich et al., "Genetic elimination of field-cage populations of Mediterranean fruit flies", Proc. R. Soc., vol. 281, No. 1792, 21 pages, 2014.
Lemon, S. M. et al., Vector-Borne Diseases: Understanding the Environmental, Human Health, and Ecological Connections, Workshop Summary (Forum on Microbial Threats), National Academies Press, 2008.
Lewin, Genes V, Oxford University Press, Oxford, pp. 847-873, Fifth Edition.
Li, F. et al. An Anti-Chitinase Malaria Transmission-Blocking Single-Chain Antibody as an Effector Molecule for Creating a *Plasmodium falciparum*-Refractory Mosquito. J. Infect. Dis. 192, pp. 878-887 (2005).
Lin, H. et al., Cellular toxicity induced by SRFmediated transcriptional squelching, Toxicological sciences, vol. 96, No. 1, pp. 83-91, 2007.
Lines et al., "Genetic sexing systems in Anopheles arabiensis Patton (Diptera: Culicidae)", Journal of Economic Entomology, vol. 78, pp. 848-851, 1985.

(56) References Cited

OTHER PUBLICATIONS

Lo, P. C. et al., A role for the COUP-TF-related gene seven-up in the diversification of cardioblast identities in the dorsal vessel of *Drosophila*, Mech Dev, vol. 104, pp. 49-60, 2001.
Lockless, S. W. et al., Traceless protein splicing utilizing evolved split inteins, Proc Natl Acad Sci U S A, vol. 106, No. 27, pp. 10999-11004, 2009.
Luan, H. et al., Refined spatial manipulation of neuronal function by combinatorial restriction of transgene expression, Neuron, vol. 52, No. 3, pp. 425-436, 2006.
Lyon, M. F. et al., Mutagenic effects of repeated small radiation doses to mouse spermatogonia I. Specific-locus mutation rates, Mutation Research/Fundamental and Molecular Mechanisms of Mutagenesis, vol. 15, No. 2, pp. 185-190, 1972.
Lyttle, T. Experimental population genetics of meiotic drive systems I. Pseudo-Y chromosomal drive as a means of eliminating cage populations of *Drosophila melanogaster*, Genetics, vol. 86, pp. 413-445, (1977).
Magnusson et al., "Transcription regulation of sex-biased genes during ontogeny in the malaria vector Anopheles gambiae", PLoS One, vol. 6, No. 6, e21572, 2011.
Magori, K. et al., Genetically engineered underdominance for manipulation of pest populations: a deterministic model. Genetics, vol. 172, No. 4, pp. 2613-2620, 2006.
Malavasi, A. Project Aedes transgenic population control in Juazeiro and, Jacobina Bahia, Brazil. BMC Proc. 8, 011 (2014).
Marois et al. High-throughput sorting of mosquito larvae for laboratory studies and for future vector control interventions, Malaria Journal, vol. 11, No. 1, pp. 302-308, 2012.
Marris, E., Transgenic fish go large, Nature, vol. 467, No. 7313, pp. 259, 2010.
Marshall, J. M. et al., Confinement of gene drive systems to local populations: a comparative analysis, J Theor Biol, vol. 294, pp. 153-171, 2012.
Marshall, J. M. et al., Inverse Medea as a novel gene drive system for local population replacement: a theoretical analysis, J Hered, vol. 102, No. 3, pp. 336-341, 2011.
Marshall, J. M. et al., Perspectives of people in Mali toward genetically-modified mosquitoes for malaria control, Malar J, vol. 9, No. 128, 2010a.
Marshall, J. M. et al., Towards a quantitative assessment of public attitudes to transgenic mosquitoes: Questions based on a qualitative survey in Mali, Asia Pacific J. Mol. Biol. Biotechnol, vol. 18, pp. 251-273, 2010b.
Marshall, J. M., The Cartagena Protocol and genetically modified mosquitoes, Nat. Biotechnol., vol. 28, No. 9, pp. 896-897, 2010.
Marshall, J. M., The effect of gene drive on containment of transgenic mosquitoes, J. of Theor. Biol., vol. 258, No. 2, pp. 250-265, 2009.
Marshall, J. et al The Impact of Dissociation on Transposon-Mediated Disease Control Strategies. Genetics vol. 178, pp. 1673-1682 (2008).
Marshall, J.M. et al., General principles of single-construct chromosomal gene drive, Evolution; vol. 66 No. 7, pp. 2150-2166; 2012b.
Marshall, J.M. et al., Semele: a killer-male, rescue-female system for suppression and replacement of insect disease vector populations, Genetics, vol. 187 No. 2, pp. 535-551; 2011.
Martinez et al., Biodegradation of lignocellulosics: microbial, chemical, and enzymatic aspects of the fungal attack of lignin, Int Microbiol 8:195-204 (2005).
Marygold, S. J. et al., The ribosomal protein genes and Minute loci of *Drosophila melanogaster*, Genome Biol, vol. 8, No. 10, R216, 2007.
Mathur, G. et al., Transgene-mediated suppression of dengue viruses in the salivary glands of the yellow fever mosquito, *Aedes aegypti*. Insect Mol. Biol. 19, pp. 753-763 (2010).

Matzen, K.J. Engineering of Dengue virus refractoriness in Aedes aegypti and development of an underdominant gene drive system (Doctoral dissertation), California Institute of Technology, Pasadena, CA, 2012.
McCauley, et al., Analysis of a Human Sperm CD52 Glycoform in Primates: Identification 1-30 of an Animal Model for Immunocontraceptive Vaccine.Development, Biology of Reproduction, vol. 66, pp. 1681-1688, (2002).
McDonald et al., "A Genetic-Sexing Strain Based on Malathion Resistance for Culex-Tarsalis", Mosquito News, vol. 42, No. 4, pp. 531-536, 1982.
McManus, M. T. et al., Gene silencing using micro-RNA designed hairpins, RNA, vol. 8, No. 6, 842-850, 2002.
Medici et al., "Studies on Aedes albopictus larval mass-rearing optimization", Journal of Economic Entomology, vol. 104, No. 1, pp. 266-273, 2011.
Merkens et al., Vanillate metabolism in Corynebacterium glutamicum, Curr Microbiol 51:59-65 (2005).
Miller, L. H. et al., Perspective on malaria eradication: is eradication possible without modifying the mosquito? Journal of Infectious Diseases, vol. 200, No. 11, pp. 1644-1645, 2009.
Miller, T. A., Let high-tech genetically modified insects counter dengue, BioScience, vol. 61, No. 8, pp. 586-587, 2011.
Moreira, L. A. et al., Bee venom phospholipase inhibits malaria parasite development in transgenic mosquitoes, J Biol Chem, vol. 277, No. 43, pp. 40839-40843, 2002.
Moreno, E., Design and construction of "synthetic species," PLoS One, vol. 7, No. 7, e39054, 2012.
Morrison, N. I. et al., Genetic improvements to the sterile insect technique for agricultural pests, Asia-Pacific Journal of Molecular Biology and Biotechnology, vol. 18, No. 2, pp. 275-295, 2010.
Morrison et al., "Engineered repressible lethality for controlling the pink bollworm, a lepidopteran pest of cotton," PLoS One 7:e50922 (2012).
Mumford, J. D. Science, regulation, and precedent for genetically modified insects, PLoS neglected tropical diseases, vol. 6, No. 1, e1504, 2012.
Murray, C. J. et al., Global malaria mortality between 1980 and 2010: a systematic analysis, the Lancet, vol. 379, No. 9814, pp. 413-431, 2012.
Nath, R., Generation and characterisation of plant produced recombinant antibodies specific to LHRH for treatment of sex hormone dependent diseases. (MS thesis), Fachhochschule Aachen, Aachen, Germany, 2003.
Ndiath, M. O., et al., Resistance to DDT and pyrethroids and increased kdr mutation frequency in an. gambiae after the implementation of permethrin-treated nets in Senegal, PloS one, vol. 7, No. 2, e31943, 2012.
Neely, G. G. et al., A Global In Vivo *Drosophila* RNAi Screen Identifies NOT3 as a Conserved Regulator of Heart Function, Cell, vol. 141, No. 1, pp. 142-153, 2010.
Nern, A. et al., Multiple new site-specific recombinases for use in manipulating animal genomes, Proceedings of the National Academy of Sciences, vol. 108, No. 34, pp. 14198-14203, 2011.
Ni, J. Q. et al., A genome-scale shRNA resource for transgenic RNAi in *Drosophila*, Nat Methods, vol. 8, No. 5, pp. 405-407, 2011.
Nicholson, G.M. et al., Fighting the global pest problem: preface to the special Toxicon issue on insecticidal toxins and their potential for insect pest control, Toxicon, vol. 49 No. 4, pp. 413-422; 2007.
Nishimura et al., "Molecular cloning of Streptomyces genes encoding vanillate demethylase," Biosci Biotech Bioch 70:2316-2319 (2006).
Noble, C. et al., "Evolutionary dynamics of CRISPR gene drives", Science Advances, 5, vol. 3, e1601964, (2017).
Notice of Allowance Dated Feb. 13, 2017 in U.S. Appl. No. 14/206,011.
Nuckolls, N. L., M. A. Bravo Nunez, M. T. Eickbush, J. M. Young, J. J. Lange, J. S. Yu, G. R. Smith, S. L. Jaspersen, H. S. Malik, and S. E. Zanders. 2017. "Wtf Genes Are Prolific Dual Poison-Antidote Meiotic Drivers." eLife 6. https://doi.org/10.7554/eLife.26033.
Oberhofer, G. et al., Behavoir for Homin Endoclease Gene Drives targeting Genes Required for Viability or Femal Fertility with Multiplexted Guide RNAs, (2018).

(56) References Cited

OTHER PUBLICATIONS

Office Action Dated Apr. 9, 2015 in U.S. Appl. No. 14/206,011.
Office Action Dated Sep. 21, 2015 in U.S. Appl. No. 14/206,011.
Office Action Dated Feb. 4, 2016 in U.S. Appl. No. 14/631,171.
Office Action Dated Apr. 7, 2016 in U.S. Appl. No. 14/206,011.
Office Action Dated Jun. 2, 2016 in U.S. Appl. No. 14/170,118.
Office Action Dated Aug. 18, 2016 in U.S. Appl. No. 14/631,171.
Office Action Dated Sep. 2, 2016 in U.S. Appl. No. 14/206,011.
Office Action Dated Dec. 28, 2016 in U.S. Appl. No. 14/170,118.
Office Action Dated Apr. 6, 2017 in U.S. Appl. No. 14/631,171.
Office Action Dated Sep. 21, 2017 in U.S. Appl. No. 14/837,941.
Office Action Dated Jan. 26, 2018 in U.S. Appl. No. 14/837,941.
Office Action Dated May 30, 2018 in U.S. Appl. No. 14/170,118.
Office Action Dated Aug. 16, 2018 in U.S. Appl. No. 15/164,452.
Office Action Dated Aug. 24, 2018 U.S. Appl. No. 14/837,941.
Office Action Dated Oct. 19, 2018 in U.S. Appl. No. 14/170,118.
Office Action Dated Mar. 22, 2019 U.S. Appl. No. 15/164,452.
Oye, K.A. et al., Biotechnology. Regulating gene drives, Science vol. 345 No. 6197, pp. 626-628; 2014.
Papathanos et al., "Sex Ratio Manipulation for Insect Population Control", Transgenic Insects: Techniques and Applications, pp. 83-100, Publication date Oct. 29, 2014.
Papathanos, et al., "Sex Separation Strategies: past experience and new approaches", Malaria Journal, vol. 8, Suppl 2, No. S5, 2009.
Pardo, R. et al., The role of means and goals in technology acceptance, a differentiated landscape of public perceptions of pharming, EMBO Rep, vol. 10, No. 10, pp. 1069-1075, 2009.
Parvy, J. P. et al., *Drosophila melanogaster* Acetyl-CoA-Carboxylase Sustains a Fatty Acid-Dependent Remote Signal to Waterproof the Respiratory System, PLoS genetics, vol. 8, No. 8, e1002925, 2012.
Perrimon, N. et al., In vivo RNAi: today and tomorrow, Cold Spring Harbor perspectives in biology, vol. 2, No. 8, a003640, 2010.
Pfeiffer, B. D. et al., Refinement of tools for targeted gene expression in *Drosophila*, Genetics, vol. 186, No. 2, pp. 735-755, 2010.
Pfeiffer, B. D. et al., Using translational enhancers to increase transgene expression in *Drosophila*. Proc Natl Acad Sci U S A, vol. 109, No. 17, pp. 6626-6631, 2012.
Pomiankowski et al., "The evolution of the *Drosophila* sex-determination pathway", Genetics, vol. 166, pp. 1761-1773, 2004.
Poindexter, "Biological properties and classification of the Caulobacter group," Bacteriol Rev 28:231-295 (1964).
Popovici, J. et al., Assessing key safety concerns of a Wolbachia-based strategy to control dengue transmission by Aedes mosquitoes. Mem. Inst. Oswaldo Cruz 105, pp. 957-964, (2010).
Port, F. et al., Optimized CRISPR/Cas Tools for Efficient Germline and Somatic Genome Engineering in *Drosophila*. Proceedings of the National Academy of Sciences of the United States of America 111 (29), pp. E2967-E2976. (2014).
Preston, Christine R., Carlos C. Flores, and William R. Engels. 2006. "Differential Usage of Alternative Pathways of Double-Strand Break Repair in *Drosophila*." Genetics 172 (2): 1055-68.
Ran, F. A. et al., Genome engineering using the CRISPR-Cas9 system, Nature protocols, vol. 8, No. 11, pp. 2281-2308, 2013.
Randolph, S.E. et al., "The arrival, establishment and spread of exotic diseases: patterns and predictions," Nat Rev Microbiol., vol. 8 No. 5, pp. 361-371; (2010).
Reeves, R. G., J. Bryk, P. M. Altrock, J. A. Denton, and F. A. Reed. 2014. "First Steps towards Underdominant Genetic Transformation of Insect Populations." PloS One 9 (5): e97557.
Rendon et al., "Medfly (Diptera: Tephritidae) genetic sexing: large-scale field comparison of males-only and bisexual sterile fly releases in Guatemala", Journal of Economic Entomology, vol. 97, No. 5, pp. 1544-1553, 2004.
Resnik, D., Ethical Issues in Field Trials of Genetically Modified Disease-Resistant Mosquitoes, Dev. World Bioeth, vol. 14, pp. 37-46, (2014).
Restriction Requirement Dated Feb. 23, 2015 in U.S. Appl. No. 14/206,011.
Restriction Requirement Dated Sep. 14, 2015 in U.S. Appl. No. 14/631,171.
Restriction Requirement Dated Jan. 11, 2018 in U.S. Appl. No. 15/164,452.
Riehle, M. M. et al., Anopheles gambiae APL1 is a family of variable LRR proteins required for Rel1-mediated protection from the malaria parasite, *Plasmodium berghei*, PLoS One, vol. 3, No. 11, e3672, 2008.
Ringrose, L., et al., Quantitative comparison of DNA looping in vitro and in vivo: chromatin increases effective DNA flexibility at short distances, The EMBO Journal, vol. 18, No. 23, 6630-6641, 1999.
Robinson et al., "Cytological, linkage and insecticide studies on a genetic sexing line in Anopheles stephensi Liston", Heredity, vol. 58, pp. 95-101, 1987.
Robinson A.S., A reassessment of the use of chromosome inversions for insect control, Journal of Heredity, vol. 66, pp. 35-37, 1975.
Robinson, A. S. et al., Insect transgenesis and its potential role in agriculture and human health, Insect biochemistry and molecular biology, vol. 34, No. 2, pp. 113-120, 2004.
Robinson, A.S. et al., Controlled Crosses and Cage Experiments with a Translocation in *Drosophila*, Genetica, vol. 44, pp. 591-601; 1973.
Robinson, A.S., Progress in the use of chromosomal translocations for the control of insect pests. Biological Reviews, vol. 51, No. 1, pp. 1-24, 1976.
Rong, Y. S. et al., The homologous chromosome is an effective template for the repair of mitotic DNA double-strand breaks in *Drosophila*, Genetics, vol. 165, No. 4, pp. 1831-1842, 2003.
Rørth, P, Gal4 in the *Drosophila* female germline, Mechanisms of development, vol. 78, No. 1, pp. 113-118, 1998.
Royden, C., et al., The Tko Locus, Site of a Behavioral Mutation in *D. melanogaster*, Codes for a Protein Homologous to Prokaryotic Ribosomal Protein S12. Cell 51 (2), pp. 165-173, (2004).
Sambrook et al., Molecular Cloning, a Laboratory Manual, Cold Springs Harbor Press, Cold Springs Harbor, N. Y. 1989, Second Edition.
Schmid-Hempel, P., Evolutionary ecology of insect immune defenses, Annu Rev Entomol, vol. 50, pp. 529-551, 2005.
Schnutgen, F. et al., Adopting the good reFLEXes when generating conditional alterations in the mouse genome, Transgenic research, vol. 16, No. 4, pp. 405-413, 2007.
Schwartz, E. C. et al., Post-translational enzyme activation in an animal via optimized conditional protein splicing, Nat Chem Biol, vol. 3, No. 1., pp. 50-54, 2007.
Seawright et al., "Genetic method for the preferential elimination of females of anopheles albimanus", Science, vol. 200, No. 4347, pp. 1303-1304, 1978.
Sebrovskii, A. et al. A New Possible Method of Pest Control. Zool Zh, vol. 19, pp. 618-630, (1940).
Segura et al., "Genetic analysis of a chromosomal region containing vanA and vanB, genes required for conversion of either ferulate or vanillate to protocatechuate in Acinetobacter," J Bacteriol 181:3494-3504 (1999).
Seidel, H. S., M. Ailion, J. Li, A. van Oudenaarden, M. V. Rockman, and L. Kruglyak. 2011. "A Novel Sperm-Delivered Toxin Causes Late-Stage Embryo Lethality and Transmission Ratio Distortion in C. Elegans." PLoS Biology 9 (7): e1001115.
Sellin, J. et al., Dynamics of heart differentiation, visualized utilizing heart enhancer elements of the *Drosophila melanogaster* bHLH transcription factor Hand, Gene Expr Patterns, vol. 6, No. 4, pp. 360-375, 2006.
Shaner, N. et al., Improved Monomeric Red, Orange and Yellow Fluorescent Proteins Derived from *Discosoma* Sp. Red Fluorescent Protein, Nature Biotechnology, 22 (12), pp. 1567-1572, (2004).
Shetty, "Genetic sexing system for the preferential elimination of females in Culex quinquefasciatus", Journal of the American Mosquito Control Association, vol. 3, No. 1, pp. 84-86, 1987.
Sherizen, D. et al., Meiotic recombination in *Drosophila* females depends on chromosome continuity between.
Shmakov, S. et al., Discovery and Functional Characterization of Diverse Class 2 CRISPR-Cas Systems. Mol. Cell 60, 385-397 (2015).

(56) References Cited

OTHER PUBLICATIONS

Shmakov, S. et al., Diversity and evolution of class 2 CRISPR-Cas systems. Nat. Rev. Microbiol. 15, pp. 169-182 (2017).
Simoni, A. et al., Development of synthetic selfish elements based on modular nucleases in *Drosophila melanogaster*. Nucleic Acids Res. vol. 42, pp. 7461-7472 (2014).
Singleton et al., Dictionary of Microbiology and Molecular Biology, J. Wiley & Sons, New York, N. Y., 1994, Second Edition.
Sinkins, S. P. et al., Gene drive systems for insect disease vectors, Nat Rev Genet, vol. 7, No. 6, pp. 427-435, 2006.
Spradling, A. C. et al., Transposition of cloned P elements into *Drosophila* germ line chromosomes. Science, vol. 218, No. 4570, pp. 341-347, 1982.
Steller et al., "A Transposable P Vector That Confers Selectable G418 Resistance to *Drosophila* Larvae", EMBO Journal, vol. 4, No. 1, pp. 167-171, 1985.
Sun, N., and H. Zhao. 2014. "A Single-Chain TALEN Architecture for Genome Engineering." Molecular bioSystems 10 (3): 446-53.
Szymczak, A. L. et al., Correction of multi-gene deficiency in vivo using a single 'self-cleaving' 2A peptide-based retroviral vector, Nature biotechnology, vol. 22, No. 5, pp. 589-594, 2004.
Tatem, A.J. et al., Global transport networks and infectious disease spread, Adv Parasitol, vol. 62, pp. 293-343; 2006.
Thanbichler et al., "A comprehensive set of plasmids for vanillate- and xylose-inducible gene expression in Caulobacter crescentus," Nucleic Acids Res 35:e137 (2007).
Theilmann et al., "Molecular analysis of the trans-activating IE-2 gene of Orgyia pseudotsugata multicapsid nuclear polyhedrosis virus", Virology, vol. 187, pp. 84-96, 1992.
Thomas et al., "Insect population control using a dominant, repressible, lethal genetic system," Science 287:2474-2476 (2000).
Thorpe, H. M. et al., Control of directionality in the sitespecific recombination system of the Streptomyces phage φC31, Molecular microbiology, vol. 38, No. 2, pp. 232-241, 2000.
Tolle, M. A., Mosquito-borne diseases. Current problems in pediatric and adolescent health care, vol. 39, No. 4, pp. 97-140, 2009.
Travanty, E., et al., Using RNA interference to develop dengue virus resistance in genetically modified Aedes aegypti. Insect Biochem. Mol. Biol. 34, pp. 607-613, (2004).
Tripet, F. et al., Ecological immunology of mosquito-malaria interactions, Trends Parasitol vol. 24 No. 5-3, pp. 219-227; 2008.
Uemura, M. et al., Chromosomal manipulation by site-specific recombinases and fluorescent protein-based vectors, PloS one vol. 5 No. 3, e9846; 2010.
Van Dyke, D. L. et al., The frequency and mutation rate of balanced autosomal rearrangements in man estimated from prenatal genetic studies for advanced maternal age, American journal of human genetics, vol. 35, No. 2, pp. 301-308, 1983.
Wade, M. J., and R. W. Beeman. 1994. "The Population Dynamics of Maternal-Effect Selfish Genes." Genetics 138 (4): 1309-14.
Walker, T. et al., The wMel Wolbachia strain blocks dengue and invades caged Aedes aegypti populations, Nature, vol. 476, No. 7361, pp. 450-453, 2011.
Wang, S. et al., Genetic approaches to interfere with malaria transmission by vector mosquitoes, Trends in biotechnology, vol. 31, No. 3, pp. 185-193, 2013.
Ward, Catherine M., Jessica T. Su, Yunxin Huang, Alun L. Lloyd, Fred Gould, and Bruce A. Hay. 2011. "Medea Selfish Genetic Elements as Tools for Altering Traits of Wild Populations: A Theoretical Analysis." Evolution; International Journal of Organic Evolution 65 (4): 1149-62.
Weber, E. et al., A modular cloning system for standardized assembly of multigene constructs, PLoS one, vol. 6, No. 2, e16765, 2011.
Whitten, M. J., Insect control by genetic manipulation of natural populations, Science, vol. 171, No. 3972, pp. 682-684, 1971.
WHO World Malaria Report dated 2014, accessed on the world wide web at <who.int/malaria/publications/world_malaria_report_2014/en/>.
Willis, N.L. et al., Reciprocal translocations and partial correlation of chromosomes in the stable fly, J Hered vol. 72 No. 2, pp. 104-106; 1981.
Windbichler, Nikolai, Philippos Aris Papathanos, Flaminia Catteruccia, Hilary Ranson, Austin Burt, and Andrea Crisanti. 2007. "Homing Endonuclease Mediated Gene Targeting in Anopheles Gambiae Cells and Embryos." Nucleic Acids Research 35 (17): 5922-33.
Windbichler, N. et al., A synthetic homing endonuclease-based gene drive system in the human malaria mosquito, Nature, vol. 473, No. 7346, pp. 212-215, 2011.
Windbichler, N., P. A. Papathanos, and A. Crisanti. 2008. "Targeting the X Chromosome during Spermatogenesis Induces Y Chromosome Transmission Ratio Distortion and Early Dominant Embryo Lethality in Anopheles Gambiae." PLoS Genetics.
World Health Organization Global Burden of Disease Study, Retrieved Apr. 30, 2014, from who.int/evidence/bod, 2000.
Xie, et al., "Antagonistic control of a dual-input mammalian gene switch by food additives." Nucleic acids research (2014): gku545.
Yamada et al., "Genetic sex separation of the malaria vector, Anopheles arabiensis, by exposing eggs to dieldrin", Malaria Journal, vol. 11, No. 1, pp. 208-219, 2012.
Yen, P. et al. Synthetic miRNAs induce dual arboviral-resistance phenotypes in the vector mosquito *Aedes aegypti*. Commun. Biol. 1, pp. 11 (2018).
Yu, Y. et al., Engineering chromosomal rearrangements in mice, Nat Rev Genet, vol. 2, No. 10, pp. 780-790, 2001.
Zeh et al., "From father to son: transgenerational effect of tetracycline on sperm viability," Sci Rep 2:375 (2012).
Zettler, J. et al., The naturally split Npu DnaE intein exhibits an extraordinarily high rate in the protein trans-splicing reaction, FEBS Lett, vol. 583, No. 5, pp. 909-914, 2009.
Zhou, X. et al., Optimization of the Tet-On system for regulated gene expression through viral evolution, Gene therapy, vol. 13, No. 19, pp. 1382-1390, 2006.
Zhu, X. D. et al., Cleavage-dependent ligation by the FLP recombinase; characterization of a mutant flp protein with an alteration in a catalytic amino acid, Journal of Biological Chemistry, vol. 270, No. 39, pp. 23044-23054, 1995.
File History of U.S. Appl. No. 14/170,118.
File History of U.S. Appl. No. 14/206,011.
File History of U.S. Appl. No. 14/631,171.
File History of U.S. Appl. No. 14/837,941.
File History of U.S. Appl. No. 15/164,452.
Gould, F., et al., Pest Management By Genetic Addiction, Proceedings of the National Academy of Sciences of the United States of America, vol. 116, No. 13, pp. 5849-5851, 2019.
Nowak, C.M., et al., Guide RNA Engineering for Versatile Cas9 functionality, Nucleic Acids Research, vol. 44, No. 20, pp. 9555-9564, 2016.
Oberhofer, G., et al., Cleave and Rescue, a Novel Selfish Genetic Element and General Strategy for Gene Drive, Proceedings of the National Academy of Sciences of the United States of America, vol. 116, No. 13, pp. 6250-6259, 2019.
Oberhofer, G., et al., Cleave and Rescue, a Novel Selfish Genetic Element and General Strategy for Gene Drive, Supplementary Information for Proceedings of the National Academy of Sciences of the United States of America, vol. 116, No. 13, pp. 6250-6259, 2019.
Oberhofer, G., et al., Gene Drive and Resilience Through Renewal With Next Generation Cleave and Rescue Selfish Genetic Elements, Proceedings of the National Academy of Sciences of the United States of America, vol. 117, No. 16, pp. 9013-9021, 2020.
Peng, J., et al., High-throughput screens in mammalian cells using the CRISPR-Cas9 system, The FEBS Journal, vol. 282, pp. 2089-2096, 2015.
Bonneau et al., "The Effects of Immunization Against Luteinizing Hormone-Releasing Hormone on Performance, Sexual Development, and Levels of Boar Taint-Related Compounds in Intact Male Pigs," Journal of Animal Science 72:14-20, 1994.
Carvajal-Vallejos, et al. Unprecedented Rates and Efficiencies Revealed for New Natural Split Inteins from Metagenomic Sources, The journal of Biological Chemistry, vol. 287, No. 34, pp. 28686-28696, 2012.

(56) References Cited

OTHER PUBLICATIONS

Hu et al., A Large Gene Family in Fission Yeast Encodes Spore Killers That Subvert Mendel's Law, 2017.
Notice of Allowance Dated Feb. 3, 2021 in U.S. Appl. No. 15/164,452.
Oberhofer et al., "Split versions of Cleave and Rescue selfish genetic elements for measured self limiting gene drive," BA.PLoS Genet., Feb. 18, 2021;17(2):e1009385. doi: 10.1371/journal.pgen.1009385.
Biswajit, P., megaTAL-mediate Gene Editing at the CCR5 locus, PhD Dissertation, University of Washington, pp. 1-113, 2016.
Burt and Trivers, Genes in Conflict, 2008.
Centers for Disease Control and Prevention (2014). About malaria. Retrieved Apr. 30, 2014, from cdc.gov/malaria/about/facts.html.
Centers for Disease Control and Prevention (2012). Dengue fact sheet. Retrieved Apr. 30, 2014, from cdc.gov/Dengue/faqFacts/fact.html.
Chen et al, An Enhanced Gene Targeting Toolkit for *Drosophila*: Golic+, Genetics, vol. 199, pp. 683-694, 2015.
Farasat, I, Salis HM,A Biophysical Model of CRISPR/Cas9Activity for Rational Design of Genome Editing and Gene Regulation. PLoS Comput Biol 12(1):e1004724, 2016.
Gratz et al, CRISPR-Cas9 Genome Editing in Unit 31.2 *Drosophila*, Current Protocols in Molecular Biology 31.2.1-31.2.20, 2015.
Lack et al., A Thousand Fly Genomes: An Expanded Drosophila Genome Nexus. Mol Biol Evol33(12):3308-3313.Marshall, J. M. 2009. "The Effect of Gene Drive on Containment of Transgenic Mosquitoes." Journal of Theoretical Biology 258 (2): 250-65, 2016.
Naveira et al., The Theoretical Distribution of Lengths of Intact Chromosome Segments Around a Locus Held Heterozygous With Backcrossing in a Diploid Species, Genetics, vol. 130:205-209, 1992.
Pacher et al., Two Unlinked Double-Strand Breaks Can Induce Reciprocal Exchanges in Plant Genomes via Homologous Recombination and Nonhomologous End Joining, Genetics 175: 21-29, 2007.
Restriction Requirement in U.S. Appl. No. 17/004,698 dated Nov. 28, 2022.
Gould and Schliekelman, Population Genetics of Autocidal Control and Strain Replacement, Annu. Rev. Entomol. 49: 193-217, 2004.
Serebrovsky, A.S., On the possibility of a new method for the control of insect pests. Zool. Zh. 19,4, pp. 123-137, 1940.
World Health Organization (2014b). Dengue factsheet. Retrieved Apr. 30, 2014, from who.int/mediacentre/factsheets/fs117/en/index.html.
International Preliminary Reporton Patentability in PCT/US2018/030990 mailed on Nov. 14, 2019.

\* cited by examiner

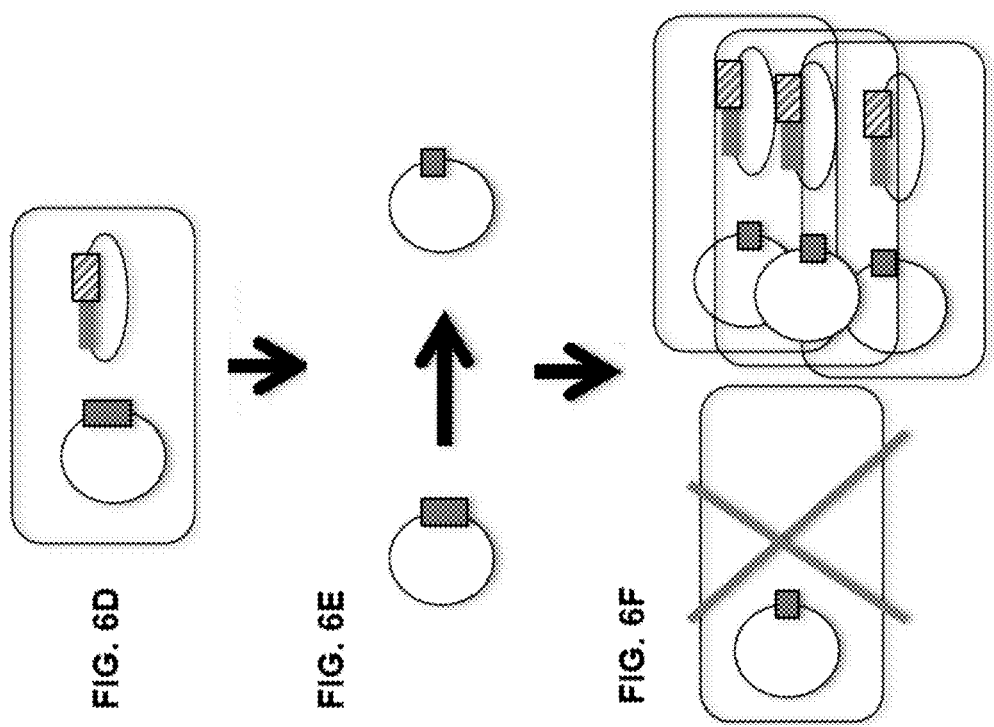
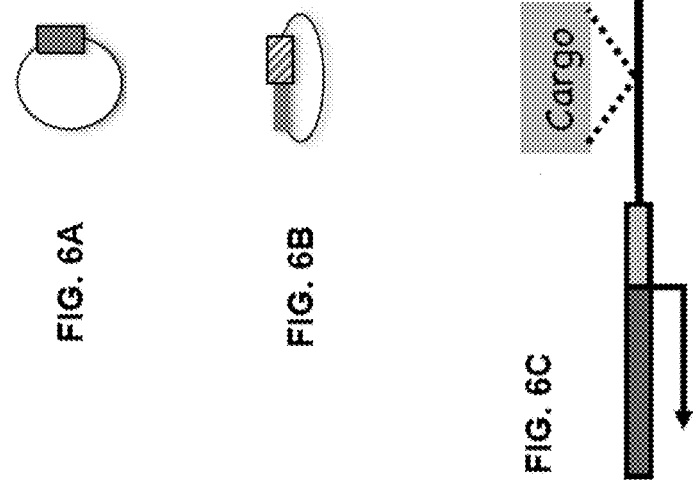
FIG. 6A – FIG. 6F

```
                      PAM           gRNA1
                      CCGtgg        aatggcatcgctgcagc
reference accgccgtccgtgg--------------aatggcatcgctgcagcagatgcaccgcagcggaccgcacataaagacgcgt
w[1118] control ACCGCCGTCCGTGG--------------AATGGCATCGCTGCAGCAGATGCACCGCAGCGGACCGCACATAAAGACGCGT
                ACCGCCGTCCGTCCGTGG------------A--CATCGCTGCAGCAGATGCACCGCAGCGGACCGCACATAAAGACGCGT
                ACCGCCGTCCGTCCGT-----------------------------------------ACCGTCCGTACACGGACCGCACATAAAGACGCGT
                ACCGCCGTCCGTCCGT-----------------------------------------ACCGTCCGTACACGGACCGCACATAAAGACGCGT
                ACCGCCGTCCGTCCGT-----------------------------------------ACCGTCCGTACACGGACCGCACATAAAGACGCGT
                ACCGCCGTCCGTCCGTGG-------------ATCGCTGCAGCAGATGCACCGCAGCGGACCGCACATAAAGACGCGT
                ACCGCCGTCCGTCCGT-----------------------------------------ACCGTCCGTACACGGACCGCACATAAAGACGCGT
                ACCGCCGTCCGTCCGT---------------CGGCATCGCTGCAGCAGATGCACCGCAGCGGACCGCACATAAAGACGCGT
                ACCGCCGTCCGTCCGT---------------CGGCATCGCTGCAGCAGATGCACCGCAGCGGACCGCACATAAAGACGCGT
                ACCGCCGTCCGTCCGTGG-------------GGCATCGCTGCAGCAGATGCACCGCAGCGGACCGCACATAAAGACGCGT
♂X/Y;Clvrko    ACCGCCGTCCGTCCGTGG------------A--GGCATCGCTGCAGCAGATGCACCGCAGCGGACCGCACATAAAGACGCGT
offspring from ACCGCCGTCCGTCCGTGG------------A--GGCATCGCTGCAGCAGATGCACCGCAGCGGACCGCACATAAAGACGCGT
♀Clvrko/+ XX ♂w[1118] ACCGCCGT-----------------------------------------------------------CCGCACATAAAGACGCGT
                ACCGCCGT-----------------------------------------------------------CCGCACATAAAGACGCGT
                ACCGC---------------------------------------------------------------------------CGT
                ACCGC---------------------------------------------------------------------------CGT
                ACCGCCGTCCGTCCGTGGACCGACATGCAGCGGCATCGCTGCAGCAGATGCACCGCAGCGGACCGCACATAAAGACGCGT
                ACCGCCGTCCGTCCGTGGACCGACATGCAGCGGCATCGCTGCAGCAGATGCACCGCAGCGGACCGCACATAAAGACGCGT
                ACCGCCGTCCGTCCGTG-------------ACCGACATGCAGCGGCATCGCTGCAGCAGATGCACCGCAGCGGACCGCACATAAAGACGCGT
                ACCGCCGTCCGTCCGTG-------------ACCGACATGCAGCGGCATCGCTGCAGCAGATGCACCGCAGCGGACCGCACATAAAGACGCGT
```

DNA SEQUENCE MODIFICATION-BASED GENE DRIVE

CROSS-REFERENCE TO RELATED APPLICATIONS

This application claims the benefit of U.S. Provisional Application 62/502,338 filed on May 5, 2017, which is hereby incorporated by reference in its entirety.

STATEMENT REGARDING FEDERALLY SPONSORED R&D

This invention was made with government support from the US Department of Agriculture, National Institute of Food and Agriculture specialty crop initiative under USDA NIFA Award No. 2012-51181-20086. The government has certain rights in the invention.

REFERENCE TO ELECTRONIC SEQUENCE LISTING

The present application is being filed along with an Electronic Sequence Listing. The Electronic Sequence Listing is provided as a file entitled CALTE130ASEQLIST.txt which is 83,106 bytes in size, created on May 3, 2018. The information in the Electronic Sequence Listing is incorporated herein by reference in its entirety.

BACKGROUND

Field

The disclosure is generally related to DNA sequence modification-based modification of a population.

Description of the Related Art

Gene drive occurs when genetic elements—including genes, gene complexes, entire chromosomes and endosymbiotic bacteria—are transmitted to viable, fertile progeny at rates greater than those due to Mendelian transmission, resulting in an increase in their frequency in the population over time, even if their presence results in a fitness cost to carriers.

SUMMARY

In some embodiments, a vector is provided. In some embodiments, the vector comprises a first gene encoding a DNA sequence modifying enzyme, wherein the DNA modifying enzyme modifies an endogenous copy of an essential gene, a first promoter operably linked to the first gene encoding the DNA sequence modifying enzyme, a second gene encoding a rescue transgene, a second promoter operably linked to the rescue transgene, and optionally, one or more cargo sequences, wherein the vector is configured to be positioned in a chromosome or an extra-chromosomal element.

In some embodiments of the vector, the DNA sequence modifying enzyme is a nuclease or a base editor. In some embodiments of the vector, the nuclease cleaves and generates one or more double strand breaks in the endogenous copy of the essential gene. In some embodiments of the vector, the one or more double strand breaks are repaired to create an altered sequence of the essential gene. In some embodiments of the vector, the base editor creates one or more base changes in the endogenous copy of the essential gene to create an altered sequence of the essential gene. In some embodiments of the vector, the one or more base changes comprise one or more point mutations in the endogenous copy of the essential gene.

In some embodiments of the vector, the rescue transgene is either a recoded copy of the essential gene or is a gene of unrelated sequence, wherein the rescue transgene encodes a protein that is functionally equivalent to a protein encoded by the essential gene, and wherein the DNA sequence modifying enzyme does not modify the rescue transgene.

In some embodiments of the vector, the chromosome is an autosome, X chromosome, Y chromosome, or supernumerary chromosome. In some embodiments of the vector, the extra-chromosomal element is a plasmid or a virus.

In some embodiments of the vector, the one or more cargo sequences comprise one or more foreign gene sequences, or one or more alleles of an endogenous chromosomal or extra-chromosomal gene to which the vector has been linked through nearby insertion on the chromosome or extra-chromosomal element that carries the endogenous allele of interest.

In some embodiments of the vector, the DNA sequence modifying enzyme is selected from the group consisting of Cas9, Cas-9-related RNA-guided nucleases, ZFN, TALEN, homing endonuclease, restriction enzymes, natural site-specific nucleases, engineered site-specific nucleases, base editing enzymes, cytidine deaminase, and adenine deaminase.

In some embodiments, the vector further comprises one or more additional sequences, wherein the one or more additional sequences allow the vector to be positioned in the chromosome or the extra-chromosomal element. In some embodiments of the vector, the one or more additional sequences is selected from the group consisting of transposase binding site, LTRs, recombinase binding site, a sequence with homology to a desired location on the chromosome or the extra-chromosomal element.

In some embodiments of the vector, the first promoter is selected from the group consisting of a germline promoter, a male specific germline promoter, a female specific germline promoter, a cell-type specific promoter, a tissue-specific promoter, a ubiquitous promoter, a promoter activated at a specific stage of mitosis, and a promoter activated at a specific stage of meiosis.

In some embodiments of the vector, the double strand break is repaired by a mechanism selected from the group consisting of non-homologous end joining, microhomology-mediated end joining, and incomplete homologous recombination.

In some embodiments of the vector, the size of the one or more cargo sequences ranges from about 0.5 kb to about 500 kb.

In some embodiments of the vector, the nuclease comprises at least one nuclease domain and one or more DNA binding domains. In some embodiments of the vector, when the nuclease is Cas9 or a Cas9-related enzyme, the vector further comprise one or more genes encoding a guide RNA, wherein the guide RNA enables the nuclease to target specific sequences within the essential gene through Watson-Crick base pairing. In some embodiments of the vector, when the nuclease is Cas9, the nuclease domain of Cas9 is inactivated through one or more mutations, and the vector comprises a different nuclease domain. In some embodiments of the vector, the different nuclease domains is single chain variant of FokI. In some embodiments of the vector, when the DNA binding domain is a TALE, the nuclease domain is provided as a single active nuclease domain, such as single chain variants of FokI.

In some embodiments, a method of modifying a population by a vector is provided. In some embodiments, the method comprises obtaining an organism of the population, positioning the vector, configured to be positioned in at least one chromosome or extra-chromosomal element in the organism, comprising a first gene encoding a DNA sequence modifying enzyme, wherein the DNA modifying enzyme modifies an endogenous copy of an essential gene, a first promoter operably linked to the first gene encoding the DNA sequence modifying enzyme, a second gene encoding a rescue transgene, a second promoter operably linked to the rescue transgene, and optionally, one or more cargo sequences, expressing the DNA sequence modifying enzyme in the organism, inducing one or more sequence modifications in the essential gene in one or more cells in the organism, such that the one or more sequence modifications result in the essential gene being rendered partially or wholly non-functional and result in a defect in survival, growth control, fertility, or differentiation of the one or more cells if the one or more cells lack the rescue transgene, rescuing the defects in survival, growth control, or differentiation of the one or more cells in which the essential gene has been rendered partially or wholly non-functional, by the rescue transgene, generating an altered organism, wherein the altered organism carries one or more copies of the vector, and wherein the defects in survival, growth control, or differentiation of the one or more cells in which the essential gene has been rendered partially or wholly non-functional have been rescued by the rescue transgene, introducing the altered organism in an environment wherein an increase in a frequency of the altered organism is desired relative to a frequency of a wild type organism in the population; replacing the wild type organism with the altered organism in the population in the environment wherein the altered organism is introduced, thereby modifying the population.

In some embodiments of the method, an organism with the defect in survival, growth control, fertility, or differentiation of the one or more cells is eliminated if the one or more cells of the organism lack the rescue transgene.

In some embodiments of the method, the DNA sequence modifying enzyme does not modify the rescue transgene.

In some embodiments of the method, rescuing the defects in survival, growth control, or differentiation is achieved by restoring normal survival, growth control, fertility, or differentiation of the one or more cells by the rescue transgene.

In some embodiments of the method, the one or more cells comprise somatic cells, germline cells, gametes, or a combination thereof.

In some embodiments of the method, the DNA sequence modifying enzyme is a nuclease or a base editor. In some embodiments of the method, the nuclease cleaves and generates one or more double strand breaks in the endogenous copy of the essential gene.

In some embodiments of the method, the one or more double strand breaks are repaired to create an altered sequence comprising insertions, deletions, base alterations, or a combination thereof.

In some embodiments of the method, the base editor creates one or more base changes or small insertions/deletions in the endogenous copy of the essential gene. In some embodiments of the method, the one or more base changes comprise one or more point mutations, or deaminated bases that are replaced with nucleotides of a different sequence.

In some embodiments of the method, the altered organism is heterozygous or homozygous for the vector. In some embodiments of the method, the organism is haploid, diploid, or polyploid. In some embodiments of the method, the organism is selected from the group consisting of prokaryotes, fungi, plants, and animals.

In some embodiments of the method, the environment comprises an open environment, a bioreactor, a multicellular body, or a colony of individual cells.

In some embodiments of the method, the wild type organism is replaced at a high frequency with the altered organism in the environment wherein the wild type organism is present. In some embodiments of the method, the high frequency is defined as replacement of at least 90% of the wild type organism with the altered organism after 100 generations in the population. In some embodiments of the method, the wild type organism is replaced at a rapid rate with the altered organism in the environment wherein the wild type organism is present. In some embodiments of the method, the rapid rate is defined as replacement of at least 90% of the wild type organisms by organisms carrying the vector in the population after at most 100 generations.

In some embodiments of the method, the one or more sequence modifications in the one or more cells is a result of the one or more cells carrying the first gene encoding the DNA sequence modifying enzyme or is a result of the DNA sequence modifying enzyme being transmitted to the one or more cells from one or more cells expressing the DNA sequence modifying enzyme through diffusion, active transport, or movement of the DNA sequence modifying enzyme from a cell that expresses the DNA sequence modifying enzyme to a cell that does not express the DNA sequence modifying enzyme.

In some embodiments of the method, the vector is positioned on the chromosome or the extra-chromosomal element by a homologous recombination-dependent integration. In some embodiments of the method, the vector is positioned on the chromosome or extra-chromosomal element by random integration, integration using transposition, integration using a recombinase, or a combination thereof.

In some embodiments of the method, the one or more cargo sequences comprise one or more foreign gene sequences, or one or more alleles of an endogenous chromosomal or extra-chromosomal gene to which the vector has been linked through nearby insertion on the chromosome or extra-chromosomal element that carries the endogenous allele of interest.

In some embodiments of the method, the vector is positioned on the chromosome or the extra-chromosomal element, the first gene operably linked to the first promoter, the second gene operably linked to the second promoter, and the one or more cargo transgenes are genetically linked.

In some embodiments of the method, the nuclease cleaves and generates one or more double strand breaks in the endogenous copy of the essential gene with a high cleavage efficiency. In some embodiments of the method, the high cleavage frequency is defined as the nuclease cleaving the endogenous copy of the essential gene in at least 30% of the organisms carrying the vector and the endogenous copy of the essential gene in each generation. In some embodiments of the method, the base editor creates one or more base changes in the endogenous copy of the essential gene with a high base editing frequency. In some embodiments of the method, the high base editing frequency is defined as the base editor modifying the endogenous copy of the essential gene in at least 20% of the organisms carrying the vector and the endogenous copy of the essential gene in each generation.

BRIEF DESCRIPTION OF THE DRAWINGS

FIG. 1A shows a schematic of the mechanism of action an embodiment of a vector (transgenic construct) that brings about drive of a vector-bearing Y chromosome through cleavage of an essential gene on the X chromosome.

FIG. 1B shows a schematic of an embodiment of inheritance, and viable or non-viable progeny, of an X chromosome cleavage mediated Y chromosome drive process. X (linear) and Y (kinked) chromosomes are indicated.

FIG. 1C shows a graph of an embodiment of a population frequency modeling of X cleavage mediated Y drive for different fitness costs and introduction frequencies. The heat map to the right indicates the number of generations required for the vector to reach a population frequency of >99%.

FIG. 2A shows a schematic of the mechanism of action an embodiment of a vector (transgenic construct) for cleavage mediated X drive with the vector located on the X.

FIG. 2B shows a schematic of inheritance, and viable or non-viable progeny, of a cleavage mediated X drive process with the vector located on the X.

FIG. 2C shows a graph of an embodiment of a population frequency modeling of cleavage mediated X drive with the vector located on the X.

FIG. 3A shows a schematic of the mechanism of action an embodiment of a vector (transgenic construct) for cleavage mediated autosomal drive.

FIG. 3B shows a schematic of inheritance and viable or non-viable progeny of a cleavage mediated autosomal drive process.

FIG. 3C shows a graph of an embodiment of a population frequency modeling of cleavage mediated autosomal drive.

FIG. 4A shows a schematic of the mechanism of action an embodiment of a vector (transgenic construct) for cleavage mediated 2-locus autosomal drive.

FIG. 4B shows a schematic of inheritance, and viable or non-viable progeny, of a cleavage mediated 2-locus autosomal drive process.

FIG. 4C shows a graph of an embodiment of a population frequency modeling of cleavage mediated 2-locus autosomal drive.

FIG. 5A shows a schematic of the mechanism of action an embodiment of a vector (transgenic construct) for cleavage mediated haplolethal drive.

FIG. 5B shows a schematic of inheritance and viable or non-viable progeny of a cleavage mediated haplolethal drive process.

FIG. 5C shows a graph of an embodiment of a population frequency modeling of cleavage mediated haplolethal drive.

FIG. 6A-FIG. 6F show a schematic of an embodiment of maintenance of extrachromosomal element.

FIG. 17 shows an embodiment of an alignment of the target gene (*Drosophila melanogaster* tko—Examples 15 and 16) with the recoded rescue based on *Drosophila virilis* tko. Target exon in red, recoded rescue exon in green, gRNA target sites in pink, PAM in bold letters, additional silent point mutations introduced into the rescue copy to reduce homology in blue.

FIG. 19 shows an embodiment of the results of Sanger sequencing from Example 17.

DETAILED DESCRIPTION

Figure 1A:
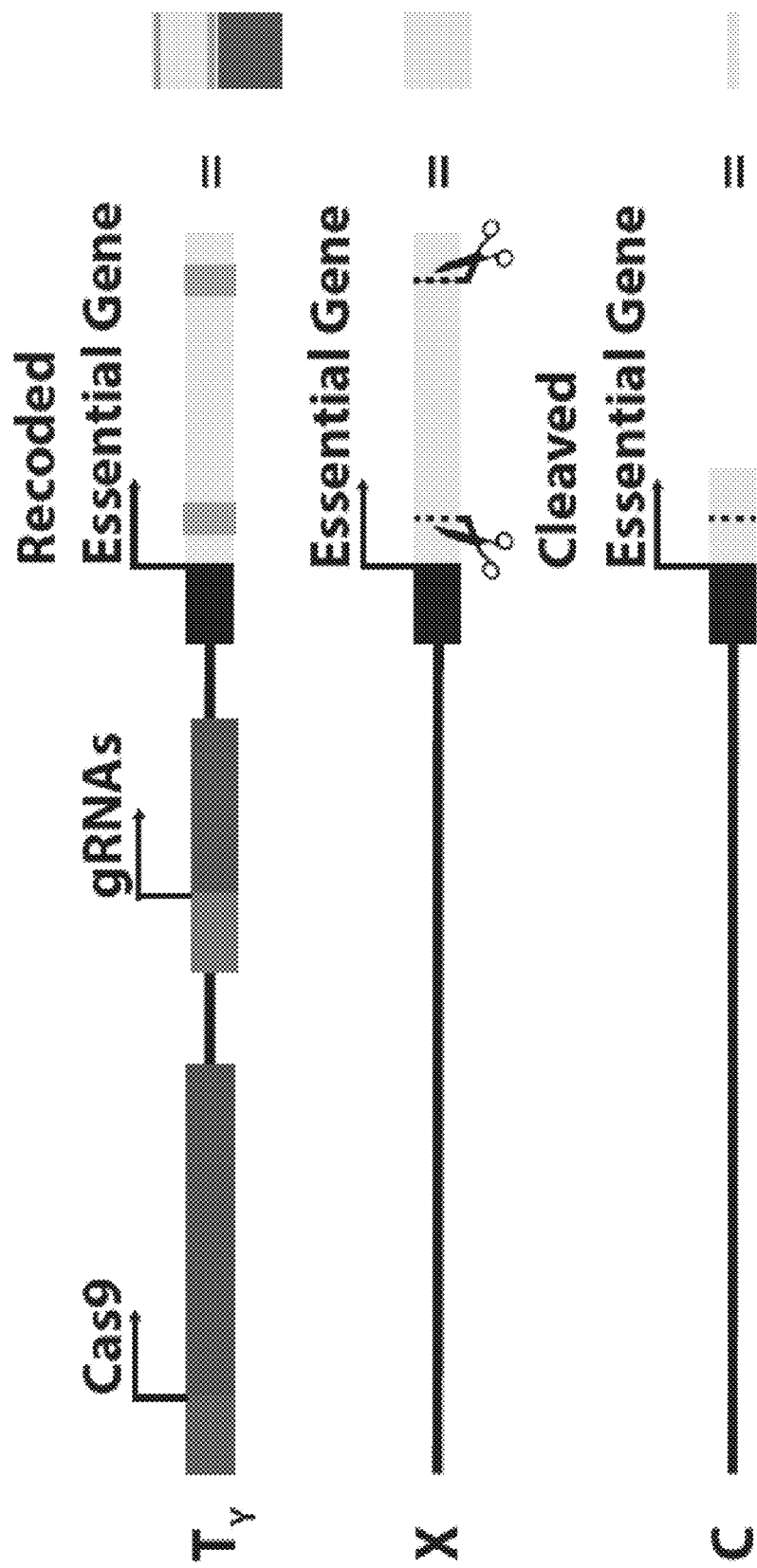
FIG. 1A-FIG. 1C show an embodiment of an X cleavage mediated Y drive. The vector is present on the Y chromosome. Cleavage of an essential gene located on the X chromosome is brought about by Cas9 and associated gRNAs. The Y chromosome also carries a recoded version of the essential gene that is resistant to cleavage by Cas9.

In nature gene drive is brought about by a number of mechanisms, in a number of contexts (Ben-David et al. 2017; Burt and Trivers 1998; Seidel et al. 2011; Nuckolls et al. 2017; Hu et al. 2017). A number of novel methods of engineering gene drive have also been proposed, and in several cases implemented.

There are two general contexts in which gene drive is considered as a technological tool. In one, the goal is population replacement: to spread a trait throughout an extant population. For organisms such as beneficial insects such traits include insecticide, natural pathogen resistance or resistance to other stresses. For a pest/disease vector traits of interest include insecticide sensitivity, the inability to carry or transmit specific pathogens, or a change in life history that preclude pathogen transmission. Genes that confer conditional lethality in response to an environmental cue, so as to ultimately bring about population suppression, are also of interest. A second goal is population suppression or elimination. Targets of interest include invasive species of plants and animals, pests that cause damage directly to plants or animals, and vectors of plant or animal disease. Finally, gene drive is also of interest as a tool for maintaining the presence of a trait in a population in which the genetic element (plasmid, chromosome, virus) in which the gene drive element and any associated cargo genes are sometimes lost, for example during cell division. This is related to population replacement.

A number of methods have been considered for bringing about self-sustaining population replacement. Many of these take as their starting point naturally occurring selfish genetic elements to which cargo genes could be linked (Braig and Yan 2001; Burt and Trivers 1998; Chen et al. 2007). Others involve the use of novel, engineered systems, many of which utilize, in one way or another, the phenomenon of underdominance (heterozygote disadvantage) (Gould and Schliekelman 2004; Marshall and Hay 2011; Marshall and Hay 2012; Marshall et al. 2011; Akbari et al. 2013; Altrock et al. 2010; Altrock et al. 2011; Davis et al. 2001; Gokhale et al. 2014; Reeves et al. 2014). An important characteristic of any gene drive mechanism is its level of invasiveness: its ability to increase in frequency both at the point of release and in surrounding areas linked to the release site by various levels of migration, when introduced at various population frequencies. Here we divide gene drive mechanisms somewhat arbitrarily into low and high threshold variants, with the understanding that these distinctions lie along a continuum. Low threshold gene drive mechanisms require that only a small fraction of individuals in the population carry the drive element in order for spread to occur locally (Marshall 2009; Marshall and Hay 2012). Examples include transposons, engineered Medea chromosomal elements (Chen et al. 2007; Wade and Beeman 1994; Ward et al. 2011), several other possible single locus chromosomal elements (Marshall and Hay 2012), site-specific nucleases that home into their target site (Burt 2003; Gantz and Bier 2015; Gantz et al. 2015; Hammond et al. 2016; Simoni et al. 2014; Windbichler et al. 2011), and site-specific nucleases located on the Y chromosome that cleave and thereby (somehow) block development of X-bearing sperm, resulting in sex ratio distortion (Galizi et al. 2014). These mechanisms are predicted to be invasive because low levels of migration of drive element-bearing individuals into areas outside the release area may, depending on the threshold and the migration rate (Beaghton et al. 2016; Beaghton et al. 2017; Godfray et al. 2017; Marshall 2009; Marshall and Hay 2012), result in these areas being seeded with enough transgene-bearing individuals that drive is likely to occur. Low threshold, invasive gene drive mechanisms are attractive when the goal is to spread transgenes over a large area, and migration rates between the release site and surrounding areas of interest are low. However, for these same reasons, it is likely to be challenging to restore the population to the pre-transgenic state if desired. High (or higher) threshold gene drive mechanisms require, as their name implies, that transgenes make up a much larger fraction of the total insect population (important examples range from ~15-70%) before gene drive occurs. Below this frequency transgenes are instead actively eliminated from the population. These drive mechanisms thus behave as frequency-dependent bistable switches. High transgene frequencies are needed to initiate drive at the release site, limiting the possibility that unintended release of a few individuals could initiate replacement (Marshall 2009). Furthermore, once replacement has occurred at the release site, spread to high frequency in areas connected to the release site by low levels of migration is prevented because the transgene never reaches the threshold frequency needed for drive (Altrock et al. 2010; Altrock et al. 2011; Marshall and Hay 2012). Finally, transgenes can be eliminated from the population if the release of wildtypes results in the frequency of transgenics being driven below the threshold required for drive. A number of gene drive mechanisms that could in principal bring about high threshold gene drive have been proposed. Examples include a number of single locus toxin-antidote gene drive mechanisms (Marshall and Hay 2011; Marshall and Hay 2012; Marshall et al. 2011), reciprocal chromosome translocations, inversions and compound chromosomes (Gould and Schliekelman 2004), and several forms of engineered underdominance (Akbari et al. 2013; Altrock et al. 2010; Altrock et al. 2011; Davis et al. 2001; Gokhale et al. 2014; Marshall and Hay 2012; Reeves et al. 2014). Two of these, $UD^{MEL}$(double Medea), and engineered reciprocal translocations, have recently been shown to drive reversible population replacement into populations of wildtype *Drosophila* (Akbari et al. 2013; Buchman et al. 2018). A third system has been shown to drive high threshold population replacement in *Drosophila* in a split configuration (Reeves et al. 2014). In each of these systems gene drive occurs when transgene-bearing chromosomes experience frequency-dependent changes in fitness with respect to non-transgene-bearing counterparts, with the former having high fitness at high frequency and lower fitness at low frequency. These systems all rely, in one way or another, on the phenomena of underdominance, in which transgene-bearing heterozygotes (or some fraction of them or their progeny) have a lower fitness than either homozygous wildtypes or homozygous transgenics (or transgene-bearing trans-heterozygote in some three allele cases). If the frequency of one allele or pair of alleles or chromosome type is above a critical threshold it spreads to genotype, and in some cases allele fixation. Conversely, if it falls below the critical threshold it is lost in favor of the other allele or chromosome type, usually wildtype. In broad outline, this behavior occurs because when transgene-bearing individuals are common they mate mostly with each other, producing transgene-bearing offspring of high fitness (high survival and/or fecundity), while wildtypes mate mostly with transgene-bearing individuals, producing a preponderance of heterozygous offspring of low fitness (inviable and/or with reduced fecundity). However, when the frequency of wildtypes is high the tables are turned, with transgene-bearing individuals producing high frequencies of unfit heterozygous progeny, and wildtypes producing a high frequency of fit homozygous progeny.

The only gene drive mechanisms shown to drive population replacement in otherwise wildtype organisms are Medea (Akbari et al. 2012; Buchman et al. 2018; Chen et al. 2007), UDMEL (Akbari et al. 2013), and reciprocal chromosome translocations (Buchman et al. 2018), all in *Drosophila melanogaster* or *Drosophila suzukii*. Several other methods, including engineered underdominance (Reeves et al. 2014) and homing endonucleases (Windbichler et al. 2011; Windbichler et al. 2007; Simoni et al. 2014; Gantz and Bier 2015; Gantz et al. 2015; Hammond et al. 2016; Champer et al. 2017; Chan et al. 2011; Chan et al. 2013), have seen important progress, though population replacement has not been demonstrated.

There is a need for robust mechanisms of gene drive that can easily be developed for diverse species, and that are robust to mechanisms that can cause failure of gene drive to occur. Thus, while Medea elements have been generated in *Drosophila*, it has not yet been possible to develop them in other insects. In addition, Medea is inherently challenging because it requires that early zygotic promoters be available, along with antidotes, which together are capable of rescuing maternal lethality. These reagents, as well as specific mechanisms for bringing about toxicity in embryos but not oocytes, are challenging to identify and create, and their implementation requires that one have detailed biological knowledge of the species under consideration (Hay et al. 2010). UDMEL represents a more complicated version of Medea, and therefore suffers from the same problems (Akbari et al. 2013). Homing-based population replacement is challenging for several reasons. First, it requires that DNA cleavage be followed by DNA repair using homologous recombination, and that homologous recombination proceed through the entire gene drive element that must be copied. Since the cell utilizes multiple repair pathways, and HR is inefficient, complete copying through HR often does not happen. Second, because homing requires the targeting and cleavage of a specific sequence, its efficacy is sensitive to genomic sequence variation. Variation can occur as pre existing sequence polymorphisms in a population. It can also arise from mutation, and as a result of break repair through non-homologous end joining, which is error prone (Preston et al. 2006; Windbichler et al. 2011). Regardless of the mechanism, sequence variants that are not cleaved are resistant to homing, and may retain some or complete wildtype gene function. The presence of such resistant alleles can block HEG spread and thereby prevent population replacement. Thus, the question of how to bring about high frequency homing that is gene specific, but insensitive to some level of sequence variation within the gene, is central to the development of HEG-based population replacement technologies, and remains to be solved. Translocations can only provide high threshold population replacement. They also require a significant amount of chromosomal engineering, in that two large chromosome fragments must become linked to each other, while maintaining high levels of organism fitness (Buchman et al. 2018; Marshall and Hay 2012). Finally, shredding of the X chromosome through the use of a P-linked transgene that thereby causes the loss of X-bearing sperm has also been proposed (Burt 2003), and significant progress has been made (Galizi et al. 2014; Galizi et al. 2016; Windbichler et al. 2008). However, this approach is limited to population suppression and species that have clear X and Y chromosomes in which males are Y. Many species of interest lack this configuration. In summary, gene drive for population replacement is an important technological goal, but methods for easily engineering it in diverse species are lacking.

As a specific example of the need for population replacement gene drive, despite a myriad of approaches to controlling mosquito-borne infections, ranging from insecticide treated bed nets, new anti-malarial drugs such as artemisinin, and suppression attempts using sterile males, there are still over 600,000 deaths from malaria each year [WHO World Malaria Report 2014]. This stems from a combination of lack of human compliance, emerging drug resistance, and selection for mosquitoes preferring to bite outdoors. These failures show the need for novel molecular approaches to combating insect-borne disease [Alphey, 2014].

However, the approaches proposed face substantial barriers to their development. In toxin-antidote systems, the toxin has to be strong enough to suppress one or both copies of the target gene and the recoded 'antidote' version of this gene has to have strong enough and timely zygotic expression to compensate for the loss of the maternal product Chen et al 2007, [Akbari, 2013; Akbari, 2014]. These are already difficult requirements for the development of the original gene drive, let alone successive drives in case the original mutates to inactivity. Additionally, what works in one species, such as the Medea$^{myd88}$ in *Drosophila melanogaster*, does not necessarily work in other species, such as *Aedes aegypti*, despite sharing the molecular components involved in the drive.

HEG approaches are elegant in that they increase their frequency not through the destruction of competing alleles as in toxin-antidote drives but by copying themselves onto non HEG containing homologs, thus forcing heterozygotes for the HEG to become homozygous. However, they suffer from the being limited in what they can target due to their inherent base specificity and from potential replication errors every time they are copied.

HEG based approaches to gene drive are predicted to be very powerful, driving from low frequency and in relatively few generations. The emergence of TALENs and ZFNs have vastly expanded the number of possible target sites while maintaining specificity, but their multiple repeats make them prone to mutation due to recombination [Simoni, 2014; Esvelt, 2014]. An alternative now being very actively explored utilizes the CRISPR nuclease Cas9 and gRNAs that target Cas9 to specific sequences for cleavage based on Watson-Crick base pairing interactions. While HEGs based on Cas9 can target virtually any sequence, a Cas9 drive construct is likely to be quite large, making homing more difficult and the construct much more prone to copying errors.

While drives like Medea can incorporate new toxins in addition to old ones to perform additional stages of replacement, adding additional gRNAs will buffer a Cas9 HEG against NHEJ resistant alleles but will only make the construct even larger and thus more prone to other problems, such as abortive gap repair.

Cas9 can be used at the heart of any of the gene drives previously proposed for use as HEGs, with a substantially larger pool of potential targets while maintaining specificity. However, these strategies have the major drawback of susceptibility to DNA loss or drive dysfunction due to the imperfect copying of Cas9 during homology directed repair.

Described herein is a novel mechanism for gene drive that is very simple, yet powerful, and utilizes only two simple components that can be readily engineered in any organism for which genetic engineering can be achieved. The first component is a gene expressing an enzyme that bring about DNA sequence modification, and thus inactivation, of an essential gene. The second component is a transgene (the rescue transgene) that is able to rescue the loss of function phenotype due to inactivation of the endogenous copies of the essential gene, and is insensitive to enzyme-mediated DNA sequence modification. This method requires only two components: a site-specific DNA modifying enzyme that targets a gene required for viability or fertility in any way (an essential gene), and a second, functional version of the essential gene that includes sequences that are resistant to modification by the site-specific DNA modifying enzyme (the rescue transgene). When these two elements are linked together, for example, in a vector (e.g., plasmid), organisms that carry the vector always survive because they always carry the rescue transgene. In contrast, organisms that do not carry the rescue transgene will die or be sterile if they only carry inactive copies of the essential gene that are inherited from vector-bearing parents or created de novo through site-specific DNA modifying enzyme activity that is brought into these cells through diffusion, transport, or cell-cell movement.

In some embodiments, the gene drive disclosed herein is an alternative form of gene drive that utilizes Cas9 or other nucleases to bring about cleavage and repair of an essential gene that does not involve or require homing. This form of gene drive can also make use of base editing enzymes such as adenosine or cytosine deaminase to modify specific bases to create non-functional versions of an essential gene. Without being limited by any particular theory, the mechanism simply involves DNA sequence modifying enzyme such as Cas9, a set of gRNAs targeting an essential gene for cleavage, (or a sequence targeted base editor) and a recoded version of the target that is immune to modification linked as a single construct. In some embodiments, individuals carrying one or more copies of this construct bring about modification of the sequence of one or more copies of the endogenous version of the essential gene such that it is no longer functional. Individuals who end up inheriting only non-functional versions of the essential gene die or are sterile, while those that carry one or more copies of the construct, which includes a rescue transgene, will survive and/or be fertile. Over multiple generations this behavior is predicted to result in the spread of the construct/vector into the population at the expense of the wildtype version of the same chromosome.

In some embodiments, characterized and disclosed herein are multiple forms of this DNA sequence modification mediated drive. A discrete generation, deterministic population frequency model is used to demonstrate that there are a variety of conditions, that include various fitness costs, DNA sequence modification frequencies, and introduction frequencies, under which population replacement is predicted to occur.

Definitions

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below. It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, "regulatory element" refers to nucleic acid elements that can influence the expression of a coding sequence (for example, a gene) in a particular host organism. These terms are used broadly and encompass all elements that promote or regulate transcription, including promoters, core elements required for basic interaction of RNA polymerase and transcription factors, upstream elements, enhancers, and response elements (see, for example, Lewin, "Genes V" (Oxford University Press, Oxford) pages 847-873).

As used herein, the term "insertion site" refers a nucleic acid sequence that allows for insertion of the constructs as provided herein into a genome of a multicellular organism (for example, an insect genome). In some embodiments, a construct as provided herein can comprise a "insertion sequence" that allows for insertion of the construct into a genome of the host organism. Some embodiments that can be employed include the piggybac transposable element, mariner type transposable elements, and the P-element. Also, plasmids can be site specifically integrated into the genome using attb/attp or even by using CRISPR/Cas9, TALEN, MegaTAL and homologous recombination.

As used herein, a "vector," interchangeably referred to as a transgenic construct, a targeting construct, or simply a construct, is a nucleic acid. As used herein, "nucleic acid" refers to deoxyribonucleic acid (DNA). In some embodiments, nucleic acid may refer to ribonucleic acid (RNA). In some embodiments, the construct as provided herein comprise one or more regulatory elements. Exemplary regulatory elements in prokaryotes include promoters, operators and ribosome binding sites. Regulatory elements that are used in eukaryotic cells can include, without limitation, transcriptional and translational control sequences, such as promoters, terminators, enhancers, insulators, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell. For example, a promoter is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions (for example, a change in temperature).

As used herein, "homologous recombination" refers to exchange of nucleotide sequences between two identical nucleic acid sequences. Homologous recombination also refers to exchange of nucleotide sequences between two similar nucleic acid sequences. In some embodiments, when the two nucleic acid sequences are similar, a similarity between the two nucleic acid sequences can be about 90% to about 99.9%. In some embodiments, the similarity between the two nucleic acid sequences can be about 90, 91, 92, 93, 94, 95, 96, 97, 98, 99, 99.1, 99.2, 99.3, 99.4, 99.5, 99.6, 99.7, 99.8 or 99.9%.

As used herein, "gene drive" refers to a situation in which genetic elements—including alleles of specific genes, gene complexes, entire chromosomes or endosymbiotic bacteria—are transmitted to viable, fertile progeny at rates greater than those due to Mendelian transmission, resulting in an increase in their frequency in the population over time, even if their presence results in a fitness cost to carriers. Without being limited by any particular theory, gene drive can occur by a number of mechanisms. In some embodiments gene drive has evolved in wild populations of various organisms, through a variety of mechanisms that are still under study (Burt and Trivers, 2006). In some embodiments, the gene drive is engineered. In some embodiments, the gene drive represents a naturally occurring mechanism or is engineered depending on the context and environment in which it occurs. A number of novel methods of engineering gene drive have also been proposed, and in several cases implemented.

In some embodiments, the present disclosure is related to vectors and methods for DNA sequence modification-based modification of populations, and beneficial and commercial applications of the vectors and methods.

In one implementation of this system, detailed below in the examples and sometimes referred to as CleaveR (also referred to herein as ClvR), the nuclease includes a member of the RNA-guided nucleases, such as Cas9. In this implementation Cas9 is expressed in the germline of male, females, or both sexes. Multiple gRNAs are also expressed, preferably three or four of them. They are designed to engage in Watson-Crick base pairing with, and therefore target for cleavage, distinct sequences within a target gene, so as to bring about its cleavage at multiple sites. These multiple breakages are expected to result in the creation of repair products—deletions, base changes, small additions—that create a non-functional version of the targeted gene. In summary, the purpose of the nuclease is to bring about loss-of-function mutants of the targeted gene. There are two important characteristics of the system described thus far. First, the cassette encoding the nuclease can sit at any position in the genome. Second, the gene being targeted for inactivation is in some sense an essential gene: required for organism survival or fertility, broadly defined as fitness.

The second component of the CleaveR gene drive system is the existence of a version of the targeted essential gene that can rescue the lethality or infertility of those individuals in which both copies (for a diploid) of the essential gene have been inactivated, but that is itself resistant to cleavage by the RNA-guided Cas9 component of the construct. Resistance to cleavage is brought about by recoding the transgene so that it no longer productively interacts with the guide RNA Cas9 complex, according to rules that are well known in the field. Further recoding of the rescue transgene, in both the coding region and non-coding and regulatory regions, is also carried out. This recoding is done so as to minimize homology between the wildtype, endogenous version of the gene and the rescue version of the gene. This recoding is also done so as to minimize/eliminate the possibility that the cleaved version of the wildtype endogenous essential gene can be repaired and restored to functionality through ectopic homologous recombination, using the rescue transgene as a template for repair based on existing homology at the broken ends of the former. The literature provides guidance on the level of homology needed to prevent or promote homologous recombination. Without being limited by any particular theory, recoding can successfully achieved even when the rescue transgene has essentially no nucleotide homology to the endogenous copy of the gene. Demonstration that this can be achieved comes from multiple reports showing that bacterial and/or human versions of a large number of essential genes can successfully replace their yeast counterparts, resulting in yeast with high fitness.

In the CleaveR construct, also often referred to as the vector or the construct, when these two genes are located near each other (tightly linked), they behave, as illustrated below, as a novel selfish genetic element, able to spread itself into a population and/or maintain itself in a population (bring about population replacement) under a variety of conditions that include varying levels of fitness cost associated with carrying the vector and any associated cargo genes, and introduction frequencies. The details of these characters are described in more below.

Overview of CleaveR-Based Gene Drive

Without being limited by any particular theory, when the CleaveR construct is present in an organism, wildtype copies of the essential are a risk for cleavage and inactivation. The individuals carrying CleaveR themselves do not experience any cost from this cleavage, which happens in the germline and also in some cases in somatic cells, because they also carry a tightly linked copy of the rescue transgene. However, the gametes they pass on will in many cases not carry a functional copy of the endogenous essential gene, and they may also lack the CleaveR construct. In some cases the Cas9/gRNA complexes will also be deposited into oocytes/eggs, resulting in cleavage of the endogenous copy of the essential gene in early embryos that do not carry the CleaveR construct. In all of these cases, which arise through normal Mendelian segregation of chromosomes during meiosis in males and females, and in some cases diffusion or transport of Cas9/gRNA into daughter cells or products of cell-cell fusion (fertilization), progeny are often created that carry no functional copies of the essential gene. These individuals are of low fitness (dead, sterile or otherwise dysfunctional [flightless]) and do not contribute further to the population.

The above behavior results in some loss in each generation of chromosomes and individuals that do not carry the CleaveR. This results, over multiple generations, in a progressive increase in the frequency of CleaveR-bearing individuals. Modeling, discussed further below, shows that under a variety of conditions CleaveR is predicted to spread to high frequency such that most or all individuals in the population bear at least one copy of the CleaveR chromosome. The CleaveR chromosome is in some sense "held" in the population because as it has been spread (and the mechanism by which it has been spreading) it has necessarily caused inactivation of most or all of the wildtype copies of the essential gene. Thus the population has become "locked" into a configuration in which it now depends on the presence of CleaveR in order to maintain viability or fertility.

A similar principle, cleavage associated with rescue of those who carry the CleaveR vector, allows CleaveR to act as a gamete killer (known as spore killers in yeast), and to force its inheritance in conditions in which it is episomal (as in a plasmid). In both cases the presence of the CleaveR element selects for those who carry it, and against those who fail to inherit it.

In some embodiments, the method of gene drive described herein is agnostic as to the mechanism by which sequence modification-dependent inactivation of the essential gene is brought about. It can involve cleavage and error-prone repair, as discussed above. It can also involve the use of base editing enzymes known from the literature. It can also utilize other DNA modifying enzymes such as sequence targeted transposases, recombinases, integrases, topoisomerases, or other enzymes that can be targeted to specific sequences in DNA to bring about sequence changes. Importantly, the exact nature of the sequence changes brought about is not critical since there are many ways of rendering nonfunctional any particular gene through sequence modification.

Vectors

Figure 15A:
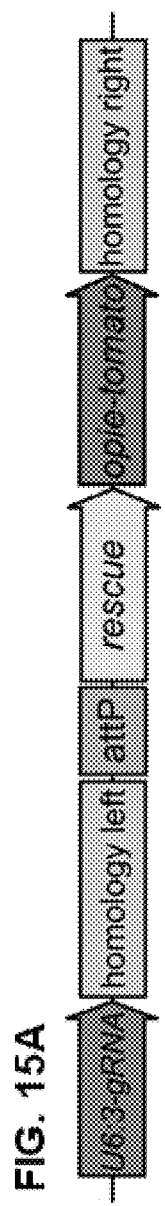
FIG. 15A-FIG. 15C show an embodiment of DNA sequence modification based gene drive (herein referred to as ClvR when a nuclease is used for DNA sequence modification) construct design and principle according to the present disclosure.
Figure 15B:
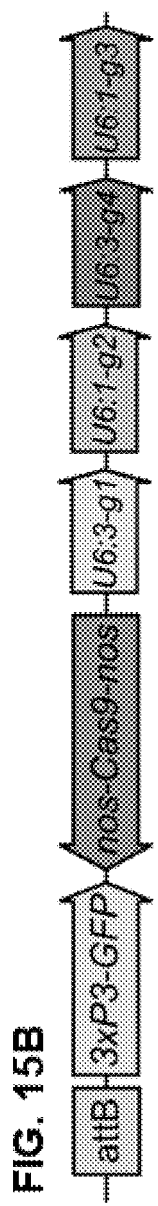
Figure 15C:
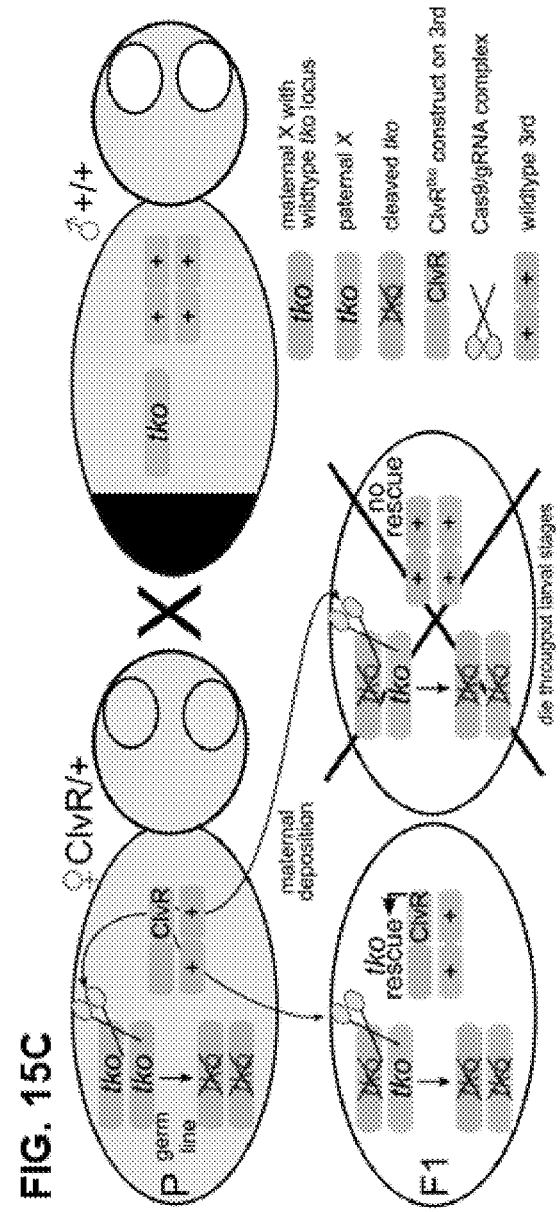

FIG. 15A-FIG. 15C show an embodiment of ClvR construct design and principle according to the present disclosure (Example 15). In some embodiments, the disclosure is related to a vector. In some embodiments, the vector comprises a first gene encoding a DNA sequence modifying enzyme. In some embodiments, the DNA modifying enzyme modifies the sequence of an endogenous copy of an essential gene. As used herein, an "essential gene" is defined as a gene that is critical for survival, growth or fertility, and whose loss of function is either lethal, prevents growth or is sterilizing. Some essential genes are critical for survival under all circumstances. Some essential genes are critical for survival only under particular circumstances and/or particular environmental conditions (e.g., in the presence of toxic drugs, toxins, etc., or in the absence of nutrients, vitamins, etc.). In some embodiments, more than one or more endogenous copies of the essential gene are present. In some embodiments, when one or more endogenous copies of the essential gene are present they are alleles or allelic variants of the essential gene. As used herein, the "endogenous copy" refers to the wild type version of the essential gene.

In some embodiments, vector comprises first promoter operably linked to the first gene encoding the DNA sequence modifying enzyme. In some embodiments, the first gene is operably linked to one or more additional regulatory elements. In some embodiments, the vector further comprises a second gene encoding a rescue transgene. In some embodiments of the vector, a second promoter is operably linked to the rescue transgene. In some embodiments, the second gene is operably linked to one or more additional regulatory elements.

In some embodiments, the vector optionally comprises one or more cargo sequences. In some embodiments, a cargo sequence is a nucleic acid. In some embodiments, the vector is configured to be positioned in a chromosome. In some embodiments, the vector is configured to be positioned in an extra-chromosomal element. Non-limiting examples of cargo genes include are sequences encoding antibodies against *Plasmodium*, the causal agent of malaria (Isaacs et. al. 2011, Hollingdale et. al. 1984, and Li et. al. 2005), or non-coding RNAs to bring about cleavage of the dengue virus RNA genome (Yen et. al. 2018, Franz et. al. 2006, Mathur et. al. 2010, Travanty et. al. 2004, and Castillo et. al. 2016). In some embodiments, the vector is configured to be positioned in a chromosome and an extra chromosomal element. In some embodiments, the vector is configured to be positioned in a chromosome but not in an extra chromosomal element. In some embodiments, the vector is configured to be positioned in an extra chromosomal element but not in a chromosome.

In some embodiments, the DNA sequence modifying enzyme is a nuclease. Non-limiting examples of nucleases include Flap endonucleases, restriction endonucleases (e.g., F-EcoT5I, F-EcoT5II, F-EcoT5IV, F-SceI, F-TevI, F-TevII, I-AchMI, I-AniI, I-BasI, I-BmoI, I-Bth0305I, I-BthII, I-BthORFAP, I-CeuI, I-ChuI, I-CpaI, I-CpaII, I-CreI, I-CsmI, I-CvuI, I-DdiI, I-DmoI, I-GpiI, I-GzeI, I-HjeMI, I-HmuI, I-HmuII, I-LlaI, I-LtrI, I-LtrWI, I-MpeMI, I-MsoI, I-NanI, I-NitI, I-NjaI, I-OnuI, I-PakI, I-PanMI, I-PnoMI, I-PogTE7I, I-PorI, I-PpoI, I-ScaI, I-SceI, I-SceII, I-SceIII, I-SceVI, I-SpomI, I-SscMI, I-Ssp6803I, I-TevI, I-TevII, I-TevIII, I-TslI, I-TslWI.AY76, I-Vdi141I, PI-AvaI, PI-BciPI, PI-HvoWI, PI-MleSI, PI-MtuI, PI-PkoI, PI-PkoII, PI-PspI, PI-SceI, PI-TfuI, PI-TfuII, PI-TliI, PI-TliII, PI-TmaI, PI-TmaKI), Cas9, and Cas9-like enzymes (including but not limited to CPf1, C2c1, C2c2, and C2c3 (Shmakov et. al. 2015, Shmakov et. al. 2017, Koonin et. al. 2017-1, Koonin et. al. 2017-2), ZFNs, MegaTALs, TALENs, HEGs, meganucleases, etc.

In some embodiments, DNA modifications are achieved through cleavage by site-specific nucleases. Without being limited by any particular theory, it should be understood that equivalent effects can be obtained through the use of any enzyme that brings about modification of a target DNA sequence. Non-limiting examples include cytosine and adenine base changes brought about through the targeted use of deaminases and site-specific integrases.

In some embodiments, the nuclease cleaves the endogenous copy of the essential gene. In some embodiments, the nuclease generates one or more double strand breaks in the endogenous copy of the essential gene. In some embodiments, the nuclease cleaves and generates one or more double strand breaks in the endogenous copy of the essential gene. In some embodiments, the one or more double strand breaks in the endogenous copy of the essential gene are staggered. In some embodiments, the one or more double strand breaks in the endogenous copy of the essential gene are not staggered. In some embodiments, the nuclease cleaves and generates one or more single strand breaks in the endogenous copy of the essential gene.

In some embodiments, the one or more double strand breaks (DSBs) are repaired. In some embodiments, the one or more DSBs are repaired to create an altered sequence of the essential gene. In some embodiments, the one or more DSBs are repaired by one or more of non-homologous end joining (NHEJ), microhomology-mediated end joining (MMEJ), homologous recombination (HR), complete HR, and incomplete HR. In some embodiments, the altered sequence comprises substitutions, insertions, deletions, frame-shifts, or a combination thereof.

In some embodiments, the DNA sequence modifying enzyme is a base editor. Non-limiting examples of a base editor include cytosine deaminase, and adenine deaminases.

In some embodiments, the base editor creates one or more base changes in endogenous copy of the essential gene. In some embodiments, the one or more base changes comprise transitions, transversions, or both. In some embodiments, the one or more base changes occur due to tautomerism, depurination, deamidation, or a combination thereof. In some embodiments, the one or more base changes creates an altered sequence of the essential gene. In some embodiments, the one or more base changes comprise one or more point mutations in the endogenous copy of the essential gene. In some embodiments, the one or more point mutations comprise frameshift mutation, nonsense mutation, missense mutation, neutral mutation, silent mutation, or a combination thereof.

In some embodiments, the promoter of the first gene expresses within females such that the DNA-modifying enzyme produced by the first gene is deposited into eggs and can modify target sequences inherited from a father who lacks the vector. This activity, while unnecessary, for the majority of cases wherein this drive method successfully replaces a population, results in more rapid population replacement than without, for a given fitness cost and/or introduction frequency. Where the DNA-modifying enzyme is a version of Cas9 or a Cas9-related enzyme (guided to a target sequence by a guide RNA), both Cas9 and any and all associated gRNAs are deposited into the eggs of such females together to enable modification of alleles inherited from a non-vector bearing male.

In some embodiments, there is paternal carryover of the DNA modifying enzyme, allowing for modification of alleles inherited from the mother, even in those who have not inherited the vector.

In some embodiments, the rescue transgene is a recoded copy of the essential gene. In some embodiments, when the rescue transgene is a recoded copy of the essential gene, the protein encoded by the recoded copy of the essential gene (recoded protein) is about 90% to about 99.9% identical to protein encoded by the endogenous copy of the essential gene (endogenous protein). In some embodiments, the recoded protein is about 90, 91, 92, 93, 94, 95, 96, 97, 98, 99, 99.1, 99.2, 99.3, 99.4, 99.5, 99.6, 99.7, 99.8, or 99.9% to the endogenous protein. In some embodiments, the rescue transgene is a gene of unrelated sequence. In some embodiments, when the rescue transgene is a gene of unrelated sequence, the protein encoded by the recoded copy of the essential gene (recoded protein) is functionally equivalent to the protein encoded by the endogenous copy of the essential gene (endogenous protein). In some embodiments, the DNA sequence modifying enzyme does not modify the rescue transgene.

In some embodiments, the chromosome in which the vector is positioned is one or more of an autosome, X chromosome, Y chromosome, or supernumerary chromosome. In some embodiments, the vector is positioned in one or more combinations of an autosome, X chromosome, Y chromosome, or supernumerary chromosome. For example, in some embodiments, the vector is positioned in an autosome and an X chromosome, in some embodiments, the vector is positioned in an autosome and a Y chromosome, in some embodiments, the vector is positioned in an autosome and a supernumerary chromosome, in some embodiments, the vector is positioned in an X chromosome and a Y chromosome, in some embodiments, the vector is positioned in an X chromosome and a supernumerary chromosome, in some embodiments, the vector is positioned in an Y chromosome and a supernumerary chromosome, and in some embodiments, the vector is positioned in an autosome, X chromosome, Y chromosome, and supernumerary chromosome.

In some embodiments, the vector is positioned in an extra-chromosomal element. In some embodiments, the extra-chromosomal element is a plasmid. In some embodiments, the extra-chromosomal element is a virus. In some embodiments, the extra-chromosomal element is a plasmid and a virus. In some embodiments, the vector is positioned in combinations of one or more chromosomes and one or more extra-chromosomal elements.

In some embodiments, the vector optionally comprises one or more cargo sequences. In some embodiments, the one or more cargo comprise foreign gene sequences, or one or more alleles of an endogenous chromosomal or extra-chromosomal gene.

In some embodiments the cargo comprises one or more alleles of an endogenous chromosomal or extra-chromosomal gene to which the vector has been linked through nearby insertion on the chromosome or extra-chromosomal element that carries the endogenous allele of interest.

In some embodiments, the cargo can be physically part of the vector prior to its insertion in a chromosomal or an extra-chromosomal element. In some embodiments, the cargo can be a chromosomal/extra-chromosomal allele of a gene that becomes linked to the vector after the insertion of the vector near that allele. In some embodiments, a fraction of the cargo can be physically part of the vector prior to its insertion in a chromosomal or an extra-chromosomal element, and a remainder of the cargo can be a chromosomal/extra-chromosomal allele of a gene that becomes linked to the vector after the insertion of the vector near that allele. In some embodiments, the cargo does not have to be a part of the vector, i.e., in some embodiments, the cargo is optional and can be physically part of the vector prior to its insertion in a chromosomal or an extra chromosomal element. In some embodiments, the cargo does not have to be a part of the vector, i.e., in some embodiments, a fraction of the cargo can optionally be physically part of the vector prior to its insertion in a chromosomal or an extra chromosomal element, and a remainder of the cargo can be a chromosomal/extra-chromosomal allele of a gene that becomes linked to the vector after the insertion of the vector near that allele.

In some embodiments herein, the vector comprising the first gene encoding the DNA sequence modifying enzyme and the second gene encoding the rescue transgene is referred to as CLeaveR (e.g., FIG. 6C), which comprises and/or consists of two components: (1) a site-specific DNA modifying enzyme designed to alter the sequence of an endogenous gene required for survival, proliferation, fertility, or differentiation so as to render it non-functional (left); (2) a recoded version of the essential gene resistant to cleavage, and having reduced nucleotide identity with the endogenous gene (right). Optionally, one or more cargo sequences are present (center).

In some embodiments, DNA sequence modifying enzyme is, without limitation, Cas9, Cas-9-related RNA-guided nucleases, ZFNs, TALENs, homing endonucleases, restriction enzymes, natural site-specific nucleases, engineered site-specific nucleases, base editing enzymes, cytidine deaminase, and adenine deaminase.

In some embodiments, the vector further comprises one or more additional sequences. In some embodiments, the one or more additional sequences allow the vector to be positioned in the chromosome. In some embodiments, the one or more additional sequences allow the vector to be positioned in the extra-chromosomal element. In some embodiments, the one or more additional sequences allow the vector to be positioned in the chromosome and the extra-chromosomal element. In some embodiments, the one or more additional sequences allow the vector to be positioned in the chromosome but not the extra-chromosomal element. In some embodiments, the one or more additional sequences allow the vector to be positioned in the extra-chromosomal element but not the chromosome.

In some embodiments, the one or more additional sequences is, without limitations, transposase binding site, LTRs, recombinase binding site, a sequence with homology to a desired location on the chromosome or a sequence with homology to a desired location on the extra-chromosomal element, or combinations thereof.

In some embodiments, the vector further comprises one or more additional sequences, wherein the one or more additional sequences serve as dominant marker genes that allow individuals carrying the vector to be easily identified either visually, as with expression of a fluorescent protein, or by virtue of surviving a negative selection procedure, as with expression of a gene that encodes resistance to a toxin (such as an antibiotic, insecticide, herbicide), in the presence of the toxin. In some embodiments, the vector comprises one or more sequences that encode marker proteins that can be expressed under the control of suitable regulatory elements. Non-limiting examples of marker proteins include dsRed, GFP, EGFP, CFP, ECFP, BFP, EBFP, mHoneydew, mBanana, mOrange, tdTomato, mTangering, mStrawberry, mCherry, mGrape1, mGrape2, mRaspberry, mPlum, YFP or EYFP, and can be chosen by one of skilled in the art according to need. Fluorescent marker protein can be visualized by illuminating with a suitable excitatory wavelength and observing the fluorescence (e.g., by fluorescence microscopy). In some embodiments, a marker protein would allow for easy identification of organisms carrying the vector.

In some embodiments, the first promoter is, without limitations, a germline promoter, a male specific germline promoter, a female specific germline promoter, a cell-type specific promoter, a tissue-specific promoter, a ubiquitous promoter, a promoter activated at a specific stage of mitosis, a promoter activated at a specific stage of meiosis, or combinations thereof.

In some embodiments, the size of the one or more cargo sequences ranges from about is about 0.5 kb to about 500 kb. In some embodiments, the size ranges from about 1 kb to about 1000 kb. In some embodiments, the size ranges from about 5 kb to about 5000 kb. In some embodiments, the size ranges from about 10 kb to about 10000 kb. In some embodiments, the size is about 0.1, 0.5, 1, 5, 10, 25, 50, 75, 100, 250 500, 750 1000, 2500, 5000, 7500, or 10000 kb.

In some embodiments, the nuclease comprises at least one nuclease domain. In some embodiments, the nuclease comprises one or more DNA binding domains. In some embodiments, the nuclease comprises at least one nuclease domain and one or more DNA binding domains.

In some embodiments, when the nuclease is Cas9 or a Cas9-related enzyme, the vector further comprise one or more genes encoding a guide RNA. In some embodiments, the guide RNA enables the nuclease to target specific DNA sequences through Watson-Crick base pairing, thereby allowing targeting of very many positions in any genome. In some embodiments, the guide RNA enables the nuclease to target specific sequences within the endogenous copy of the essential gene. In some embodiments, the guide RNA enables the nuclease to target specific sequences within the protein coding region of endogenous copy of the essential gene. In some embodiments, the guide RNA allows the nuclease to target specific sequences within the non-coding region of endogenous copy of the essential gene. In some embodiments, the guide RNA allows the nuclease to target specific sequences outside the endogenous copy of the essential gene.

In some embodiments, when the nuclease is Cas9, the nuclease domain of Cas9 is inactivated through one or more mutations and the vector comprises a different nuclease domain. In some embodiments, the different nuclease domain is single chain variant of FokI. In some embodiments, when the DNA binding domain is a TALE, the nuclease domain is provided as a single active nuclease domain. In some embodiments, the single active nuclease domain is a single chain variants of FokI. In some embodiments of the vector, when the DNA binding domain is a TALE, the nuclease domain is provided as a single active nuclease domain, such as single chain variants of FokI (Sun and Zhao 2014).

Methods

One of ordinary skill in the art would appreciate that any of the methods disclosed herein can be performed by any of the vectors provided herein.

In some embodiments, a method of modifying a population by a vector is provided. In some embodiments, the method comprises obtaining an organism of the population. In some embodiments, the organism is, without limitations, bacteria, archaea, fungi, plants and animals, including rodents, amphibians, mammals, reptiles, insects, mosquitoes, fish, etc.

In some embodiments, the method comprises positioning the vector in at least one chromosome or extra-chromosomal element in the organism. In some embodiments, the vector is any of the embodiments of the vectors provided herein.

In some embodiments, the DNA sequence modifying enzyme is expressed in the organism. In some embodiments, the organism is unicellular or multicellular. In some embodiments, when the organism is multicellular, the DNA sequence modifying enzyme is expressed in all cells of the organism. In some embodiments, the DNA sequence modifying enzyme is not expressed in all cells of the multicellular organism. In some embodiments, the DNA sequence modifying enzyme is expressed in a fraction of cells of the multicellular organism. In some embodiments, the DNA sequence modifying enzyme is expressed only in the male or female germline, or in the germline of both sexes.

In some embodiments, the expression of the DNA sequence modifying enzyme induces one or more sequence modifications. In some embodiments, the expression of the DNA sequence modifying enzyme induces one or more sequence modifications in an essential gene. In some embodiments, the expression of the DNA sequence modifying enzyme induces one or more sequence modifications in an essential gene in one or more cells in the organism. In some embodiments, the one or more sequence modifications result in the essential gene being rendered partially nonfunctional. In some embodiments, the one or more sequence modifications result in the essential gene being rendered wholly non-functional. In some embodiments, the one or more sequence modifications result in the essential gene being rendered partially non-functional in some circumstances and wholly non-functional in other circumstances. In some embodiments, the result of the essential gene being rendered partially or wholly non-functional is in a defect in the organism. In some embodiments, the defect is, without limitations, a defect in survival, growth control, fertility, differentiation, or combinations thereof.

In some embodiments, the defect occurs when the one or more cells in which the essential gene being rendered partially or wholly non-functional lack a rescue transgene. In some embodiments, the rescue transgene expresses a recoded protein that rescues the defects in survival, growth control, differentiation, or combinations thereof.

In some embodiments, the expression of the recoded protein by the rescue transgene results in the generations of an altered organism. In some embodiments, the altered organism expresses the recoded protein in the one or more cells in which the essential gene has been rendered partially non-functional. In some embodiments, the altered organism expresses the recoded protein in the one or more cells in which the essential gene has been rendered wholly non-functional. In some embodiments, the altered organism expresses the recoded protein in the one or more cells in which the essential gene has been rendered partially non-functional in some circumstances and wholly non-functional in other circumstances.

In some embodiments, the altered organism carries one or more copies of the vector, and wherein the defects in survival, growth control, or differentiation of the one or more cells in which the essential gene has been rendered partially non-functional have been rescued the rescue transgene expressed from the one or more copies of the vector. In some embodiments, the altered organism carries one or more copies of the vector, and wherein the defects in survival, growth control, or differentiation of the one or more cells in which the essential gene has been rendered wholly non-functional have been rescued the rescue transgene expressed from the one or more copies of the vector. In some embodiments, the altered organism carries one or more copies of the vector, and wherein the defects in survival, growth control, or differentiation of the one or more cells in which the essential gene has been rendered partially non-functional in some circumstances and wholly non-functional in other circumstances have been rescued the rescue transgene expressed from the one or more copies of the vector.

In some embodiments, the altered organism is introduced in a population. In some embodiments, the altered organism is introduced in a population in which an increase in a frequency of the altered organism is desired relative to a frequency of a wild type organism. In some embodiments, the altered organism is introduced in a population in a particular environment. In some embodiments, the altered organism is introduced in a population in a particular environment in which an increase in a frequency of the altered organism is desired relative to a frequency of a wild type organism in the population in the particular environment. In some embodiments, the altered organisms is introduced in the population such that the percent of the altered organism in the population ranges from about 0.0001% to about 50%. In some embodiments, the percent is about 0.00001, 0.0005, 0.0001, 0.0005, 0.001, 0.005, 0.01, 0.05, 0.1, 0.5, 1, 5, 10, 20, 30, 40, or 50%. In some embodiments, the percent is greater than 100%, so as to achieve a more rapid change in the population.

In some embodiments, introducing the altered organism in the population results in replacement of the wild type organism with the altered organism in the population. In some embodiments, introducing the altered organism in the population results in replacement of the wild type organism with the altered organism in the population in the particular environment.

In some embodiments, the altered organism exhibits one or more altered traits. In some embodiments, the altered organism introduces and spreads one or more traits of interest in the population. In some embodiments, the one or more traits of interest is a novel trait not previously prevalent in the population, a trait that is a modified version of a trait previously present in the population (e.g., an enhance or a suppressed version of a trait previously present in the population) or a combination thereof. In some embodiments, the population is modified by the introduction of the altered organism in the population. In some embodiments, the population is modified by the introduction of the altered organism in the population in the particular environment. In Non-limiting examples of traits of interest include but are not limited to pathogen resistance, insecticide resistance, environmentally triggered death or sterility, herbicide resistance, fungicide resistance, phage resistance, resistance to viral infection, resistance to abiotic environmental factors, such as cold, heat, and stress.

In some embodiments, an organism with the defect in survival, growth control, fertility, or differentiation of the one or more cells is eliminated if the one or more cells of the organism lack the rescue transgene.

In some embodiments, the DNA sequence modifying enzyme does not modify the rescue transgene.

In some embodiments, rescuing the defects in one or more of survival, growth control, or differentiation is achieved by restoring one or more of normal survival, growth control, fertility, or differentiation of the one or more cells by the rescue transgene.

In some embodiments, the one or more cells comprise somatic cells, germline cells, gametes, or a combination thereof.

In some embodiments, the DNA sequence modifying enzyme is a nuclease or a base editor according to the embodiments herein.

In some embodiments, the nuclease cleaves and generates one or more double strand breaks in the endogenous copy of the essential gene as described herein.

In some embodiments, the one or more double strand breaks are repaired to create an altered sequence comprising insertions, deletions, base alterations, or a combination thereof.

In some embodiments, the base editor creates one or more base changes or small insertions/deletions in the endogenous copy of the essential gene.

In some embodiments, the one or more base changes comprise one or more point mutations, or deamidated bases that are replaced with nucleotides of a different sequence.

In some embodiments, the altered organism is heterozygous or homozygous for the vector.

In some embodiments, the organism is haploid. Non-limiting example of haploid organisms include prokaryotes. In some embodiments, the organism is diploid. Non-limiting example of diploid organisms include insects, fungi, many plants and animals. In some embodiments, the organism is polyploidy. Non-limiting example of polyploidy organisms include some fungi and animals and many plants.

In some embodiments, the organism is selected from the group consisting of prokaryotes, fungi, plants, and animals. In some embodiments, the organism is, without limitations, a prokaryote (bacteria, archaea), fungi, insect, mammal, rodent, fish, amphibian, reptile or plant. In some embodiments, any of the embodiments of the vectors and and/or methods can be one or more of the following: *Autographa gamma* Silver Y moth *Chilo suppressalis* Asiatic rice borer *Diabrotica speciosa* Cucurbit beetle *Harpophora maydis* Late wilt of corn *Helicoverpa armigera* Old world bollworm *Heteronychus arator* Black maize beetle *Peronosclerospora maydis* Java downy mildew *Peronosclerospora philippinensis* Philippine downy mildew *Punctodera chalcoensis* Mexican corn cyst nematode *Sclerophthora rayssiae* var. *zeae* Brown stripe downy mildew *Spodoptera littoralis* Egyptian cottonworm *Spodoptera litura* Cotton cutworm *Thaumatotibia leucotreta* False codling moth *Anthonomus grandis* Boll weevil *Autographa gamma* Silver Y moth *Eutetranychus orientalis* Citrus brown mite *Helicoverpa armigera* Old World bollworm *Oxycarenus hyalinipennis* Cotton seed bug *Pectinophora gossypiella* Pink bollworm *Spodoptera littoralis* Egyptian cottonworm *Spodoptera litura* Cotton cutworm *Thaumatotibia leucotreta* False codling moth *Adoxophyes orana* Summer fruit *tortrix* moth *Aeolesthes sarta* City longhorned beetle *Agrilus biguttatus* Oak splendour beetle *Archips xylosteanus* Variegated golden *tortrix Epiphyas postvittana* Light brown apple moth *Lymantria dispar asiatica* Asian gypsy moth *Lymantria mathura* Rosy moth *Massicus raddei* Mountain oak longhorned beetle *Phytophthora quercina* Oak decline *Platypus quercivorus* Oak ambrosia beetle *Raffaelea quercivora* Japanese oak wilt *Scolytus intricatus* European oak bark beetle *Spodoptera littoralis* Egyptian cottonworm *Thaumatotibia leucotreta* False codling moth *Thaumetopoea processionea* Oak processionary moth *Tortrix viridana* Green oak *tortrix Tremex fuscicornis Tremex* woodwasp Candidatus Phytoplasma pini Pine witches' broom *Cronartium flaccidum* Scots pine blister rust *Dendroctonus micans* Great spruce bark beetle *Dendrolimus pini* Pine-tree lappet *Dendrolimus punctatus* Masson pine moth *Dendrolimus sibiricus* Siberian silk moth *Diprion pini* Pine sawfly *Hylobius abietis* Large pine weevil *Lymantria mathura* Rosy moth *Monochamus saltuarius* Japanese pine sawyer *Monochamus sutor* Small white-marmorated longhorned beetle *Mycosphaerella gibsonii* Needle blight of pine *Panolis flammea* Pine beauty moth *Tomicus destruens* No common name, a pine shoot beetle *Autographa gamma* Silver Y moth *Cernuella virgate* Maritime garden snail *Cochlicella* spp. Exotic species *Diabrotica speciosa* Cucurbit beetle *Helicoverpa armigera* Old world bollworm *Heterodera filipjevi* Cereal cyst nematode *Heterodera latipons* Mediterranean cereal cyst nematode *Heteronychus arator* Black maize beetle *Lobesia botrana* European grape vine moth *Meloidogyne artiellia* British root-knot nematode *Nysius huttoni* Wheat bug *Peronosclerospora philippinensis* Philippine downy mildew *Spodoptera littoralis* Egyptian cottonworm *Spodoptera litura* Cotton cutworm *Adoxophyes orana* Summer fruit *tortrix* moth *Alectra vogelii* Yellow witchweed *Autographa gamma* Silver Y moth *Cernuella virgata* Maritime garden snail *Chrysodeixis chalcites* Golden twin spot moth *Crocidosema aporema* Bud borer *Diabrotica speciosa* Cucurbit beetle *Eutetranychus orientalis* Citrus brown mite *Helicoverpa armigera* Old world bollworm *Spodoptera littoralis* Egyptian cottonworm *Adoxophyes orana* Summer fruit *tortrix* moth *Autographa gamma* Silver Y moth Candidatus Phytoplasma australiense Australian grapevine yellows *Cryptoblabes gnidiella Epiphyas* Honeydew moth *postvittana Eupoecilia ambiguella* Candidatus Phytoplasma vitis 1 Light brown apple moth *Heteronychus arator Lobesia botrana Pseudopezicula tracheiphila Spodoptera* European grape berry moth *littoralis Spodoptera litura Thaumatotibia leucotreta* Flavescence doree Black maize beetle European grape vine *Bursaphelenchus cocophilus* Red ring nematode Candidatus Phytoplasma palmae Palm lethal yellowing Cocadviroid Coconut cadang cadang Coconut cadang cadang viroid *Darna pallivitta* Nettle caterpillar *Haplaxius crudus* American palm cixiid *Metamasius hemipterus* West Indian cane weevil *Oryctes rhinoceros* Coconut *rhinoceros* beetle *Paysandisia archon* No common name, a palm borer *Raoiella indica* Red palm mite *Rhabdoscelus obscurus* New Guinea sugarcane weevil *Rhynchophorus ferrugineus* Red palm weevil *Rhynchophorus palmarum* South American palm weevil *Autographa gamma* Silver-Y moth Candidatus Phytoplasma australiense Australian grapevine yellows *Chrysodeixis chalcites* Golden twin spot moth *Globodera pallida* Pale cyst nematode *Globodera rostochiensis* Golden nematode *Helicoverpa armigera* Old world bollworm *Meloidogyne fallax* False Columbia root-knot nematode *Meloidogyne* minor Root-knot nematode *Neoleucinodes elegantalis* Tomato fruit borer *Ralstonia solanacearum* race 3 Bacterial wilt/Southern biovar 2 bacterial Wilt *Spodoptera littoralis* Egyptian cottonworm *Spodoptera litura* Cotton cutworm *Synchytrium endobioticum* Potato wart *Tecia solanivora* Guatemalan potato tuber moth *Thaumatotibia leucotreta* False codling moth *Tuta absoluta* Tomato leaf miner *Adoxophyes orana* Summer fruit *tortrix Argyresthia pruniella* Cherry blossom moth *Bactrocera zonata* Peach fruit fly Candidatus Phytoplasma prunorum European stone fruit yellows *Enarmonia formosana* Cherry bark *tortrix Epiphyas postvittana* Light brown apple moth *Grapholita funebrana* (Syn.: Plum fruit moth *Cydia funebrana*) *Leucoptera malifoliella* Pear leaf blister moth *Lobesia botrana* European grape vine moth *Monilia polystroma* Asiatic brown rot *Monilinia fructigena* Brown rot, Apple brown rot *Potyvirus* Plum Pox Virus Plum pox *Rhagoletis cerasi* European cherry fruit fly *Thaumatotibia leucotreta* False codling moth *Globodera pallida* Pale cyst nematode *Globodera rostochiensis* Golden nematode *Heterodera cajani* Pigeonpea cyst nematode *Heterodera ciceri* Chickpea cyst nematode *Heterodera filipjevi* Cereal cyst nematode *Heterodera latipons* Mediterranean cereal cyst nematode *Heterodera sacchari* Sugarcane cyst nematode *Punctodera chalcoensis* Mexican corn cyst nematode *Agrilus auroguttatus* Goldspotted oak borer *Agrilus biguttatus* Oak splendour beetle *Agrilus planipennis* Emerald ash borer *Anoplophora chinensis* Citrus longhorned beetle *Anoplophora glabripennis* Asian longhorned beetle *Chlorophorus annularis* Bamboo borer *Chlorophorus strobilicola* Slender-banded pine cone longhorn beetle *Dendroctonus micans* Great spruce bark beetle *Ips sexdentatus* Six-toothed bark beetle *Ips typographus* European spruce bark beetle *Megaplatypus mutatus* No common name, an ambrosia beetle *Monochamus alternatus* Japanese pine sawyer *Monochamus saltuarius* Japanese pine sawyer *Monochamus sutor* Small white-marmorated longhorned beetle *Orthotomicus erosus* Mediterraneran pine engraver *Pityogenes chalcographus* Sixtoothed spruce bark beetle *Platypus quercivorus* Oak ambrosia beetle *Scolytus intricatus* European oak bark beetle *Tetropium castaneum* Black spruce beetle *Tetropium fuscum* Brown spruce longhorned beetle *Tomicus destruens* No common name, a pine shoot beetle *Tomicus minor* Lesser pine shoot beetle *Tomicus piniperda* Pine shoot beetle *Trichoferus campestris*

Velvet longhorned beetle *Trypodendron* European hardwood ambrosia beetle *domesticum* Redbay ambrosia beetle *Belocaulus* spp. No common name, leatherleaf slugs *Cernuella* spp. No common name, hygromiid snails *Cochlicella* spp. No common name, cochlicellid snails *Colosius* spp. No common name, leatherleaf slugs *Laevicaulis* spp. No common name, leatherleaf slugs *Lissachatina fulica* Giant African snail *Meghimatium pictum* Chinese slug *Monacha* spp. No common name, hygromiid snails *Sarasinula* spp. No common name, leatherleaf slugs *Semperula* spp. No common name, leatherleaf slugs *Veronicella* spp. No common name, leatherleaf slugs *Dendrolimus pini* Pine-tree lappet *Dendrolimus punctatus* Masson pine moth *Dendrolimus sibiricus* Siberian silk moth *Lymantria albescens* Okinawa gypsy moth *Lymantria dispar asiatica* Asian gypsy moth *Lymantria dispar japonica* Japanese gypsy moth *Lymantria mathura* Rosy moth *Lymantria monacha* Nun moth *Lymantria postalba* White-winged gypsy moth *Lymantria umbrosa* Hokkaido gypsy moth *Lymantria xylina* Casuarina tussock moth.

In some embodiments, an insect can be a direct pest or indirect pest. A "direct pest" refers to insects that can cause damage at one or more stage of their life cycle by, for example, eating crops or damaging animals. The New World screw-worm fly *Cochliomyia hominivorax*, for example, is a direct pest of cattle, and the spotted wing *Drosophila, Drosophila suzukii* is pest of many fruit crops. An "indirect pest" refers to insects that transmit human diseases, for example, mosquitoes which carry malaria. Indirect pests of organisms other than humans, such as livestock or plants are also known.

In some embodiments, insect refers to, without limitations, one or more of *Drosophila*, mosquitoes, bumblebees, hoverflies, grasshoppers, dragonfly, dancefly, weevil, cricket, wasp, moth, beetles, honey bee, robberfly or butterfly. Additional examples of insects include, but are not limited to, Asian citrus psyllid (*diaphorini citrii*, Australian sheep blowfly (*Lucilia cuprina*, Asian tiger mosquito (*Aedes albopictus*); Japanese beetle (*Popilla japonica*), White-fringed beetle (*Graphognatus* spp.), Citrus blackfly (*Aleurocanthus woglumi*), Oriental fruit fly (*Dacus dorsalis*), Olive fruit fly (*Dacus oleae*), tropical fruit fly (*Dacus cucurbitae, Dacus zonatus*), Mediterranean fruit fly (*Ceratitis capitata*), Natal fruit fly (*Ceratitis rosa*), Chemy fruit fly (*Rhagoletis cerasi*), Queensland fruit fly (*Bactrocera tryoni*), Caribbean fruit fly (*Anastrepha suspensa*), imported fire ants (*Solenopis richteri, Solenopis invictai*, Gypsy moth (*Lyman tria dispar*), Codling moth (*Cydia pomonella*), Brown tail moth (*Euproctis chrysorrhoea*), yellow fever mosquito (*Aedes aegypti*), malaria mosquitoes (*Anopheles gambiae, Anopheles stephensi*), New world screwworm (*Cochliomyia hominivorax*), Old World Screwworm (*Chrysomya bezziana*), Tsetse fly (*Glossina* spp), Boll weevil (*Anthonomous grandis*), Damsel fly (*Enallagma hageni*), Dragonfly (*Libellula luctuosa*), and rice stem borer (*Tryporyza incertulas*). In some embodiments, the insect either transmits human disease or are agricultural pests. In some embodiments, the insects are wild insect populations.

In some embodiments, the insects are mosquitoes or flies (for example fruit flies, tsetse flies, sand flies). The mosquitoes can be, for example, *Aedes* sp. or *Anopheles* sp. In some embodiments, the mosquito is yellow fever mosquito (*Aedes aegypti*), malaria mosquito (*Anopheles gambiae, Anopheles stephensi*), Asian tiger mosquito (*Aedes albopictus*) or Culex mosquitoes. In some embodiments, the insect is one that transmits a disease of a mammal. The disease can be any disease, for example, malaria and/or yellow fever. In some embodiments, the insect is a Spotted wing *Drosophila* (*Drosophila suzukii*).

In some embodiments, insect refers to an insect that spreads a disease of humans. In some embodiments, insect refers to an insect that spreads a disease of economically important animals. In some embodiments, insect refers to an insect that spreads a disease of companion animals. In some embodiments, insect refers to an insect that spreads a disease of plants.

In some embodiments, mosquitoes can be, without limitations, of *Aedes, Anopheles, Culex, Coquillettidia, Haemagogus, Mansonia, Ochlerotatus, Psorophora* or other genera that transmit diseases. In some embodiments, the diseases transmitted by mosquitoes can be one or more of Malaria, Chikungunya, Dog Heartworm, Dengue, Yellow Fever, Eastern Equine Encephalitis, St. Louis Encephalitis, LaCrosse Encephalitis, Western Equine Encephalitis, West Nile Virus, or Zika Virus, lymphatic filariasis.

In some embodiments, the population has about 10,000 to about 100,000,000,000 organisms. In some embodiments, the population has about 500, 1000, 1500, 2000, 2500, 3000, 3500, 4000, 4500, 5000, 5500, 6000, 6500, 7000, 7500, 8000, 8500, 9000, 9500, 10,000, 100,000, 500,000, 1,000,000, 100,000,000, 1,000,000,000, 100,000,000,000 or 1,000,000,000,000 organisms, or a number within a range defined by any two of the aforementioned values.

In some embodiments, the environment comprises an open environment, a bioreactor, or a multicellular body, a closed container, or combinations thereof. In some embodiments, the environment is a combination of an open environment, a bioreactor, or a multicellular body, a closed container, and the environment changes sequentially from one to the other.

In some embodiments, the wild type organism is replaced at a high frequency with the altered organism in the population wherein the wild type organism is present. In some embodiments, the wild type organism is replaced at a high frequency with the altered organism in the population in a particular environment wherein the wild type organism is present. In some embodiments, high frequency is defined as replacement of at least 90% of the wild type organism with the altered organism after 50 generations. In some embodiments, high frequency is defined as replacement of at least 80% of the wild type organism with the altered organism after 50 generations. In some embodiments, high frequency is defined as replacement of at least 70% of the wild type organism with the altered organism after 50 generations. In some embodiments, high frequency is defined as replacement of at least 60% of the wild type organism with the altered organism after 50 generations. In some embodiments, high frequency is defined as replacement of at least 50% of the wild type organism with the altered organism after 50 generations.

In some embodiments, the wild type organism is replaced at a rapid rate with the altered organism in the population wherein the wild type organism is present. In some embodiments, the wild type organism is replaced at a rapid rate with the altered organism in the population in a particular environment wherein the wild type organism is present. In some embodiments, rapid rate is defined as replacement of at least 90% of the wild type organism with the altered organism after 50 generations. In some embodiments, rapid rate is defined as replacement of at least 80% of the wild type organism with the altered organism after 50 generations. In some embodiments, rapid rate is defined as replacement of at least 70% of the wild type organism with the altered organism after 50 generations. In some embodiments, rapid rate is defined as replacement of at least 60% of the wild type organism with the altered organism after 50 generations. In some embodiments, rapid rate is defined as replacement of at least 50% of the wild type organism with the altered organism after 50 generations.

In some embodiments, at least 90% of the wild type organism is replaced with the altered organism after 50 generations. In some embodiments, at least 90% of the wild type organism is replaced with the altered organism after 50 generations. In some embodiments, at least 80% of the wild type organism is replaced with the altered organism after 50 generations. In some embodiments, at least 70% of the wild type organism is replaced with the altered organism after 50 generations. In some embodiments, at least 60% of the wild type organism is replaced with the altered organism after 50 generations. In some embodiments, at least 50% of the wild type organism is replaced with the altered organism after 50 generations.

In some embodiments, the one or more sequence modifications in the one or more cells is a result of the one or more cells carrying the first gene encoding the DNA sequence modifying enzyme. In some embodiments, the one or more sequence modifications in the one or more cells is a result of the DNA sequence modifying enzyme being transmitted to the one or more cells from one or more cells expressing the DNA sequence modifying enzyme through diffusion. In some embodiments, the one or more sequence modifications in the one or more cells is a result of the DNA sequence modifying enzyme being transmitted to the one or more cells from one or more cells expressing the DNA sequence modifying enzyme through active transport. In some embodiments, the one or more sequence modifications in the one or more cells is a result of the one or more cells carrying the first gene encoding the DNA sequence modifying enzyme and is a result of the DNA sequence modifying enzyme being transmitted to the one or more cells from one or more cells expressing the DNA sequence modifying enzyme through diffusion. In some embodiments, the one or more sequence modifications in the one or more cells is a result of the one or more cells carrying the first gene encoding the DNA sequence modifying enzyme and is a result of the DNA sequence modifying enzyme being transmitted to the one or more cells from one or more cells expressing the DNA sequence modifying enzyme through active transport. In some embodiments, the one or more sequence modifications in the one or more cells is a result of the DNA sequence modifying enzyme being transmitted to the one or more cells from one or more cells expressing the DNA sequence modifying enzyme through diffusion and is a result of the DNA sequence modifying enzyme being transmitted to the one or more cells from one or more cells expressing the DNA sequence modifying enzyme through active transport. In some embodiments, the one or more sequence modifications in the one or more cells is a result of the DNA sequence modifying enzyme being transmitted to the one or more cells from one or more cells expressing the DNA sequence modifying enzyme through intercellular movement.

In some embodiments, the vector is positioned in the chromosome or the extra-chromosomal element by a homologous recombination-dependent integration, random integration, integration using transposition, integration using a recombinase, or combinations thereof.

In some embodiments, the one or more cargo sequences comprise a one or more foreign gene sequences, or one or more alleles of an endogenous chromosomal or extra-chromosomal gene to which the vector has been linked through nearby insertion on the chromosome or extra-chromosomal element that carries the endogenous allele of interest.

In some embodiments, when the vector is positioned on the chromosome or the extra-chromosomal element, the first gene operably linked to the first promoter, the second gene operably linked to the second promoter, and the one or more cargo transgenes are genetically linked.

In some embodiments of the method, the vector and cargo are located in a small chromosomal inversion. In some embodiments of the method, the vector and cargo are located in a small chromosomal inversion further limits the possibility that the vector and cargo can separate from each other during any stage of DNA replication, mitosis, and/or or meiosis.

In some embodiments, the nuclease cleaves and generates one or more double strand breaks in the endogenous copy of the essential gene with a high cleavage efficiency. In some embodiments, the high cleavage frequency is defined as at least 30% of individuals carrying the nuclease cleave the endogenous copy of the essential gene in each generation. In some embodiments, the high cleavage frequency is defined as at least 40% of individuals carrying the nuclease cleave the endogenous copy of the essential gene being cleaved in each generation. In some embodiments, the high cleavage frequency is defined as at least 50% of individuals carrying the nuclease cleave the endogenous copy of the essential gene being cleaved in each generation. In some embodiments, the high cleavage frequency is defined as at least 60% of individuals carrying the nuclease cleave the endogenous copy of the essential gene being cleaved in each generation.

In some embodiments, the high cleavage frequency is defined as the nuclease cleaving one or more alleles of the endogenous copy of the essential gene in at least 30% of organisms carrying the vector and the one or more alleles of the endogenous copy of the essential gene in each generation. In some embodiments, the high cleavage frequency is defined as the nuclease cleaving one or more alleles of the endogenous copy of the essential gene in at least 40% of organisms carrying the vector and the one or more alleles of the endogenous copy of the essential gene in each generation. In some embodiments, the high cleavage frequency is defined as the nuclease cleaving one or more alleles of the endogenous copy of the essential gene in at least 50% of organisms carrying the vector and the one or more alleles of the endogenous copy of the essential gene in each generation. In some embodiments, the high cleavage frequency is defined as the nuclease cleaving one or more alleles of the endogenous copy of the essential gene in at least 60% of organisms carrying the vector and the one or more alleles of the endogenous copy of the essential gene in each generation.

In some embodiments, the base editor creates one or more base changes in endogenous copy of the essential gene with a high base editing frequency. In some embodiments, the high base editing frequency is defined as base editing in at least 20% of organisms that carry the vector in each generation. In some embodiments, the high base editing frequency is defined as base editing in at least 30% of organisms that carry the vector in each generation. In some embodiments, the high base editing frequency is defined as base editing in at least 40% of organisms that carry the vector in each generation. In some embodiments, the high base editing frequency is defined as base editing in at least 50% of organisms that carry the vector in each generation.

In some embodiments, the high base editing frequency is defined as the base editor modifying one or more alleles of the endogenous copy of the essential gene in at least 20% of the organisms carrying the vector and the one or more alleles of the endogenous copy of the essential gene in each generation. In some embodiments, the high base editing frequency is defined as the base editor modifying one or more alleles of the endogenous copy of the essential gene in at least 30% of the organisms carrying the vector and the one or more alleles of the endogenous copy of the essential gene in each generation. In some embodiments, the high base editing frequency is defined as the base editor modifying one or more alleles of the endogenous copy of the essential gene in at least 40% of the organisms carrying the vector and the one or more alleles of the endogenous copy of the essential gene in each generation. In some embodiments, the high base editing frequency is defined as the base editor modifying one or more alleles of the endogenous copy of the essential gene in at least 50% of the organisms carrying the vector and the one or more alleles of the endogenous copy of the essential gene in each generation.

In some embodiments of the method, the nuclease cleaves and generates one or more double strand breaks in the endogenous copy of the essential gene with a high cleavage efficiency. In some embodiments of the method, the high cleavage frequency is defined as the nuclease cleaving the endogenous copy of the essential gene in at least 30% of the organisms carrying the vector in each generation. In some embodiments of the method, the base editor creates one or more base changes in the endogenous copy of the essential gene with a high base editing frequency. In some embodiments of the method, the high base editing frequency is defined as the base editor modifying the endogenous copy of the essential gene in at least 20% of the organisms carrying the vector in each generation.

In some embodiments, the promoter of the first gene is a female-specific promoter such that the first gene encoding the DNA sequence modifying enzyme is expressed within females only. In some embodiments, female-specific expression of the DNA sequence modifying enzyme results in the DNA-modifying enzyme being present in the eggs. In some embodiments, when an egg expressing the DNA sequence modifying enzyme is fertilized by a male gamete, the DNA sequence modifying enzyme from the egg can modify target sequence in the paternal copy provided by the father. In some embodiments, there is paternal carryover wherein sperm contribute DNA modifying activity to eggs, resulting in modification of the copy of the target sequence provided by the mother. In some embodiments, there is potential for carryover. In some embodiments, modification of an allele in a fertilized egg is achieved even when the allele is inherited from a parent that did not carry the vector.

In some embodiments, as used herein, "fitness cost" is defined as a relative reduction in the number of offspring produced by, or survival of, individuals carrying the transgenic construct, as compared with wild type individuals. In some embodiments fitness cost is defined as a relative reduction in the number of offspring produced by, or survival of, individuals not carrying the transgenic construct, as compared with those who do. In some embodiments, fitness benefit is defined as a relative increase in the number of offspring produced by, or survival of, individuals carrying the transgenic construct as compared with wild type individuals.

In some embodiments, the first gene expresses within females (the female germline or cells that contribute components to the female germline), such that the DNA-modifying enzyme and any associated cofactors such as guide RNAs are deposited into all oocytes/eggs, and modify target sequences in the version of the essential gene provided by the father. This represents maternal carryover of DNA sequence modifying activity.

In some embodiments, paternal carryover of the DNA modifying enzyme results in modification of the maternal copy of the essential locus in eggs, including those that do not inherit the vector.

Applications

In some embodiments, the methods provided herein can be applied for modification of populations for beneficial outcomes. For example, in some embodiments, to prevent mosquito-borne diseases (e.g., malaria, dengue, etc.), mosquitoes can be engineered based on the embodiments of the vectors and methods disclosed herein to resist infection. The engineered mosquito can be used to replace wild mosquito population in order to achieve less transmission and less disease. Such a trait (e.g., refractoriness of the engineered mosquito to disease transmission) is unlikely to spread into a population in the absence of gene drive because the trait results in a fitness cost to carriers. A gene drive solution to this problem described herein is to increase the fitness cost associated with not carrying the gene of interest through DNA sequence modification-based gene drive.

In comparison to other low threshold gene drive systems (Example, 12-14), the Cas9 based gene drive mechanisms in Examples 1-5 do not require any homing to occur (homing is known to vary in its relative rate compared to other forms of DNA repair in different species), and they are predicted to rapidly take over wild type populations even when the associated cargo results in significant fitness costs. The presently proposed DNA sequence modification-based drives are all predicted to replace wild type populations quickly while bearing substantial fitness costs, and each of the five drives displays characteristics that qualify them for different scenarios.

While all five of these mechanisms have been considered in the context of Cas9, these drive results could apply to any endonuclease or base editor used to disrupt the function of an endogenous gene. For some embodiments, one of the biggest advantages of these drives is their adaptability to new species. This is because the primary requirements are the identification of an essential gene (thousands in each organism), a recoded or sequence unrelated version of the gene (including associated regulatory sequences) that has wildtype or close to wildtype function, and a promoter and DNA sequence-modifying enzyme capable of bringing about sequence alteration of the endogenous copy of the essential gene in the germline, or germline and early embryo cells exposed to the enzyme.

Additional Embodiments

Without being limited by any particular theory, one implementation of a DNA sequence-based modification-based gene drive is as follows: a cell expresses a DNA sequence modifying enzyme that alters the sequence of an essential gene, inactivating it. The DNA sequence modifying enzyme is transmitted through cytoplasm to offspring (either maternally, paternally, or both), where it modifies the target gene, regardless of whether the gene encoding the DNA sequence modifying enzyme is transmitted to these progeny. Progeny that inherit the DNA sequence modifying enzyme-encoding gene also inherit a rescue copy of the wildtype gene that has been cleaved. This rescue copy is both functional and uncleavable. In this way key features required for gene drive are brought about In some embodiments, the above system is applicable to insects. A DNA sequence modifying enzyme is expressed under the control of a germline promoter. The promoter may be expressed in both the male and female germline. However, let us also consider a case in which the nuclease is expressed under the control of a late female germline specific promoter. In this case the DNA sequence modifying enzyme is transmitted from the oocyte, where its mRNA (and any associated co-factors such as gRNAs) is synthesized, to the mature oocyte/fertilized egg. In the zygote (fertilized egg) the DNA sequence modifying enzyme alters wildtype copies of the gene, resulting in their inactivation. This inactivation can occur in the nuclei that will ultimately give rise to cells of various somatic tissues of the animal. It can also occur in the cells that will give rise to the embryonic germline. Without being limited by any particular theory, provided that endogenous copies of the essential gene are altered in a sufficient number of nuclei, and are inactivated in both copies (for diploid organisms), which can happen early in embryogenesis (at the single diploid nucleus stage) or later, after some number of nuclei have been generated, then development will be disrupted, resulting in animal death. However, if the zygote inherits along with the DNA sequence modifying enzyme-encoded gene a tightly linked copy of the rescue transgene that cannot be modified, the progeny will survive, even if both copies of the wildtype copy of the gene have been modified. This occurs because for most genes in diploids heterozygosity for one wildtype copy of the gene is sufficient to provide enough function to allow the organisms to survive and thrive. Good evidence for this conclusion comes from several sources: the many examples of phenotypically normal heterozygotes in many species; and the ability to create and maintain healthy stocks for deletions that eliminate, one at a time, one copy of most regions of the *drosophila* genome (flybase.org). If there is a modest fitness cost associated with heterozygosity this will be decreased over time as the construct spreads. This is because as spread occurs the frequency of homozygotes for the construct rises, in which case individuals now carry two copies of the rescue gene of interest and are therefore have increased fitness.

Without being limited by any particular theory, the model can be generalized and extrapolated to prokaryotes or other haploids carrying a plasmid that encodes a DNA sequence modifying enzyme and a recoded or sequence unrelated version of an essential gene. In this case progeny that fail to inherit the plasmid will still inherit the chromosomal mutation that results in loss of function of the wildtype copy of the gene. They may also inherit the DNA sequence modifying enzyme, in which case the sequence of any wildtype copies of the essential gene (incorporated through horizontal gene transfer, transduction, transformation, or conjugation) will be altered and the cell will die. However, those cells that inherit the plasmid inherit a functional copy of the gene, even though the chromosomal version of the gene has been altered.

Without being limited by any particular theory, the model can be generalized and extrapolated to organisms such as yeast that go from a haploid to diploid phase and back to haploid through sporulation. A chromosomal copy of the DNA sequence modifying enzyme and a recoded or sequence unrelated version of the rescue will be transmitted to only some progeny during sporulation. Those haploids that fail to inherit the rescue copy of the gene will die because the DNA sequence modifying enzyme, which is transmitted through cytoplasm, will cause alteration of the wildtype copy. The wildtype copy of the gene will likely also have been cleaved during the diploid stage in which case cytoplasmic inheritance of the nuclease is not essential. In any case, only haploids that inherit the tightly linked rescue construct will survive. This constitutes a kind of gamete killing. Most generally, the system described applies to any biological situation in which a DNA sequence modifying enzyme alters the sequence of an essential gene so as to disrupt essential functions in haploid, diploid or polyploid cells. This modification can occur in the parental cell, which can be haploid, diploid, tetraploid, or polyploid. Alternatively the DNA sequence modifying enzyme, the transcript and/or protein for which is produced in the parental cell, can alter the sequence of the essential gene in the progeny cells in which it becomes located through cytoplasmic diffusion or active transport. The operative principle in all cases is that in the relevant cell type, or in a multicellular organism, in some fraction of these cells, all or most copies of the endogenous copies of the essential gene are altered so as to produce non-functional copies of the gene. This results in death of all cells that fail to inherit one or more copies of the rescue transgene. The DNA sequence modifying enzyme and the rescue transgene are tightly linked and behave as a single genetic unit.

In some embodiments, the model is extrapolated to a diploid animal such as a rodent, mosquito, fish, amphibian, or other organism in which spermatogenesis utilizes haploid-specific promoters to drive the expression of genes essential for spermatogenesis. In some embodiments, the DNA sequence modifying enzyme is expressed in the germline at some point. It is not critical when, or in which sex. What matters is that ultimately one will end up with post-meiotic cells that carry a copy of the rescue transgene, while their post-meiotic brothers do not. To the extent that it is true that the product of the rescue transgene, which will have all the endogenous regulatory sequences of the endogenous gene, does not diffuse into the meiotic brothers to which they are still connected by cytoplasmic bridges, those sperm will die, be resorbed, or be ejaculated in a state that is non-functional. This will result in nuclease and rescue transgene-bearing meiotic products being preferentially represented in the next generation, a form of population replacement.

Figure 11:
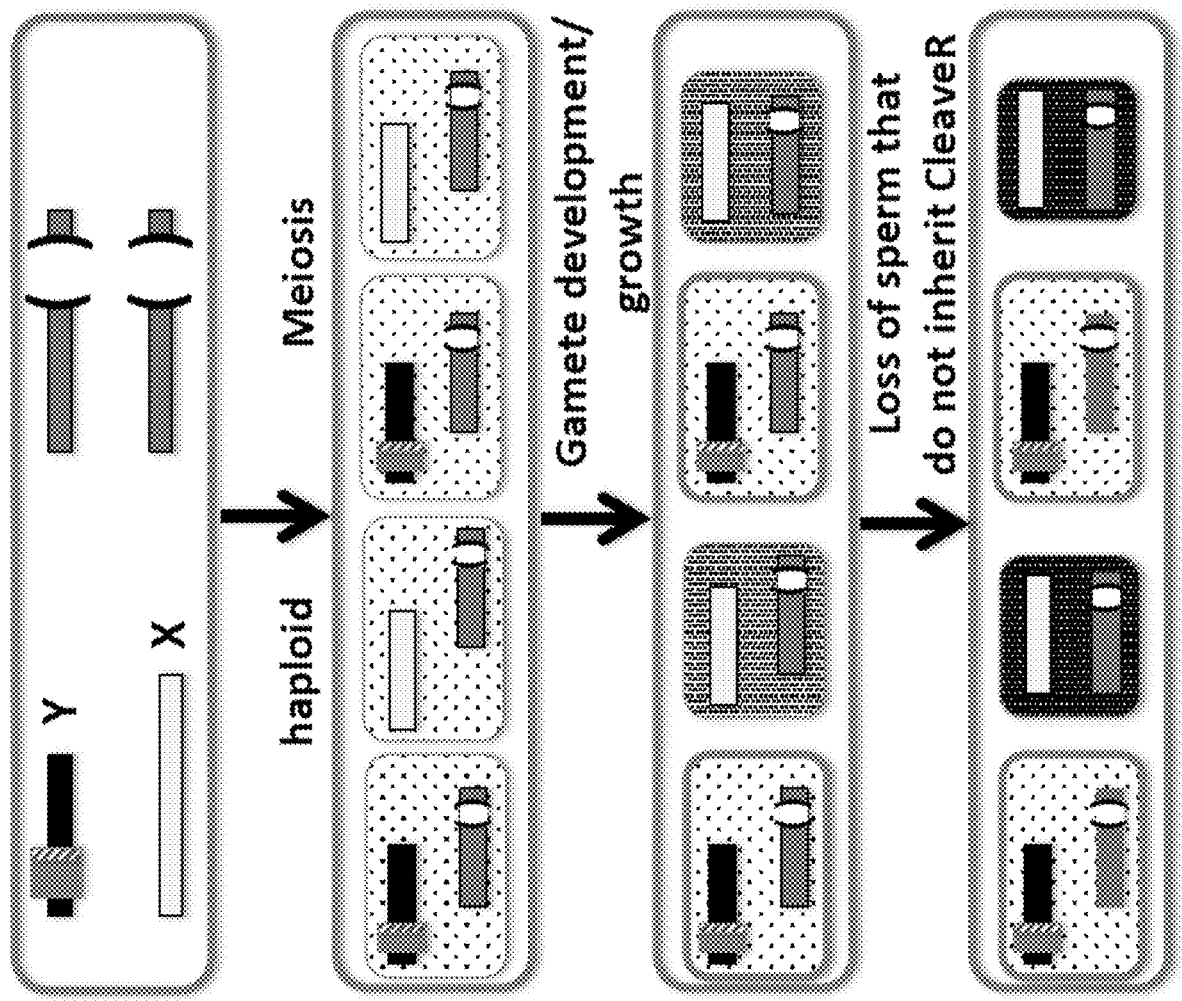
FIG. 11 shows a schematic of an embodiment of vector-mediated sex ratio distortion.

In some embodiments, a rescue version of a post-meiotic expressed gene that is normally present on an autosome can be expressed from the Y chromosome along with the DNA sequence modifying enzyme. Provided the DNA sequence modifying enzyme alters the wildtype endogenous copy of the gene in the germline then only Y-bearing sperm will generate this product. This holds even if the haplo-expressed gene is on the autosome (FIG. 11). In early generations there may be some reduced sex ratio bias if some wildtype copies are not cleaved, and depending on when in germline development the nuclease acts (before or after this generations post-meiotic expression). However, the bottom line is the same. Eventually, wildtype copies of the haplo-expressed gene are lost and the only remaining functional copies are those on the Y chromosome. This can result in sex ratio distortion if the sperm in which the gene has been inactivated are unable to carry out fertilization.

In some embodiments, the model is applicable to chickens with ZW sex chromosomes. W is the sex chromosome. Males are ZZ. A W chromosome that carries a rescue cassette and a nuclease. It is inherited only into females. Males that inherit the Z chromosome inherit a cleaved copy of an essential Z gene, or cleaved copies of an autosomal essential gene. In any case, ultimately a population in which there are only females is obtained because males do not inherit a rescue construct. The male eggs simply do not develop. A big male egg is still obtained because the actual embryo with chickens is quite small. However, baby male chickens are not obtained. Ultimately female chickens carrying the rescue construct and no wildtype copies of the gene are mated with wildtype males. Female progeny survive. Male progeny do not survive if there is maternal carryover that causes killing of the wildtype loci inherited from the male. If W-bearing females are mated with to wildtype males, which is what is done in a breeding or hybrid generation situation, the males will all die if the gene that is essential is normal on the Z and there is enough maternal carryover of the DNA sequence modifying enzyme to cause the wildtype copy of whatever chromosome carries the wildtype copy of the gene from males to undergo sequence modification such that males inherit no good copies of the essential gene.

EXAMPLES

Outlined in Examples 1-5 are the designs of five proposed cleavage mediated gene drives. Discrete generation, deterministic population frequency models were developed for each of the five drive mechanisms that demonstrate the range of fitness costs and Cas9 cleavage efficiencies for which they will take over a wildtype population.

Example 1—X Chromosome Cleavage Mediated Y Chromosome Drive

X chromosome cleavage mediated Y chromosome Drive (also referred to herein as X cleavage mediated Y drive) consists of Cas9, gRNAs which target an essential (i.e. recessive lethal) gene on the X chromosome, and a recoded copy of this target X gene which is immune to gRNA targeting, which are situated together at the same locus on the Y chromosome (FIG. 1A). The transgenic construct (TY) is situated on the Y chromosome and consists of Cas9 (long green rectangle), gRNAs (short green rectangle) targeting an essential gene on the X chromosome, and a recoded version of the target gene (yellow rectangle with recoded gRNA target sites in orange) (FIG. 1A). Potential cleavage sites on the target essential gene (X) are indicated by dashed lines and scissors, and the cleaved locus (C) is a null form of the target gene made of what remains of the gene from the outer ends of the cleavage sites (FIG. 1A).

Figure 1B:
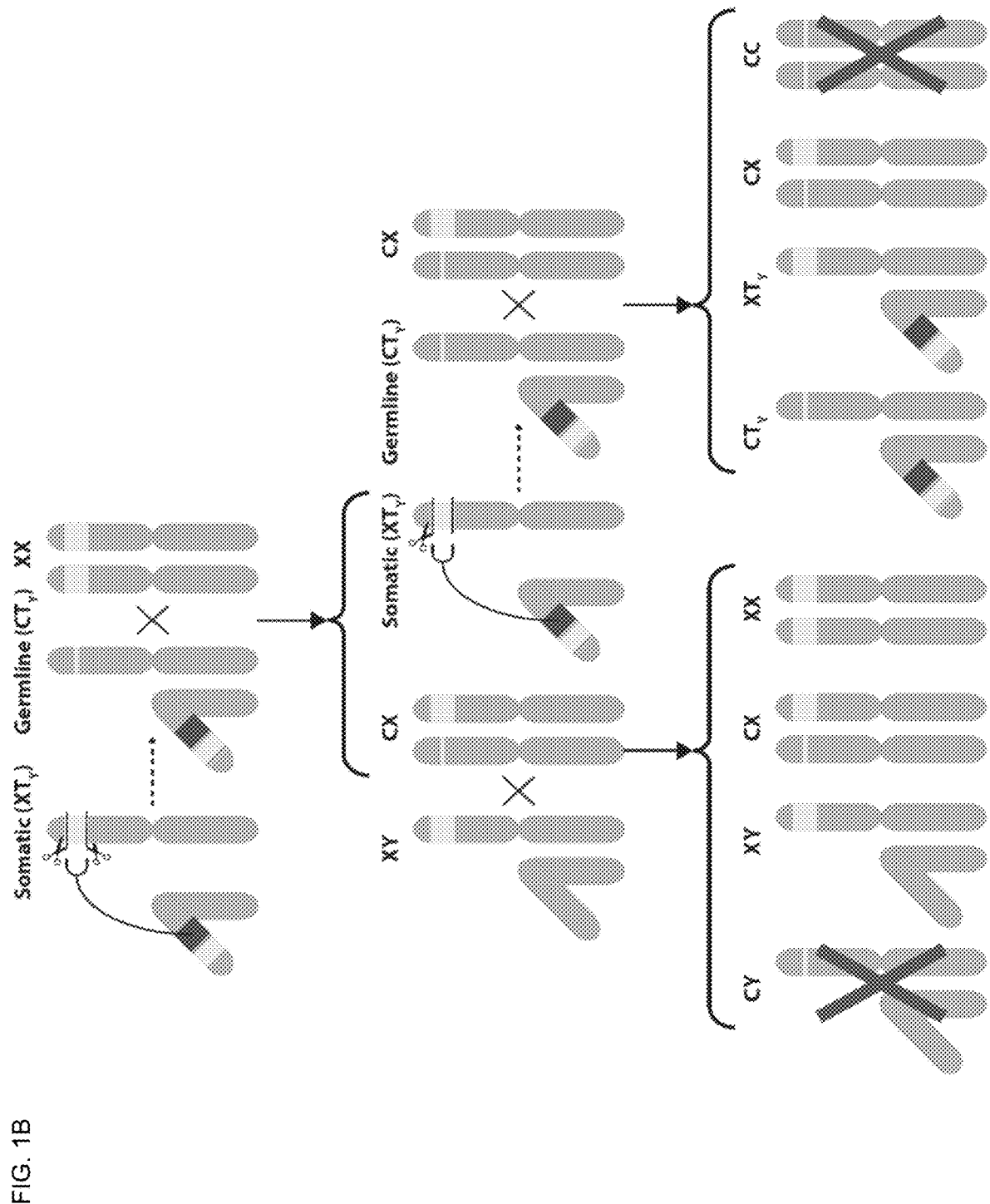

In males who carry this construct (TY) and a normal X chromosome (X), the target gene is cleaved multiple times during spermatogenesis, destroying the wild type copy of the gene on the X chromosome (C) and resulting in either TY or C bearing sperm (FIG. 1B). In transgenic males that bear wild type X chromosomes, Cas9 (stacked green square and yellow square with orange bars) can find and cleave a copy of the target gene (yellow square). The resulting cleaved locus (yellow bar) is passed on instead of the original target wildtype locus. When two individuals bearing a cleaved locus mate and the cleaved X loci are paired together (CC) or when the cleaved locus is passed on to a male (CY), the resulting offspring is unviable, removing wild type alleles are from the population (FIG. 1B) As TY males mate with wild type females, C's will begin to accumulate in heterozygotes (CX). All CY males and all CC females will die from the absence of a functional copy of the target essential X gene, leaving the viable genotypes CTY, XTY, XY, CX, and XX (FIG. 1B). Events proceed from left to right. The vector on the Y expresses a site-specific nuclease (dark square) and a rescue transgene (light square). The nuclease has the ability to cleave a wildtype version of the essential gene on the X at multiple positions (scissors). Cleavage does not necessarily happen in somatic cells. The left-most panel (X,Ty) simply indicates where cleavage occurs. Cleavage occurs in germline cells (CTy), resulting in the creation of an X chromosome that lacks a functional copy of the essential gene (thin light line). When a male carrying these chromosomes mates with a wildtype female new opportunities for cleavage of a wildtype X are created (second line). In the third generation matings are shown that result in the death of several genotypes.

Figure 1C:
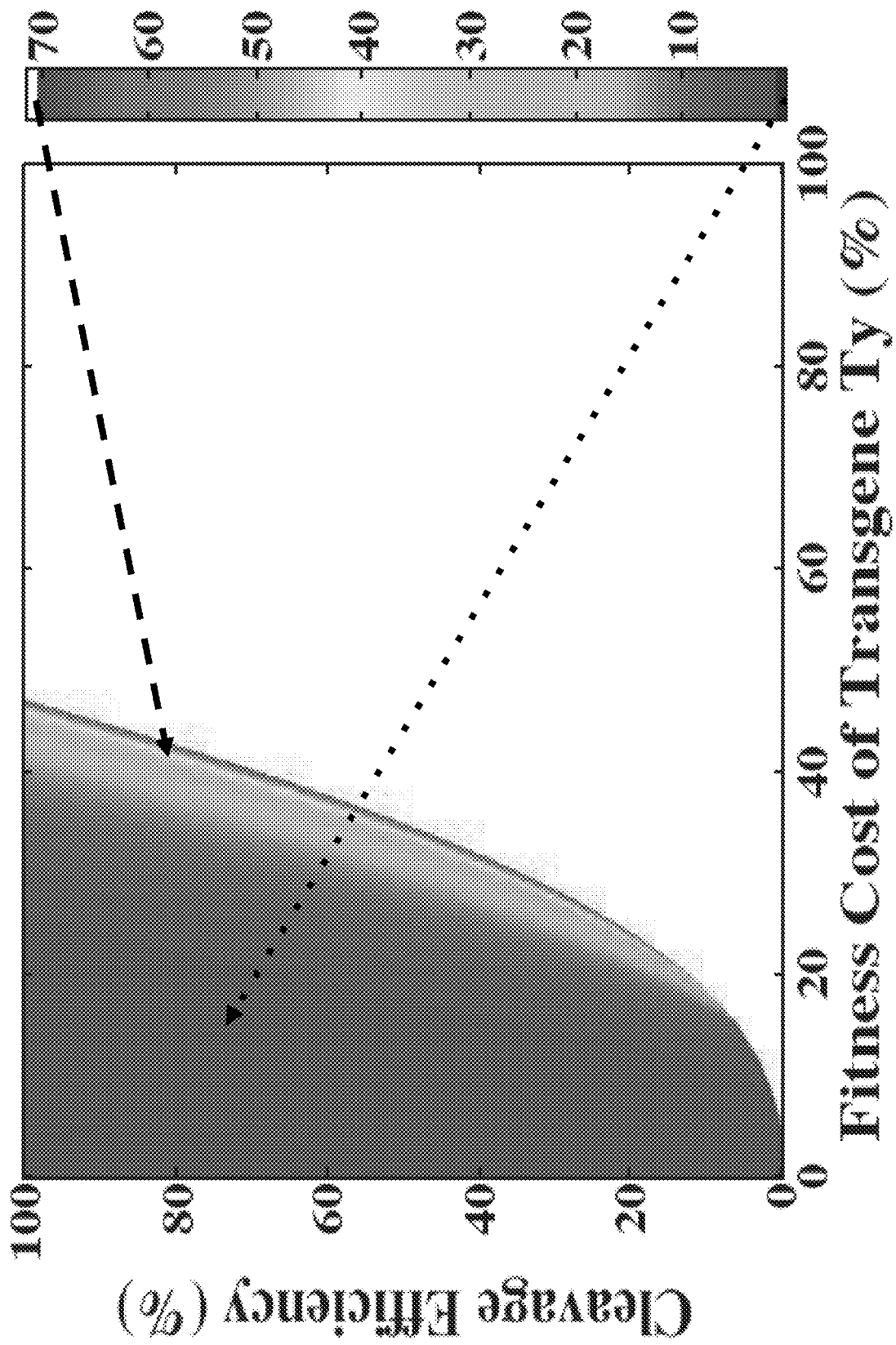

The discrete generation, deterministic population frequency model for this drive mechanism demonstrates that if Cas9 cleaves the target gene with 100% efficiency, TY can drive to fixation amongst Y chromosomes with just a few moderate releases of CTY males while bearing a fitness cost of up to approximately 45% (FIG. 1C). TY can still drive male replacement when Cas9 is cleaving at non-optimal rates, but it can only tolerate correspondingly reduced fitness costs as a result (FIG. 1C). Discrete generation, deterministic population frequency modeling of X cleavage mediated Y drive is shown in FIG. 1C. Each data point uses a few moderate releases of transgenic mosquitoes (three releases of CTY males at 50% of the population) with the specified fitness cost and Cas9 cleavage efficiency. The color of each data point indicates the number of generations (as indicated by the colorbar) before TY bearing individuals make up >99% of all males. White indicates the inability of TY to take over under the specified conditions or failure to do so within 70 generations (FIG. 1C).

The X CM Y drive is capable of quickly driving a transgene to fixation on the Y chromosome while bearing ~40% fitness costs at high cleavage efficiency. As males are the only transgenics, it cannot be used as a replacement mechanism for attacking mosquitoes because only the females are vectors. However, it can still be useful in the context of suppression if the cargo is a lethal gene under an environmentally triggered promoter. In this way, the transgene can spread to fixation in males, killing all males once the environmental trigger activates and resulting in a population crash. Alternatively, this construct can be used in ZW species where the female is the heterogametic sex, such as the pink bollworm.

Example 2—Cleavage Mediated X Drive

Figure 2A:
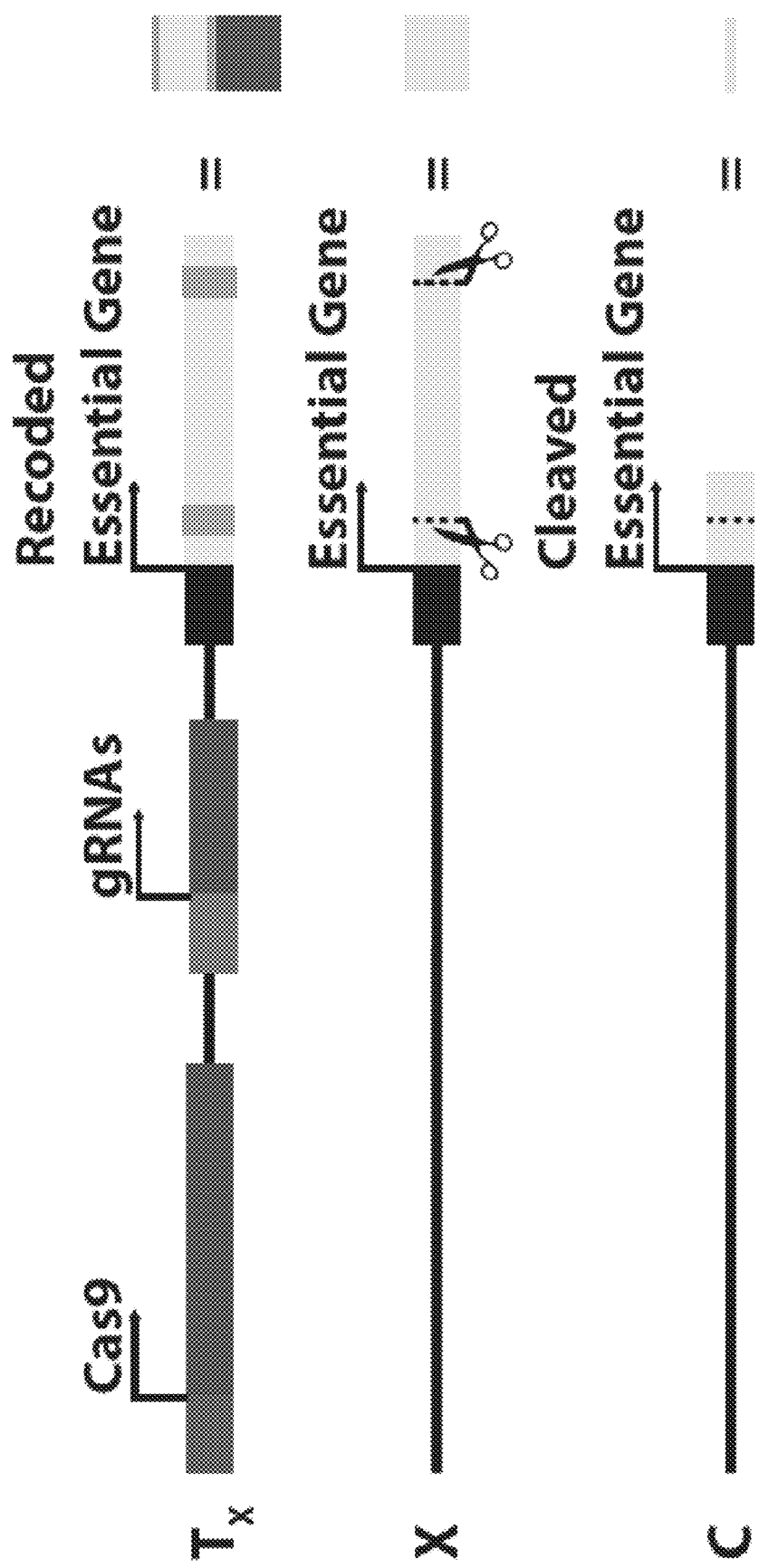
FIG. 2A-FIG. 2C show an embodiment of a cleavage mediated X drive with the vector also located on the X.

Cleavage mediated X drive consists of Cas9, gRNAs which target an essential gene on the X chromosome, and a recoded or sequence unrelated copy of this target X gene which is immune to gRNA targeting, which are situated together at the same locus as the target gene (FIG. 2A). The transgenic construct (TX) is situated on the X chromosome and consists of Cas9 (long green rectangle), gRNAs (short green rectangle) targeting an essential gene on the X chromosome (at the same locus as TX), and a recoded version of the target gene (yellow rectangle with recoded gRNA target sites in orange) (FIG. 2A). Potential cleavage sites on the target essential gene (X) are indicated by dashed lines and scissors, and the cleaved locus (C) is a null form of the target gene made of what remains of the gene from the outer ends of the cleavage sites (FIG. 2A).

Figure 2B:
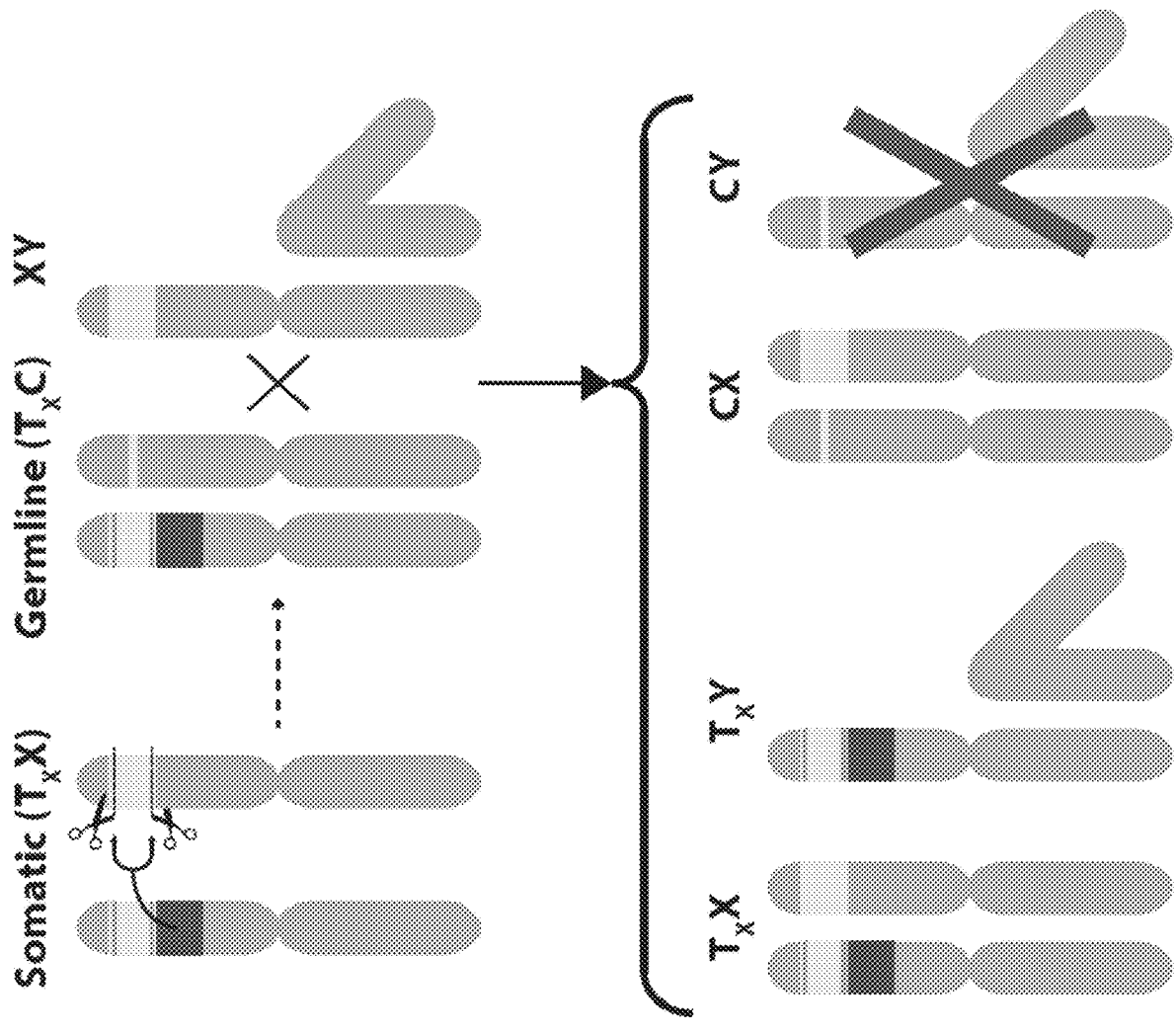

In females who carry this construct (TX) and a normal X chromosome (X), the target gene is cleaved multiple times during oogenesis, destroying the wild type copy of the gene on the X chromosome (C) and resulting in either TX or C bearing eggs (FIG. 2B). In transgenic females that bear wild type X chromosomes (TX X) Cas9 can find and cleave a copy of the target gene. The resulting cleaved locus is passed on instead of the original target wildtype locus. When the cleaved locus is passed on to a male (CY), the resulting offspring is unviable, removing a wild type allele are from the population (FIG. 2B). As transgenic individuals mate with wild types, cleaved copies of the essential X gene will begin to accumulate in females (CX). All males that receive a cleaved X chromosome (CY) will die from the absence of a functional copy of the target essential X, leaving the viable genotypes TXY, XY, TXTX, TXC, TXX, CX, and XX (FIG. 2B).

Figure 2C:
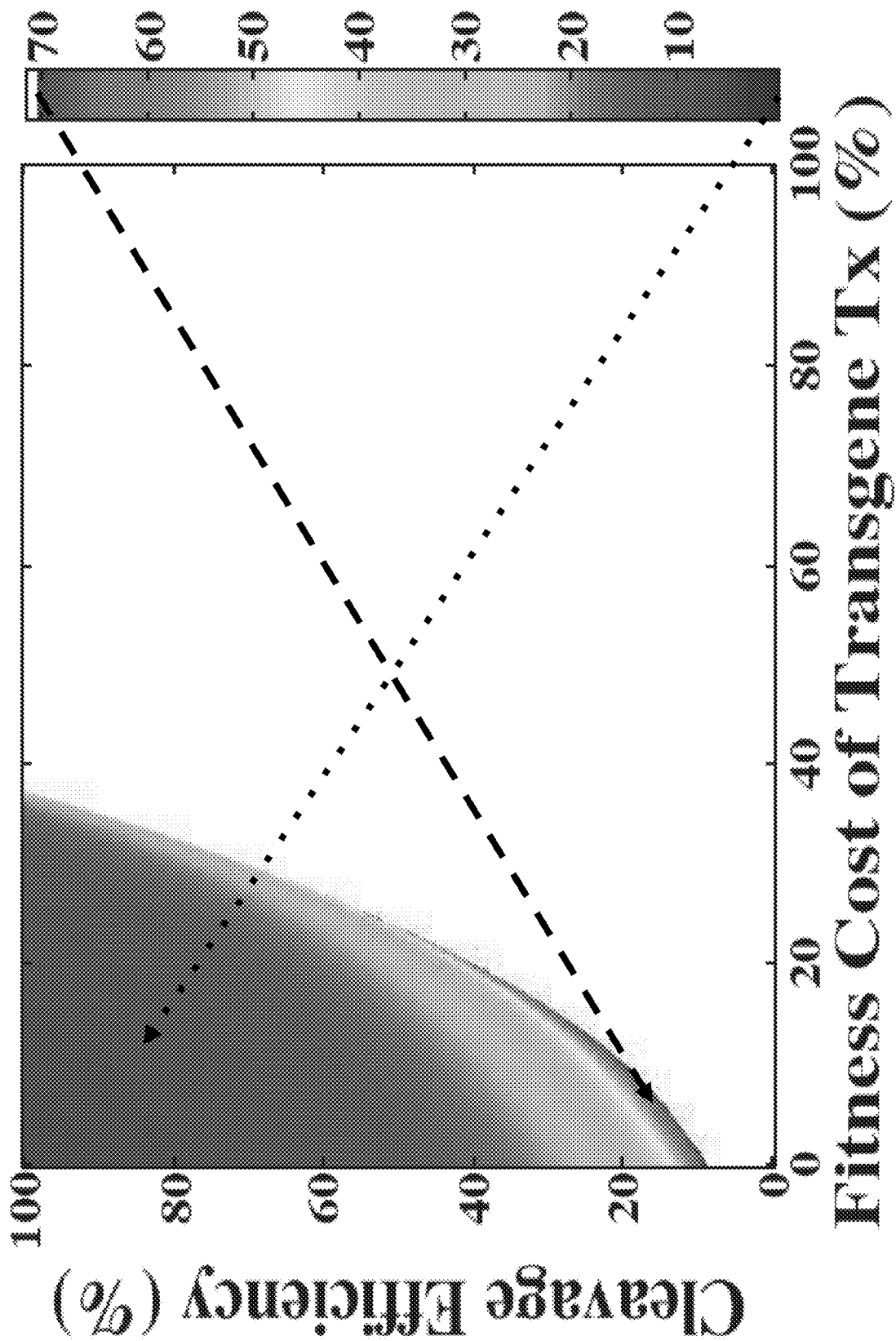

The discrete generation, deterministic population frequency model for this drive mechanism demonstrates that if Cas9 cleaves the target gene with 100% efficiency, TX can drive to fixation with just a few moderate releases of TXY males while bearing a fitness cost of up to approximately 35% (FIG. 2C). TX can still drive population replacement when Cas9 is cleaving at non-optimal rates, but it can only tolerate correspondingly reduced fitness costs as a result (FIG. 2C). Discrete generation, deterministic population frequency modeling of cleavage mediated X drive is shown in FIG. 2C. Each data point uses a few moderate releases of transgenic mosquitoes (three releases of TXY males at 50% of the population) with the specified fitness cost and Cas9 cleavage efficiency. The color of each data point indicates the number of generations (as indicated by the colorbar) before TX bearing individuals make up >99% of the population. White indicates the inability of TX to take over under the specified conditions or failure to do so within 70 generations (FIG. 2C).

The X drive can tolerate ~35% fitness costs at high cleavage efficiency. This drive is well suited to replacement in XY species of mosquitoes such as Anopheles gambiae.

Example 3—Autosomal Cleavage Mediated Autosomal Drive

Figure 3A:
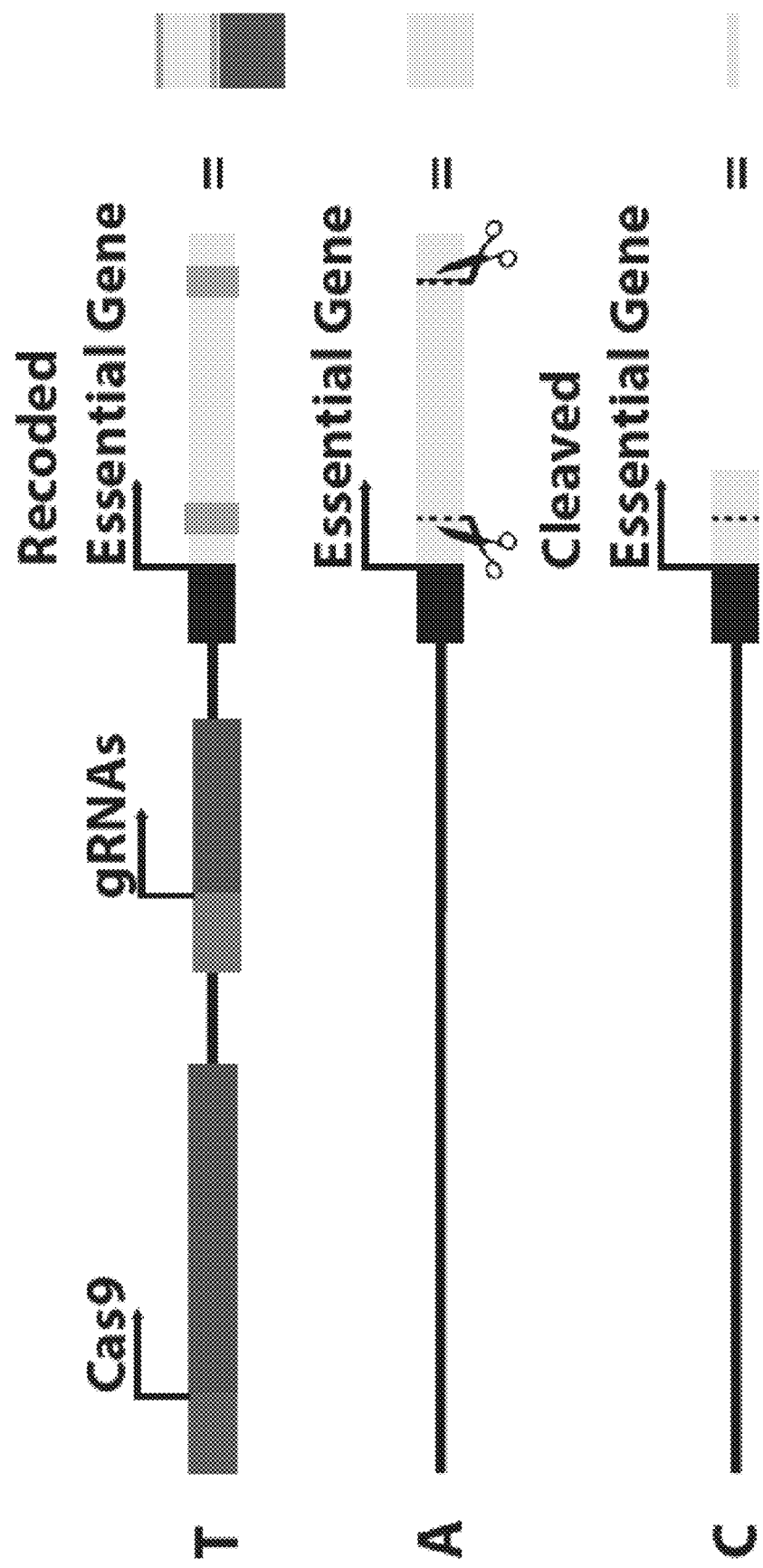
FIG. 3A-FIG. 3C show an embodiment of a cleavage mediated autosomal drive.

Cleavage mediated autosomal drive consists of Cas9, gRNAs which target an essential autosomal gene, and a recoded or sequence unrelated copy of this target gene which is immune to gRNA targeting, which are situated together at the same locus as the target gene (FIG. 3A). The transgenic construct (T) is situated on an autosome and consists of Cas9 (long green rectangle), gRNAs (short green rectangle) targeting an essential gene (at the same autosomal locus as T), and a recoded version of the target gene (yellow rectangle with recoded gRNA target sites in orange) (FIG. 3A). Potential cleavage sites on the target essential gene (A) are indicated by dashed lines and scissors, and the cleaved locus (C) is a null form of the target gene made of what remains of the gene from the outer ends of the cleavage sites (FIG. 3A).

Figure 3B:
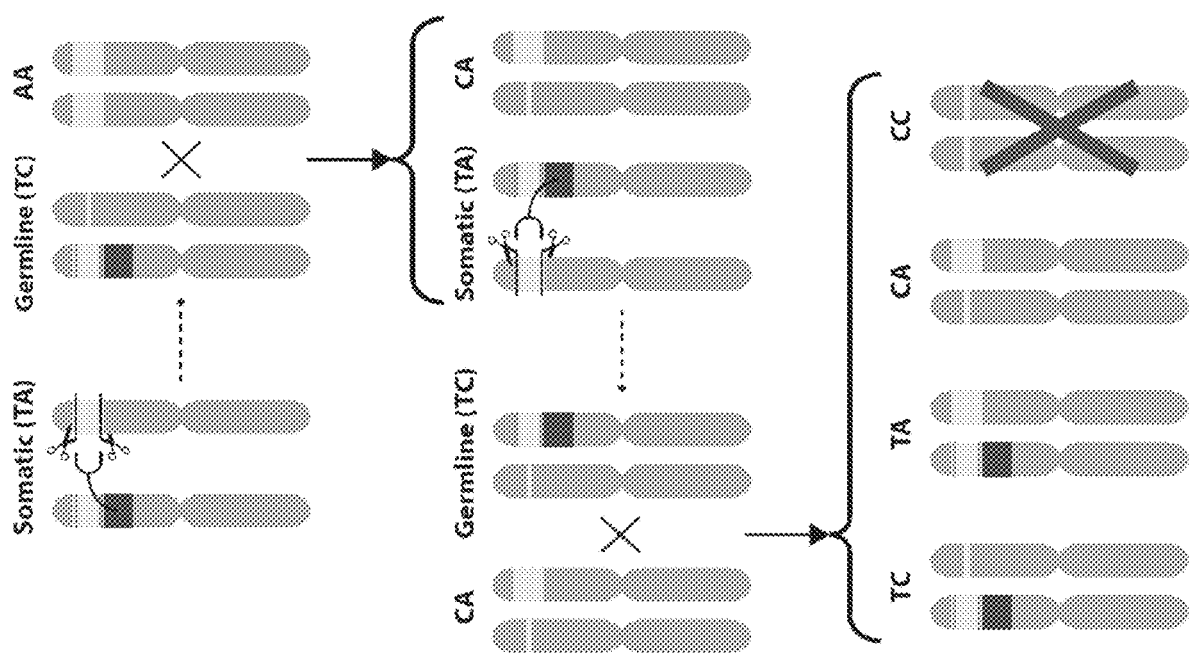

In males and females who carry the construct (T) and a wild type copy of the its target (A), the target gene is cleaved multiple times during gametogenesis, destroying the wild type copy of the gene (C) and resulting in either T or C bearing gametes (FIG. 3B). As transgenic individuals mate with wild types, cleaved copies of the essential gene will begin to accumulate in heterozygotes (CA individuals). All individuals that receive two cleaved autosomes (CC) will die from the absence of a functional copy of the target essential autosomal gene, leaving the viable genotypes TT, TC, TA, CA, and AA (FIG. 3B). In heterozygotes (TA) Cas9 can find and cleave a copy of the target gene. The resulting cleaved locus is passed on instead of the original target wildtype locus. When two individuals bearing cleaved locus mate and the cleaved loci are paired together (CC), the resulting offspring is unviable, removing two wild type alleles are from the population (FIG. 3B).

Figure 3C:
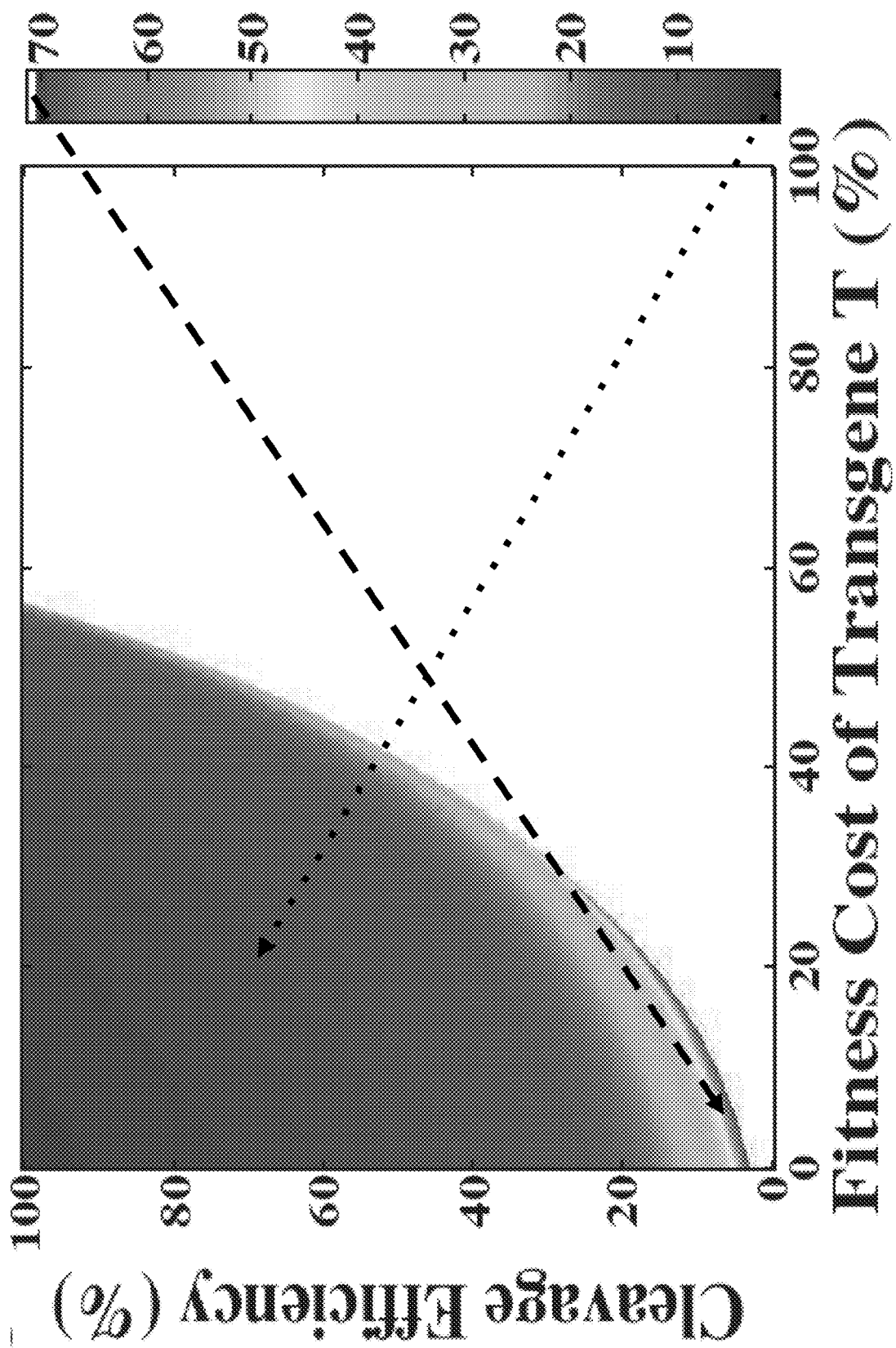

The discrete generation, deterministic population frequency model for this drive mechanism demonstrates that if Cas9 cleaves the target gene with 100% efficiency, T can drive to fixation with just a few moderate releases of TT males while bearing a fitness cost of up to approximately 55% (FIG. 3C). T can still drive population replacement when Cas9 is cleaving at non-optimal rates, but it can only tolerate correspondingly reduced fitness costs as a result (FIG. 3C). Discrete generation, deterministic population frequency modeling of cleavage mediated autosomal drive is shown in FIG. 3C. Each data point uses a few moderate releases of transgenic mosquitoes (three releases of TT males at 50% of the population) with the specified fitness cost and Cas9 cleavage efficiency. The color of each data point indicates the number of generations (as indicated by the colorbar) before T bearing individuals make up >99% of the population. White indicates the inability of T to take over under the specified conditions or failure to do so within 70 generations (FIG. 3C).

The autosomal drive is very potent, capable of driving even with ~55% fitness costs at high cleavage efficiency. Because the construct is autosomal, it can be used to drive replacement in any species, importantly covering both Anopheles gambiae and Aedes aegypti. It is also perhaps the easiest to implement, as the only knowledge it requires about the target species are an essential gene on an autosome and an appropriate promoter to drive expression of the DNA sequence modifying enzyme (either pre-meiotic or gametogenic).

Example 4—Cleavage Mediated 2-Locus Autosomal Drive

Figure 4A:
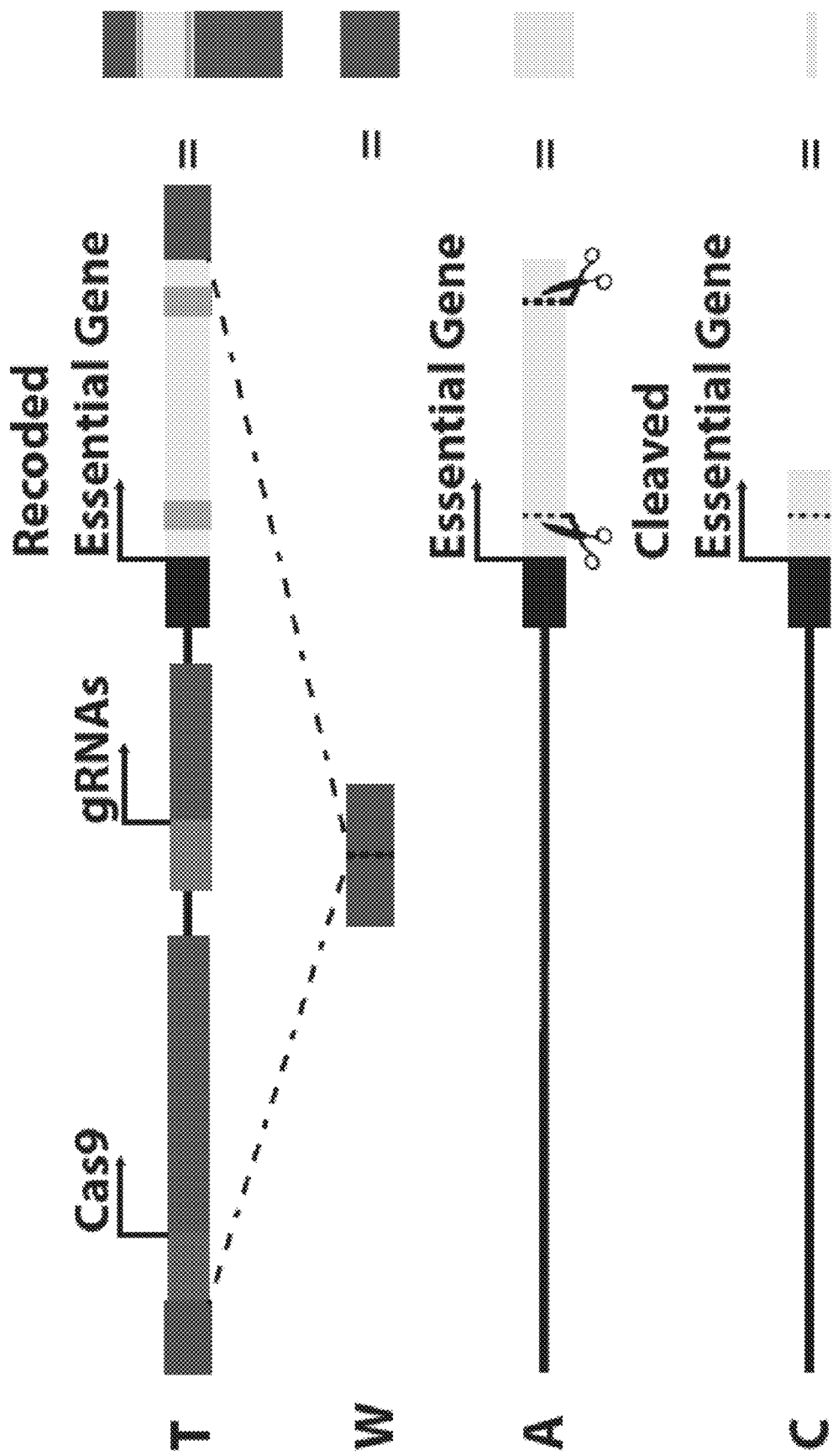
FIG. 4A-FIG. 4C show an embodiment of a cleavage mediated 2-locus autosomal drive.

Cleavage mediated 2-locus autosomal drive consists of Cas9, gRNAs which target an essential autosomal gene, and a recoded or sequence unrelated copy of this target gene which is immune to gRNA targeting, which are situated together on a different autosome (wild type W) than the target gene (FIG. 4A). The transgenic construct (T) is situated on an autosome and consists of Cas9 (long green rectangle), gRNAs (short green rectangle) targeting an essential gene (at a different autosomal locus than T), and a recoded version of the target gene (yellow rectangle with recoded gRNA target sites in orange). The transgenic construct T is generated by targeted insertion at a wild type locus indicated by the blue rectangle (W). Potential cleavage sites on the target essential gene (A) are indicated by dashed lines and scissors, and the cleaved locus (C) is a null form of the target gene made of what remains of the gene from the outer ends of the cleavage sites (FIG. 4A).

Figure 4B:
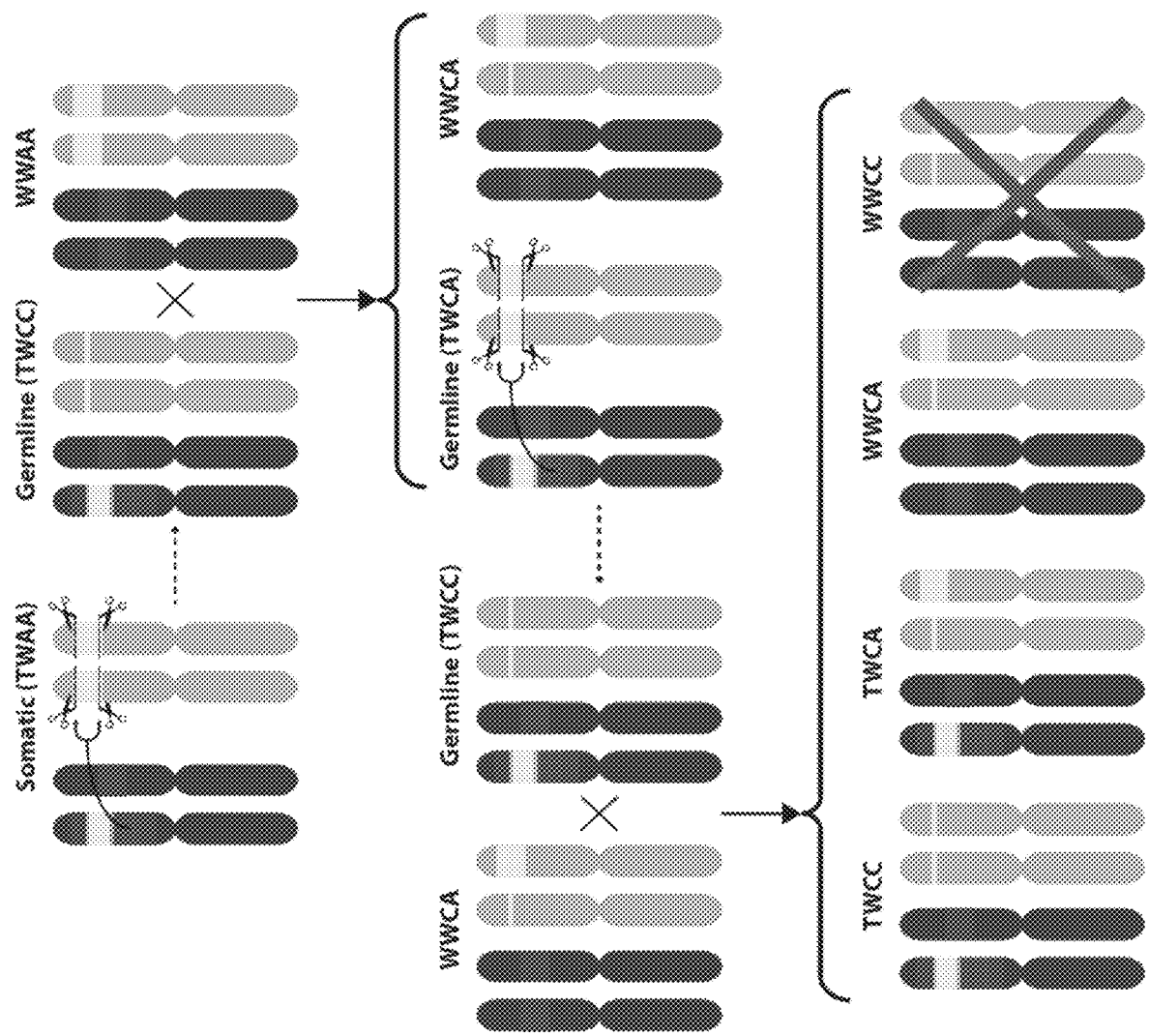

In males and females who carry at least one copy of the construct (T) and at least one copy of the wild type target (A), the target gene is cleaved multiple times during gametogenesis, destroying the wild type copy of the gene (C) and resulting in C bearing gametes (FIG. 4B). As transgenic individuals mate with wild types, cleaved copies of the essential gene will begin to accumulate in heterozygotes (—CA individuals). Only individuals who do not bear a T and receive two cleaved genes (WWCC) will die from the absence of a functional copy of the target essential autosomal gene, leaving the viable genotypes TTCC, TTCA, TTAA, TWCC, TWCA, TWAA, WWCA, and WWAA (FIG. 4B). In individuals which possess at least one T and at least one A, Cas9 can find and cleave a copy of the target gene. The resulting cleaved locus is passed on instead of the original target wildtype locus. When two individuals bearing the cleaved locus mate and the cleaved loci are paired together in the absence of the transgene (WWCC), the resulting offspring is unviable, removing two wild type alleles are from the population (FIG. 4B).

Figure 4C:
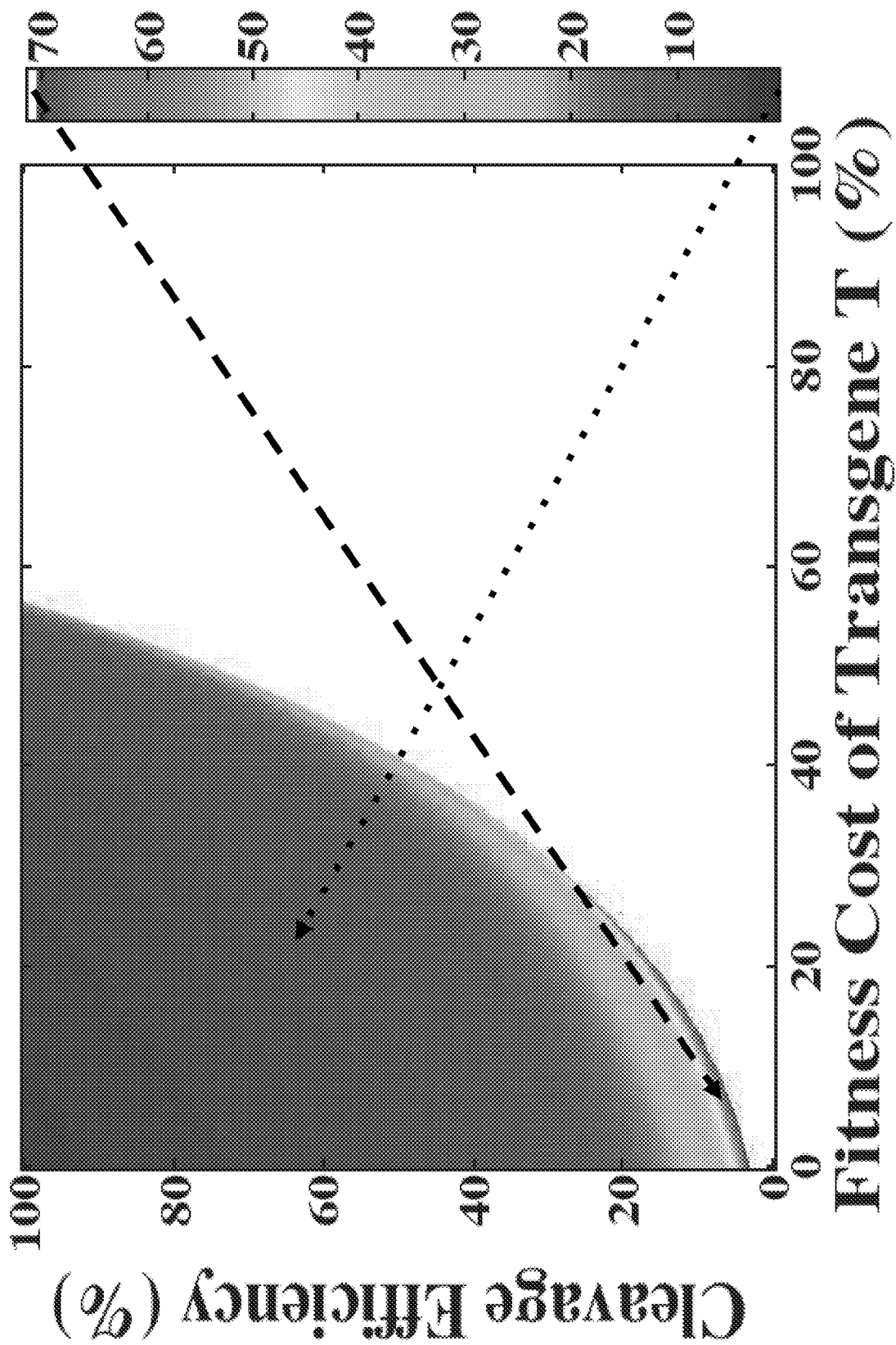

The discrete generation, deterministic population frequency model for this drive mechanism demonstrates that if Cas9 cleaves the target gene with 100% efficiency, this drive mechanism is identical to the single locus cleavage based autosomal drive mechanism. However, if Cas9 cleavage efficiency is imperfect, then this 2-locus cleavage based drive can tolerate larger fitness costs than the single locus version (FIG. 4C, as compared to FIG. 3C). Discrete generation, deterministic population frequency modeling of cleavage mediated 2-locus autosomal drive is shown in FIG. 4C. Each data point uses a few moderate releases of transgenic mosquitoes (three releases of TTCC males at 50% of the population) with the specified fitness cost and Cas9 cleavage efficiency. The color of each data point indicates the number of generations (as indicated by the colorbar) before T bearing individuals make up >99% of the population. White indicates the inability of T to take over under the specified conditions or failure to do so within 70 generations (FIG. 4C).

The dynamics of the 2-locus autosomal drive makes it identical to the autosomal drive when the cleavage efficiency of Cas9 is perfect, but when that cleavage efficiency is reduced 2-locus drive becomes the stronger drive. As a result, it can maintain higher fitness costs at reduced cleavage efficiencies while sharing the same applicability to species and ease of creation as with single locus versions.

Example 5—Cleavage Mediated Haplolethal Drive

Figure 5A:
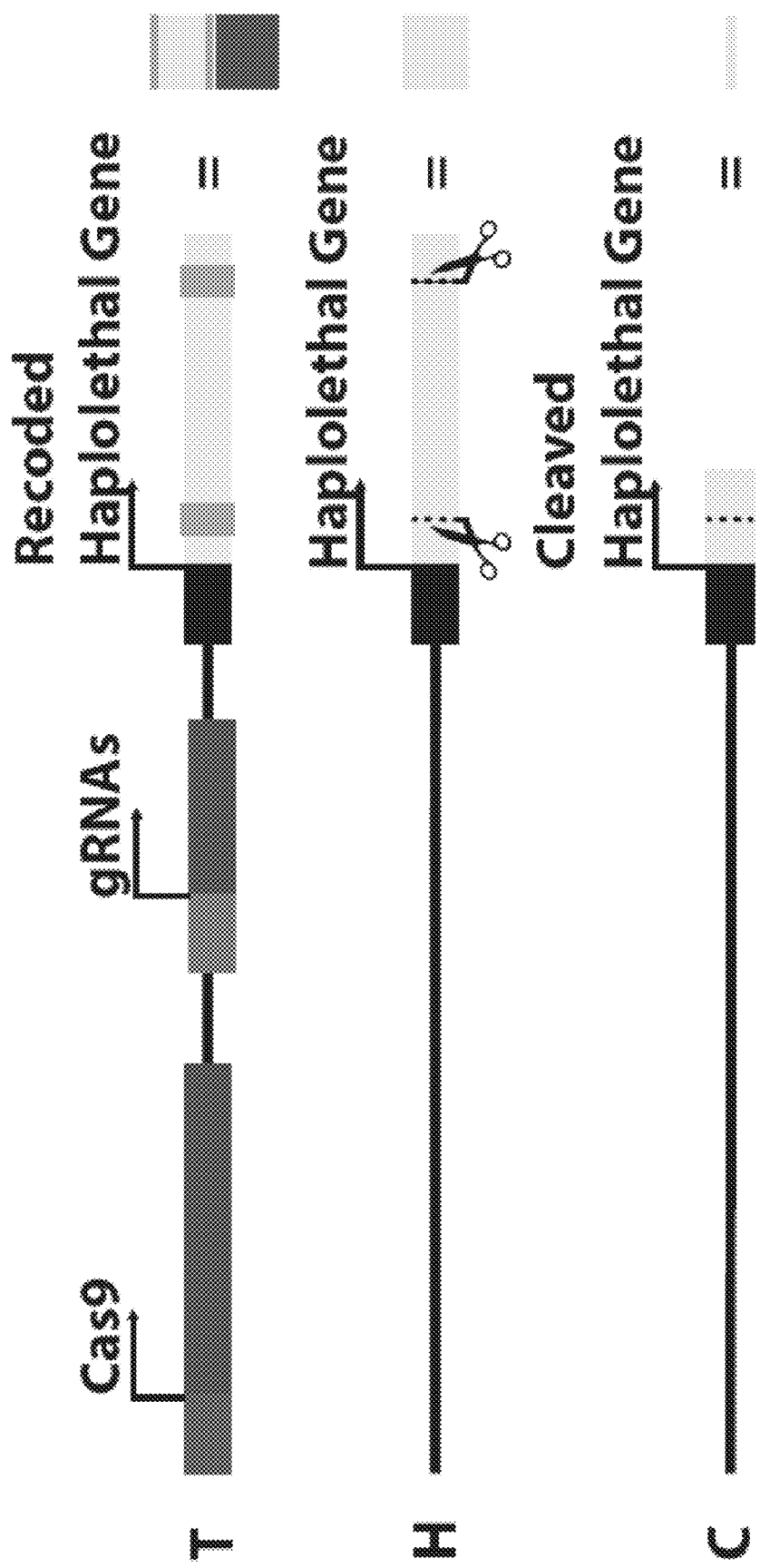
FIG. 5A-FIG. 5C show an embodiment of a cleavage mediated haplolethal drive.

Cleavage mediated haplolethal drive is slightly different from the other four cleavage based mechanisms. It consists of Cas9, gRNAs which target an autosomal haplolethal gene (instead of a recessive lethal gene), and a recoded or sequence unrelated copy of this haplolethal target gene which is immune to gRNA targeting, which are situated together at the same locus as the target gene (FIG. 5A). The transgenic construct (T) is situated on an autosome and consists of Cas9 (long green rectangle), gRNAs (short green rectangle) targeting a haplolethal gene (at the same autosomal locus as T), and a recoded version of the target gene (yellow rectangle with recoded gRNA target sites in orange). Potential cleavage sites on the target haplolethal gene (long yellow rectangle, H) are indicated by dashed lines and scissors, and the cleaved locus (short yellow rectangle, C) is a null form of the target gene made of what remains of the gene from the outer ends of the cleavage sites (FIG. 5A).

Figure 5B:
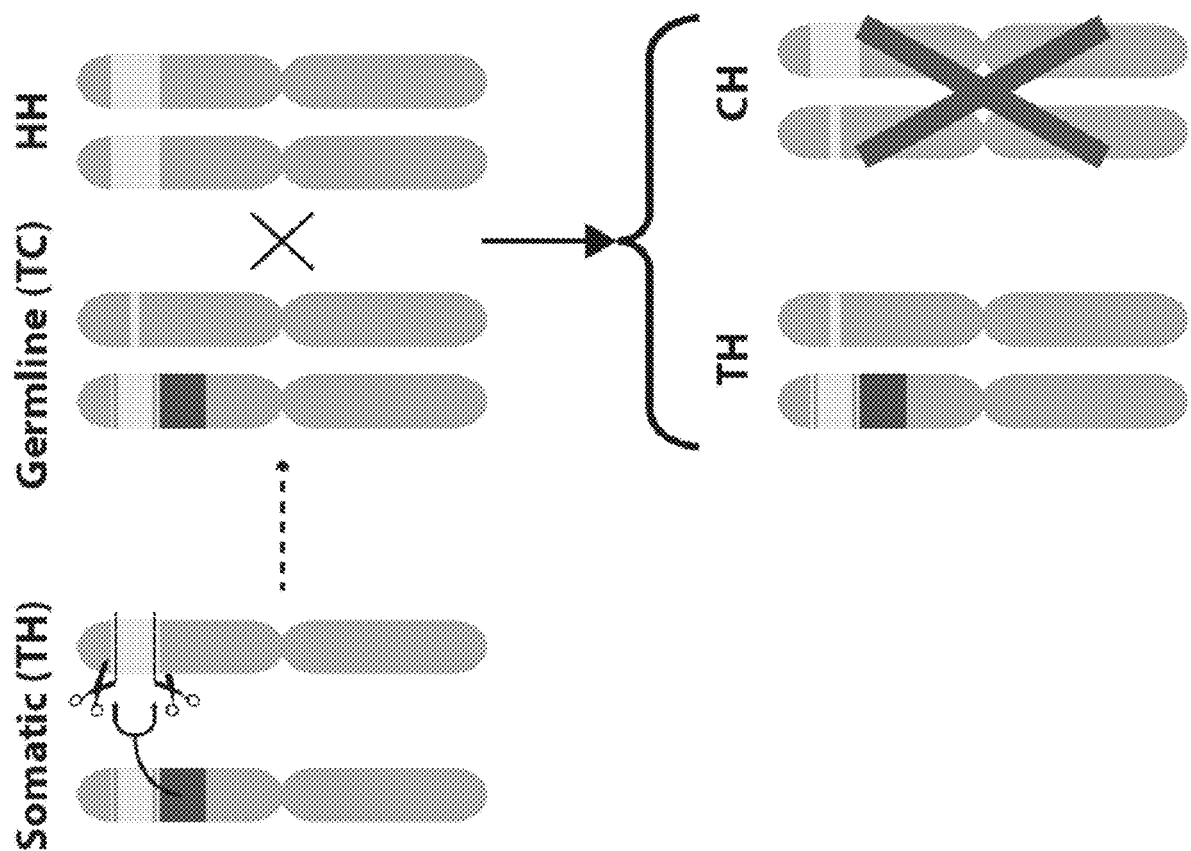

Cleavage is male specific, so in males who carry the construct (T) and a wild type copy of its target (H), the target gene is cleaved multiple times during spermatogenesis, destroying the wild type copy of the gene (C) and resulting in either T or C bearing sperm (FIG. 5B). As transgenic males mate, cleaved copies of the haplolethal gene will immediately result in the death of their carrier (both TC and CH genotypes), leaving the viable genotypes TT, TH, and HH (FIG. 5B). In heterozygotes (TH) Cas9 can find and cleave a copy of the target essential gene. The resulting cleaved locus is passed on instead of the original wildtype locus, and any offspring that receives the cleaved locus is unviable, removing either a transgene and a cleaved locus (TC) or two wild type alleles (CH) from the population (FIG. 5B). Related constructs can be implemented, as described above for the two-locus autosomal situation, in which the construct is located at a position different from that of the gene being targeted.

Figure 5C:
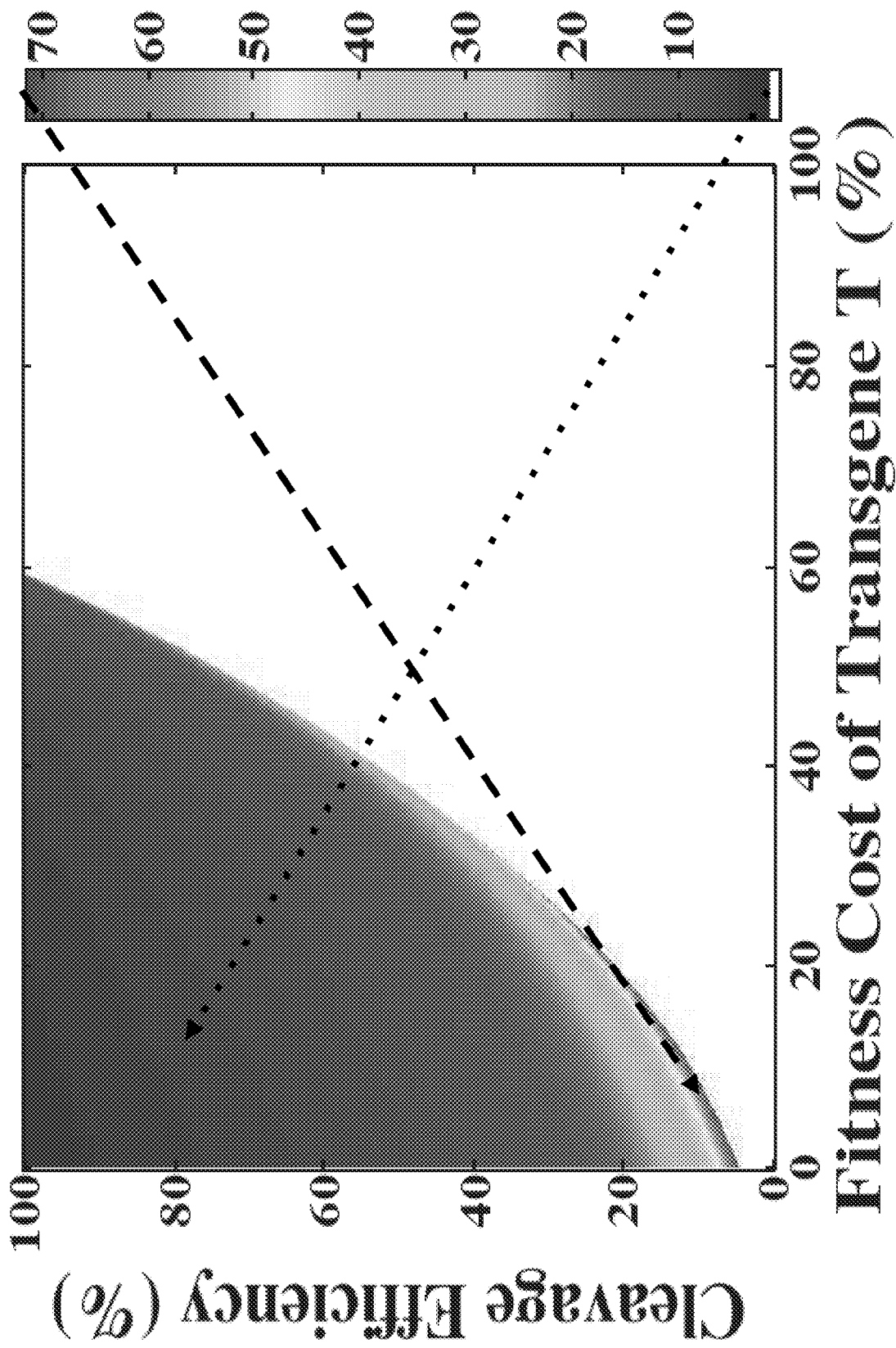

The discrete generation, deterministic population frequency model for this drive mechanism demonstrates that if Cas9 cleaves the target gene with 100% efficiency, T can drive to fixation with just a few moderate releases of TT males while bearing a fitness cost of up to approximately 60% (FIG. 5C). T can still drive population replacement when Cas9 is cleaving at non-optimal rates, but it can only tolerate correspondingly reduced fitness costs as a result (FIG. 5C). Discrete generation, deterministic population frequency modeling of cleavage mediated haplolethal drive is shown in FIG. 5C. Each data point uses a few moderate releases of transgenic mosquitoes (three releases of TT males at 50% of the population) with the specified fitness cost and Cas9 cleavage efficiency. The color of each data point indicates the number of generations (as indicated by the colorbar) before T bearing individuals make up >99% of the population. White indicates the inability of T to take over under the specified conditions or failure to do so within 70 generations.

The haplolethal drive is even stronger than the autosomal drive, capable of driving even with ~60% fitness costs at high cleavage efficiency. However, at reduced cleavage efficiency it withstands a smaller range of fitness costs than the 2-locus drive. Additionally, haplolethal drives rely on identifying a haploethal locus on which to base this drive mechanism as well as a pre-meiotic promoter to drive expression of either Cas9 and a post-meiotic promoter for the gRNAs, with one or both promoters also driving male specific expression. The latter two requirements are necessary for getting cleavage of the haplolethal locus in sperm without causing cleavage in the rest of the individual, thereby resulting in death of the construct-bearing individual. In some implementations Cas9 expression is limited to stages of spermatogenesis after those that require activity of the gene being targeted.

Example 6—Maintenance of Extrachromosomal Element

FIG. 6A shows a chromosome (circle) carrying essential gene (green rectangle). In this example a prokaryotic chromosome carries a wildtype copy of an essential gene. FIG. 6B shows an extra-chromosomal element such as a plasmid carrying the construct (red and green rectangles) and any other genes (e.g., one or more cargo sequences) to be maintained in the population. An extrachromosomal element carries the vector, which carries a recoded or sequence unrelated version of the essential gene (diagonal lines) and the DNA modifying enzyme driven by a promoter (solid rectangle). FIG. 6C shows the construct, which consists of two components: (1) a site-specific DNA modifying enzyme designed to alter the sequence of an endogenous gene required for survival, proliferation, fertility, or differentiation so as to render it non-functional (left); (2) a recoded or sequence unrelated version of the essential gene resistant to cleavage, and having reduced nucleotide identity with the endogenous gene (right). Optionally, one or more cargo sequences are present (center). FIG. 6D shows the chromosome (FIG. 6A) and the extra extra-chromosomal element (FIG. 6B) in a cell and forced inheritance of the extra-chromosomal element. The endogenous copy of essential gene is altered within the cell by CleaveR to render it non-functional (FIG. 6E). However, cells that inherit CleaveR survive, proliferate, differentiate, or are fertile, whereas those that fail to inherit C fail are survive, proliferate, differentiate, or are sterile (FIG. 6F). An expanded view of the vector shown in (FIG. 6B). Recoded essential gene (or functional equivalent that lacks significant sequence homology) transcribes to the right. DNA sequence modifying enzyme transcribes to the left. A cargo gene is located in between the two in the figure, though the actual arrangement between cargo, rescue and DNA modifying enzyme can take a number of forms. FIG. 6D shows a cell carrying the wildtype chromosome and the extrachromosomal element including the vector. FIG. 6E shows DNA modifying activity of the element results in sequence changes to the wildtype copy of essential chromosomal gene (horizontal arrow leading to a chromosome carrying a smaller version of the essential gene). FIG. 6F shows the extrachromosomal element is spontaneously lost from some cells (left). These cells die because they lack essential gene activity. Those on the right, that carry the vector and associated rescue transgene survive and proliferate.

Example 7

Figure 7:
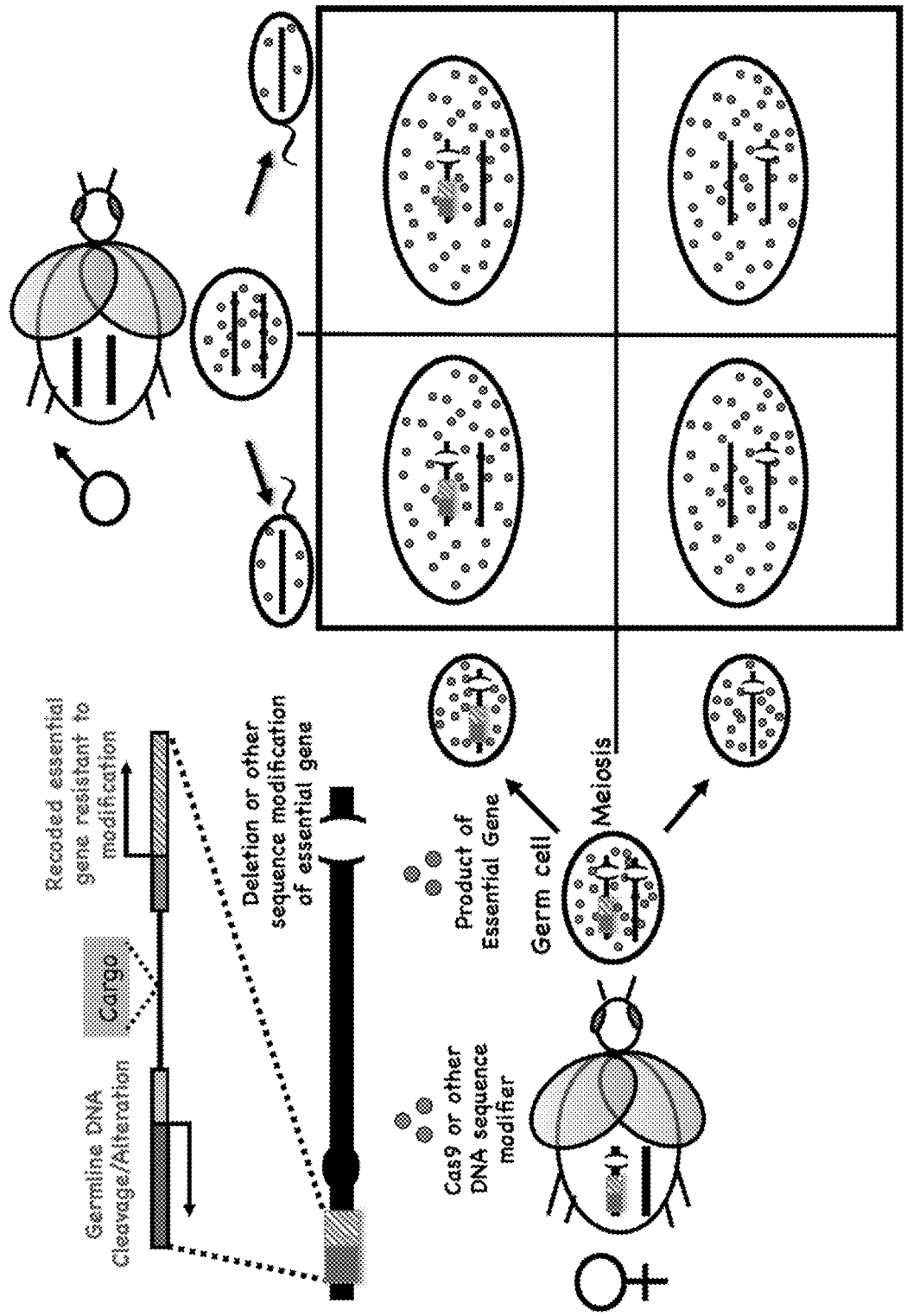
FIG. 7 shows a schematic of an embodiment the results of a cross between a female insect heterozygous for the vector with germline expression of the DNA sequence modifying enzyme and a wild type male when there is no carryover of DNA cleavage/alteration activity from germline into embryo.

FIG. 7 shows a schematic of an embodiment the results of a cross between organisms (in this example insects) heterozygous for the construct and a wild type organism when there is no carryover of DNA cleavage/alteration activity from germline into embryo. DNA sequence modified (parentheses) version of the essential gene is created in the female germline of heterozygotes. Both copies are cleaved, but the diploid germline cell survives because it carries one copy of the rescue transgene. Female haploid meiotic products (oocytes) survive because the essential product is provided to them from the rescue transgene. These products are inherited by progeny. All individuals inherit chromosomes carrying one sequence modified version of the essential gene. No progeny die. However, crosses between heterozygotes for the nonfunctional version of the essential gene in subsequent generations will create dead homozygotes (not shown). Note that in this example the essential locus is located on the same chromosome as the vector. This is simply for illustrative purposes as it decreases the number of genotypes that need to be shown to capture important aspects of vector behavior. As noted in the figures above, the vector can be located on any chromosome, and act to bring about sequence modifications of any essential gene, on any chromosome or extrachromosomal element. All progeny express one or both versions of the essential gene in the example provided. Therefore, all progeny survive.

Example 8

Figure 8A:
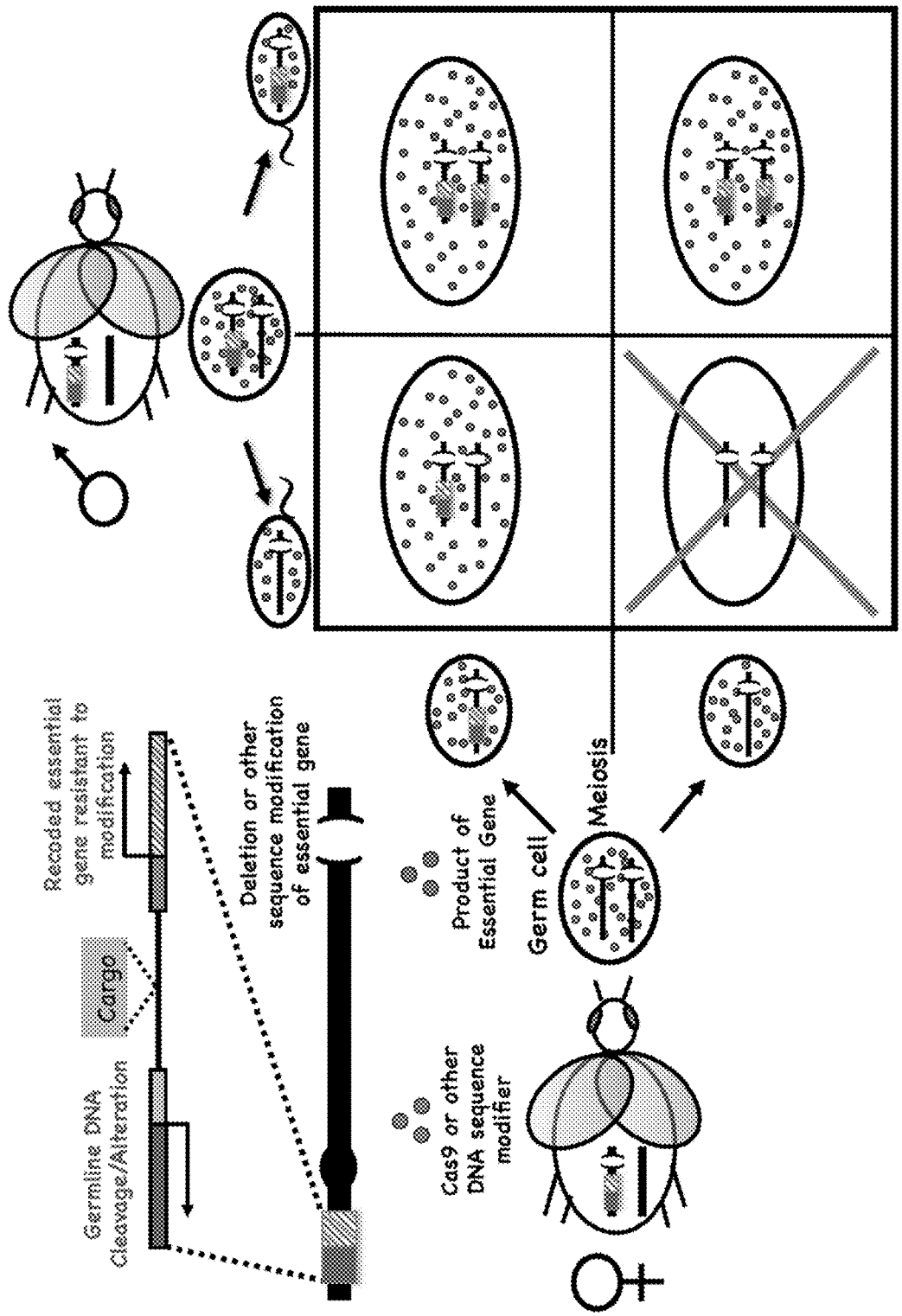
FIG. 8A shows a schematic of an embodiment the results of a cross between an insect heterozygous for the vector with germline expression of the DNA sequence modifying enzyme an a second insect heterozygous for the vector when there is no maternal transfer of DNA cleavage/alteration activity from germline into embryo. Individuals that inherit no functional copies of the essential gene die, while those that inherit at least one copy of the vector and its associated rescue transgene survive.
Figure 8B:
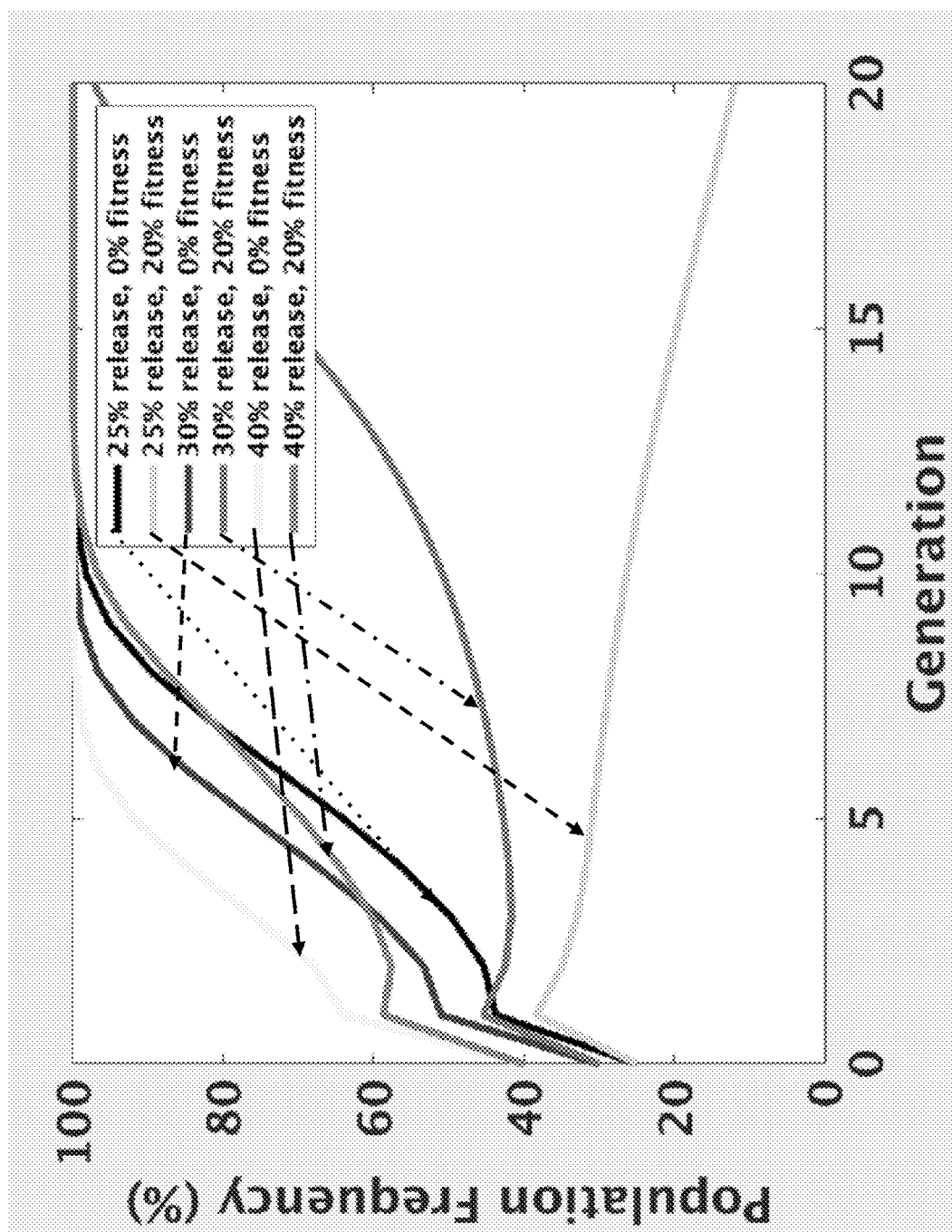
FIG. 8B shows a graph of an embodiment of vector-mediated gene drive/population replacement for an autosomal two locus scenario, with different fitness costs and introduction frequencies, and without maternal transfer of DNA cleavage/alteration activity.

FIG. 8A shows a schematic of an embodiment of the results of a cross between heterozygous organisms when there is no carryover of DNA cleavage/alteration activity from germline into embryo. Cleavage of the essential gene occurs in the parental cell resulting in survival of progeny that express the recoded protein survive and death of offspring that do no inherit CleaveR (FIG. 8A). The outcome of a cross between heterozygotes is the same whether or not there is maternal carryover. Progeny that inherit the construct survive while those that do not die. FIG. 8B shows an graph of an embodiment of CleaveR gene drive for different fitness costs and introduction frequencies without maternal transfer of DNA cleavage/alteration activity.

Example 9

Figure 9A:
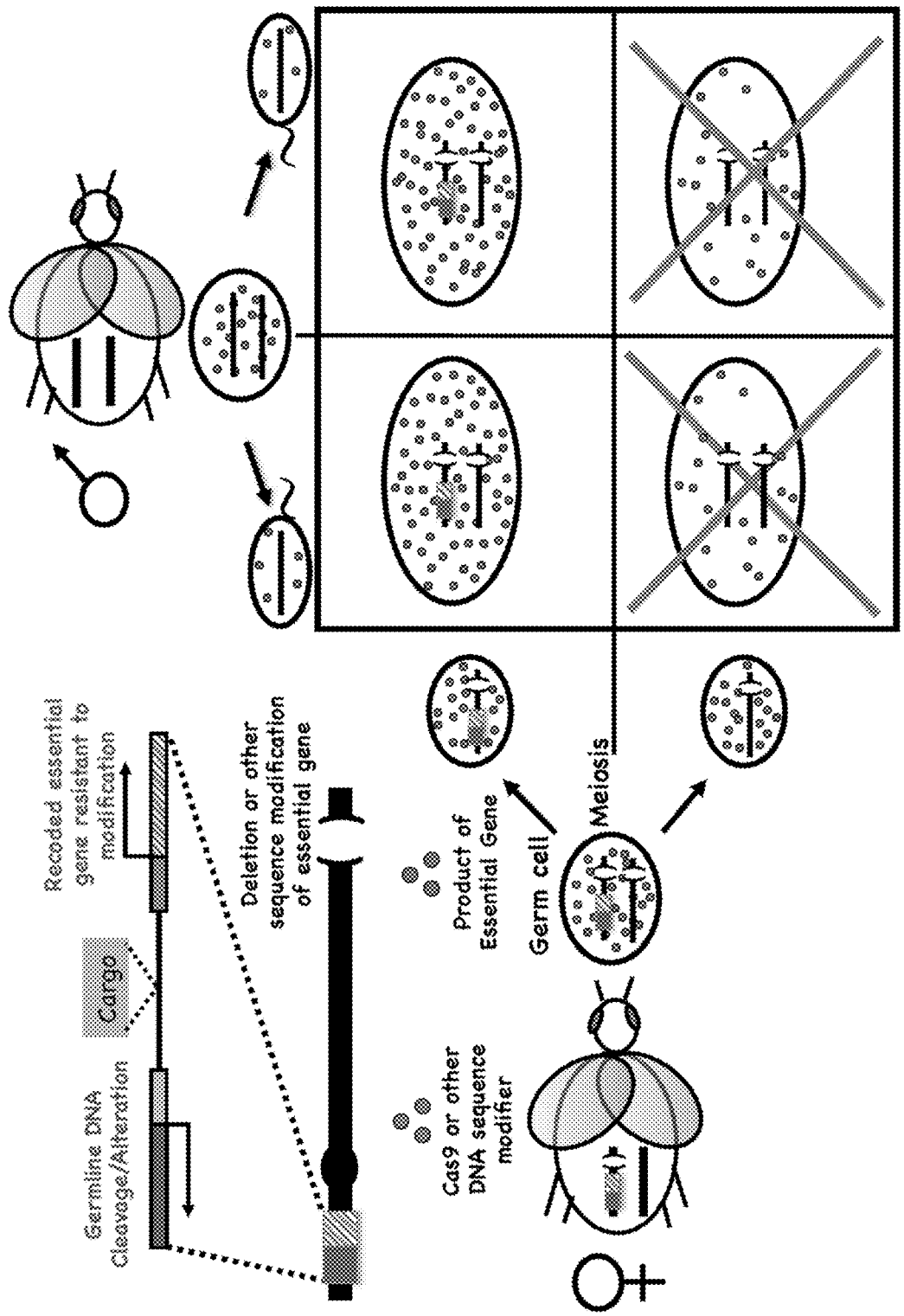
FIG. 9A shows a schematic of an embodiment the results of a cross when there is maternal transfer of DNA cleavage/alteration activity from germline into embryo.
Figure 9B:
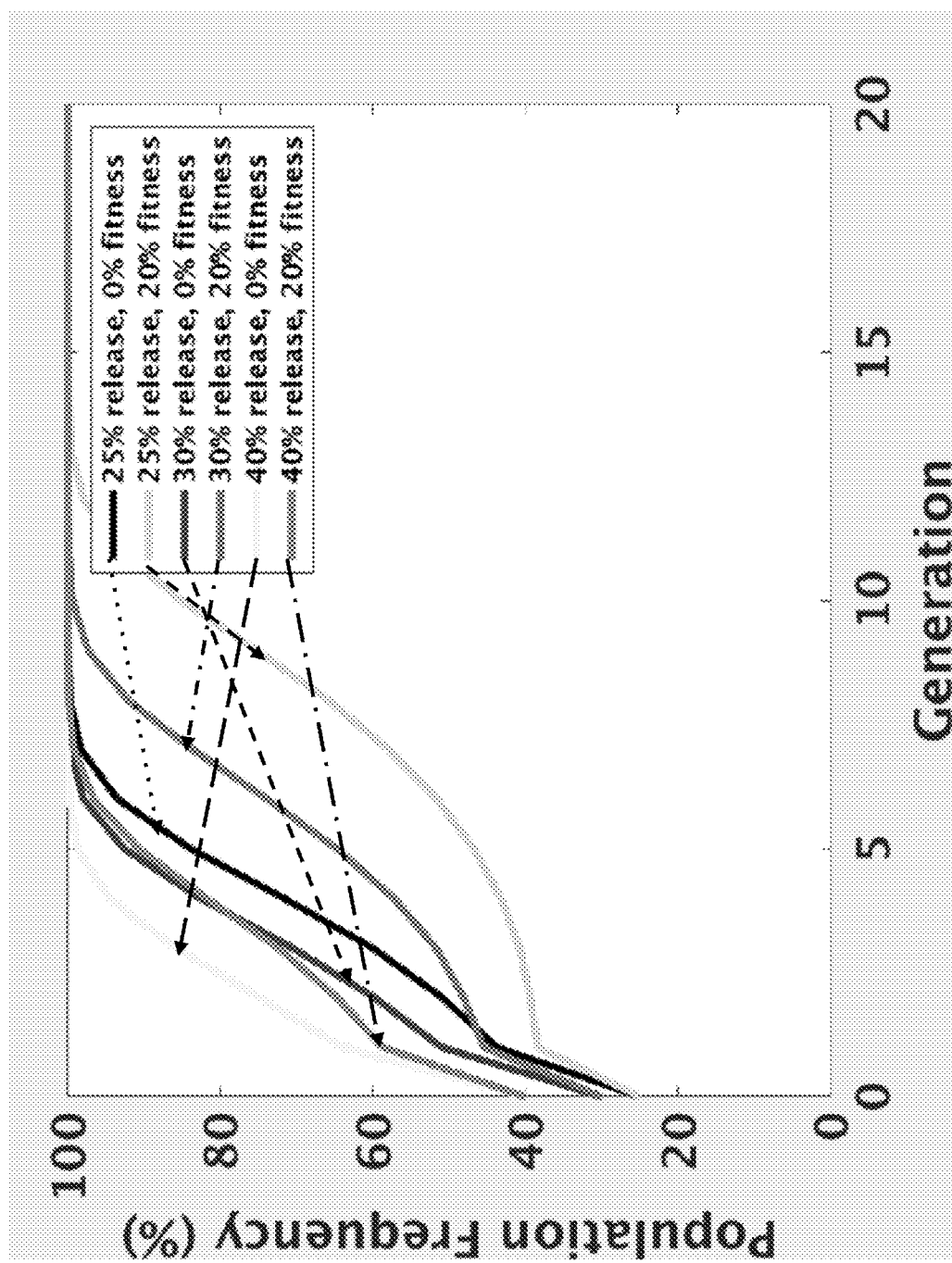
FIG. 9B shows a graph of an embodiment of vector-mediated gene drive/population replacement for different fitness costs and introduction frequencies with maternal transfer of DNA cleavage/alteration activity.

FIG. 9A shows a schematic of an embodiment the results of a cross when there is maternal transfer of DNA cleavage/ alteration activity from germline into embryo. Cleavage of the essential gene occurs in the parental cell and in products of cell fusion/fertilization into which the DNA cleavage/ alteration activity (or the encoding RNA(s)) is introduced during oogenesis, resulting in death of offspring that do no inherit the construct (FIG. 9A). Only progeny that express the recoded protein survive. FIG. 9B shows a graph of an embodiment of gene drive for different fitness costs and introduction frequencies with maternal transfer of DNA cleavage/alteration activity.

Example 10—Meiotic Gene Drive

Figure 10:
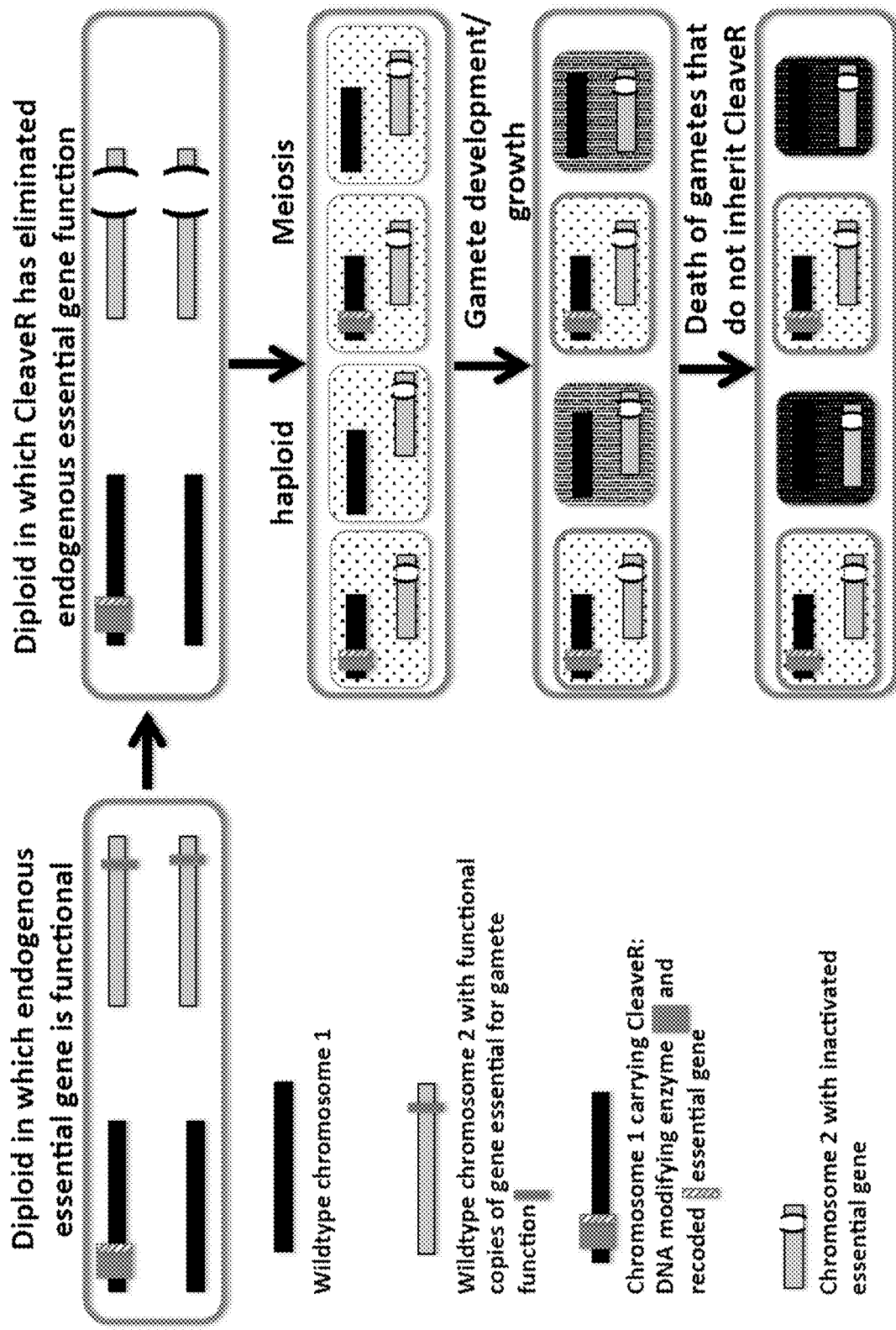
FIG. 10 shows a schematic of an embodiment of a meiotic gene drive. Spores that fail to inherit a functional copy of the essential gene die.

FIG. 10 shows a schematic of an embodiment of a meiotic gene drive. Cleavage of the essential gene occurs in the parental cell. As a result, gametes that fail to inherit CleaveR do not survive. In such a system chromosomes that carry the vector have a selective advantage and increase in frequency. Such a system can also be used to guarantee that gametes arising from a transgenic individual always carry the transgenes of interest (by virtue of tight genetic linkage to the construct). This ability has applications in agriculture, as it provides a method for regulating gene flow between populations of different genotypes.

Example 11—Sex Ratio Distortion

FIG. 11 shows a schematic of an embodiment of vector-mediated sex ratio distortion. A gene essential for post-meiotic sperm development is expressed on the Y chromosome as a part of the drive element. Only Y-bearing sperm, generated from diploids in which the drive element/vector has eliminated a gene required in haploid stages for sperm function, will express the product of this essential gene and be able to complete spermatogenesis/carry out fertilization. This results in sex-ratio distortion if sperm in which the gene has been inactivated fail to develop/undergo fertilization. Such a technology has many uses when the goal is to bring about population reduction or elimination by biasing the sex ratio towards males. A related approach can also be used to bias sex ratios towards males in species in which males are the homogametic sex (ZZ) and females the heterogametic sex (ZW). It can also be used for similar ends in species in which maleness is determined by a dominant allele of a male-determining locus. The primary requirement is that it be possible to eliminate and replace the activity of a gene required in haploid stages of sperm function, and that this product not be able to rescue meiotic brothers to which they may be linked by cytoplasmic bridges until late in spermatogenesis.

Example 12—Comparison of DNA Sequence Modification-Based Gene Drive with Homing-Based Gene Drive—1

Figure 12:
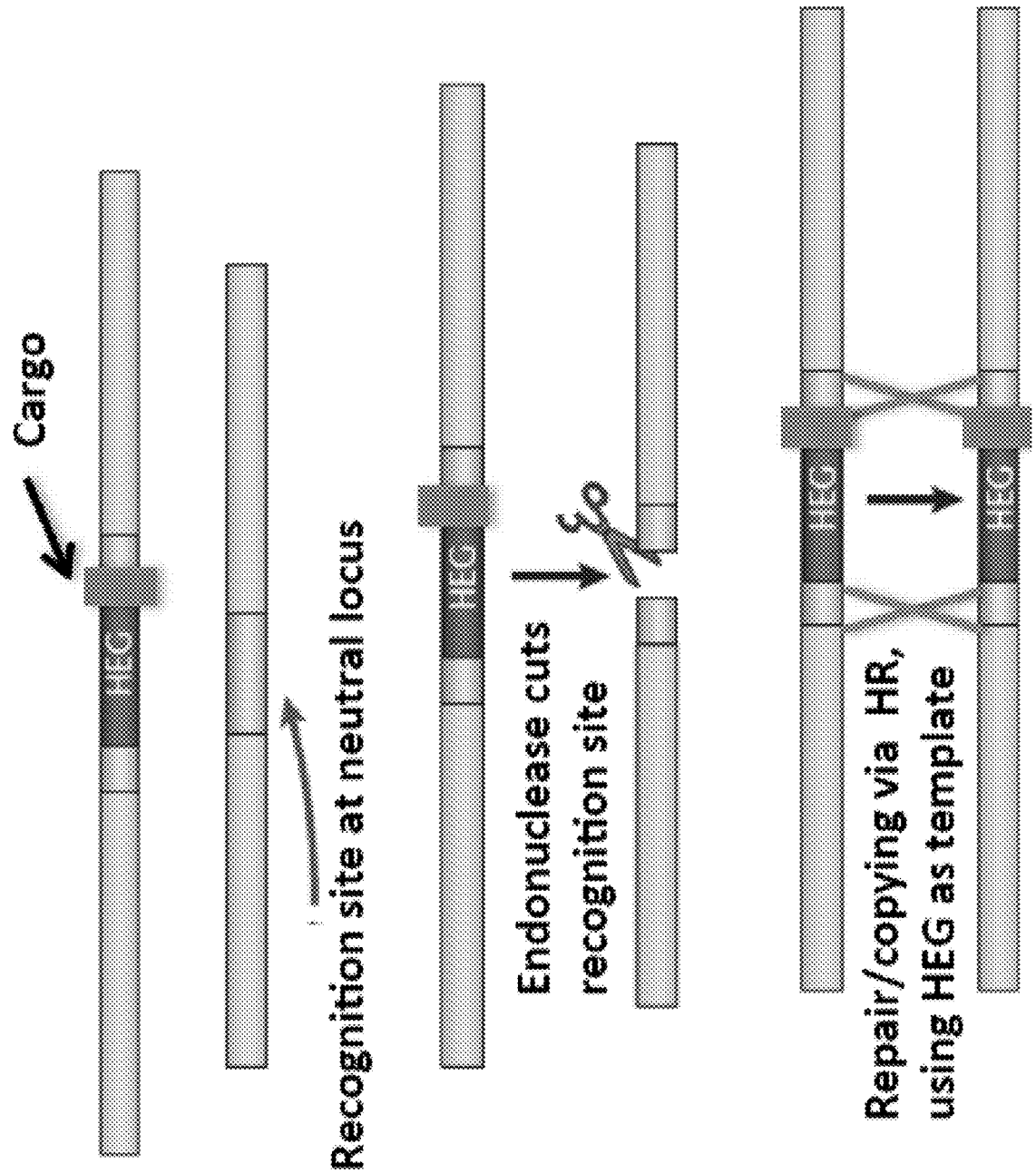
FIG. 12 shows a schematic of an embodiment of homing endonuclease gene (HEG)-based population replacement in which the cargo gene is included as a component of the HEG.

FIG. 12 shows a schematic of an embodiment of a homing endonuclease-based cleavage of target gene for gene drive. The HEG cuts at a neutral locus in the wildtype chromosome, located at the same position in the genome as the HEG. The presence of the HEG disrupts the HEG cleavage site. In this example, the HEG carries a cargo gene located between the homology arms. In the middle panel, the HEG cleaves the wildtype allele. In the lower panel homologous recombination (HR) is used to repair the DNA break using the HEG-bearing chromosome as a template. Successful HR results in copying of the HEG into the cleaved chromosome. Cleavage of neutral locus by the homing nuclease results in the homing of gene drive and cargo genes into cleaved chromosome. This results in an increase in the population frequency of the HEG and its cargo transgene. However, homing to the neutral locus is required, which may be inefficient. Additionally, the cargo gene needs to be copied, which may not always occur, and development of resistance of neutral locus sequences to cleavage is very common. In contrast, with the DNA sequence modification-based drive method described herein (FIG. 8A, FIG. 9A), cleavage of the essential gene results in death of progeny that lack functional copies of the essential gene, i.e., both endogenous copies are cleaved and the recoded copy of the essential gene is not inherited, and results in survival of only those progeny that inherit cargo and recoded copy of the essential gene. Additionally, there is no need for the cargo to be copied as the cargo transmitted with the chromosome. Additionally, homing is not required or utilized, and occurrence of essential genes resistant to cleavage would be rare. Additionally, some species have low rate of germline HDR, greatly if not completely hindering homing based strategies.

Example 13—Comparison of DNA Sequence Modification-Based Gene Drive with Homing-Based Gene Drive—2

Figure 13:
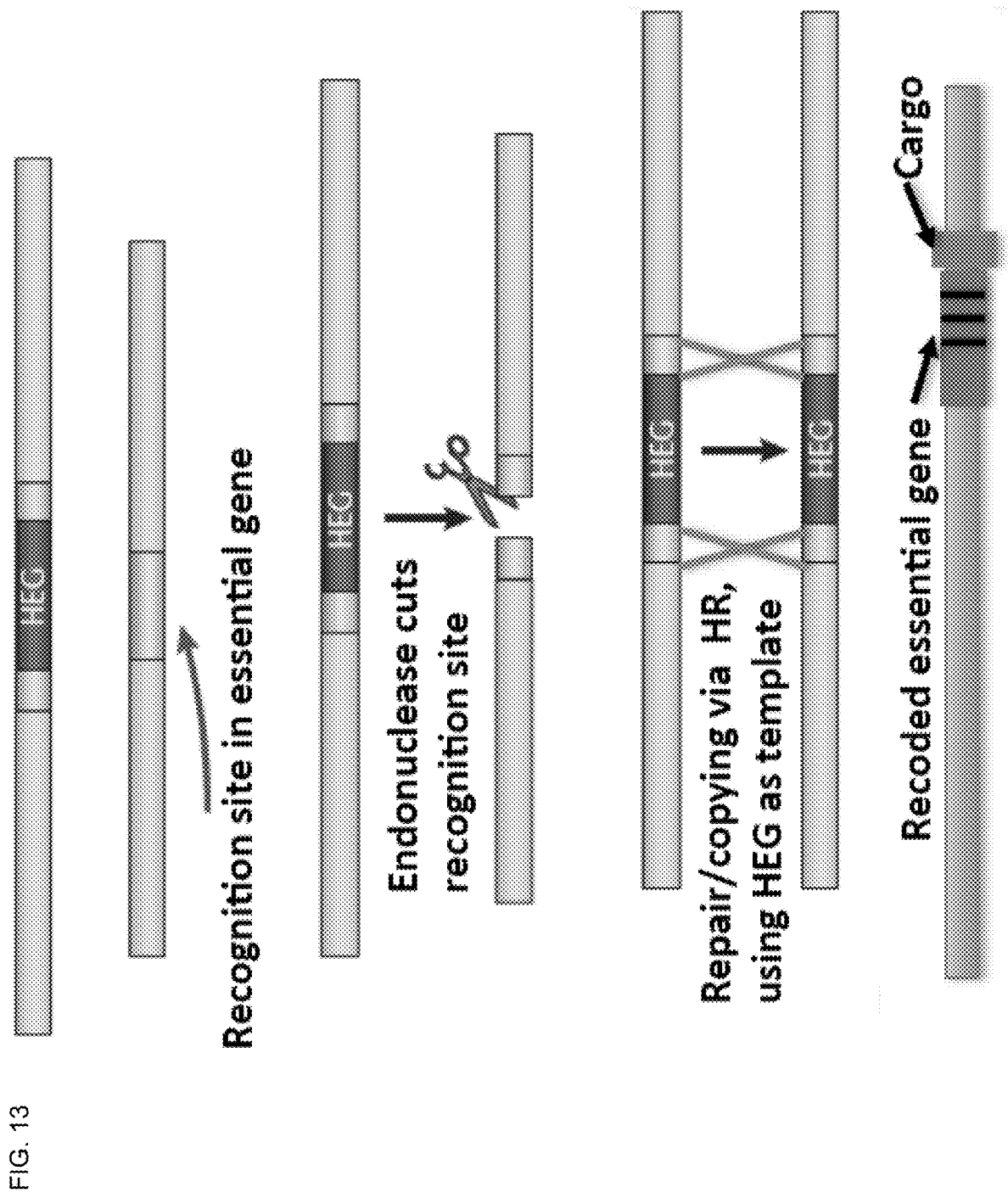
FIG. 13 shows a schematic of an embodiment of HEG-based population replacement in which the cargo is located at a different site in the genome.

FIG. 13 shows a schematic of an embodiment of a homing endonuclease-based cleavage of target gene for gene drive. The HEG cleaves an essential gene. Homing occurs into the cleaved essential gene, resulting in loss of essential gene function, and an increase in the frequency of the HEG, but only under specific conditions, since loss of both copies of an essential gene results in death or infertility. The recoded essential gene and a cargo are located elsewhere in the genome. As the frequency of the HEG increases, versions of the other chromosome that carry the recoded rescue and cargo are selected for, resulting in their spread. It is important to note that homing is required for this version of population replacement to work. Cleavage alone is not sufficient as it only results in loss of essential gene function, but not an increase in HEG frequency. It is only with homing that the frequency of the HEG increases. Progeny that inherit the chromosome with recoded essential gene and cargo survive but may experience a fitness cost in an otherwise background, which would result in their loss. Only progeny that inherit two inactive copies of the essential gene die. In contrast, with the DNA sequence modification-based drive method described herein (CleaveR; FIG. 8A, FIG. 9A), only cleavage is required, and cleavage of the essential gene results in death of progeny that lack functional copies of the essential gene, i.e., both endogenous copies are cleaved and the recoded copy of the essential gene is not inherited, and results in survival of only those progeny that inherit cargo and recoded copy of the essential gene, which are tightly linked. The DNA sequence modification-based drive mechanism described herein does not utilize or depend on homing, only DNA sequence modification and tight linkage to a rescuing transgene.

Example 14—Comparison of DNA Sequence Modification-Based Gene Drive with Medea

Figure 14:
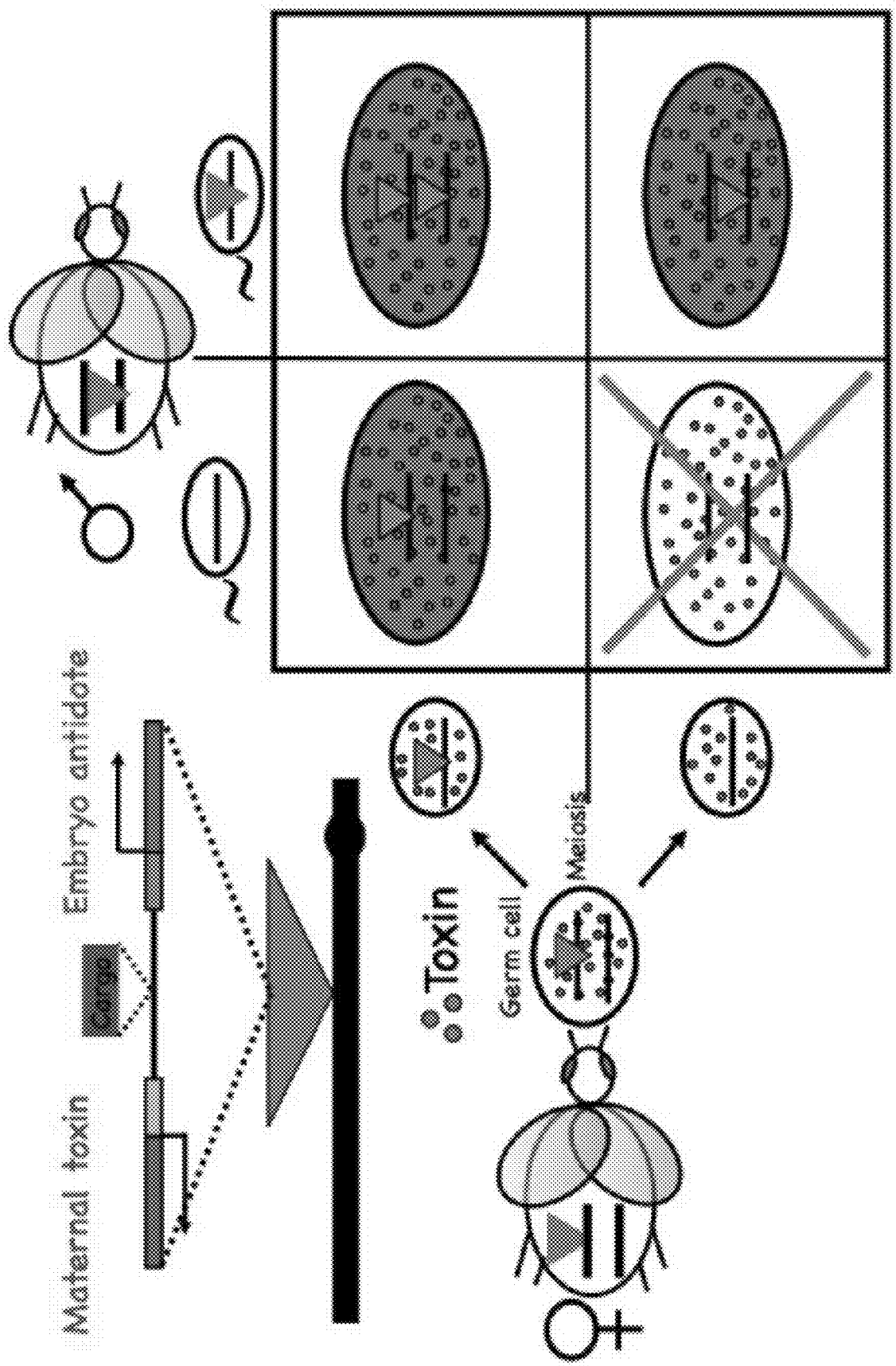
FIG. 14 shows a schematic of an embodiment of a Medea-based gene drive.

FIG. 14 shows a schematic of an embodiment of a Medea-based gene drive. In Medea-based gene drive a maternally deposited toxin (which may consist of maternally expressed miRNAs that result in a loss of an essential gene, as well as a protein-based toxin, (c.f. Chen et al., 2007)) has the potential to cause the death of all embryos. However, those that inherit a tightly linked antidote survive (which may include a version of the maternally expressed gene being targeted by the maternally expressed miRNAs (c.f. Chen et al., 2007)) because they turn on expression of the antidote just in time to prevent toxin action. In this drive mechanism there is no DNA sequence modification of an endogenous locus. The mechanism of action requires that a maternal (or paternal) toxin be deposited into the embryo. In the Medea-based system, a toxin is expressed in maternal germline resulting in the toxin being present in all oocytes/eggs. Embryos that inherit Medea survive because they express an antidote in the early embryo, while those that do not inherit Medea die. In the Medea-based system, maternal expression of a toxin which can kill embryos but not oocytes is required, and rescue is achieved through early embryo expression of an antidote. In contrast, with the DNA sequence modification-based drive method described herein (CleaveR; FIG. 8A, FIG. 9A), cleavage of the essential gene results in death of progeny that lack functional copies of the essential gene, i.e., both endogenous copies are cleaved and the recoded copy of the essential gene is not inherited, and results in survival of only those progeny that inherit cargo and recoded copy of the essential gene. The DNA sequence modification-based drive mechanism described herein only requires DNA sequence modification and does not require maternal or paternal deposition of a toxin. Additionally, germline expression of a DNA modifying enzyme that targets an essential gene occurs, and rescue achieved through inheritance of a recoded version of an essential gene.

Example 15—Cleavage Mediated Drive Targeting an Essential Gene on the X-Chromosome, Proof of Concept in Drosophila melanogaster Example 15 is an embodiment of a CleaveR drive system showing reduction to practice. FIG. 15A shows a schematic of an embodiment of a Construct A with a U6:3-gRNA, an attP site, the tko rescue copy from Drosophila virilis (Dv) and a ubiquitous opie2-td-tomato marker. Only elements between the homology arms were inserted into the germline via Cas9 mediated HR. FIG. 15B shows an embodiment of a Construct B with an attB site, a 3×P3-GFP marker, Cas9 driven by nanos regulatory elements, and a set of four U6 driven gRNAs. Construct B was integrated into the attP landing site of construct A via phiC31 integrase. FIG. 15C shows an embodiment of the principle of ClvR. Females heterozygous for the ClvR construct create cleaved tko alleles in the germline. Additionally, active Cas9/gRNA complex is deposited maternally to all embryos. Offspring without the rescue copy will die.

Figure 17:
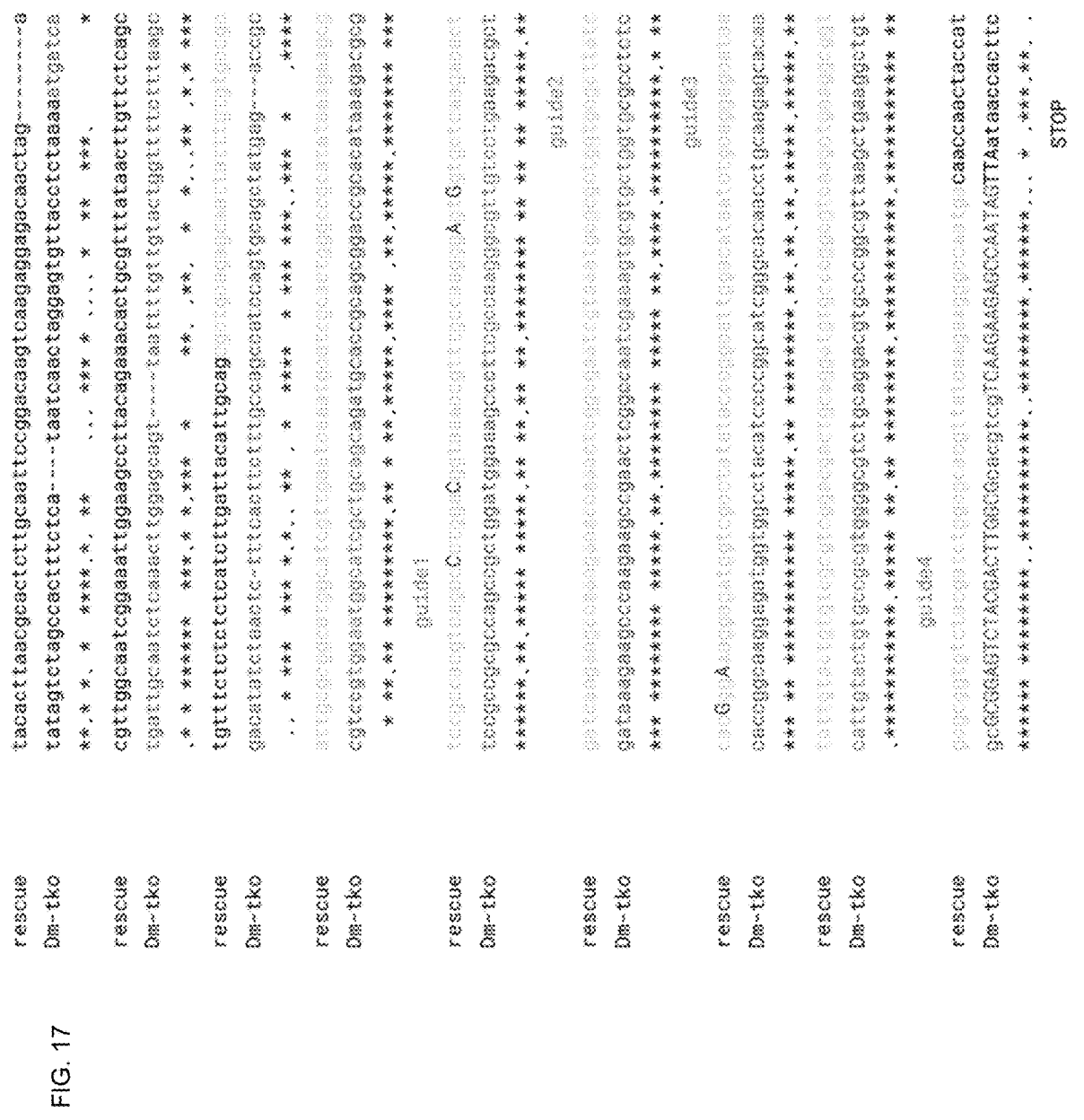

The cleavage mediated 2-locus autosomal drive described herein (referred to as CleaveR) consists of Cas9, 4 gRNAs which target an essential gene on the X-chromosome, and a recoded copy of this target gene which is immune to gRNA targeting, which are situated together on a different autosome (chromosome 3) than the target gene (FIG. 15C). FIG. 17 shows an embodiment of an alignment of the target gene (Drosophila melanogaster tko [second line]—Examples 15 and 16) with the recoded rescue based on Drosophila virilis tko.

In males and females who carry at least one copy of the construct and at least one copy of the wild type target, the target gene is cleaved multiple times during gametogenesis, destroying the wild type copy of the gene and resulting in gametes bearing cleaved tko alleles (FIG. 15C). As transgenic individuals mate with wild types, cleaved copies of the essential gene will begin to accumulate in heterozygotes.

Additionally, if the CleaveR drive system is inherited through the female germline, all of the offspring will inherit Cas9 and gRNASs. Only offspring that carries the rescue encoded by CleaveR will survive (FIG. 15C).

Target Gene Selection and gRNA Design

Two versions of the ClvR constructs were constructed using tko (technical knockout) as the target. The tko gene encodes a mitochondrial ribosome protein (Royden, Pirrotta, and Jan 1987). It is a recessive lethal. Benchling software suite was used to design gRNAs targeting the exonic regions of the genes at 4 sites. gRNAs were used based on on-target activity ranking (Doench et al. 2016). In addition gRNAs were selected so as to not cut in the rescue constructs (see below).

Cloning of ClvR Constructs and Fly Germline Transformation

All plasmids were assembled with standard molecular cloning techniques and Gibson assembly (Gibson et al. 2009). All restriction enzymes, enzymes for Gibson Assembly mastermix and Q5 polymerase used in PCRs were from NEB. Gel extraction kits and JM109 cells for cloning from Zymo Research. The gRNA cassette and Cas9 were based on pCFD3(4)-dU6:3gRNA and pnos-Cas9-nos which were a gift from Simon Bullock (Port et al. 2014) (Addgene #49410 and #62208) and modified as described previously (Oberhofer, Ivy, and Hay 2018). Construct A (FIG. 15A) was inserted into the fly germline via Cas9 mediated homologous recombination. Construct B (FIG. 15B) was integrated into an attP landing site within construct A using the phiC31 system.

The experiment was started with a plasmid having a dU6:3 promoter and a modified guide scaffold (Dang et al. 2015) separated by BsmBI cutsites from our previous work (Oberhofer, Ivy, and Hay 2018), which was based on pCFD3-dU6:3gRNA, a gift from Simon Bullock (Addgene plasmid #49410) (Port et al. 2014). Restriction digestion was performed with BsmBI and ligated annealed oligos (P0-68E FWD+P0-68E REV) as described on flycrispr.molbio.wisc.edu. This gRNA targets a region on the third chromosome (68E) which was chosen based on the location of an attP landing site in a widely used fly strain, zh-68E (Bischof et al. 2007). Next, the plasmid was cut with HindIII and SpeI and the following 4 fragments were assembled in a Gibson reaction (Gibson et al. 2009) to yield plasmid p68-tko-step1 (see FIG. 15A):

Two homology arms, approximately 1 kb in length up and downstream of the above gRNA target site were amplified from genomic DNA with primers P9+P10 and P15+P16; an attP site with primers P11+P12; a 4.2 kb rescue fragment with primers P13+P14. The rescue fragment was based on the tko genomic region of Drosophila virilis, a distant Drosophila species (Drosophila 12 Genomes Consortium et al. 2007). Additionally, 6 silent point mutations were introduced in the ORF of Dv-tko in order to avoid homology stretches >14 bp. The rescue was gene synthesized by IDT as two gBlock fragments with an additional 2 point mutations introduced in the intron to work around a synthesis complexity issue. Finally, a td-tomato marker (Shaner et al. 2004) driven by the ubiquitous opie2 promoter (Theilmann and Stewart 1992) with primers P15+P16 was used as the dominant marker.

Construct p68-tko-step1 (see FIG. 15A) was injected into a fly strain expressing Cas9 in the germline under nanos regulatory regions (Bloomington stock #54591) (Port et al. 2014). All injections were carried out by Rainbow Transgenic Flies.

Male injected G0 flies were outcrossed to w− and the progeny was scored for ubiquitous td-tomato expression. Male transformants were crossed to a TM3,Sb/TM6b,Tb balancer stock. Flies carrying the marker over TM3,Sb, were pooled and used as the injection strain for the 2nd construct following below.

For construct tko-step2 (FIG. 15B), two constructs having two gRNAs each were subcloned. Construct pU6:3-U6:1-tandem (Oberhofer, Ivy, and Hay 2018) (based on (Port et al. 2014)) was digested with BsmBI and ligated back in two gRNAs encoded in the primer overhangs: P21+P22 and P23+P24.

A plasmid that had a 3×P3-GFP marker gene, an attB site as well as parts of nos-Cas9-nos flanked by gypsy insulators was digested with EcoRV and BglII. In a three fragment Gibson reaction full length nos-Cas9-nos, as well as the two gRNA cassettes from above were assembled to yield the final construct ptko-B. Cas9 was amplified with primers P25-nosCas9 FWD+P26-nos-Cas9 REV, guide cassette A with P27-guidesA FWD+P28-guidesA REV, and guide cassette B with P29-guidesB FWD+P30-guidesB REV.

Construct B was injected along with a phiC31 helper plasmid (Rainbow Transgenic Flies). Injected G0 flies were outcrossed to w− and the progeny was screened for 3×P3-GFP expression. Transgenic males were used to cross to the balancer stock TM3,Sb/TM6b,Tb as well as w[1118]. Flies carrying the GFP marker over TM3,Sb were pooled to generate the balanced stock and flies homozygous for the ClvR construct were collected in the next generation. All primers are shown in TABLE 1, and vector sequences are provided in SEQ ID NO: 39 (p68-tko-step1; FIG. 15A), SEQ ID NO: 40 (tko-step2; FIG. 15B), and SEQ ID NO: 41 (Dvir-rescue-modified; "rescue" in FIG. 15A and FIG. 17).

TABLE 1

PRIMERS

| Primer | Sequence | SEQ ID NO: |
|---|---|---|
| P0-68E FWD | gtcgTGCACAACCAGAGACTGGAG | 1 |
| P0-68E REV | aaacCTCCAGTCTCTGGTTGTGCA | 2 |
| P9-68E-hr-left FWD | cttattacgtggccaactaggtgcccaaaatgtgtgtgga | 3 |
| P10-68E-hr-left REV | GCTTCGGTGTGTCCGTCAGTgagaggttttgccgcgattt | 4 |
| P11-attP FWD | aaatcgcggcaaaacctctcACTGACGGACACACCGAAGCC | 5 |
| P12-attP REV | ccttgctgcccgcctgcagcAGTCGCGCTCGCGCGACTGA | 6 |

TABLE 1 -continued

PRIMERS

| Primer | Sequence | SEQ ID NO: |
|---|---|---|
| P13-dv-tko FWD | TCAGTCGCGCGAGCGCGACTgctgcaggcgggcagcaagg | 7 |
| P14-dv-tko REV | gcagtgcaaaaaagttggtggggtcggacctcaagttgcatatgg | 8 |
| P15-68E-hr-right FWD | tgcaacttgaggtccgaccccaccaacttttttgcactgc | 9 |
| P16-68E-hr-right REV | gggcgaattgggtacaagctaggatgatgggatgctggaa | 10 |
| P21-tko-guidesA FWD | ctattttcaatttaacgtcgctgcagcgatgccattccaGTTTCagagctaTGCTGgaaa | 11 |
| P22-tko-guidesA REV | ttcCAGCAtagctctGAAACtcgccaagggcgagtcctgCgaagttcacccggatatct | 12 |
| P23-tko-guidesB FWD | ctattttcaatttaacgtcgcaacattgtactgtgccgcgGTTTCagagctaTGCTGgaa | 13 |
| P24-tko-guidesB REV | ttcCAGCAtagctctGAAACatcgaaagtgcgtgctggtgCgaagttcacccggatatct | 14 |
| P25-nosCas9 FWD | GTTGTCTATACTATAAGATCTATAGGCACGGGATAACGCT | 15 |
| P26-nos-Cas9 REV | GCAATCACAGGTGAGCAAAAAAGCTTGGATTTCACTGGAACT | 16 |
| P27-guidesA FWD | AGTTCCAGTGAAATCCAAGCtttttgctcacctgtgattgc | 17 |
| P28-guidesA REV | aatcacaggtgagcaaaaaaattaaccctcactaaaggga | 18 |
| P29-guidesB FWD | ccctttagtgagggttaattttttttgctcacctgtgatt | 19 |
| P30-guidesB REV | gcagcctcgagatcgatgattgccgagcacaattgtctag | 20 |
| tko-seq1 | aagcgttccaagctgcacag | 21 |
| tko-seq2 | cgcacatccatttccaattg | 22 |
| tko-seq3 | cacacacacaggtgcgttc | 23 |
| tko-seq4 | acaactagacgttggcaatcTCACACCTTCCTCTTCTTCTT | 24 |
| tko-seq5 | tcagcgggattagtgtaagt | 25 |
| tko-seq6 | catatgcaacttgaggtccg | 26 |
| s2-attB-rev | ttcgagaccgtgacctacat | 27 |
| s2-u631-seq | AGTTCCAGTGAAATCCAAGC | 28 |
| T3-seq REV | gttcccttagtgagggttaatt | 29 |
| T3-seq FWD | ATTAACCCTCACTAAAGGGA | 30 |
| CAS91F | ATGGACAAGAAGTACTCCATTG | 31 |
| CAS91R | GATCGGTATTGCCCAGAACT | 32 |
| CAS92F2 | AGCGCTAGGCTGTCCAAATC | 33 |
| CAS93F | GAGAAAATCCTCACATTTCGG | 34 |
| CAS94F2 | AGAGTGGAAAGACAATCCTGG | 35 |
| CAS95F | CTGAACGCCAAACTGATCAC | 36 |
| CAS96F | TGGACGCCACACTGATTCAT | 37 |
| CAS96R | TCACACCTTCCTCTTCTTCTT | 38 |

Example 16—ClvR Effect in Females and Males

To determine the rate of germline cleavage and carryover effect in females carrying the ClvR element, heterozygous females were crossed to w[1118] males and scored the progeny for the dominant opie2-td-tomato marker of the ClvR construct. Under normal mendelian rules only half of the progeny should carry this marker. Among the 2580 progeny from these crosses all carried the opie2-td-tomato dominant marker, showing that the system works efficiently when transmitted through females (see FIG. 9A and FIG. 16A), data in the Punnett square below each cross figure.

To determine the cleavage rate in the male germline, crosses were set up between males heterozygous for the ClvR element and females carrying a mutant copy of tko over the FM7a X-chromosome balancer (tko$^3$/FM7a/Dp(1; 2;Y)w+, BDSC_4283). Female offspring of this cross will inherit one X-chromosome from the father and one from the mother. Female offspring inheriting the mutant tko allele from the mother and not carrying the ClvR element with the rescue copy of tko will be dead, if tko was cleaved in the male germline (see FIG. 16B).

Figures 16A, 16B:
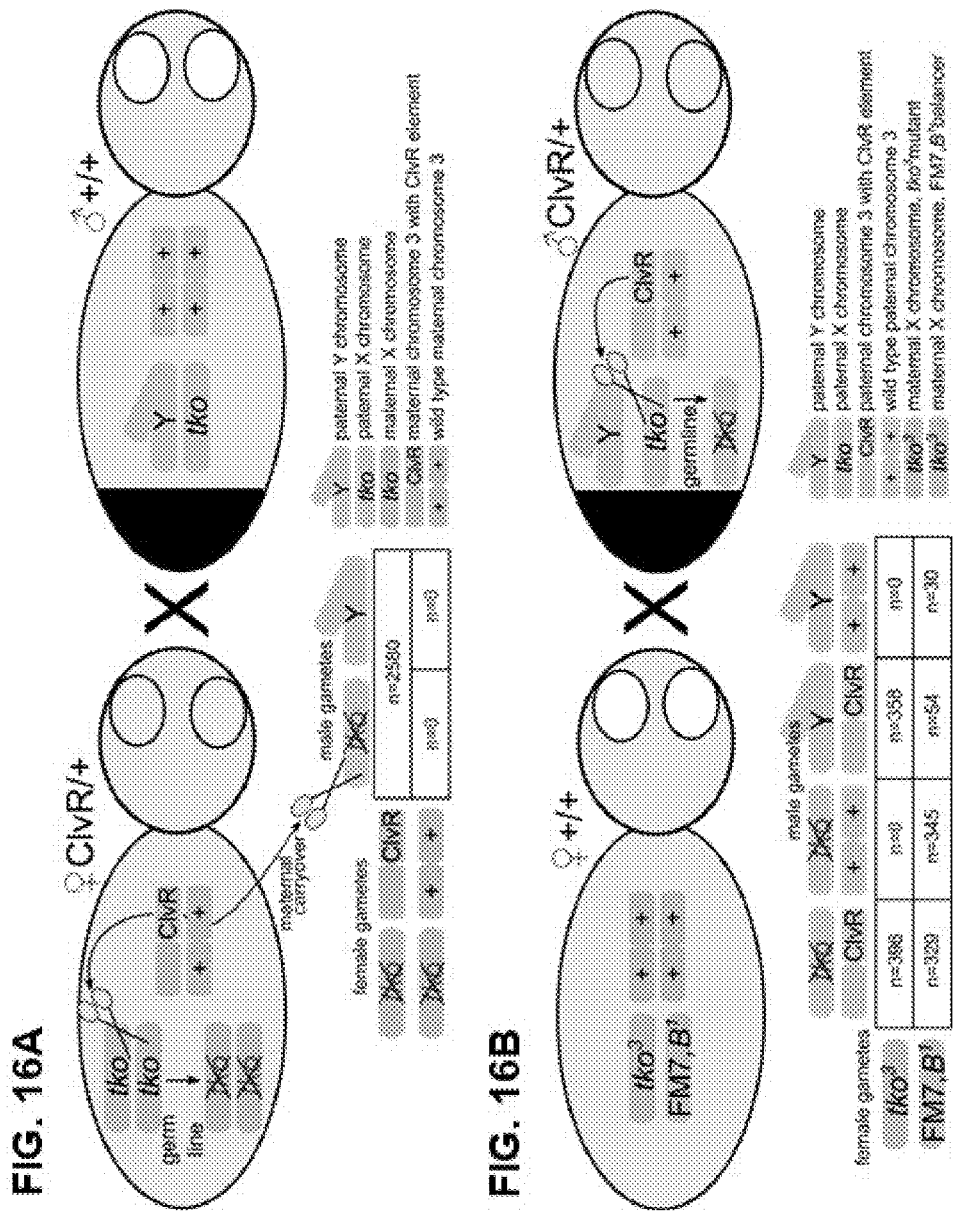
FIG. 16A-FIG. 16B show an embodiment of a determination of the effects of a CleaveR drive when transmitted through the female (FIG. 16A) or male (FIG. 16B) germline.

For FIG. 16A, B all female chromosomes in red, male chromosomes in blue, Cas9/gRNA complex indicated as green scissors. Top row in Panel A and B indicates the cross, lower row shows a punnett square with gametes indicated and numbers of scored progeny in the corresponding fields. Numbers showing the effect of CleaveR are indicated in red (FIG. 16A) Females heterozygous for the CleaveR system were crossed to wildtype males. The Cas9/gRNA complex encoded by the CleaveR element, cleaves all wildtype copies of tko in the female germline. In addition active complexes get deposited maternally into all embryos, leading to subsequent cleavage of the paternal tko allele in the zygote. Only offspring that inherited the rescue copy from the CleaveR construct were viable, showing that the CleaveR system works efficiently in the female germline and also brings about maternal carryover-dependent cleavage. In FIG. 16B, males heterozygous for the CleaveR element were crossed to a tko mutant. The only copy of wildtype tko on the single male X-chromosome was cleaved in the male germline by the CleaveR system. When the cleaved tko allele was paired with the maternal mutant X-chromosome (tko3), only those animals that also inherit the rescue encoded by the CleaveR element survived, all others died. Actual data is shown in the Punnet squares below each cross. Results showed successful implementation of the DNA sequence modification-based gene drive according to the embodiments disclosed herein.

Example 17—ClvR Effect in Females and Males

Figure 18A:
FIG. 18A show a schematic of an embodiment of the components of the DNA sequence modification-based gene drive (Example 17).
Figure 18B:
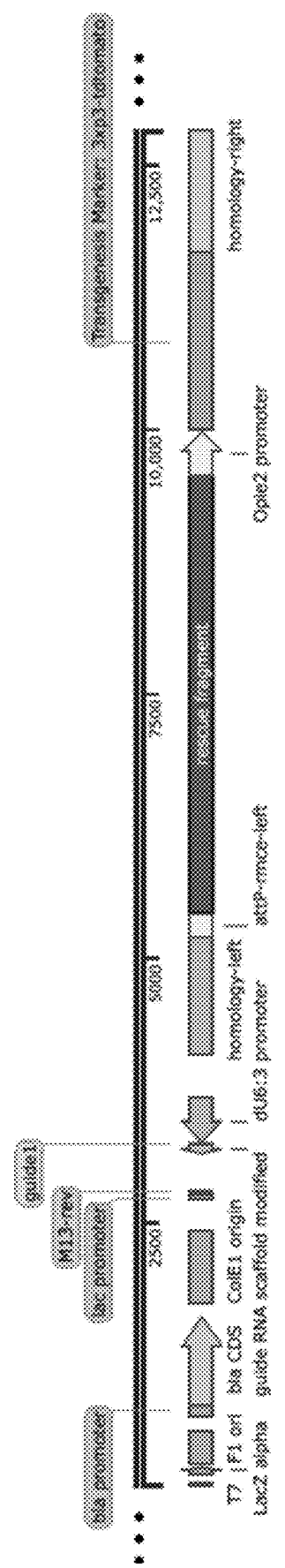
FIG. 18B shows a schematic of an embodiment of the components of the step 1 of FIG. 18A (Example 17).
Figure 18C:
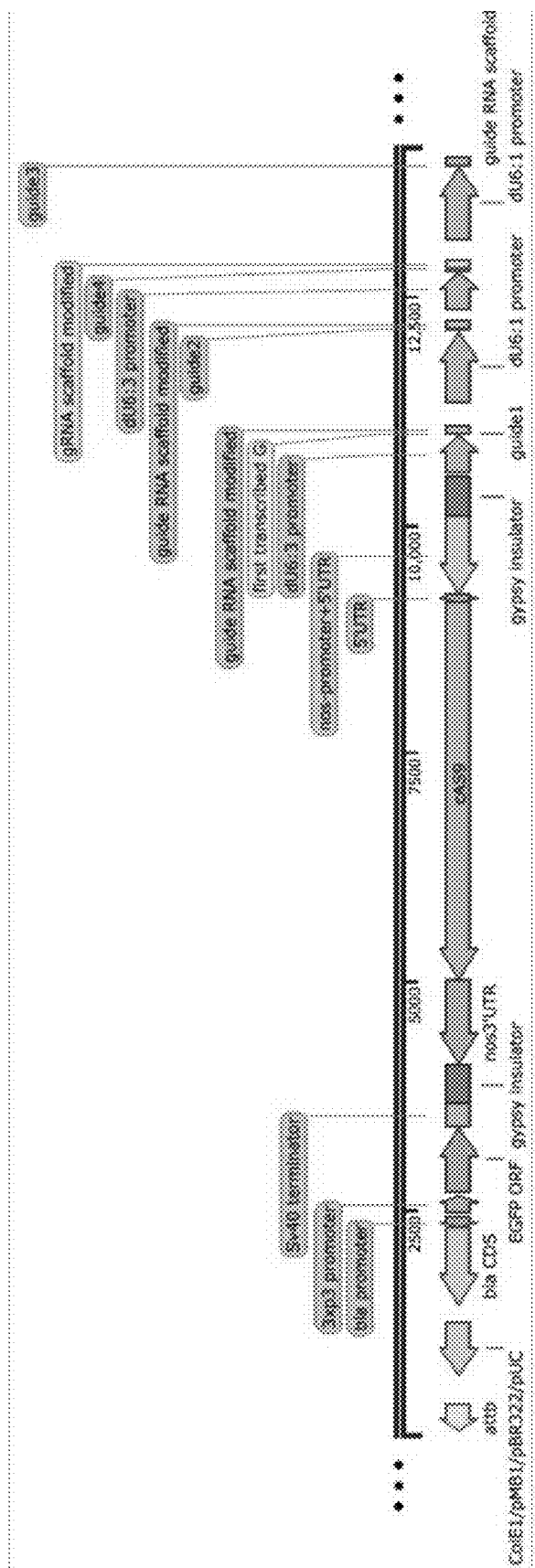
FIG. 18C shows a schematic of an embodiment of the components of the step 2 of FIG. 18A (Example 17).

FIG. 18A show a schematic of an embodiment of the components of the DNA sequence modification-based gene drive implemented in the example below, targeting the X-linked locus tko in *Drosophila*, using a third chromosome-based gene drive element. FIG. 18B (SEQ ID NO: 42) shows a schematic of an embodiment of the components of the step 1 transgenic created for the DNA sequence modification-based gene drive implemented for targeting the X-linked locus tko in *Drosophila*, using a third chromosome-based gene drive element. This construct was inserted into the *Drosophila* genome using homologous recombination, based on the left and right homology arms. FIG. 18C (SEQ ID NO: 43) shows a schematic of an embodiment of the components of the step 2 construct created for the DNA sequence modification-based gene drive implemented for targeting the X-linked locus tko in *Drosophila*, using a third chromosome-based gene drive element. This construct was inserted into the step 1 genomic region using the attb site-specific integrase target site. FIG. 19 shows an embodiment Sanger sequencing results of the gRNA1 target region of the *Drosophila* wildtype version of the tko gene and offspring: ♂ClvR$^{tko}$/+ offspring from ♀ClvR$^{tko}$/+XX ♂w[1118] parents. The wildtype sequence is shown as well as products of ClvR action, which contain indels. Two flies were sequenced from 9 different single fly crosses each. All 18 analyzed flies showed indels of varying sizes at the gRNA1 target site. Results showed successful implementation of the DNA sequence modification-based gene drive according to the embodiments disclosed herein.

REFERENCES

WHO World Malaria Report 2014. WHO at <who.int/malaria/publications/world_malaria_report_2014/en/>

Alphey, L. Genetic Control of Mosquitoes. Annu. Rev. Entomol. 59, 205-224 (2014).

Resnik, D. B. Ethical Issues in Field Trials of Genetically Modified Disease-Resistant Mosquitoes. Dev. World Bioeth. 14, 37-46 (2014).

Malavasi, A. Project *Aedes* transgenic population control in Juazeiro and Jacobina Bahia, Brazil. BMC Proc. 8, O11 (2014).

Popovici, J. et al. Assessing key safety concerns of a *Wolbachia*-based strategy to control dengue transmission by *Aedes* mosquitoes. Mem. Inst. Oswaldo Cruz 105, 957-964 (2010).

Walker, T. et al. The wMel *Wolbachia* strain blocks dengue and invades caged *Aedes aegypti* populations. Nature 476, 450-453 (2011).

Hoffmann, A. A. et al. Successful establishment of *Wolbachia* in *Aedes* populations to suppress dengue transmission. Nature 476, 454-457 (2011).

Sebrovskii, A. S. A New Possible Method of Pest Control. Zool Zh 19, 618-630 (1940).

Curtis, C. F. Possible Use of Translocations to fix Desirable Genes in Insect Pest Populations. Nature 218, 368-369 (1968).

Gould, F. & Schliekelman, P. POPULATION GENETICS OF AUTOCIDAL CONTROL AND STRAIN REPLACEMENT. Annu. Rev. Entomol. 49, 193-217 (2004).

Sinkins, S. P. & Gould, F. Gene drive systems for insect disease vectors. Nat. Rev. Genet. 7, 427-435 (2006).

Chen, C.-H. et al. A Synthetic Maternal-Effect Selfish Genetic Element Drives Population Replacement in *Drosophila*. Science 316, 597-600 (2007).

Gould, F., Huang, Y., Legros, M. & Lloyd, A. L. A Killer-Rescue system for self-limiting gene drive of anti-pathogen constructs. Proc. R. Soc. B Biol. Sci. 275, 2823-2829 (2008).

Marshall, J. M. & Hay, B. A. GENERAL PRINCIPLES OF SINGLE-CONSTRUCT CHROMOSOMAL GENE DRIVE: SINGLE-CONSTRUCT GENE DRIVE. Evolution 66, 2150-2166 (2012).

Marshall, J. M. The Impact of Dissociation on Transposon-Mediated Disease Control Strategies. Genetics 178, 1673-1682 (2008).

Davis, S., Bax, N. & Grewe, P. Engineered Underdominance Allows Efficient and Economical Introgression of Traits into Pest Populations. j. Theor. Biol. 212, 83-98 (2001).

Magori, K. Genetically Engineered Underdominance for Manipulation of Pest Populations: A Deterministic Model. Genetics 172, 2613-2620 (2005).

Brelsfoard, C. L. & Dobson, S. L. *Wolbachia*-based strategies to control insect pests and disease vectors. Asia Pac j Mol Biol Biotechnol 17, 55-63 (2009).

Huang, Y., Magori, K., Lloyd, A. L. & Gould, F. INTRODUCING DESIRABLE TRANSGENES INTO INSECT POPULATIONS USING Y-LINKED MEIOTIC DRIVE?A THEORETICAL ASSESSMENT. Evolution 61, 717-726 (2007).

Lyttle, T. W. Experimental population genetics of meiotic drive systems I. Pseudo-Y chromosomal drive as a means of eliminating cage populations of *Drosophila melanogaster*. Genetics 86, 413-445 (1977).

Magnusson, K. et al. Demasculinization of the *Anopheles gambiae* X chromosome. BMC Evol. Biol. 12, 69 (2012).

Simoni, A. et al. Development of synthetic selfish elements based on modular nucleases in *Drosophila melanogaster*. Nucleic Acids Res. 42, 7461-7472 (2014).

Burt, A. & Koufopanou, V. Homing endonuclease genes: the rise and fall and rise again of a selfish element. Curr. Opin. Genet. Dev. 14, 609-615 (2004).

Gimble, F. S. Invasion of a multitude of genetic niches by mobile endonuclease genes. FEMS Microbiol. Lett. 185, 99-107 (2000).

Galizi, R. et al. A synthetic sex ratio distortion system for the control of the human malaria mosquito. Nat. Commun. 5, (2014).

Akbari, O. S. et al. A Synthetic Gene Drive System for Local, Reversible Modification and Suppression of Insect Populations. Curr. Biol. 23, 671-677 (2013).

Akbari, O. S. et al. Novel Synthetic Medea Selfish Genetic Elements Drive Population Replacement in *Drosophila*; a Theoretical Exploration of Medea-Dependent Population Suppression. ACS Synth. Biol. 3, 915-928 (2014).

Esvelt, K. M., Smidler, A. L., Catteruccia, F. & Church, G. M. Concerning RNA-guided gene drives for the alteration of wild populations. eLife e03401 (2014). doi:10.7554/eLife.03401

Isaacs, A. T. et al. Engineered Resistance to *Plasmodium falciparum* Development in Transgenic *Anopheles stephensi*. PLOS Pathog. 7, e1002017 (2011).

Hollingdale, M. R., Nardin, E. H., Tharavanij, S., Schwartz, A. L. & Nussenzweig, R. S. Inhibition of entry of *Plasmodium falciparum* and *P. vivax* sporozoites into cultured cells; an in vitro assay of protective antibodies. J. Immunol. 132, 909-913 (1984).

Li, F., Patra, K. P. & Vinetz, J. M. An Anti-Chitinase Malaria Transmission-Blocking Single-Chain Antibody as an Effector Molecule for Creating a *Plasmodium falciparum*-Refractory Mosquito. J. Infect. Dis. 192, 878-887 (2005).

Yen, P.-S., James, A., Li, J.-C., Chen, C.-H. & Failloux, A.-B. Synthetic miRNAs induce dual arboviral-resistance phenotypes in the vector mosquito *Aedes aegypti*. Commun. Biol. 1, 11 (2018).

Franz, A. W. E. et al. Engineering RNA interference-based resistance to dengue virus type 2 in genetically modified *Aedes aegypti*. Proc. Natl. Acad. Sci. 103, 4198-4203 (2006).

Mathur, G. et al. Transgene-mediated suppression of dengue viruses in the salivary glands of the yellow fever mosquito, *Aedes aegypti*. Insect Mol. Biol. 19, 753-763 (2010).

Travanty, E. A. et al. Using RNA interference to develop dengue virus resistance in genetically modified *Aedes aegypti*. Insect Biochem. Mol. Biol. 34, 607-613 (2004).

Castillo, J. A. et al. Complex interaction between dengue virus replication and expression of miRNA-133a. BMC Infect. Dis. 16, (2016).

Shmakov, S. et al. Discovery and Functional Characterization of Diverse Class 2 CRISPR-Cas Systems. Mol. Cell 60, 385-397 (2015).

Koonin, E. V., Makarova, K. S. & Zhang, F. Diversity, classification and evolution of CRISPR-Cas systems. Curr. Opin. Microbiol. 37, 67-78 (2017).

Shmakov, S. et al. Diversity and evolution of class 2 CRISPR-Cas systems. Nat. Rev. Microbiol. 15, 169-182 (2017).

Koonin, E. V., Makarova, K. S. & Wolf, Y. I. Evolutionary Genomics of Defense Systems in Archaea and Bacteria. Annu. Rev. Microbiol. 71, 233-261 (2017).

Bischof, Johannes, Robert K. Maeda, Monika Hediger, François Karch, and Konrad Basler. 2007. "An Optimized Transgenesis System for *Drosophila* Using Germ-Line-Specific phiC31 Integrases." Proceedings of the National Academy of Sciences of the United States of America 104 (9): 3312-17.

Dang, Ying, Gengxiang Jia, Jennie Choi, Hongming Ma, Edgar Anaya, Chunting Ye, Premlata Shankar, and Haoquan Wu. 2015. "Optimizing sgRNA Structure to Improve CRISPR-Cas9 Knockout Efficiency." Genome Biology 16 (December): 280.

Doench, John G., Nicolo Fusi, Meagan Sullender, Mudra Hegde, Emma W. Vaimberg, Katherine F. Donovan, Ian Smith, et al. 2016. "Optimized sgRNA Design to Maximize Activity and Minimize off-Target Effects of CRISPR-Cas9." Nature Biotechnology 34 (2): 184-91.

*Drosophila* 12 Genomes Consortium, Andrew G. Clark, Michael B. Eisen, Douglas R. Smith, Casey M. Bergman, Brian Oliver, Therese A. Markow, et al. 2007. "Evolution of Genes and Genomes on the *Drosophila* Phylogeny." Nature 450 (7167): 203-18.

Gibson, Daniel G., Lei Young, Ray-Yuan Chuang, J. Craig Venter, Clyde A. Hutchison, and Hamilton O. Smith. 2009. "Enzymatic Assembly of DNA Molecules up to Several Hundred Kilobases." Nature Methods 6 (5): 343-45.

Oberhofer, Georg, Tobin Ivy, and Bruce A. Hay. 2018. "Behavior of Homing Endonuclease Gene Drives Targeting Genes Required for Viability or Female Fertility with Multiplexed Guide RNAs." bioRxiv. https://doi.org/10.1101/289546.

Port, Fillip, Hui-Min Chen, Tzumin Lee, and Simon L. Bullock. 2014. "Optimized CRISPR/Cas Tools for Efficient Germline and Somatic Genome Engineering in *Drosophila.*" Proceedings of the National Academy of Sciences of the United States of America 111 (29): E2967-76.

Royden, C. S., V. Pirrotta, and L. Y. Jan. 1987. "The Tko Locus, Site of a Behavioral Mutation in *D. Melanogaster*, Codes for a Protein Homologous to Prokaryotic Ribosomal Protein S12." Cell 51 (2): 165-73.

Shaner, Nathan C., Robert E. Campbell, Paul A. Steinbach, Ben N. G. Giepmans, Amy E. Palmer, and Roger Y. Tsien. 2004. "Improved Monomeric Red, Orange and Yellow Fluorescent Proteins Derived from *Discosoma* Sp. Red Fluorescent Protein." Nature Biotechnology 22 (12): 1567-72.

Theilmann, D. A., and S. Stewart. 1992. "Molecular Analysis of the Trans-Activating IE-2 Gene of *Orgyia pseudotsugata* Multicapsid Nuclear Polyhedrosis Virus." Virology 187 (1): 84-96.

Akbari, Omar S., Chun-Hong Chen, John M. Marshall, Haixia Huang, Igor Antoshechkin, and Bruce A. Hay. 2012. "Novel Synthetic Medea Selfish Genetic Elements Drive Population Replacement in *Drosophila*; a Theoretical Exploration of Medea-Dependent Population Suppression." *ACS Synthetic Biology*, December. https://doi.org/10.1021/sb300079h.

Akbari, Omar S., Kelly D. Matzen, John M. Marshall, Haixia Huang, Catherine M. Ward, and Bruce A. Hay. 2013. "A Synthetic Gene Drive System for Local, Reversible Modification and Suppression of Insect Populations." *Current Biology*: CB 23 (8): 671-77.

Altrock, P. M., A. Traulsen, and F. A. Reed. 2011. "Stability Properties of Underdominance in Finite Subdivided Populations." *PLoS Computational Biology* 7 (11): e1002260.

Altrock, P. M., A. Traulsen, R. G. Reeves, and F. A. Reed. 2010. "Using Underdominance to Bi-Stably Transform Local Populations." *Journal of Theoretical Biology* 267 (1): 62-75.

Beaghton, A., P. J. Beaghton, and A. Burt. 2016. "Gene Drive through a Landscape: Reaction-Diffusion Models of Population Suppression and Elimination by a Sex Ratio Distorter." *Theoretical Population Biology* 108 (April): 51-69.

Beaghton, A., A. Hammond, T. Nolan, A. Crisanti, H. C. Godfray, and A. Burt. 2017. "Requirements for Driving Antipathogen Effector Genes into Populations of Disease Vectors by Homing." *Genetics* 205 (4): 1587-96.

Ben-David, E., A. Burga, and L. Kruglyak. 2017. "A Maternal-Effect Selfish Genetic Element in *Caenorhabditis elegans*." *Science* 356 (6342): 1051-55.

Braig, H. R., and G. Yan. 2001. "The Spread of Genetic Constructs in Natural Insect Populations." In *Genetically Engineered Organisms: Assessing Environmental and Human Health Effects*, edited by D. K. Letourneau and B. E. Burrows, 251-314. CRC Press.

Buchman, A. B., T. Ivy, J. M. Marshall, O. S. Akbari, and B. A. Hay. 2018. "Engineered Reciprocal Chromosome Translocations Drive High Threshold, Reversible Population Replacement in *Drosophila*." *ACS Synthetic Biology*. https://doi.org/10.1021/acssynbio.7b00451.

Burt, A. 2003. "Site-Specific Selfish Genes as Tools for the Control and Genetic Engineering of Natural Populations." *Proceedings. Biological Sciences/The Royal Society* 270 (1518): 921-28.

Burt, A., and R. Trivers. 1998. "Genetic Conflicts in Genomic Imprinting." *Proceedings. Biological Sciences/The Royal Society* 265 (1413): 2393-97.

Champer, J., R. Reeves, S. Y. Oh, C. Liu, J. Liu, A. G. Clark, and P. W. Messer. 2017. "Novel CRISPR/Cas9 Gene Drive Constructs Reveal Insights into Mechanisms of Resistance Allele Formation and Drive Efficiency in Genetically Diverse Populations." *PLoS Genetics* 13 (7): e1006796.

Chan, Yuk-Sang, David S. Huen, Ruth Glauert, Eleanor Whiteway, and Steven Russell. 2013. "Optimising Homing Endonuclease Gene Drive Performance in a Semi-Refractory Species: The *Drosophila melanogaster* Experience." *PloS One* 8 (1): e54130.Chan, Yuk-Sang, Daniel A. Naujoks, David S. Huen, and Steven Russell. 2011. "Insect Population Control by Homing Endonuclease-Based Gene Drive: An Evaluation in *Drosophila melanogaster*." *Genetics* 188 (1): 33-44.

Chen, C. H., H. Huang, C. M. Ward, J. T. Su, L. V. Schaeffer, M. Guo, and B. A. Hay. 2007. "A Synthetic Maternal-Effect Selfish Genetic Element Drives Population Replacement in *Drosophila*." *Science* 316 (5824): 597-600.

Davis, Stephen, Nicholas Bax, and Peter Grewe. 2001. "Engineered Underdominance Allows Efficient and Economical Introgression of Traits into Pest Populations." *Journal of Theoretical Biology* 212 (1): 83-98.

Galizi, R., L. A. Doyle, M. Menichelli, F. Bernardini, A. Deredec, A. Burt, B. L. Stoddard, N. Windbichler, and A. Crisanti. 2014. "A Synthetic Sex Ratio Distortion System for the Control of the Human Malaria Mosquito." *Nature Communications* 5: 3977.

Galizi, R., A. Hammond, K. Kyrou, C. Taxiarchi, F. Bernardini, S. M. O'Loughlin, P. A. Papathanos, T. Nolan, N. Windbichler, and A. Crisanti. 2016. "A CRISPR-Cas9 Sex-Ratio Distortion System for Genetic Control." *Scientific Reports* 6: 31139.Gantz, V. M., and E. Bier. 2015. "The Mutagenic Chain Reaction: A Method for Converting Heterozygous to Homozygous Mutations." *Science* 348 (6233): 442-44.

Gantz, V. M., N. Jasinskiene, O. Tatarenkova, A. Fazekas, V. M. Macias, E. Bier, and A. A. James. 2015. "Highly Efficient Cas9-Mediated Gene Drive for Population Modification of the Malaria Vector Mosquito *Anopheles stephensi*." *Proceedings of the National Academy of Sciences of the United States of America* 112 (49): E6736-43.

Godfray, H. C. J., A. North, and A. Burt. 2017. "How Driving Endonuclease Genes Can Be Used to Combat Pests and Disease Vectors." *BMC Biology* 15 (1): 81.

Gokhale, Chaitanya S., Richard Guy Reeves, and Floyd A. Reed. 2014. "Dynamics of a Combined Medea-Underdominant Population Transformation System." *BMC Evolutionary Biology* 14: 98.

Gould, Fred, and Paul Schliekelman. 2004. "Population Genetics of Autocidal Control and Strain Replacement." *Annual Review of Entomology* 49: 193-217.

Hammond, A., R. Galizi, K. Kyrou, A. Simoni, C. Siniscalchi, D. Katsanos, M. Gribble, et al. 2016. "A CRISPR-Cas9 Gene Drive System Targeting Female Reproduction in the Malaria Mosquito Vector *Anopheles gambiae*." *Nature Biotechnology* 34 (1): 78-83.

Hay, Bruce A., Chun-Hong Chen, Catherine M. Ward, Haixia Huang, Jessica T. Su, and Ming Guo. 2010. "Engineering the Genomes of Wild Insect Populations: Challenges, and Opportunities Provided by Synthetic Medea Selfish Genetic Elements." *Journal of Insect Physiology* 56 (10): 1402-13.

Hu, W., Z. D. Jiang, F. Suo, J. X. Zheng, W. Z. He, and L. L. Du. 2017. "A Large Gene Family in Fission Yeast Encodes Spore Killers That Subvert Mendel's Law." *eLife* 6. https://doi.org/10.7554/eLife.26057.

Marshall, J. M. 2009. "The Effect of Gene Drive on Containment of Transgenic Mosquitoes." *Journal of Theoretical Biology* 258 (2): 250-65.

Marshall, J. M., and B. A. Hay. 2011. "Inverse Medea as a Novel Gene Drive System for Local Population Replacement: A Theoretical Analysis." *The Journal of Heredity* 102 (3): 336-41.

Marshall, J. M., and B. A. Hay. 2012. "Confinement of Gene Drive Systems to Local Populations: A Comparative Analysis." *Journal of Theoretical Biology* 294: 153-71.

Marshall, John M., and Bruce A. Hay. 2012a. "Confinement of Gene Drive Systems to Local Popu . . . [J Theor Biol. 2012]—PubMed—NCBI." *Journal of Theoretical Biology* 294 (February): 153-71.

Marshall, J. M., and B. A. Hay. 2012b. "General Principles of Single-Construct Chromosomal Gene Drive [Evolution. 2012]—PubMed—NCBI." *Evolution; International Journal of Organic Evolution* 66 (7): 2150-66.

Marshall, John M., Geoffrey W. Pittman, Anna B. Buchman, and Bruce A. Hay. 2011. "Semele: A Killer-Male, Rescue-Female System for Suppression and Replacement of Insect Disease Vector Populations." *Genetics* 187 (2): 535-51.

Nuckolls, N. L., M. A. Bravo Nunez, M. T. Eickbush, J. M. Young, J. J. Lange, J. S. Yu, G. R. Smith, S. L. Jaspersen, H. S. Malik, and S. E. Zanders. 2017. "Wtf Genes Are Prolific Dual Poison-Antidote Meiotic Drivers." *eLife* 6. https://doi.org/10.7554/eLife.26033.

Preston, Christine R., Carlos C. Flores, and William R. Engels. 2006. "Differential Usage of Alternative Pathways of Double-Strand Break Repair in *Drosophila*." *Genetics* 172 (2): 1055-68.

Reeves, R. G., J. Bryk, P. M. Altrock, J. A. Denton, and F. A. Reed. 2014. "First Steps towards Underdominant Genetic Transformation of Insect Populations." *PloS One* 9 (5): e97557.

Seidel, H. S., M. Ailion, J. Li, A. van Oudenaarden, M. V. Rockman, and L. Kruglyak. 2011. "A Novel Sperm-Delivered Toxin Causes Late-Stage Embryo Lethality and Transmission Ratio Distortion in *C. Elegans*." *PLoS Biology* 9 (7): e1001115.

Simoni, A., C. Siniscalchi, Y. S. Chan, D. S. Huen, S. Russell, N. Windbichler, and A. Crisanti. 2014. "Development of Synthetic Selfish Elements Based on Modular Nucleases in *Drosophila melanogaster*." *Nucleic Acids Research* 42 (11): 7461-72.

Wade, M. J., and R. W. Beeman. 1994. "The Population Dynamics of Maternal-Effect Selfish Genes." *Genetics* 138 (4): 1309-14.

Ward, Catherine M., Jessica T. Su, Yunxin Huang, Alun L. Lloyd, Fred Gould, and Bruce A. Hay. 2011. "Medea Selfish Genetic Elements as Tools for Altering Traits of Wild Populations: A Theoretical Analysis." *Evolution; International Journal of Organic Evolution* 65 (4): 1149-62.

Windbichler, Nikolai, Philippos Aris Papathanos, Flaminia Catteruccia, Hilary Ranson, Austin Burt, and Andrea Crisanti. 2007. "Homing Endonuclease Mediated Gene Targeting in *Anopheles gambiae* Cells and Embryos." *Nucleic Acids Research* 35 (17): 5922-33.

Windbichler, N., M. Menichelli, P. A. Papathanos, S. B. Thyme, H. Li, U. Y. Ulge, B. T. Hovde, et al. 2011. "A Synthetic Homing Endonuclease-Based Gene Drive System in the Human Malaria Mosquito." *Nature* 473 (7346): 212-15.

Windbichler, N., P. A. Papathanos, and A. Crisanti. 2008. "Targeting the X Chromosome during Spermatogenesis Induces Y Chromosome Transmission Ratio Distortion and Early Dominant Embryo Lethality in *Anopheles gambiae*." *PLoS Genetics* 4 (12): e1000291. Sun, N., and H. Zhao. 2014. "A Single-Chain TALEN Architecture for Genome Engineering." Molecular bioSystems 10 (3): 446-53.

---

What is claimed is:

1. A vector, comprising:

a first gene sequence encoding a DNA sequence modifying enzyme, wherein the DNA sequence modifying enzyme induces one or more sequence modifications in an endogenous copy of an essential gene, wherein the DNA sequence modifying enzyme is Cas9 nuclease;

a first promoter operably linked to the first gene sequence encoding the DNA sequence modifying enzyme, wherein the first promoter is selected from the group consisting of a germline promoter, a male specific germline promoter, and a female specific germline promoter;

a second rescue transgene sequence;

a second promoter operably linked to the rescue transgene sequence;

a sequence encoding at least one guide RNA, wherein the guide RNA enables the Cas9 nuclease to target specific sequences within the essential gene, one or more additional sequences that allow the vector to be positioned in a chromosome or an extra-chromosomal element that is different from the location of the endogenous copy of the essential gene comprise sequences that are not homologous to sequences flanking the endogenous copy of the essential gene, and one or more cargo sequences;

wherein the one or more sequence modifications being cleavage of the essential gene resulting in the essential gene being rendered partially or wholly non-functional and resulting in a defect in survival, growth control, fertility, or differentiation in absence of the rescue transgene, wherein a rescue of the defect occurs by the rescue transgene being positioned in a chromosomal or an extrachromosomal element that is different from the location of the endogenous copy of the essential gene, wherein the rescue transgene is either a recoded copy of the essential gene or is a gene of unrelated sequence, wherein the rescue transgene encodes a protein that is functionally equivalent to a protein encoded by the essential gene, and wherein the DNA sequence modifying enzyme does not modify the rescue transgene, and wherein the vector is capable of performing a gene spread by increasing in relative frequency in a population following introduction into an organism by causing the death of those who inherit only non-functional alleles of the essential gene and fail to inherit the vector.

2. The vector of claim 1, wherein the Cas9 nuclease cleaves and generates one or more single or double strand breaks in the endogenous copy of the essential gene.

3. The vector of claim 2, wherein the one or more single or double strand breaks are repaired to create an altered sequence of the essential gene.

4. The vector of claim 1, wherein the chromosome is an autosome, X chromosome, Y chromosome, or supernumerary chromosome.

5. The vector of claim 1, wherein the extra-chromosomal element is a plasmid or a virus.

6. The vector of claim 1, wherein the one or more cargo sequences comprise a one or more foreign gene sequences, or one or more alleles of an endogenous chromosomal or extra-chromosomal gene to which the vector has been linked through nearby insertion on the chromosome or extra-chromosomal element that carries the endogenous allele of interest.

7. The vector of claim 1, wherein the one or more additional sequences is selected from the group consisting of transposase binding site, LTRs, recombinase binding site, and a sequence with homology to a desired location on the chromosome or the extra-chromosomal element.

8. The vector of claim 1, wherein the Cas9 nuclease comprises at least one nuclease domain and one or more DNA binding domains.

* * * * *

SEQUENCE LISTING

```
<160> NUMBER OF SEQ ID NOS: 43

<210> SEQ ID NO 1
<211> LENGTH: 24
<212> TYPE: DNA
<213> ORGANISM: Artificial
<220> FEATURE:
<223> OTHER INFORMATION: P0-68E FWD

<400> SEQUENCE: 1
gtcgtgcaca accagagact ggag                                          24

<210> SEQ ID NO 2
<211> LENGTH: 24
<212> TYPE: DNA
<213> ORGANISM: Artificial
<220> FEATURE:
<223> OTHER INFORMATION: P0-68E REV

<400> SEQUENCE: 2
aaacctccag tctctggttg tgca                                          24

<210> SEQ ID NO 3
<211> LENGTH: 40
<212> TYPE: DNA
<213> ORGANISM: Artificial
<220> FEATURE:
<223> OTHER INFORMATION: P9-68E-hr-left FWD

<400> SEQUENCE: 3
cttattacgt ggccaactag gtgcccaaaa tgtgtgtgga                          40

<210> SEQ ID NO 4
<211> LENGTH: 40
```

```
<212> TYPE: DNA
<213> ORGANISM: Artificial
<220> FEATURE:
<223> OTHER INFORMATION: P10-68E-hr-left REV

<400> SEQUENCE: 4
gcttcggtgt gtccgtcagt gagaggtttt gccgcgattt                    40

<210> SEQ ID NO 5
<211> LENGTH: 41
<212> TYPE: DNA
<213> ORGANISM: Artificial
<220> FEATURE:
<223> OTHER INFORMATION: P11-attP FWD

<400> SEQUENCE: 5
aaatcgcggc aaaacctctc actgacggac acaccgaagc c                  41

<210> SEQ ID NO 6
<211> LENGTH: 40
<212> TYPE: DNA
<213> ORGANISM: Artificial
<220> FEATURE:
<223> OTHER INFORMATION: P12-attP REV

<400> SEQUENCE: 6
ccttgctgcc cgcctgcagc agtcgcgctc gcgcgactga                    40

<210> SEQ ID NO 7
<211> LENGTH: 40
<212> TYPE: DNA
<213> ORGANISM: Artificial
<220> FEATURE:
<223> OTHER INFORMATION: P13-dv-tko FWD

<400> SEQUENCE: 7
tcagtcgcgc gagcgcgact gctgcaggcg ggcagcaagg                    40

<210> SEQ ID NO 8
<211> LENGTH: 45
<212> TYPE: DNA
<213> ORGANISM: Artificial
<220> FEATURE:
<223> OTHER INFORMATION: P14-dv-tko REV

<400> SEQUENCE: 8
gcagtgcaaa aagttggtg gggtcggacc tcaagttgca tatgg               45

<210> SEQ ID NO 9
<211> LENGTH: 40
<212> TYPE: DNA
<213> ORGANISM: Artificial
<220> FEATURE:
<223> OTHER INFORMATION: P15-68E-hr-right FWD

<400> SEQUENCE: 9
tgcaacttga ggtccgaccc caccaacttt tttgcactgc                    40

<210> SEQ ID NO 10
<211> LENGTH: 40
<212> TYPE: DNA
<213> ORGANISM: Artificial
<220> FEATURE:
<223> OTHER INFORMATION: P16-68E-hr-right REV

<400> SEQUENCE: 10
```

```
gggcgaattg ggtacaagct aggatgatgg gatgctggaa                    40
```

<210> SEQ ID NO 11
<211> LENGTH: 60
<212> TYPE: DNA
<213> ORGANISM: Artificial
<220> FEATURE:
<223> OTHER INFORMATION: P21-tko-guidesA FWD

<400> SEQUENCE: 11

```
ctattttcaa tttaacgtcg ctgcagcgat gccattccag tttcagagct atgctggaaa    60
```

<210> SEQ ID NO 12
<211> LENGTH: 60
<212> TYPE: DNA
<213> ORGANISM: Artificial
<220> FEATURE:
<223> OTHER INFORMATION: P22-tko-guidesA REV

<400> SEQUENCE: 12

```
ttccagcata gctctgaaac tcgccaaggg cgttgtcctg cgaagttcac ccggatatct    60
```

<210> SEQ ID NO 13
<211> LENGTH: 60
<212> TYPE: DNA
<213> ORGANISM: Artificial
<220> FEATURE:
<223> OTHER INFORMATION: P23-tko-guidesB FWD

<400> SEQUENCE: 13

```
ctattttcaa tttaacgtcg caacattgta ctgtgccgcg gtttcagagc tatgctggaa    60
```

<210> SEQ ID NO 14
<211> LENGTH: 60
<212> TYPE: DNA
<213> ORGANISM: Artificial
<220> FEATURE:
<223> OTHER INFORMATION: P24-tko-guidesB REV

<400> SEQUENCE: 14

```
ttccagcata gctctgaaac atcgaaagtg cgtgctggtg cgaagttcac ccggatatct    60
```

<210> SEQ ID NO 15
<211> LENGTH: 40
<212> TYPE: DNA
<213> ORGANISM: Artificial
<220> FEATURE:
<223> OTHER INFORMATION: P25-nosCas9 FWD

<400> SEQUENCE: 15

```
gttgtctata ctataagatc tataggcacg ggataacgct                    40
```

<210> SEQ ID NO 16
<211> LENGTH: 42
<212> TYPE: DNA
<213> ORGANISM: Artificial
<220> FEATURE:
<223> OTHER INFORMATION: P26-nos-Cas9 REV

<400> SEQUENCE: 16

```
gcaatcacag gtgagcaaaa aagcttggat ttcactggaa ct                 42
```

<210> SEQ ID NO 17
<211> LENGTH: 42
<212> TYPE: DNA
<213> ORGANISM: Artificial

```
<220> FEATURE:
<223> OTHER INFORMATION: P27-guidesA FWD

<400> SEQUENCE: 17
agttccagtg aaatccaagc tttttttgctc acctgtgatt gc                          42

<210> SEQ ID NO 18
<211> LENGTH: 41
<212> TYPE: DNA
<213> ORGANISM: Artificial
<220> FEATURE:
<223> OTHER INFORMATION: P28-guidesA REV

<400> SEQUENCE: 18
aatcacaggt gagcaaaaaa aattaaccct cactaaaggg a                            41

<210> SEQ ID NO 19
<211> LENGTH: 40
<212> TYPE: DNA
<213> ORGANISM: Artificial
<220> FEATURE:
<223> OTHER INFORMATION: P29-guidesB FWD

<400> SEQUENCE: 19
ccctttagtg agggttaatt ttttttgctc acctgtgatt                              40

<210> SEQ ID NO 20
<211> LENGTH: 40
<212> TYPE: DNA
<213> ORGANISM: Artificial
<220> FEATURE:
<223> OTHER INFORMATION: P30-guidesB REV

<400> SEQUENCE: 20
gcagcctcga gatcgatgat tgccgagcac aattgtctag                              40

<210> SEQ ID NO 21
<211> LENGTH: 20
<212> TYPE: DNA
<213> ORGANISM: Artificial
<220> FEATURE:
<223> OTHER INFORMATION: tko-seq1

<400> SEQUENCE: 21
aagcgttcca agctgcacag                                                    20

<210> SEQ ID NO 22
<211> LENGTH: 20
<212> TYPE: DNA
<213> ORGANISM: Artificial
<220> FEATURE:
<223> OTHER INFORMATION: tko-seq2

<400> SEQUENCE: 22
cgcacatcca tttccaattg                                                    20

<210> SEQ ID NO 23
<211> LENGTH: 19
<212> TYPE: DNA
<213> ORGANISM: Artificial
<220> FEATURE:
<223> OTHER INFORMATION: tko-seq3

<400> SEQUENCE: 23
cacacacaca ggtgcgttc                                                     19
```

```
<210> SEQ ID NO 24
<211> LENGTH: 41
<212> TYPE: DNA
<213> ORGANISM: Artificial
<220> FEATURE:
<223> OTHER INFORMATION: tko-seq4

<400> SEQUENCE: 24
acaactagac gttggcaatc tcacaccttc ctcttcttct t          41

<210> SEQ ID NO 25
<211> LENGTH: 20
<212> TYPE: DNA
<213> ORGANISM: Artificial
<220> FEATURE:
<223> OTHER INFORMATION: tko-seq5

<400> SEQUENCE: 25
tcagcgggat tagtgtaagt                                  20

<210> SEQ ID NO 26
<211> LENGTH: 20
<212> TYPE: DNA
<213> ORGANISM: Artificial
<220> FEATURE:
<223> OTHER INFORMATION: tko-seq6

<400> SEQUENCE: 26
catatgcaac ttgaggtccg                                  20

<210> SEQ ID NO 27
<211> LENGTH: 20
<212> TYPE: DNA
<213> ORGANISM: Artificial
<220> FEATURE:
<223> OTHER INFORMATION: s2-attB-rev

<400> SEQUENCE: 27
ttcgagaccg tgacctacat                                  20

<210> SEQ ID NO 28
<211> LENGTH: 20
<212> TYPE: DNA
<213> ORGANISM: Artificial
<220> FEATURE:
<223> OTHER INFORMATION: s2-u631-seq

<400> SEQUENCE: 28
agttccagtg aaatccaagc                                  20

<210> SEQ ID NO 29
<211> LENGTH: 23
<212> TYPE: DNA
<213> ORGANISM: Artificial
<220> FEATURE:
<223> OTHER INFORMATION: T3-seq REV

<400> SEQUENCE: 29 gttccctta gtgagggtta att                               23

<210> SEQ ID NO 30
<211> LENGTH: 20
<212> TYPE: DNA
<213> ORGANISM: Artificial
<220> FEATURE:
<223> OTHER INFORMATION: T3-seq FWD
```

<400> SEQUENCE: 30 attaccctc actaaaggga                                              20

<210> SEQ ID NO 31
<211> LENGTH: 22
<212> TYPE: DNA
<213> ORGANISM: Artificial
<220> FEATURE:
<223> OTHER INFORMATION: CAS91F

<400> SEQUENCE: 31
atggacaaga agtactccat tg                                          22

<210> SEQ ID NO 32
<211> LENGTH: 20
<212> TYPE: DNA
<213> ORGANISM: Artificial
<220> FEATURE:
<223> OTHER INFORMATION: CAS91R

<400> SEQUENCE: 32
gatcggtatt gcccagaact                                             20

<210> SEQ ID NO 33
<211> LENGTH: 20
<212> TYPE: DNA
<213> ORGANISM: Artificial
<220> FEATURE:
<223> OTHER INFORMATION: CAS92F2

<400> SEQUENCE: 33
agcgctaggc tgtccaaatc                                             20

<210> SEQ ID NO 34
<211> LENGTH: 21
<212> TYPE: DNA
<213> ORGANISM: Artificial
<220> FEATURE:
<223> OTHER INFORMATION: CAS93F

<400> SEQUENCE: 34
gagaaaatcc tcacatttcg g                                           21

<210> SEQ ID NO 35
<211> LENGTH: 21
<212> TYPE: DNA
<213> ORGANISM: Artificial
<220> FEATURE:
<223> OTHER INFORMATION: CAS94F2

<400> SEQUENCE: 35
agagtggaaa gacaatcctg g                                           21

<210> SEQ ID NO 36
<211> LENGTH: 20
<212> TYPE: DNA
<213> ORGANISM: Artificial
<220> FEATURE:
<223> OTHER INFORMATION: CAS95F

<400> SEQUENCE: 36
ctgaacgcca aactgatcac                                             20

<210> SEQ ID NO 37

```
<211> LENGTH: 20
<212> TYPE: DNA
<213> ORGANISM: Artificial
<220> FEATURE:
<223> OTHER INFORMATION: CAS96F

<400> SEQUENCE: 37
tggacgccac actgattcat                                                 20

<210> SEQ ID NO 38
<211> LENGTH: 21
<212> TYPE: DNA
<213> ORGANISM: Artificial
<220> FEATURE:
<223> OTHER INFORMATION: CAS96R

<400> SEQUENCE: 38
tcacaccttc ctcttcttct t                                               21

<210> SEQ ID NO 39
<211> LENGTH: 12817
<212> TYPE: DNA
<213> ORGANISM: Artificial
<220> FEATURE:
<223> OTHER INFORMATION: p68-tko-step1

<400> SEQUENCE: 39
agcttgtacc caattcgccc tatagtgagt cgtattacaa ttcactggcc gtcgttttac     60
aacgtcgtga ctgggaaaac cctggcgtta cccaacttaa tcgccttgca gcacatcccc    120
ctttcgccag ctggcgtaat agcgaagagg cccgcaccga tcgcccttcc caacagttgc    180
gcagcctgaa tggcgaatgg gacgcgccct gtagcggcgc attaagcgcg gcgggtgtgg    240
tggttacgcg cagcgtgacc gctacacttg ccagcgccct agcgcccgct cctttcgctt    300
tcttcccttc ctttctcgcc acgttcgccg gctttccccg tcaagctcta atcgggggc    360 tccctttagg gttccgattt agtgctttac ggcacctcga ccccaaaaaa cttgattagg    420
gtgatggttc acgtagtggg ccatcgccct gatagacggt ttttcgccct ttgacgttgg    480
agtccacgtt ctttaatagt ggactcttgt tccaaactgg aacaacactc aaccctatct    540
cggtctattc ttttgattta agggatttt tgccgatttc ggcctattgg ttaaaaaatg    600
agctgattta acaaaaattt aacgcgaatt ttaacaaaat attaacgctt acaatttagg    660
tggcactttt cggggaaatg tgcgcggaac ccctatttgt ttatttttct aaatacattc    720
aaatatgtat ccgctcatga acaataaacc tgataaatg cttcaataat attgaaaaag    780
gaagagtatg agtattcaac atttccgtgt cgcccttatt cccttttttg cggcattttg    840
ccttcctgtt tttgctcacc cagaaacgct ggtgaaagta aaagatgctg aagatcagtt    900
gggtgcacga gtgggttaca tcgaactgga tctcaacagc ggtaagatcc ttgagagttt    960
tcgccccgaa gaacgttttc caatgatgag cacttttaaa gttctgctat gtggcgcggt   1020
attatcccgt attgacgccg ggcaagagca actcggtcgc cgcatacact attctcagaa   1080
tgacttggtt gagtactcac cagtcacaga aaagcatctt acggatggca tgacagtaag   1140
agaattatgc agtgctgcca taaccatgag tgataacact gcggccaact tacttctgac   1200
aacgatcgga ggaccgaagg agctaaccgc ttttttgcac aacatggggg atcatgtaac   1260
tcgccttgat cgttgggaac cggagctgaa tgaagccata ccaaacgacg agcgtgacac   1320
cacgatgcct gtagcaatgg caacaacgtt gcgcaaacta ttaactggcg aactacttac   1380
tctagcttcc cggcaacaat taatagactg gatggaggcg gataaagttg caggaccact   1440
```

```
tctgcgctcg gcccttccgg ctggctggtt tattgctgat aaatctggag ccggtgagcg    1500
tgggtctcgc ggtatcattg cagcactggg gccagatggt aagccctccc gtatcgtagt    1560
tatctacacg acgggagtc aggcaactat ggatgaacga aatagacaga tcgctgagat     1620
aggtgcctca ctgattaagc attggtaact gtcagaccaa gtttactcat atatacttta    1680
gattgattta aaacttcatt tttaatttaa aaggatctag gtgaagatcc ttttgataa     1740 tctcatgacc aaaatccctt aacgtgagtt ttcgttccac tgagcgtcag accccgtaga    1800
aaagatcaaa ggatcttctt gagatccttt ttttctgcgc gtaatctgct gcttgcaaac    1860
aaaaaaacca ccgctaccag cggtggtttg tttgccggat caagagctac caactctttt    1920
tccgaaggta actggcttca gcagagcgca gataccaaat actgtccttc tagtgtagcc    1980
gtagttaggc caccacttca agaactctgt agcaccgcct acatacctcg ctctgctaat    2040
cctgttacca gtggctgctg ccagtggcga taagtcgtgt cttaccgggt tggactcaag    2100
acgatagtta ccggataagg cgcagcggtc gggctgaacg gggggttcgt gcacacagcc    2160
cagcttggag cgaacgacct acaccgaact gagatacctà cagcgtgagc tatgagaaag    2220
cgccacgctt cccgaaggga gaaaggcgga caggtatccg gtaagcggca gggtcggaac    2280
aggagagcgc acgagggagc ttccagggg aaacgcctgg tatctttata gtcctgtcgg    2340
gtttcgccac ctctgacttg agcgtcgatt tttgtgatgc tcgtcagggg ggcggagcct    2400
atggaaaaac gccagcaacg cggccttttt acggttcctg gccttttgct ggccttttgc    2460
tcacatgttc tttcctgcgt tatccctga ttctgtggat aaccgtatta ccgcctttga     2520
gtgagctgat accgctcgcc gcagccgaac gaccgagcgc agcgagtcag tgagcgagga    2580
agcggaagag cgcccaatac gcaaaccgcc tctccccgcg cgttggccga ttcattaatg    2640
cagctggcac gacaggtttc ccgactggaa agcgggcagt gagcgcaacg caattaatgt    2700
gagttagctc actcattagg cacccaggc tttacacttt atgcttccgg ctcgtatgtt      2760
gtgtggaatt gtgagcggat aacaatttca cacaggaaac agctatgacc atgattacgc    2820
caagcgcgca attaaccctc actaaaggga acaaaagctg gagctcctgc aggttgttgg    2880
ttggcacacc acaaatatac tgttgccgag cacaattgtc tagaatgcat acgcattaag    2940
cgaacattaa aaagatgtga aaacataact attatgtcta aataaacaca cgtcagatgt    3000
atgtacgtca acggaaaacc attgtctata tattacaatt actaaataca taccaaattg    3060
aatacatatt gatgaaaaat aataaatact ggcgaaagca aaaaacgaa acattttat      3120 tttattgaac aactctcagg ctccaggtag gcaaaaaagc accgactcgg tgccacttt     3180 tcaagttgat aacggactag ccttatttca acttgctatg ctgtttccag catagctctg    3240
aaacctccag tctctggttg tgcacgacgt taaattgaaa ataggtctat atatacgaac    3300
tgagtctgga aaagaagtt gagaattata aaagtagtg agcactggcg ccctctctgc      3360
ttggcgagct aaccttttcg cctcttggct gagtaggtgg cgtttcattc tactctgtaa    3420
aattaatgta gaattgaaac actatggtca aaaatactt aggggcataa gttataaaac     3480
gtatgaaatg aatttttatc aacctgggct attcaaaaat tttcgaatta ttttatgtat    3540
tttttttaat cgttttcat tataggttaa atacacttt aaaaggaatt ctttcctgta      3600
aaataaatat aaataaatat gcttattga cagaaaattt gatgttttg tatttgagta      3660 ggagcaatca caggtgagca aaaagaatt catcaattga tcggctaaat ggtatggcaa     3720
gaaaaggtat gcaatataat aatctttat tgggtatgca acgaaaattt gtttcgtcaa    3780
```

```
cgtatgcaat attctttatt aaaagagggt atgcaatgta tttattaaaa aacgggtatg    3840
caatataata atcttttatt gggtatgcaa cgaaaatttg tttcgtcaaa gtatgcaata    3900
ttttttatta aaagagggta tgcaatgtat tttattaaaa acgggtatgc aataaaaaat    3960
tatttggttt ctctaaaaag tatgcagcac ttatttttg  ataaggtatg caacaaaatt    4020
ttactttgcc gaaaatatgc aatgtttttg cgataaatt  caacgcacac ttattacgtg    4080
gccaactagg tgcccaaaat gtgtgtggac tacgaaattt tccaaattta agatgctatc    4140
tttaaaccaa tgaaatatgg ttcgtatact atgaattttc aattaggcga acatcaatga    4200 ttccccccc  agaaaaccga catagcagag cacacgagca ggcgcaaatt gagaaaccca    4260
tccgcgtgaa gtcggttaat tgcccatct  tcttctggac gcgttcgtgc acccgctgct    4320
catccggcgg agtattgtac cattgtgtac ggccgtagtc cgtgtgcctt cgttttggcg    4380
ttcatgcatg agcagcccaa ttccttgctg ccccattcgg ttacattgca cagtggacac    4440
aaaagctagt tttgtagtca aagtacagaa ttcacaaatt atataaactg atatagttca    4500
tagatagtat aaactgatac caagtaacag atacacattt aaataggtaa actgtgtctg    4560
tgatcaaact gtttcttttc gtgtcgaaga atcaattaaa aatgattgaa tcattatatt    4620
tatttccgtt aaaagctgtg caggctgttc aaaatgtttt aatgaaaaaa tacgaatttt    4680
tagactgtct gaatcacagt gtgctcgctt acatttccgc tttcctcttt tggcaactcg    4740
atgtcgcctt tggggctctt ttggagaccg gaaaaaggca acattttcta ttcgattctt    4800
tttgccaatt gcccgagact gtgtcctgtc ggcatatgac gaatacgtaa cgtacgtgac    4860
ggcgacgtta ctcatacgca ccgtgggtag ctgcagacat ctcagcaccc acgttcgcga    4920
attattttga attcgactcc ctgggcgata tttgtttttc gcttttgcat attttgcggg    4980
caatttgggt aaaaggattt ccgcactctg cgacgccgtc ttcagtttgc ggctttcgtt    5040
tttttcctag tagttcggca cacattttcc tcgccgcttc ggcaaatcgc tcacgtaaaa    5100
tatgcatgcg tttccttggc ggttttgcgc tctcaagtgc ctgcaattca attacatttc    5160
gattgatttt catgtttggc cccaaatcgc ggcaaaacct ctcactgacg gacacaccga    5220
agccccggcg gcaaccctca gcggatgccc cggggcttca cgttttccca ggtcagaagc    5280
ggttttcggg agtagtgccc caactggggt aacctttgag ttctctcagt tggggcgta    5340 gggtcgccga catgacacaa ggggttgtga ccggggtgga cacgtacgcg ggtgcttacg    5400
accgtcagtc gcgcgagcgc gactgctgca ggcgggcagc aaggcgtccc atccgcatta    5460
cgtgcccagc tatttgccag ctatgcccga tcctcatgcc tatattcgaa cgcccacgca    5520
caagcagccc gtaaccgaat acgaggcaat aagggaaaag gcagccagtc agaagcgtga    5580
cgttgagaag gcgctgacca aatttctgtg caaaacaaca gaaacaaaca atctctttcc    5640
caccgaggac aacatgtttc cgtgtaagta agcgctgcga ttaatggttc ttggttcttt    5700
attcaaatgt ttcgacttct ttttctgaat gcaacagtaa tcgcctgtaa gcccgccttt    5760
ccggcgtatg cagctgcctt gaatcccaca gatcaggtat ttgacttcga ggagctggag    5820
taccactact tggtggccaa tcgtacggaa gatgtgccca gtaaaggtag gtccaaattg    5880
tacacaatag atattccaat gaacacaggc tctacttttca tttgcagagg agggcgagga    5940
gggtgacagt gagaatgagg aactggatgg cgacaagtcc aaggaggaga gcccgagct    6000 ggagatcaag cccaattcaa caacaaataa agctatttta gagaatccca atatagacaa    6060
tccctacttg cgtgccgcta cactgccaaa gcgttccaag ctgcacagtg agtgcactac    6120
accacgcatg gtgccctcac gaagtataca ctcggcttca cccacgacac cgacgccctc    6180
```

```
aactctagag ataaccaaaa gtagtgctta gttataatta taaatagatg cattgtaatt    6240
gtgtatagtt ttttaaaaaa aaaatattgg ataaacaaac tcttttcttc ttatcgatag    6300
ttcgtgcttt tgcttaaaat ggtgtgcgat ggcagcgctg cggcaacaaa cagctgtttc    6360
gatataaaag tacattttac ttatcgatag ctcgtgctat tgcataaaat gatgttaggt    6420
ggcaacgctg cggcaacaat cagctgttta ccaggccgca gcaacgttac agtgcatttt    6480
acattttacc aagttgaatt aataaaattg cttttaaaa gtgtttacta aattaaaaag     6540
ccaacaaatt gttgttgttt tcgttgctta caagcggctg ctgtacataa attatacata    6600
ttagcgctaa acgtgctcaa catgaatttc ctgcgccaaa cattcaacgt tacgaaacaa    6660
ttgacggcac aaggtaagtt ttaacaaaaa tccctattta aaacattgcg ttgcggctat    6720
ttattcaact tcgagtcccg tgttctatat acatacgcgc ccacgcgcct aattgccaac    6780
catgtgaggc agccggtagc cgcttgcgca catccatttc caattggtga ctgtgcgcat    6840
tttgtgttta tccaaggatc ctgcgttcca ttgtgtgcac acaatgattt gtattgtctg    6900
ttgtttgcct gcgatctcaa ctcttttaca tgggcgcgtg gccggcttgc gagcctgtcg    6960
cccgtctgcc agttctctag ttgtcgtcgt accccccttc cccctgccca gccccttatc    7020
gtgtgtctag tctgtgaata tttttataag cattttctca tgtgtgtttc ctgtttgtgt    7080
gttttaatgt gtcctcaaaa ctgttcacgg agcctacaaa gtgtgtattg agaatatata    7140
tatatatata tagtccatct gtccatcttg gatatttgtc attggaacgg gcgagcgaaa    7200
aaagggtttg tcaatgaaaa acttatcatt ttcattatgt gcaacattta ctaaccaaat    7260
ctattcaata cataggttgg acaaacttgc cttctgttct tcgagataac ttcagcaaag    7320
tctgccaatg cgatctgaag tccattcaat ttttggccta gcaaaaaacg cattcgtttt    7380
tctgcttgtt ttaattaaaa ttcacaacaa atccgcata acatgaggcc cacccctcaac    7440
aataggaatt gcatgacat gcacacaata aggaaaaaac aacacaagaa aaaaaaatta    7500
tgagaaaagg acacacacac acacacaggt gcgttcggat cgcggcagac aatgcacgga    7560
gctgtgattg gcatagttct tgctgtgcgc ctgctcccat tgtaagcgat tgtccagcgt    7620
tatggtaatt attacctgtg tgtacgtgtg tgtgtgtgtg tgtggcattt aattaaaaat    7680
tgttgtcgtt tgcgattttg gctgcagtac agtcgagtcc agtcgggagt ccagctgaac    7740
agaaatctga gcatcagaca gtcaaccccc gtgcatggct aaaggttctc aatgcttaaa    7800
aggcttgaga actgcagttg ccgctgaccc acagccgcgt catttggctg caattatttg    7860
tgaaaataac cttatatatg catgatatgt ggatggatat ggatggatat atggatgtgc    7920
gcagcataac aattattttg cgattttcac agagattagc cacaacaaaa ggcgaatggc    7980
cattgttgct tgggcatttg gaactggcca actgtttctg accctttgt catgttgtgt     8040
ccgttctctc gtttgtgtca atgttttta gccgctcgct gcggctgcgc tcacacatgc     8100
ggcagcagct accatataca atttatatac caatatatgt acacatattt aattggtaca    8160
gttgtgtcca cttgcattgt atgtgtacac ttaacgcact cttgcaattc cggacaagtc    8220
aagaggagac aactagacgt tggcaatcgg aaattggaag ccttacagaa acactgcgtt    8280
tataacttgt tctcagctgt ttctctctct catcttgatt acattgcagc gctgcagagc    8340
aattatttgt gtgccgcatt gcgcggcatg gcatcgttga atcaaatgca tcgcactggg    8400
ccgcatataa agaagcgtcc gccacgtcag cccctgacg gtaaaccgtt tgccaaggga    8460
gtggtgctca agacactgat caagaagcca aagaaaccaa actcggcgaa tcgtaaatgc    8520
```

```
gcgctggtgc gcttatccac gggaaaggag atggtcgcct atatacccgg cattggacat    8580
aatctgcagg agcataatat tgtactgtgt cgcgtcggac gactgcagga tgtgcccggc    8640
gtcaagctga aggcggtgcg cggtgtctac gatctggcgc acgttatcaa gaagggccaa    8700
tgacaaccaa ctaccatgta attctcttcc ataaaaaaac aaaaaaaaaa taagaaaaga    8760
aaacaagcca aatctttgag tactctgcta ttcttgtgca gcatatatta ttatgatttt    8820
tttaatggaa aattatgcag ctcagcggga ttagtgtaag tagccaacac acaacaagtg    8880
agctctggcc tcgcctcatc ccaacttgtc ttgccgtaat cttaagtcaa caggccaaat    8940
tgcgagccaa acaattggcc agtgttgcca acgacgctgc cgaaaaagga gctaaatccc    9000
attggaaaat agctaaaaaa tagccagagc atgaattgga cgactgaaga cagctgaaat    9060
tggccagaat ttggccagaa tatagctgat atcgcaacac tgcacatttg ttgcccactc    9120
gaaatatgat tttaacggca tttttacgct ttagcaggca aatcccttt tgaagaaacg    9180 gcccgtcttt acttttaac agaatttgct tgcacaaatt ttatgccaaa taatcgttaa    9240
gcgaaatggg cgtcgacagg ccacgccaca ttttcacagt acgcagagcc tcgccacgcc    9300
tttgcaacag gatacaacaa attttgaata ggcaccgacc aggttgtcgt gcatctgggc    9360
tgaacgataa catctgtatt aaatcaatcc catattcaag cttccaaagg atttcggcaa    9420
catgccaatt ccgctattaa tcttcgggt tatcctgaat atctgggtag tcctaggtgt    9480
ggagctggtg tcgcttatgg cagagcagct gaatgctaac atatacgagc ataaaaagtt    9540
tcatcaggaa tccatatgca acttgaggtc cgaccccacc aactttttg cactgcaaaa    9600 aaacacgctt ttgcacgcgg gcccatacat agtacaaact ctacgtttcg tagactattt    9660
tacataaata gtctacaccg ttgtatacgc tccaaataca ctaccacaca ttgaacccttt    9720 ttgcagtgca aaaagtacg tgtcggcagt cacgtaggcc ggccttatcg ggtcgcgtcc    9780
tgtcacgtac gaatcacatt atcggaccgg acgagtgttg tcttatcgtg acaggacgcc    9840
agcttcctgt gttgctaacc gcagccgac gcaactcctt atcggaacag gacgcgcctc    9900
catatcagcc gcgcgttatc tcatgcgcgt gaccggacac gaggcgcccg tcccgcttat    9960
cgcgcctata aatacagccc gcaacgatct ggtaaacaca gttgaacaga tggtgagcaa   10020
gggcgaggag gtcatcaaag agttcatgcg cttcaaggtg cgcatggagg gctccatgaa   10080 cggcacgag ttcgagatcg agggcgaggg cgagggccgc ccctacgagg cacccagac   10140 cgccaagctg aaggtgacca agggcggccc cctgcccttc gcctgggaca tcctgtcccc   10200
ccagttcatg tacggctcca aggcgtacgt gaagcacccc gccgacatcc ccgattacaa   10260
gaagctgtcc ttccccgagg gcttcaagtg ggagcgcgtg atgaacttcg aggacggcgg   10320
tctggtgacc gtgacccagg actcctccct gcaggacggc acgctgatct acaaggtgaa   10380
gatgcgcggc accaacttcc cccccgacgg ccccgtaatg cagaagaaga ccatgggctg   10440
ggaggcctcc accgagcgcc tgtacccccg cgacggcgtg ctgaagggcg agatccacca   10500
ggccctgaag ctgaaggacg gcggccacta cctggtggag ttcaagacca tctacatggc   10560
caagaagccc gtgcaactgc ccggctacta ctacgtggac accaagctgg acatcacctc   10620
ccacaacgag gactacacca tcgtggaaca gtacgagcgc tccagggcc gccaccacct   10680 gttcctgggg catggcaccg gcagcaccgg cagcggcagc tccggcaccg cctcctccga   10740
ggacaacaac atggccgtta tcaaggaatt tatgcgcttc aaagttagga tggagggatc   10800
catgaacgga catgagttcg agatcgaggg agagggcgag gacgccgt atgaaggcac   10860 acaaacagcc aaactcaagg tcaccaaggg cggaccactg cccttcgcct gggatatcct   10920
```

```
gagtccccag tttatgtacg gcagcaaggc ctacgttaag caccccgctg acataccgga    10980
ctacaaaaag ctgtcctttc cggaaggctt caagtgggag cgcgtgatga atttcgaaga    11040
cggaggactg gtcactgtga cccaagatag cagtttgcag gacggtacac tgatctataa    11100
ggttaaaatg cgcggcacta actttccgcc agatggccca gtgatgcaga agaagaccat    11160
gggttgggag gcatccaccg aacgtctgta ccctcgagac ggagtgctca agggcgagat    11220
ccatcaggcc ctcaaactga agatggtgg tcactacctg gtcgaattta agaccattta     11280
catggccaag aagccggttc agctgcccgg atattattat gtggatacga aactggatat    11340
aacttcgcat aacgaagact acaccattgt cgagcagtat gagcgcagcg aaggccgaca    11400
tcacctgttc ctctacggca tggacgagct gtacaagtag gcggccgcga ctctagatca    11460
taatcagcca taccacattt gtagaggttt tacttgcttt aaaaaacctc ccacacctcc    11520
ccctgaacct gaaacataaa atgaatgcaa ttgttgttgt taacttgttt attgcagctt    11580
ataatggtta caaataaagc aatagcatca caaatttcac aaataaagca tttttttcac    11640
tgcattctag ttgtggtttg tccaaactca tcaatgtatc ttaaagcttc agtctctggt    11700
tgtgcatgga gcgtgttttt ggggcgattt acgagcgtga accgatattt tccatacgtc    11760
atgtttgcct tgctttacac tccaggaaac ctcatccgtt taatttagcc ggaagtgttg    11820
caatagatgc cacatcacaa tcgacttaat aattttttta ggagcaagtt ttaatggaaa    11880
cagtttctga taaataaata tacatatcaa cttagtacaa gaatatccag ctgaaagaat    11940
ggtatatata tatatatata tacttgtgtt tgtttctatg acagtttctt cacagctttc    12000
gattttctta tggcacatcg cgcgacagtt gaaatgaaaa actgaaatca gtgaaacccc    12060
gaaaaaactg aaaaagccac ggaaattgta cagatacaca gatacgcaga tacaccagca    12120
aatgtacaaa aaggtctata tacatatata tgtagctact cacttatgtt gtccttcgca    12180
gattgctccc tttaagcaaa taaaaaaaag ttggctccac gccgaaaaga aataaaatta    12240
aatggagaat cgcaaatcca tagtgagcca aaggcaaatc tataaaagaa atgaaacgaa    12300
attcattcat tttcgttttc gagttcgaat atttaagtta tatatataaa cgcagtattt    12360
atccatgtaa tcgaaccaca aaagcccaat gagaaaaccc tacattttat gctgagcatc    12420
acaaaatgcc tttcctttca catgaattta tgtattttaa tcaatttccc tcgctgtggc    12480
agttaaatat cctaaatttg tccaacgaaa ttgatgcttc aattattcga atgacgacgt    12540
ttaatgggct ttcgaggaat aaaagcaaaa attcacaaga aaacgcctc tgcatccatg      12600 ctcattatcg gaatcaatta aaatttcaca tgtatcgtta gcatggccat gtcagcaaat    12660
ccacgggatt cggctagagt cctccaaaat acgcccacgg gacccataca ccttcgaaat    12720
gatccaacat caatccctat ccaaatgtat acttagatat gtacatacct tgtcttttct    12780
tggtcggcga atgggggttc cagcatccca tcatcct                             12817
```

<210> SEQ ID NO 40
<211> LENGTH: 14148
<212> TYPE: DNA
<213> ORGANISM: Artificial
<220> FEATURE:
<223> OTHER INFORMATION: tko-step2

<400> SEQUENCE: 40

```
atcatcgatc tcgaggctgc atccaacgcg cgcgttggga gctctccgga tcaattcggc     60
ttcaggtacc gtcgacgatg taggtcacgg tctcgaagcc gcggtgcggg tgccagggcg    120
```

```
tgcccttggg ctccccgggc gcgtactcca cctcacccat ctggtccatc atgatgaacg      180
ggtcgaggtg gcggtagttg atcccggcga acgcgcggcg caccgggaag ccctcgccct      240
cgaaaccgct gggcgcggtg gtcacggtga gcacgggacg tgcgacggcg tcggctgggt      300
gcggatacgc ggggcagcgt cagcgggttc tcgacggtca cggcgggcat gtcgacgaca      360
tgttcgcctc atttgtgttc gtttatgtat tcgatgttat gtgtatgctc atgtgatgtt      420
tagcttgtaa gcgcgagatg tgggtagcag gagatgcagt gcagccaaca gcagtgacca      480
gatgatatat gctatgctac tactactact tatatgctat gatttgtggc gcggaggcgt      540
gtctgcgaca cataatcccg cccatttagc tttaagattc aggcactaag aagcaattcg      600
atcaataaat tattgtaacc actctgcatg tgagcaaaag gccagcaaaa ggccaggaac      660
cgtaaaaagg ccgcgttgct ggcgtttttc cataggctcc gccccctga cgagcatcac      720 aaaaatcgac gctcaagtca gaggtggcga acccgacag gactataaag ataccaggcg      780
tttccccctg gaagctccct cgtgcgctct cctgttccga ccctgccgct taccggatac      840
ctgtccgcct ttctcccttc gggaagcgtg gcgctttctc atagctcacg ctgtaggtat      900
ctcagttcgg tgtaggtcgt tcgctccaag ctgggctgtg tgcacgaacc cccgttcag      960 cccgaccgct gcgccttatc cggtaactat cgtcttgagt ccaacccggt aagacacgac      1020
ttatcgccac tggcagcagc cactggtaac aggattagca gagcgaggta tgtaggcggt      1080
gctacagagt tcttgaagtg gtggcctaac tacggctaca ctagaagaac agtatttggt      1140
atctgcgctc tgctgaagcc agttaccttc ggaaaaagag ttggtagctc ttgatccggc      1200
aaacaaacca ccgctggtag cggtggtttt tttgtttgca agcagcagat tacgcgcaga      1260
aaaaaaggat ctcaagaaga tcctttgatc ttttctacgg ggtctgacgc tcagtggaac      1320
gaaaactcac gttaagggat tttggtcatg agattatcaa aaaggatctt cacctagatc      1380
cttttaaatt aaaaatgaag ttttaaatca atctaaagta tatatgagta aacttggtct      1440
gacagttacc aatgcttaat cagtgaggca cctatctcag cgatctgtct atttcgttca      1500
tccatagttg cctgactccc cgtcgtgtag ataactacga tacgggaggg cttaccatct      1560
ggccccagtg ctgcaatgat accgcgagac ccacgctcac cggctccaga tttatcagca      1620
ataaaccagc cagccggaag ggccgagcgc agaagtggtc ctgcaacttt atccgcctcc      1680
atccagtcta ttaattgttg ccgggaagct agagtaagta gttcgccagt taatagtttg      1740
cgcaacgttg ttgccattgc tacaggcatc gtggtgtcac gctcgtcgtt tggtatggct      1800
tcattcagct ccggttccca acgatcaagg cgagttacat gatcccccat gttgtgcaaa      1860
aaagcggtta gctccttcgg tcctccgatc gttgtcagaa gtaagttggc cgcagtgtta      1920
tcactcatgg ttatggcagc actgcataat tctcttactg tcatgccatc cgtaagatgc      1980
ttttctgtga ctggtgagta ctcaaccaag tcattctgag aatagtgtat gcggcgaccg      2040
agttgctctt gcccggcgtc aatacgggat aataccgcgc cacatagcag aactttaaaa      2100
gtgctcatca ttggaaaacg ttcttcgggg cgaaaactct caaggatctt accgctgttg      2160
agatccagtt cgatgtaacc cactcgtgca cccaactgat cttcagcatc ttttactttc      2220
accagcgttt ctgggtgagc aaaaacagga aggcaaaatg ccgcaaaaaa gggaataagg      2280
gcgacacgga aatgttgaat actcatactc ttcctttttc aatattattg aagcatttat      2340
cagggttatt gtctcatgag cggatacata tttgaatgta tttagaaaaa taaacaaata      2400
ggggttccgc gcacatttcc ccgaaaagtg ccacctgacg tcgacggatc gggagatcgg      2460
cgcgggatct aattcaatta gagactaatt caattagagc taattcaatt aggatccaag      2520
```

```
cttatcgatt tcgaaccctc gaccgccgga gtataaatag aggcgcttcg tctacggagc    2580
gacaattcaa ttcaaacaag caaagtgaac acgtcgctaa gcgaaagcta agcaaataaa    2640
caagcgcagc tgaacaagct aaacaatcgg ctcgagaccg gtcgccacca tggtgagcaa    2700
gggcgaggag ctgttcaccg gggtggtgcc catcctggtc gagctggacg gcgacgtaaa    2760
cggccacaag ttcagcgtgt ccggcgaggg cgagggcgat gccacctacg gcaagctgac    2820
cctgaagttc atctgcacca ccggcaagct gcccgtgccc tggcccaccc tcgtgaccac    2880
cctgacctac ggcgtgcagt gcttcagccg ctaccccgac cacatgaagc agcacgactt    2940
cttcaagtcc gccatgcccg aaggctacgt ccaggagcgc accatcttct tcaaggacga    3000
cggcaactac aagacccgcg ccgaggtgaa gttcgagggc gacaccctgg tgaaccgcat    3060
cgagctgaag ggcatcgact tcaaggagga cggcaacatc ctggggcaca agctggagta    3120
caactacaac agccacaacg tctatatcat ggccgacaag cagaagaacg gcatcaaggt    3180
gaacttcaag atccgccaca acatcgagga cggcagcgtg cagctcgccg accactacca    3240
gcagaacacc cccatcggcg acggccccgt gctgctgccc gacaaccact acctgagcac    3300
ccagtccgcc ctgagcaaag accccaacga gaagcgcgat cacatggtcc tgctggagtt    3360
cgtgaccgcc gccgggatca ctctcggcat ggacgagctg tacaagtaaa gcggccgcga    3420
ctctagatca taatcagcca taccacattt gtagaggttt tacttgcttt aaaaaacctc    3480
ccacacctcc ccctgaacct gaaacataaa atgaatgcaa ttgttgttgt taacttgttt    3540
attgcagctt ataatggtta caaataaagc aatagcatca caatttcac aaataaagca    3600 ttttttcac tgcattctag ttgtggtttg tccaaactca tcaatgtatc ttagttgttg    3660
gttggcacac cacaaatata ctgttgccga gcacaattga tcggctaaat ggtatggcaa    3720
gaaaaggtat gcaatataat aatctttat tgggtatgca acgaaaattt gtttcgtcaa    3780
cgtatgcaat attctttatt aaagagggt atgcaatgta ttttattaaa acgggtatg    3840 caatataata atctttat gggtatgcaa cgaaaatttg tttcgtcaaa gtatgcaata    3900
ttttttatta aaagagggta tgcaatgtat tttattaaaa acgggtatgc aataaaaaat    3960
tatttggttt ctctaaaaag tatgcagcac ttatttttg ataaggtatg caacaaaatt    4020
ttactttgcc gaaaatatgc aatgtttttg cgaataaatt caacgcacac ttattacgtg    4080
gccaacgcgc ctagtggatc cttcctggcc cttttcgaga aacgccgcga gggcgaaaag    4140
gattagttgt ttcaaacgca agaaggacat tgtttccctt aaattgtaac catttcttta    4200
tttggcactc gagccattga attttcatt ttcagaatt gtgtacacat tttttaaaaa    4260
aataaaaaaa ttatataatg ctggcggttg tttcatgtgt gaaaaattga tcaatggtaa    4320
acaaaattga ataaatatat aacatatata tatagatatg tgtgttgaaa tgaatacttg    4380
cgatacatgt aataaaaata ctcttcgctt atctatcaaa agtgcggaa tgtcaaaatt    4440 taaaattta caatgaatgc gtagccgacg acgaaagtgt tccttgctat ttccttagc    4500 aagatttaaa tttagattaa attctaatga tacgattgac agttcgaaat tcaaagtgtt    4560
cctttttcaa aatttagtaa agattgtata tcaattgtag atatatcgaa attttcggc    4620 cgcaagcgaa cattttacaa aatgaaggcg accagttgca gaccaattcc attcatcaac    4680
tttcggattg taagatattt ctatcggcca cgacgattga acaagtatta cgatattgta    4740
agtcttcttt aacaaaatta gtttcccttt cacagaaaca gacataaatt cttgaattat    4800
tgacttggat ttgagtgatc gttcgttgtc tatactataa gatctatagg cacgggataa    4860
```

```
cgctctaaat ctcttaaaa tcgaacgcgc caggcgctag ttaaacgtta ctatctatct    4920
ggttaaccca gctttgatcg gaatgcgtat atatatttca tgttatataa acgctgcaaa    4980
agctgccaga gcctctgctc cagagctgga ttcgctcaca ccttcctctt cttcttgggg    5040
tcagccctgc tgtctccacc gagctgagag aggtcgattc ttgtttcata gagcccgta    5100
attgactgat gaatcagtgt ggcgtccagg acctcctttg tagaggtgta ccgctttctg    5160
tctatggtgg tgtcgaagta cttgaaggct gcaggcgcgc ccaagttggt cagagtaaac    5220
aagtggataa tgttttctgc ctgctccctg atgggcttat ccctgtgctt attgtaagca    5280
gaaagcacct tatcgaggtt agcgtcggcg aggatcactc ttttggagaa ttcgcttatt    5340
tgctcgatga tctcatcaag gtagtgtttg tgttgttcca cgaacagctg cttctgctca    5400
ttatcttcgg gagaccctt gagcttttca tagtggctgg ccagatacaa gaaattaacg    5460
tatttagagg gcagtgccag ctcgttacct ttctgcagct cgcccgcact agcgagcatt    5520
cgtttccggc cgttttcaag ctcaaagaga gagtacttgg gaagcttaat gatgaggtct    5580
ttttttgacct ctttatatcc tttcgcctcg agaaagtcga tggggttttt ttcgaagctt    5640
gatcgctcca tgattgtgat gcccagcagt tccttgacgc tttgagttt tttagacttc    5700
cctttctcca ctttggccac aaccagtaca ctgtaagcga ctgtaggaga atcgaatccg    5760
ccgtatttct tggggtccca atcttttttg cgtgcgatca gcttgtcgct gttccttttc    5820
gggaggatac tttccttgga gaagcctccg gtctgtactt cggtcttttt aacgatgttc    5880
acctgcggca tggacaggac cttccggact gtcgcgaaat ccctacccct gtcccacacg    5940
atttctcctg tttctccgtt tgtttcgata agtggtcgct tccgaatctc tccattggcc    6000
agtgtaatct cggtcttgaa aaaattcata atattgctgt aaaagaagta cttagcggtg    6060
gccttgccta tttcctgctc agactttgcg atcatttttcc taacatcgta cactttatag    6120
tctccgtaaa caaattcaga ttcaagcttg ggatatttt tgataagtgc agtgcctacc    6180
actgcattca ggtaggcatc atgcgcatgg tggtaattgt tgatctctct cacccttataa    6240
aactgaaagt cctttctgaa atctgagacc agcttagact tcagagtaat aactttcacc    6300
tctcgaatca gtttgtcatt ttcatcgtac ttggtgttca tgcgtgaatc gagaatttgg    6360
gccacgtgct tggtgatctg gcgtgtctca acaagctgcc ttttgatgaa gccggcttta    6420
tccaactcag acaggccacc tcgttcagcc ttagtcagat tatcgaactt ccgttgtgtg    6480
atcagtttgg cgttcagcag ctgccgccaa taatttttca ttttcttgac aacttcttct    6540
gaggggacgt tatcactctt ccctctattt ttatcggatc ttgtcaacac tttattatca    6600
atagaatcat ctttgagaaa agactggggc acgatatgat ccacgtcgta gtcggagagc    6660
cgattgatgt ccagttcctg atccacgtac atgtccctgc cgttctgcag gtagtacagg    6720
tagagcttct cattctgaag ctgggtgttt tcaactgggt gttccttaag gatttgggac    6780
cccagttctt ttatacccctc ttcaatcctc ttcatccttt ccctactgtt cttctgtccc    6840
ttctgggtag tttggttctc tcgggccatc tcgataacga tattctcggg cttatgcctt    6900
cccattactt tgacgagttc atccacgacc ttaacggtct gcagtattcc ctttttgata    6960
gctgggctac ctgcaagatt agcgatgtgc tcgtgaagac tgtcccctg ccagaaaact    7020
tgtgctttct ggatgtcctc cttaaaggtg agagagtcat catggatcaa ctgcatgaag    7080
ttccggttgg caaatccatc ggacttaaga aaatccagga ttgtctttcc actctgcttg    7140
tctcggatcc cattgatcag ttttcttgac agccgccccc atcctgtata tcggcgcctc    7200
ttgagctgtt tcatgacttt gtcgtcgaag agatgagcgt aagttttcaa gcgttcttca    7260
```

```
atcatctccc tatcttcaaa caacgtaagg gtgaggacaa tgtcctcaag aatgtcctcg   7320
ttctcctcat tgtccaggaa gtccttgtct ttaatgattt tcaggagatc gtgatacgtt   7380
cccagggatg cgttgaagcg atcctccact ccgctgattt caacagagtc gaaacattca   7440 atcttttga aatagtcttc tttgagctgt ttcacggtaa cttccggtt cgtcttgaag    7500
```

```
atcatctccc tatcttcaaa caacgtaagg gtgaggacaa tgtcctcaag aatgtcctcg   7320
ttctcctcat tgtccaggaa gtccttgtct ttaatgattt tcaggagatc gtgatacgtt   7380
cccagggatg cgttgaagcg atcctccact ccgctgattt caacagagtc gaaacattca   7440
atcttttga  aatagtcttc tttgagctgt ttcacggtaa ctttccggtt cgtcttgaag   7500
aggaggtcca cgatagcttt cttctgctct ccagacagga atgctggctt tctcatccct   7560
tctgtgacgt atttgacctt ggtgagctcg ttataaactg tgaagtactc gtacagcaga   7620
gagtgtttag gaagcacctt ttcgttaggc agatttttat caaagttagt catcctttcg   7680
atgaaggact gggcagaggc ccccttatcc acgacttcct cgaagttcca gggagtgatg   7740
gtctcttctg atttgcgagt catccacgcg aatctggaat tccccgggc  gaggggcct    7800
acatagtagg gtatccgaaa tgtgaggatt ttctcaatct tttccctgtt atctttcaaa   7860
aaggggtaga aatcctcttg ccgcctgagg atagcgtgca gttcgcccag gtgaatctgg   7920
tggggatgc  ttccattgtc gaaagtgcgc tgtttgcgca acagatcttc tctgttaagc   7980
tttaccagca gctcctcggt gccgtccatt ttttccaaga tgggcttaat aaatttgtaa   8040
aattcctcct ggcttgctcc gccgtcaatg tatccggcgt agccatttt  agactgatcg   8100
aagaaaattt ccttgtactt ctcaggcagt tgctgtctga aagggcctt  cagcaaagtc   8160
aagtcttggt ggtgctcatc atagcgcttg atcatactag cgctcagcgg agctttggtg   8220
atctccgtgt tcactcgcag aatatcactc agcagaatgg cgtctgacag gttcttttgcc  8280
gccaaaaaaa ggtctgcgta ctggtcgccg atctgggcca gcagattgtc gagatcatca   8340
tcgtaggtgt ctttgctcag ttgaagcttg gcatcttcgg ccaggtcgaa gttagattta   8400
aagttggggg tcagcccgag tgacagggcg ataagattac caaacaggcc gttcttcttc   8460
tccccaggga gctgtgcgat gaggttttcg agccgccggg atttggacag cctagcgctc   8520
aggattgctt tggcgtcaac tccggatgcg ttgatcgggt tctcttcgaa aagctgattg   8580
taagtctgaa ccagttggat aaagagtttg tcgacatcgc tgttgtctgg gttcaggtcc   8640
ccctcgatga ggaagtgtcc ccgaaatttg atcatatgcg ccagcgcgag atagatcaac   8700
cgcaagtcag cctatcagt  actgtctaca agcttcttcc tcagatgata tatggttggg   8760
tacttttcat ggtacgccac ctcgtccacg atattgccaa agattgggtg gcgctcgtgc   8820
ttttatcct  cctccaccaa aaaggactcc tccagcctat ggaagaaaga gtcatccacc   8880
ttagccatct cattactaaa gatctcctgc aggtagcaga tccgattctt tctgcgggta   8940
tatctgcgcc gtgctgttct tttgagccgc gtggcttcgg ccgtctcccc ggagtcgaac   9000
aggagggcgc caatgaggtt cttctttatg ctgtggcgat cggtattgcc cagaactttg   9060
aatttttgc  tcggcacctt gtactcgtcc gtaatgacgg cccagccgac gctgtttgtg   9120
ccgatatcga gcccaatgga gtacttcttg tccatggcga aaatccgggt cgaaagttac   9180
ggttatcgcg cactctactt tccacaaatc ctcacccaaa aaccaagcac agtttattca   9240
actgaagtat tcgcgatact tctttatcta ataataatgt acatgtaact aaactcgctt   9300
ttgggttaaa atcgtgacgc agaggcaaaa aaaatcgtat gtcccttaga caacttgaaa   9360
caactcgcaa gcgtacggca attccaggaa ttttgtggta aagctacgcg ccaactaacg   9420
gttcttgctt agaggtggaa taatgtagtt ttccagcgat aataaatata tcgatatttt   9480
tagtaaaatt gaaaaggtaa acttaatttt agaaaataat ttataagaaa tttaatagta   9540
tgcaaaataa ttttttacttg ctaagaatat gtgccactaa ttaaaagctg gacaccgcgc  9600
```

```
aatggaaaat agtactacaa cacagcaaca aagcctgagt tatcaacaaa aaaatacgaa    9660
aacatctccc aaaactaagc acccacacgc gccactcgcc gtcacaacac aatcactgca    9720
caccaccatt cgaatttcgc gcactgtgac aacatcacat gatatcggcg cggcaacatc    9780
ggattaccga caaaacgaac tatcgcacga gccaccgccg gcgaagagcg ctcgttttgc    9840
aacaccggcg cgcgctgaac gaagagaaca gctgactgct tgatacgtgc gtgtttcgcg    9900
gcaggaatta cataaagttt agagcctctg acgccagacc ccccgaacat tcgctccgat    9960
caaactacct gcgaacggtc acctaatccc caccatgcat ggtaggttac ctctgatccc   10020
ggtcatcact ggcgttcgct cacatccgtc cttacatgtg catatttcga ggttaaaacg   10080
gtcgaagctt ggatccgcta gcgttgttgg ttggcacacc acaaatatac tgttgccgag   10140
cacaattgat cggctaaatg gtatggcaag aaaaggtatg caatataata atctttatt    10200
gggtatgcaa cgaaaatttg tttcgtcaac gtatgcaata ttctttatta aagagggta   10260
tgcaatgtat tttattaaaa acgggtatgc aatataataa tcttttattg ggtatgcaac   10320
gaaaatttgt ttcgtcaaag tatgcaatat tttttattaa aagagggtat gcaatgtatt   10380
ttattaaaaa cgggtatgca ataaaaaatt atttggtttc tctaaaaagt atgcagcact   10440
tatttttga taaggtatgc aacaaatttt tactttgccg aaaatatgca atgttttgc     10500
gaataaattc aacgcacact tattacgtgg ccaactagcc tagttccagt gaaatccaag   10560
cacttgaggt ccgacccgat gaattctttt ttgctcacct gtgattgctc ctactcaaat   10620
acaaaaacat caaatttcct gtcaataaag catatttatt tatatttatt ttacaggaaa   10680
gaattccttt taaagtgtat tttaacctat aatgaaaaac gattaaaaaa aatacataaa   10740
ataattcgaa aattttgaa tagcccaggt tgataaaaat tcatttcata cgttttataa    10800
cttatgcccc taagtatttt ttgaccctag tgtttcaatt ctacattaat tttacagagt   10860
agaatgaaac gccacctact cagccaagag gcgaaaaggt tagctcgcca agcagagagg   10920
gcgccagtgc tcactacttt ttataattct caacttcttt ttccagactc agttcgtata   10980
tatagaccta ttttcaattt aacgtcgctg cagcgatgcc attccagttt cagagctatg   11040
ctggaaacag catagcaagt tgaaataagg ctagtccgtt atcaacttga aaaagtggca   11100
ccgagtcggt gcttttttgc ctacctggag cctgagagtt gttcaataaa ataaaatgt    11160
ttcgtttttt tgctttcgcc agtatttatt attttcatc aatatgtatt caatttggta   11220
tgtatttagt aattgtaata tatagacaat ggttttccgt tgacgtacat acatctgacg   11280
tgtgtttatt tagacataat agttatgttt tcacatcttt ttaatgttcg cttaatgcgt   11340
atgcattcta gattttcaac gtcctcgata gtatagtggt tagtatcccc gcctgtcacg   11400
cgggagaccg gggttcaatt ccccgtcggg gagaatctgt gattcttttt tttttctttt   11460
tactttgtta tataaacaat ttttgtttta attgaatcta atttgccatt gcttttagga   11520
atctcaggca tccagcaagc gtttgtccgc cgaatcgccc atcagtgaag aagatcctgt   11580
ggcggctacg aaaatctccc cggccatgtc ggcctccacc tccagcgaaa aacccatcag   11640
cgagctggcc acctctgtgc tgacccaccg ctttccagac tccacctcct cacccggcga   11700
acatggcctt ggacgaatgc agttgtcgat ccgctacagc gccagcgtc aaaaactaga    11760
cgtgaccata cacaaaatcc agaagatacc acttcgcgat cccagcaata tccccgatcc   11820
gtatgttaag ctgtatctgt tgcctggacg caccaaggag tcgaaacgca agacgagcgt   11880
gatcaaggac aactgcaacc ccgtctacga tgcatccttt gagtacctga tttccattgc   11940
cgaactcagg cagacggaac tggaggtgac ggtgtgcacc caaaagggat tcctatccgg   12000
```

```
cggtagtccc atcattggca tggtaggtac ccgaaagcaa ccccttagtt acagacacag  12060
cgcgtacgtc cttcgcatcc ttatgattcc caagtacata ttctgcaaga gtacagtata  12120
tataggaaag atatccgggt gaacttcgca ggacaacgcc cttggcgagt ttcagagcta  12180
tgctggaaac agcatagcaa gttgaaataa ggctagtccg ttatcaactt gaaaagtgg   12240 caccgagtcg gtgctttttt gcctacctgg agcctgagag ttgttcaatc tagacaattg  12300
tgctcggcaa cagtatattt gtggtgtgcc aaccaacaac ctgcaggagc tccagctttt  12360
gttcccttta gtgagggtta attttttttg ctcacctgtg attgctccta ctcaaataca  12420
aaaacatcaa attttctgtc aataaagcat atttatttat atttatttta caggaaagaa  12480
ttccttttaa agtgtatttt aacctataat gaaaacgat  taaaaaaaat acataaaata  12540
attcgaaaat ttttgaatag cccaggttga taaaaattca tttcatacgt tttataactt  12600
atgcccctaa gtattttttg accatagtgt ttcaattcta cattaatttt acagagtaga  12660
atgaaacgcc acctactcag ccaagaggcg aaaaggttag ctcgccaagc agagagggcg  12720
ccagtgctca ctacttttta taattctcaa cttctttttc cagactcagt tcgtatatat  12780
agacctattt tcaatttaac gtcgcaacat tgtactgtgc cgcggtttca gagctatgct  12840
ggaaacagca tagcaagttg aaataaggct agtccgttat caacttgaaa agtggcacc   12900 gagtcggtgc ttttttgcct acctggagcc tgagagttgt tcaataaaat aaaaatgttt  12960 cgttttttg ctttcgccag tatttattat ttttcatcaa tatgtattca atttggtatg   13020
tatttagtaa ttgtaatata tagacaatgg ttttccgttg acgtacatac atctgacgtg  13080
tgtttattta gacataatag ttatgttttc acatcttttt aatgttcgct taatgcgtat  13140
gcattctaga ttttcaacgt cctcgatagt atagtggtta gtatcccgc ctgtcacgcg    13200 ggagaccggg gttcaattcc ccgtcgggga gaatctgtga ttctttttt  ttttctttta   13260 ctttgttata taaacaattt ttgttttaat tgaatctaat ttgccattgc ttttaggaat   13320
ctcaggcatc cagcaagcgt ttgtccgccg aatcgcccat cagtgaagaa gatcctgtgg  13380
cggctacgaa aatctccccg gccatgtcgg cctccacctc cagcgaaaaa cccatcagcg  13440
agctggccac ctctgtgctg acccaccgct ttccagactc cacctcctca cccggcgaac  13500
atggccttgg acgaatgcag ttgtcgatcc gctacagcgc ccagcgtcaa aaactagacg  13560
tgaccataca caaaatccag aagataccac ttcgcgatcc cagcaatatc cccgatccgt  13620
atgttaagct gtatctgttg cctggacgca ccaaggagtc gaaacgcaag acgagcgtga  13680
tcaaggacaa ctgcaaccc  gtctacgatg catcctttga gtacctgatt tccattgccg   13740
aactcaggca gacggaactg gaggtgacgg tgtgcaccca aaagggattc ctatccggcg  13800
gtagtcccat cattggcatg gtaggtaccc gaaagcaacc ccttagttac agacacagcg  13860
cgtacgtcct tcgcatcctt atgattccca agtacatatt ctgcaagagt acagtatata  13920
taggaaagat atccgggtga acttcgcacc agcacgcact ttcgatgttt cagagctatg  13980
ctggaaacag catagcaagt tgaaataagg ctagtccgtt atcaacttga aaagtggca   14040 ccgagtcggt gcttttttgc ctacctggag cctgagagtt gttcaatcta gacaattgtg  14100
ctcggcaaca gtatatttgt ggtgtgccgt accgggccaa ttcgagct              14148
```

<210> SEQ ID NO 41
<211> LENGTH: 4152
<212> TYPE: DNA
<213> ORGANISM: Artificial
<220> FEATURE:

<223> OTHER INFORMATION: Dvir-rescue-modified

<400> SEQUENCE: 41

```
gctgcaggcg ggcagcaagg cgtcccatcc gcattacgtg cccagctatt tgccagctat        60
gcccgatcct catgcctata ttcgaacgcc cacgcacaag cagcccgtaa ccgaatacga       120
ggcaataagg gaaaaggcag ccagtcagaa gcgtgacgtt gagaaggcgc tgaccaaatt       180
tctgtgcaaa acaacagaaa caaacaatct ctttcccacc gaggacaaca tgtttccgtg       240
taagtaagcg ctgcgattaa tggttcttgg ttctttattc aaatgtttcg acttcttttt       300
ctgaatgcaa cagtaatcgc ctgtaagccc gcctttccgg cgtatgcagc tgccttgaat       360
cccacagatc aggtatttga cttcgaggag ctggagtacc actacttggt ggccaatcgt       420
acggaagatg tgcccagtaa aggtaggtcc aaattgtaca caatagatat tccaatgaac       480
acaggctcta ctttcatttg cagaggaggg cgaggagggt gacagtgaga atgaggaact       540
ggatggcgac aagtccaagg aggagaagcc cgagctggag atcaagccca attcaacaac       600
aaataaagct attttagaga atcccaatat agacaatccc tacttgcgtg ccgctacact       660
gccaaagcgt tccaagctgc acagtgagtg cactacacca cgcatggtgc cctcacgaag       720
tatacactcg gcttcaccca cgacaccgac gccctcaact ctagagataa ccaaaagtag       780
tgcttagtta taattataaa tagatgcatt gtaattgtgt atagtttttt aaaaaaaaaa       840
tattggataa acaaactctt ttcttcttat cgatagttcg tgcttttgct taaaatggtg       900
tgcgatggca gcgctgcggc aacaaacagc tgtttcgata taaaagtaca ttttacttat       960
cgatagctcg tgctattgca taaaatgatg ttaggtggca acgctgcggc aacaatcagc      1020
tgtttaccag gccgcagcaa cgttacagtg cattttacat tttaccaagt tgaattaata      1080
aaattgcttt ttaaaagtgt ttactaaatt aaaaagccaa caaattgttg ttgttttcgt      1140
tgcttacaag cggctgctgt acataaatta tacatattag cgctaaacgt gctcaacatg      1200
aatttcctgc gccaaacatt caacgttacg aaacaattga cggcacaagg taagttttaa      1260
caaaaatccc tatttaaaac attgcgttgc ggctatttat tcaacttcga gtcccgtgtt      1320
ctatatacat acgcgcccac gcgcctaatt gccaaccatg tgaggcagcc ggtagccgct      1380
tgcgcacatc catttccaat tggtgactgt gcgcattttg tgtttatcca aggatcctgc      1440
gttccattgt gtgcacacaa tgatttgtat tgtctgttgt ttgcctgcga tctcaactct      1500
tttacatggg cgcgtggccg gcttgcgagc ctgtcgcccg tctgccagtt ctctagttgt      1560
cgtcgtaccc cccttcccccc tgcccagccc cttatcgtgt gtctagtctg tgaatatttt      1620
tataagcatt ttctcatgtg tgtttcctgt ttgtgtgttt taatgtgtcc tcaaaactgt      1680
tcacggagcc tacaaagtgt gtattgagaa tatatatata tatatatagt ccatctgtcc      1740
atcttggata tttgtcattg gaacgggcga gcgaaaaaag ggtttgtcaa tgaaaaactt      1800
atcattttca ttatgtgcaa catttactaa ccaaatctat tcaatacata ggttggacaa      1860
acttgccttc tgttcttcga gataacttca gcaaagtctg ccaatgcgat ctgaagtcca      1920
ttcaattttt ggcctagcaa aaaacgcatt cgttttctg cttgttttaa ttaaaattca      1980
caacaaaatc cgcataacat gaggcccacc ctcaacaata ggaatttgca tgacatgcac      2040
acaataagga aaaacaaca caagaaaaaa aaattatgag aaaaggacac acacacacac      2100
acaggtgcgt tcggatcgcg gcagacaatg cacggagctg tgattggcat agttcttgct      2160
gtgcgcctgc tcccattgta agcgattgtc cagcgttatg gtaattatta cctgtgtgta      2220
cgtgtgtgtg tgtgtgtgtg gcatttaatt aaaaaattgtt gtcgtttgcg attttggctg      2280
```

```
cagtacagtc gagtccagtc gggagtccag ctgaacagaa atctgagcat cagacagtca    2340
acccccgtgc atggctaaag gttctcaatg cttaaaaggc ttgagaactg cagttgccgc    2400
tgacccacag ccgcgtcatt tggctgcaat tatttgtgaa ataaccttat atatgcatg    2460
atatgtggat ggatatggat ggatatatgg atgtgcgcag cataacaatt attttgcgat    2520
tttcacagag attagccaca acaaaaggcg aatggccatt gttgcttggg catttggaac    2580
tggccaactg tttctgaccc ttttgtcatg ttgtgtccgt tctctcgttt gtgtcaaatg    2640
ttttttagccg ctcgctgcgg ctgcgctcac acatgcggca gcagctacca tatacaattt    2700
ataccaat atatgtacac atatttaatt ggtacagttg tgtccacttg cattgtatgt    2760
gtacacttaa cgcactcttg caattccgga caagtcaaga ggagacaact agacgttggc    2820
aatcggaaat tggaagcctt acagaaacac tgcgtttata acttgttctc agctgtttct    2880
ctctctcatc ttgattacat tgcagcgctg cagagcaatt atttgtgtgc cgcattgcgc    2940
ggcatggcat cgttgaatca aatgcatcgc actgggccgc atataaagaa gcgtccgcca    3000
cgtcagcccc tggacggtaa accgtttgcc aagggagtgg tgctcaagac actgatcaag    3060
aagccaaaga aaccaaactc ggcgaatcgt aaatgcgcgc tggtgcgctt atccacggga    3120
aaggagatgg tcgcctatat acccggcatt ggacataatc tgcaggagca taatattgta    3180
ctgtgtcgcg tcggacgact gcaggatgtg cccggcgtca agctgaaggc ggtgcgcggt    3240
gtctacgatc tggcgcacgt tatcaagaag ggccaatgac aaccaactac catgtaattc    3300
tcttccataa aaaacaaaa aaaaaataag aaagaaaac aagccaaatc tttgagtact    3360
ctgctattct tgtgcagcat atattattat gattttttta atggaaaatt atgcagctca    3420
gcgggattag tgtaagtagc caacacacaa caagtgagct ctggcctcgc ctcatcccaa    3480
cttgtcttgc cgtaatctta agtcaacagg ccaaattgcg agccaaacaa ttggccagtg    3540
ttgccaacga cgctgccgaa aaaggagcta aatcccattg gaaaatagct aaaaaatagc    3600
cagagcatga attggacgac tgaagacagc tgaaattggc cagaatttgg ccagaatata    3660
gctgatatcg caacactgca catttgttgc ccactcgaaa tatgatttta acggcatttt    3720
tacgctttag caggcaaatc cctttttgaa gaaacggccc gtctttactt tttaacagaa    3780
tttgcttgca caattttat gccaaataat cgttaagcga aatgggcgtc gacaggccac    3840
gccacatttt cacagtacgc agagcctcgc cacgcctttg caacaggata caacaaattt    3900
tgaataggca ccgaccaggt tgtcgtgcat ctgggctgaa cgataacatc tgtattaaat    3960
caatcccata ttcaagcttc caaaggattt cggcaacatg ccaattccgc tattaatctt    4020
tcgggttatc ctgaatatct gggtagtcct aggtgtggag ctggtgtcgc ttatggcaga    4080
gcagctgaat gctaacatat acgagcataa aaagtttcat caggaatcca tatgcaactt    4140
gaggtccgac cc                                                        4152
```

<210> SEQ ID NO 42
<211> LENGTH: 12817
<212> TYPE: DNA
<213> ORGANISM: Artificial
<220> FEATURE:
<223> OTHER INFORMATION: tko-step1-genbank

<400> SEQUENCE: 42

```
agcttgtacc caattcgccc tatagtgagt cgtattacaa ttcactggcc gtcgttttac      60
aacgtcgtga ctgggaaaac cctggcgtta cccaacttaa tcgccttgca gcacatcccc     120
```

```
ctttcgccag ctggcgtaat agcgaagagg cccgcaccga tcgcccttcc aacagttgc    180
gcagcctgaa tggcgaatgg gacgcgccct gtagcggcgc attaagcgcg gcgggtgtgg   240
tggttacgcg cagcgtgacc gctacacttg ccagcgccct agcgcccgct cctttcgctt   300
tcttcccttc ctttctcgcc acgttcgccg gctttccccg tcaagctcta atcgggggc    360
tccctttagg gttccgattt agtgctttac ggcacctcga ccccaaaaaa cttgattagg   420
gtgatggttc acgtagtggg ccatcgccct gatagacggt ttttcgccct ttgacgttgg   480
agtccacgtt ctttaatagt ggactcttgt tccaaactgg aacaacactc aaccctatct   540
cggtctattc ttttgattta agggatttt gccgatttc ggcctattgg ttaaaaaatg     600
agctgattta caaaaattt aacgcgaatt ttaacaaaat attaacgctt acaatttagg    660
tggcactttt cggggaaatg tgcgcggaac ccctatttgt ttattttct aaatacattc    720
aaatatgtat ccgctcatga caataaacc ctgataaatg cttcaataat attgaaaaag    780
gaagagtatg agtattcaac atttccgtgt cgcccttatt ccctttttg cggcattttg    840
ccttcctgtt tttgctcacc cagaaacgct ggtgaaagta aaagatgctg aagatcagtt   900
gggtgcacga gtgggttaca tcgaactgga tctcaacagc ggtaagatcc ttgagagttt   960
tcgccccgaa gaacgttttc aatgatgag cactttaaa gttctgctat gtggcgcggt    1020
attatcccgt attgacgccg ggcaagagca actcggtcgc cgcatacact attctcagaa   1080
tgacttggtt gagtactcac cagtcacaga aaagcatctt acggatggca tgacagtaag   1140
agaattatgc agtgctgcca taaccatgag tgataacact gcggccaact tacttctgac   1200
aacgatcgga ggaccgaagg agctaaccgc ttttttgcac aacatggggg atcatgtaac   1260
tcgccttgat cgttgggaac cggagctgaa tgaagccata ccaaacgacg agcgtgacac   1320
cacgatgcct gtagcaatgg caacaacgtt gcgcaaacta ttaactggcg aactacttac   1380
tctagcttcc cggcaacaat aatagactg gatggaggcg gataaagttg caggaccact   1440
tctgcgctcg gcccttccgg ctggctggtt tattgctgat aaatctggag ccggtgagcg   1500
tgggtctcgc ggtatcattg cagcactggg gccagatggt aagccctccc gtatcgtagt   1560
tatctacacg acggggagtc aggcaactat ggatgaacga aatagacaga tcgctgagat   1620
aggtgcctca ctgattaagc attggtaact gtcagaccaa gtttactcat atatacttta   1680
gattgattta aaacttcatt tttaatttaa aaggatctag gtgaagatcc ttttgataa    1740
tctcatgacc aaaatccctt aacgtgagtt ttcgttccac tgagcgtcag accccgtaga   1800
aaagatcaaa ggatcttctt gagatccttt ttttctgcgc gtaatctgct gcttgcaaac   1860
aaaaaaacca ccgctaccag cggtggtttg tttgccggat caagagctac caactctttt   1920
tccgaaggta actggcttca gcagagcgca gataccaaat actgtccttc tagtgtagcc   1980
gtagttaggc caccacttca agaactctgt agcaccgcct acatacctcg ctctgctaat   2040
cctgttacca gtggctgctg ccagtggcga taagtcgtgt cttaccgggt tggactcaag   2100
acgatagtta ccggataagg cgcagcggtc gggctgaacg gggggttcgt gcacacagcc   2160
cagcttggag cgaacgacct acaccgaact gagataccta cagcgtgagc tatgagaaag   2220
cgccacgctt cccgaaggga gaaaggcgga caggtatccg gtaagcggca gggtcggaac   2280
aggagagcgc acgagggagc ttccagggg aaacgcctgg tatctttata gtcctgtcgg    2340
gtttcgccac ctctgacttg agcgtcgatt tttgtgatgc tcgtcagggg ggcggagcct   2400
atggaaaaac gccagcaacg cggccttttt acggttcctg gccttttgct ggccttttgc   2460
tcacatgttc tttcctgcgt tatcccctga ttctgtggat aaccgtatta ccgcctttga   2520
```

```
gtgagctgat accgctcgcc gcagccgaac gaccgagcgc agcgagtcag tgagcgagga    2580
agcggaagag cgcccaatac gcaaaccgcc tctccccgcg cgttggccga ttcattaatg    2640
cagctggcac gacaggtttc ccgactggaa agcgggcagt gagcgcaacg caattaatgt    2700
gagttagctc actcattagg caccccaggc tttacacttt atgcttccgg ctcgtatgtt    2760
gtgtggaatt gtgagcggat aacaatttca cacaggaaac agctatgacc atgattacgc    2820
caagcgcgca attaaccctc actaaaggga acaaaagctg gagctcctgc aggttgttgg    2880
ttggcacacc acaaatatac tgttgccgag cacaattgtc tagaatgcat acgcattaag    2940
cgaacattaa aaagatgtga aaacataact attatgtcta aataaacaca cgtcagatgt    3000
atgtacgtca acggaaaacc attgtctata tattacaatt actaaataca taccaaattg    3060
aatacatatt gatgaaaaat aataaatact ggcgaaagca aaaaaacgaa acattttttat   3120 tttattgaac aactctcagg ctccaggtag gcaaaaaagc accgactcgg tgccacttttt   3180 tcaagttgat aacggactag ccttatttca acttgctatg ctgtttccag catagctctg    3240
aaacctccag tctctggttg tgcacgacgt taaattgaaa ataggtctat atatacgaac    3300
tgagtctgga aaagaagtt gagaattata aaagtagtg agcactggcg ccctctctgc      3360
ttggcgagct aaccttttcg cctcttggct gagtaggtgg cgtttcattc tactctgtaa    3420
aattaatgta gaattgaaac actatggtca aaaaatactt aggggcataa gttataaaac    3480
gtatgaaatg aattttatc aacctgggct attcaaaaat tttcgaatta ttttatgtat     3540
tttttttaat cgttttcat tataggttaa aatacacttt aaaaggaatt ctttcctgta     3600
aaataaatat aaataaatat gctttattga cagaaaattt gatgtttttg tatttgagta    3660
ggagcaatca caggtgagca aaaaagaatt catcaattga tcggctaaat ggtatggcaa    3720
gaaaaggtat gcaatataat aatcttttat tgggtatgca acgaaaattt gtttcgtcaa    3780
cgtatgcaat attctttatt aaagaggggt atgcaatgta ttttattaaa acgggtatg    3840 caatataata atcttttatt gggtatgcaa cgaaaatttg tttcgtcaaa gtatgcaata   3900 tttttatta aaagagggta tgcaatgtat tttattaaaa acgggtatgc aataaaaaat    3960
tatttggttt ctctaaaaag tatgcagcac ttattttttg ataaggtatg caacaaaatt   4020
ttactttgcc gaaaatatgc aatgtttttg cgaataaatt caacgcacac ttattacgtg    4080
gccaactagg tgcccaaaat gtgtgtggac tacgaaattt ccaaatttta agatgctatc    4140
tttaaaccaa tgaaatatgg ttcgtatact atgaattttc aattaggcga acatcaatga    4200
ttcccccccc agaaaaccga catagcagag cacacgagca ggcgcaaatt gagaaaccca    4260
tccgcgtgaa gtcggttaat ttgcccatct tcttctggac gcgttcgtgc acccgctgct    4320
catccggcgg agtattgtac cattgtgtac ggccgtagtc cgtgtgcctt cgttttggcg    4380
ttcatgcatg agcagcccaa ttccttgctg ccccattcgg ttacattgca cagtggacac    4440
aaaagctagt tttgtagtca agtacagaa ttcacaaatt atataaactg atatagttca     4500
tagatagtat aaactgatac caagtaacag atacacattt aaataggtaa actgtgtctg    4560
tgatcaaact gtttcttttc gtgtcgaaga atcaattaaa aatgattgaa tcattatatt    4620
tatttccgtt aaaagctgtg caggctgttc aaaatgtttt aatgaaaaaa tacgaatttt    4680
tagactgtct gaatcacagt gtgctcgctt acatttccgc tttcctctttt tggcaactcg   4740 atgtcgcctt tggggctctt ttggagaccg gaaaaggca acatttttcta ttcgattctt    4800 tttgccaatt gcccgagact gtgtcctgtc ggcatatgac gaatacgtaa cgtacgtgac    4860
```

```
ggcgacgtta ctcatacgca ccgtgggtag ctgcagacat ctcagcaccc acgttcgcga    4920
attattttga attcgactcc ctgggcgata tttgtttttc gcttttgcat attttgcggg    4980
caatttgggt aaaaggattt ccgcactctg cgacgccgtc ttcagtttgc ggctttcgtt    5040
tttttcctag tagttcggca cacattttcc tcgccgcttc ggcaaatcgc tcacgtaaaa    5100
tatgcatgcg tttccttggc ggttttgcgc tctcaagtgc ctgcaattca attacatttc    5160
gattgatttt catgtttggc cccaaatcgc ggcaaaacct ctcactgacg dcacaccga    5220 agccccggcg gcaaccctca gcggatgccc cggggcttca cgttttccca ggtcagaagc    5280
ggttttcggg agtagtgccc caactgggt aacctttgag ttctctcagt tgggggcgta    5340
gggtcgccga catgacacaa ggggttgtga ccggggtgga cacgtacgcg ggtgcttacg    5400
accgtcagtc gcgcgagcgc gactgctgca ggcgggcagc aaggcgtccc atccgcatta    5460
cgtgcccagc tatttgccag ctatgcccga tcctcatgcc tatattcgaa cgcccacgca    5520
caagcagccc gtaaccgaat acgaggcaat aagggaaaag gcagccagtc agaagcgtga    5580
cgttgagaag gcgctgacca aatttctgtg caaaacaaca gaaacaaaca atctctttcc    5640
caccgaggac aacatgtttc cgtgtaagta agcgctgcga ttaatggttc ttggttcttt    5700
attcaaatgt ttcgacttct ttttctgaat gcaacagtaa tcgcctgtaa gcccgccttt    5760
ccggcgtatg cagctgcctt gaatcccaca gatcaggtat ttgacttcga ggagctggag    5820
taccactact tggtggccaa tcgtacgaaa gatgtgccca gtaaaggtag gtccaaattg    5880
tacacaatag atattccaat gaacacaggc tctactttca tttgcagagg agggcgagga    5940
gggtgacagt gagaatgagg aactggatgg cgacaagtcc aaggaggaga gcccgagct    6000 ggagatcaag cccaattcaa caacaaataa agctatttta gagaatccca atatagacaa    6060
tccctacttg cgtgccgcta cactgccaaa gcgttccaag ctgcacagtg agtgcactac    6120
accacgcatg gtgccctcac gaagtataca ctcggcttca cccacgacac cgacgccctc    6180
aactctagag ataaccaaaa gtagtgctta gttataatta taaatagatg cattgtaatt    6240
gtgtatagtt ttttaaaaaa aaaatattgg ataaacaaac tcttttcttc ttatcgatag    6300
ttcgtgcttt tgcttaaaat ggtgtgcgat ggcagcgctg cggcaacaaa cagctgtttc    6360
gatataaaag tacattttac ttatcgatag ctcgtgctat tgcataaaat gatgttaggt    6420
ggcaacgctg cggcaacaat cagctgttta ccaggccgca gcaacgttac agtgcatttt    6480
acattttacc aagttgaatt aataaaattg cttttttaaaa gtgtttacta aattaaaaag    6540
ccaacaaatt gttgttgttt tcgttgctta caagcggctg ctgtacataa attatacata    6600
ttagcgctaa acgtgctcaa catgaatttc ctgcgccaaa cattcaacgt tacgaaacaa    6660
ttgacggcac aaggtaagtt ttaacaaaaa tccctattta aaacattgcg ttgcggctat    6720
ttattcaact tcgagtcccg tgttctatat acatacgcgc ccacgcgcct aattgccaac    6780
catgtgaggc agccggtagc cgcttgcgca catccatttc caattggtga ctgtgcgcat    6840
tttgtgttta tccaaggatc ctgcgttcca ttgtgtgcac acaatgattt gtattgtctg    6900
ttgtttgcct gcgatctcaa ctcttttaca tgggcgcgtg gccggcttgc gagcctgtcg    6960
cccgtctgcc agttctctag ttgtcgtcgt acccccttc cccctgccca gcccttatc    7020 gtgtgtctag tctgtgaata ttttatttaag cattttctca tgtgtgtttc ctgtttgtgt    7080
gttttaatgt gtcctcaaaa ctgttcacgg agcctacaaa gtgtgtattg agaatatata    7140
tatatatata tagtccatct gtccatcttg gatttgtc attggaacgg gcgagcgaaa    7200
aaagggtttg tcaatgaaaa acttatcatt ttcattatgt gcaacattta ctaaccaaat    7260
```

| | |
|---|---|
| ctattcaata cataggttgg acaaacttgc cttctgttct tcgagataac ttcagcaaag | 7320 |
| tctgccaatg cgatctgaag tccattcaat ttttggccta gcaaaaaacg cattcgtttt | 7380 |
| tctgcttgtt ttaattaaaa ttcacaacaa aatccgcata acatgaggcc caccctcaac | 7440 |
| aataggaatt tgcatgacat gcacacaata aggaaaaaac aacacaagaa aaaaaaatta | 7500 |
| tgagaaaagg acacacacac acacacaggt gcgttcggat cgcggcagac aatgcacgga | 7560 |
| gctgtgattg gcatagttct tgctgtgcgc ctgctcccat tgtaagcgat tgtccagcgt | 7620 |
| tatggtaatt attacctgtg tgtacgtgtg tgtgtgtgtg tgtggcattt aattaaaaat | 7680 |
| tgttgtcgtt tgcgattttg gctgcagtac agtcgagtcc agtcgggagt ccagctgaac | 7740 |
| agaaatctga gcatcagaca gtcaaccccc gtgcatggct aaaggttctc aatgcttaaa | 7800 |
| aggcttgaga actgcagttg ccgctgaccc acagccgcgt catttggctg caattatttg | 7860 |
| tgaaaataac cttatatatg catgatatgt ggatggatat ggatggatat atggatgtgc | 7920 |
| gcagcataac aattattttg cgattttcac agagattagc cacaacaaaa ggcgaatggc | 7980 |
| cattgttgct tgggcatttg gaactggcca actgtttctg acccttttgt catgttgtgt | 8040 |
| ccgttctctc gtttgtgtca aatgttttta gccgctcgct gcggctgcgc tcacacatgc | 8100 |
| ggcagcagct accatataca atttatatac caatatatgt acacatattt aattggtaca | 8160 |
| gttgtgtcca cttgcattgt atgtgtacac ttaacgcact cttgcaattc cggacaagtc | 8220 |
| aagaggagac aactagacgt tggcaatcgg aaattggaag ccttacagaa acactgcgtt | 8280 |
| tataacttgt tctcagctgt ttctctctct catcttgatt acattgcagc gctgcagagc | 8340 |
| aattatttgt gtgccgcatt gcgcggcatg gcatcgttga atcaaatgca tcgcactggg | 8400 |
| ccgcatataa agaagcgtcc gccacgtcag cccctggacg gtaaaccgtt tgccaaggga | 8460 |
| gtggtgctca agacactgat caagaagcca aagaaaccaa actcggcgaa tcgtaaatgc | 8520 |
| gcgctggtgc gcttatccac gggaaaggag atggtcgcct atatacccgg cattggacat | 8580 |
| aatctgcagg agcataatat tgtactgtgt cgcgtcggac gactgcagga tgtgcccggc | 8640 |
| gtcaagctga aggcggtgcg cggtgtctac gatctggcgc acgttatcaa gaagggccaa | 8700 |
| tgacaaccaa ctaccatgta attctcttcc ataaaaaaac aaaaaaaaaa taagaaaaga | 8760 |
| aaacaagcca aatctttgag tactctgcta ttcttgtgca gcatatatta ttatgatttt | 8820 |
| tttaatggaa aattatgcag ctcagcggga ttagtgtaag tagccaacac acaacaagtg | 8880 |
| agctctggcc tcgcctcatc ccaacttgtc ttgccgtaat cttaagtcaa caggccaaat | 8940 |
| tgcgagccaa acaattggcc agtgttgcca acgacgctgc cgaaaagga gctaaatccc | 9000 |
| attggaaaat agctaaaaaa tagccagagc atgaattgga cgactgaaga cagctgaaat | 9060 |
| tggccagaat ttggcagaa tatagctgat atcgcaacac tgcacatttg ttgcccactc | 9120 |
| gaaatatgat tttaacggca ttttacgct ttagcaggca aatccctttt tgaagaaacg | 9180 |
| gcccgtctttt acttttttaac agaatttgct tgcacaaatt ttatgccaaa taatcgttaa | 9240 |
| gcgaaatggg cgtcgacagg ccacgccaca ttttcacagt acgcagagcc tcgccacgcc | 9300 |
| tttgcaacag gatacaacaa attttgaata ggcaccgacc aggttgtcgt gcatctgggc | 9360 |
| tgaacgataa catctgtatt aaatcaatcc catattcaag cttccaaagg atttcggcaa | 9420 |
| catgccaatt ccgctattaa tctttcgggt tatcctgaat atctgggtag tcctaggtgt | 9480 |
| ggagctggtg tcgcttatgg cagagcagct gaatgctaac atatacgagc ataaaaagtt | 9540 |
| tcatcaggaa tccatatgca acttgaggtc cgaccccacc aacttttttg cactgcaaaa | 9600 |

```
aaacacgctt ttgcacgcgg gcccatacat agtacaaact ctacgtttcg tagactattt    9660
tacataaata gtctacaccg ttgtatacgc tccaaataca ctaccacaca ttgaaccttt    9720
ttgcagtgca aaaaagtacg tgtcggcagt cacgtaggcc ggccttatcg ggtcgcgtcc    9780
tgtcacgtac gaatcacatt atcggaccgg acgagtgttg tcttatcgtg acaggacgcc    9840
agcttcctgt gttgctaacc gcagccggac gcaactcctt atcggaacag gacgcgcctc    9900
catatcagcc gcgcgttatc tcatgcgcgt gaccggacac gaggcgcccg tcccgcttat    9960
cgcgcctata aatacagccc gcaacgatct ggtaaacaca gttgaacaga tggtgagcaa    10020
gggcgaggag gtcatcaaag agttcatgcg cttcaaggtg cgcatggagg gctccatgaa    10080
cggccacgag ttcgagatcg agggcgaggg cgagggccgc ccctacgagg gcacccagac    10140
cgccaagctg aaggtgacca agggcggccc cctgcccttc gcctgggaca tcctgtcccc    10200
ccagttcatg tacggctcca aggcgtacgt gaagcaccccg ccgacatcc ccgattacaa    10260
gaagctgtcc ttccccgagg gcttcaagtg ggagcgcgtg atgaacttcg aggacggcgg    10320
tctggtgacc gtgacccagg actcctccct gcaggacggc acgctgatct acaaggtgaa    10380
gatgcgcggc accaacttcc cccccgacgg ccccgtaatg cagaagaaga ccatgggctg    10440
ggaggcctcc accgagcgcc tgtaccccccg cgacggcgtg ctgaagggcg agatccacca    10500
ggccctgaag ctgaaggacg gcggccacta cctggtggag ttcaagacca tctacatggc    10560
caagaagccc gtgcaactgc ccggctacta ctacgtggac accaagctgg acatcacctc    10620
ccacaacgag gactacacca tcgtggaaca gtacgagcgc tccgagggcc gccaccacct    10680
gttcctgggg catggcaccg gcagcaccgg cagcggcagc tccggcaccg cctcctccga    10740
ggacaacaac atggccgtta tcaaggaatt tatgcgcttc aaagttagga tggagggatc    10800
catgaacgga catgagttcg agatcgaggg agagggcgag gacgcccgt atgaaggcac    10860
acaaacagcc aaactcaagg tcaccaaggg cggaccactg cccttcgcct gggatatcct    10920
gagtcccccag tttatgtacg gcagcaaggc ctacgttaag cacccccgctg acataccgga    10980
ctacaaaaag ctgtccttttc cggaaggctt caagtgggag cgcgtgatga atttcgaaga    11040
cggaggactg gtcactgtga cccaagatag cagtttgcag gacggtacac tgatctataa    11100
ggttaaaatg cgcggcacta actttccgcc agatggccca gtgatgcaga agaagaccat    11160
gggttgggag gcatccaccg aacgtctgta ccctcgagac ggagtgctca agggcgagat    11220
ccatcaggcc ctcaaactga aagatggtgg tcactacctg gtcgaattta gaccatttta    11280
catggccaag aagccggttc agctgccccgg atattattat gtggatacga aactggatat    11340
aacttcgcat aacgaagact acaccattgt cgagcagtat gagcgcagcg aaggccgaca    11400
tcacctgttc ctctacggca tggacgagct gtacaagtag gcggccgcga ctctagatca    11460
taatcagcca taccacattt gtagaggttt tacttgcttt aaaaaacctc ccacacctcc    11520
ccctgaacct gaaacataaa atgaatgcaa ttgttgttgt taacttgttt attgcagctt    11580
ataatggtta caaataaagc aatagcatca caaatttcac aaataaagca tttttttcac    11640
tgcattctag ttgtggtttg tccaaactca tcaatgtatc ttaaagcttc agtctctggt    11700
tgtgcatgga gcgtgttttt ggggcgattt acgagcgtga accgatattt tccatacgtc    11760
atgtttgcct tgctttacac tccaggaaac ctcatccgtt taatttagcc ggaagtgttg    11820
caatagatgc cacatcacaa tcgacttaat aattttttta ggagcaagtt ttaatggaaa    11880
cagtttctga taaataaata tacatatcaa cttagtacaa gaatatccag ctgaaagaat    11940
ggtatatata tatatatata tacttgtgtt tgtttctatg acagtttctt cacagctttc    12000
```

| | | | | | |
|---|---|---|---|---|---|
| gattttctta | tggcacatcg | cgcgacagtt | gaaatgaaaa | actgaaatca | gtgaaacccc | 12060 |
| gaaaaaactg | aaaaagccac | ggaaattgta | cagatacaca | gatacgcaga | tacaccagca | 12120 |
| aatgtacaaa | aaggtctata | tacatatata | tgtagctact | cacttatgtt | gtccttcgca | 12180 |
| gattgctccc | tttaagcaaa | taaaaaaaag | ttggctccac | gccgaaaaga | aataaaatta | 12240 |
| aatggagaat | cgcaaatcca | tagtgagcca | aaggcaaatc | tataaaagaa | atgaaacgaa | 12300 |
| attcattcat | tttcgttttc | gagttcgaat | atttaagtta | tatatataaa | cgcagtattt | 12360 |
| atccatgtaa | tcgaaccaca | aaagcccaat | gagaaaaccc | tacattttat | gctgagcatc | 12420 |
| acaaaatgcc | tttcctttca | catgaattta | tgtattttaa | tcaatttccc | tcgctgtggc | 12480 |
| agttaaatat | cctaaatttg | tccaacgaaa | ttgatgcttc | aattattcga | atgacgacgt | 12540 |
| ttaatgggct | ttcgaggaat | aaaagcaaaa | attcacaaga | aaacgcctc | tgcatccatg | 12600 |
| ctcattatcg | gaatcaatta | aaatttcaca | tgtatcgtta | gcatggccat | gtcagcaaat | 12660 |
| ccacgggatt | cggctagagt | cctccaaaat | acgcccacgg | gacccataca | ccttcgaaat | 12720 |
| gatccaacat | caatccctat | ccaaatgtat | acttagatat | gtacatacct | tgtcttttct | 12780 |
| tggtcggcga | atggggttc | cagcatccca | tcatcct | | | 12817 |

<210> SEQ ID NO 43
<211> LENGTH: 14148
<212> TYPE: DNA
<213> ORGANISM: Artificial
<220> FEATURE:
<223> OTHER INFORMATION: tko-step2-genbank

<400> SEQUENCE: 43

| | | | | | |
|---|---|---|---|---|---|
| atcatcgatc | tcgaggctgc | atccaacgcg | cgcgttggga | gctctccgga | tcaattcggc | 60 |
| ttcaggtacc | gtcgacgatg | taggtcacgg | tctcgaagcc | gcggtgcggg | tgccagggcg | 120 |
| tgcccttggg | ctccccgggc | gcgtactcca | cctcacccat | ctggtccatc | atgatgaacg | 180 |
| ggtcgaggtg | gcggtagttg | atcccggcga | acgcgcggcg | caccgggaag | ccctcgccct | 240 |
| cgaaaccgct | gggcgcggtg | gtcacggtga | gcacgggacg | tgccgacggcg | tcggctgggt | 300 |
| gcggatacgc | ggggcagcgt | cagcgggttc | tcgacggtca | cggcgggcat | gtcgacgaca | 360 |
| tgttcgcctc | atttgtgttc | gtttatgtat | tcgatgttat | gtgtatgctc | atgtgatgtt | 420 |
| tagcttgtaa | gcgcgagatg | tgggtagcag | gagatgcagt | gcagccaaca | gcagtgacca | 480 |
| gatgatatat | gctatgctac | tactactact | tatatgctat | gatttgtggc | gcggaggcgt | 540 |
| gtctgcgaca | cataatcccg | cccatttagc | tttaagattc | aggcactaag | aagcaattcg | 600 |
| atcaataaat | tattgtaacc | actctgcatg | tgagcaaaag | gccagcaaaa | ggccaggaac | 660 |
| cgtaaaaagg | ccgcgttgct | ggcgtttttc | cataggctcc | gccccctga | cgagcatcac | 720 |
| aaaaatcgac | gctcaagtca | gaggtggcga | aacccgacag | gactataaag | ataccaggcg | 780 |
| tttccccctg | gaagctccct | cgtgcgctct | cctgttccga | ccctgccgct | taccggatac | 840 |
| ctgtccgcct | ttctcccttc | gggaagcgtg | gcgctttctc | atagctcacg | ctgtaggtat | 900 |
| ctcagttcgg | tgtaggtcgt | tcgctccaag | ctgggctgtg | tgcacgaacc | ccccgttcag | 960 |
| cccgaccgct | gcgccttatc | cggtaactat | cgtcttgagt | ccaacccggt | aagacacgac | 1020 |
| ttatcgccac | tggcagcagc | cactggtaac | aggattagca | gagcgaggta | tgtaggcgt | 1080 |
| gctacagagt | tcttgaagtg | gtggcctaac | tacggctaca | ctagaagaac | agtatttggt | 1140 |
| atctgcgctc | tgctgaagcc | agttaccttc | ggaaaaagag | ttggtagctc | ttgatccggc | 1200 |

```
aaacaaacca ccgctggtag cggtggtttt tttgtttgca agcagcagat tacgcgcaga    1260
aaaaaaggat ctcaagaaga tcctttgatc ttttctacgg ggtctgacgc tcagtggaac    1320
gaaaactcac gttaagggat tttggtcatg agattatcaa aaaggatctt cacctagatc    1380
cttttaaatt aaaaatgaag ttttaaatca atctaaagta tatatgagta aacttggtct    1440
gacagttacc aatgcttaat cagtgaggca cctatctcag cgatctgtct atttcgttca    1500
tccatagttg cctgactccc cgtcgtgtag ataactacga tacgggaggg cttaccatct    1560
ggccccagtg ctgcaatgat accgcgagac ccacgctcac cggctccaga tttatcagca    1620
ataaaccagc cagccggaag ggccgagcgc agaagtggtc ctgcaacttt atccgcctcc    1680
atccagtcta ttaattgttg ccgggaagct agagtaagta gttcgccagt taatagtttg    1740
cgcaacgttg ttgccattgc tacaggcatc gtggtgtcac gctcgtcgtt tggtatggct    1800
tcattcagct ccggttccca acgatcaagg cgagttacat gatccccat gttgtgcaaa     1860 aaagcggtta gctccttcgg tcctccgatc gttgtcagaa gtaagttggc cgcagtgtta    1920
tcactcatgg ttatggcagc actgcataat tctcttactg tcatgccatc cgtaagatgc    1980
ttttctgtga ctggtgagta ctcaaccaag tcattctgag aatagtgtat gcggcgaccg    2040
agttgctctt gcccggcgtc aatacgggat aataccgcgc cacatagcag aactttaaaa    2100
gtgctcatca ttggaaaacg ttcttcgggg cgaaaactct caaggatctt accgctgttg    2160
agatccagtt cgatgtaacc cactcgtgca cccaactgat cttcagcatc ttttactttc    2220
accagcgttt ctgggtgagc aaaaacagga aggcaaaatg ccgcaaaaaa gggaataagg    2280
gcgacacgga aatgttgaat actcatactc ttcctttttc aatattattg aagcatttat    2340
cagggttatt gtctcatgag cggatacata tttgaatgta tttagaaaaa taaacaaata    2400
ggggttccgc gcacatttcc ccgaaaagtg ccacctgacg tcgacggatc gggagatcgg    2460
cgcgggatct aattcaatta gagactaatt caattagagc taattcaatt aggatccaag    2520
cttatcgatt tcgaaccctc gaccgccgga gtataaatag aggcgcttcg tctacggagc    2580
gacaattcaa ttcaaacaag caaagtgaac acgtcgctaa gcgaaagcta agcaaataaa    2640
caagcgcagc tgaacaagct aaacaatcgg ctcgagaccg gtcgccacca tggtgagcaa    2700
gggcgaggag ctgttcaccg gggtggtgcc catcctggtc gagctggacg gcgacgtaaa    2760
cggccacaag ttcagcgtgt ccggcgaggg cgagggcgat gccacctacg gcaagctgac    2820
cctgaagttc atctgcacca ccggcaagct gcccgtgccc tggcccaccc tcgtgaccac    2880
cctgacctac ggcgtgcagt gcttcagccg ctaccccgac cacatgaagc agcacgactt    2940
cttcaagtcc gccatgcccg aaggctacgt ccaggagcgc accatcttct tcaaggacga    3000
cggcaactac aagacccgcg ccgaggtgaa gttcgagggc gacaccctgg tgaaccgcat    3060
cgagctgaag ggcatcgact tcaaggagga cggcaacatc ctggggcaca agctggagta    3120
caactacaac agccacaacg tctatatcat ggccgacaag cagaagaacg gcatcaaggt    3180
gaacttcaag atccgccaca acatcgagga cggcagcgtg cagctcgccg accactacca    3240
gcagaacacc cccatcggcg acggccccgt gctgctgccc gacaaccact acctgagcac    3300
ccagtccgcc ctgagcaaag accccaacga gaagcgcgat cacatggtcc tgctggagtt    3360
cgtgaccgcc gccgggatca ctctcggcat ggacgagctg tacaagtaaa gcggccgcga    3420
ctctagatca taatcagcca taccacattt gtagaggttt tacttgcttt aaaaaacctc    3480
ccacacctcc ccctgaacct gaaacataaa atgaatgcaa ttgttgttgt taacttgttt    3540
attgcagctt ataatggtta caaataaagc aatagcatca caaatttcac aaataaagca    3600
```

```
ttttttttcac tgcattctag ttgtggtttg tccaaactca tcaatgtatc ttagttgttg    3660
gttggcacac cacaaatata ctgttgccga gcacaattga tcggctaaat ggtatggcaa    3720
gaaaaggtat gcaatataat aatcttttat tgggtatgca acgaaaattt gtttcgtcaa    3780
cgtatgcaat attctttatt aaagagggt atgcaatgta ttttattaaa aacgggtatg    3840
caatataata atcttttatt gggtatgcaa cgaaaatttg tttcgtcaaa gtatgcaata    3900
ttttttatta aagagggta tgcaatgtat tttattaaaa acgggtatgc aataaaaaat    3960
tatttggttt ctctaaaaag tatgcagcac ttattttttg ataaggtatg caacaaaatt    4020
ttactttgcc gaaaatatgc aatgttttg cgaataaatt caacgcacac ttattacgtg    4080
gccaacgcgc ctagtggatc cttcctggcc cttttcgaga aacgccgcga gggcgaaaag    4140
gattagttgt ttcaaacgca agaaggacat ttgtttcctt aaattgtaac catttcttta    4200
tttggcactc gagccattga attttttcatt ttcagaatat gtgtacacat ttttaaaaa    4260 aataaaaaaa ttatataatg ctggcggttg tttcatgtgt gaaaaattga tcaatggtaa    4320
acaaaattga ataaatatat aacatatata tatagatatg tgtgttgaaa tgaatacttg    4380
cgatacatgt aataaaaata ctcttcgctt atctatcaaa aagtgcggaa tgtcaaaatt    4440
taaaatttta caatgaatgc gtagccgacg acgaaagtgt tccttgctat ttcctttagc    4500
aagatttaaa tttagattaa attctaatga tacgattgac agttcgaaat tcaaagtgtt    4560 ccttttttcaa aatttagtaa agattgtata tcaattgtag atatatcgaa attttttcggc    4620 cgcaagcgaa catttttacaa aatgaaggcg accagttgca gaccaattcc attcatcaac    4680
tttcggattg taagatattt ctatcggcca cgacgattga acaagtatta cgatattgta    4740
agtcttcttt aacaaaatta gtttcccttt cacagaaaca gacataaatt cttgaattat    4800
tgacttggat ttgagtgatc gttcgttgtc tatactataa gatctatagg cacgggataa    4860
cgctctaaat ctcttttaaaa tcgaacgcgc caggcgctag ttaaacgtta ctatctatct    4920
ggttaaccca gctttgatcg gaatgcgtat atatatttca tgttatataa acgctgcaaa    4980
agctgccaga gcctctgctc cagagctgga ttcgctcaca ccttcctctt cttcttgggg    5040
tcagccctgc tgtctccacc gagctgagag aggtcgattc ttgtttcata gagccccgta    5100
attgactgat gaatcagtgt ggcgtccagg acctcctttg tagaggtgta ccgctttctg    5160
tctatggtgg tgtcgaagta cttgaaggct gcaggcgcgc ccaagttggt cagagtaaac    5220
aagtggataa tgttttctgc ctgctccctg atgggcttat ccctgtgctt attgtaagca    5280
gaaagcacct tatcgaggtt agcgtcggcg aggatcactc ttttggagaa ttcgcttatt    5340
tgctcgatga tctcatcaag gtagtgtttg tgttgttcca cgaacagctg cttctgctca    5400
ttatcttcgg gagacccttt gagcttttca tagtggctgg ccagatacaa gaaattaacg    5460
tatttagagg gcagtgccag ctcgttacct ttctgcagct cgcccgcact agcgagcatt    5520 cgttccggc cgttttcaag ctcaaagaga gagtacttgg gaagcttaat gatgaggtct    5580
tttttgacct ctttatatcc tttcgcctcg agaaagtcga tgggttttt ttcgaagctt    5640 gatcgctcca tgattgtgat gcccagcagt tccttgacgc ttttgagttt tttagacttc    5700
cctttctcca ctttggccac aaccagtaca ctgtaagcga ctgtaggaga atcgaatccg    5760
ccgtatttct tggggtccca atctttttg cgtgcgatca gcttgtcgct gttccttttc    5820
gggaggatac tttccttgga gaagcctccg gtctgtactt cggtctttttt aacgatgttc    5880 acctgcggca tggacaggac cttccggact gtcgcgaaat ccctacccttt gtcccacacg    5940
```

```
atttctcctg tttctccgtt tgtttcgata agtggtcgct tccgaatctc tccattggcc   6000
agtgtaatct cggtcttgaa aaaattcata atattgctgt aaaagaagta cttagcggtg   6060
gccttgccta tttcctgctc agactttgcg atcatttttcc taacatcgta cactttatag   6120
tctccgtaaa caaattcaga ttcaagcttg ggatattttt tgataagtgc agtgcctacc   6180
actgcattca ggtaggcatc atgcgcatgg tggtaattgt tgatctctct cacccttataa  6240 aactgaaagt cctttctgaa atctgagacc agcttagact tcagagtaat aactttcacc   6300
tctcgaatca gtttgtcatt ttcatcgtac ttggtgttca tgcgtgaatc gagaatttgg   6360
gccacgtgct tggtgatctg gcgtgtctca acaagctgcc ttttgatgaa gccggcttta   6420
tccaactcag acaggccacc tcgttcagcc ttagtcagat tatcgaactt ccgttgtgtg   6480
atcagtttgg cgttcagcag ctgccgccaa taatttttca ttttcttgac aacttcttct   6540
gaggggacgt tatcactctt ccctctattt ttatcggatc ttgtcaacac tttattatca   6600
atagaatcat ctttgagaaa agactggggc acgatatgat ccacgtcgta gtcggagagc   6660
cgattgatgt ccagttcctg atccacgtac atgtccctgc cgttctgcag gtagtacagg   6720
tagagcttct cattctgaag ctgggtgttt tcaactgggt gttccttaag gatttgggac   6780
cccagttctt ttatacccctc ttcaatcctc ttcatccttt ccctactgtt cttctgtccc   6840
ttctgggtag tttggttctc tcgggccatc tcgataacga tattctcggg cttatgcctt   6900
cccattactt tgacgagttc atccacgacc ttaacggtct gcagtattcc cttttttgata  6960 gctgggctac ctgcaagatt agcgatgtgc tcgtgaagac tgtccccctg gccagaaact   7020
tgtgcttcct ggatgtcctc cttaaaggtg agagagtcat catggatcaa ctgcatgaag   7080
ttccggttgg caaatccatc ggacttaaga aaatccagga ttgtctttcc actctgcttg   7140
tctcggatcc cattgatcag ttttcttgac agccgccccc atcctgtata tcggcgcctc   7200
ttgagctgtt tcatgacttt gtcgtcgaag agatgagcgt aagttttcaa gcgttcttca   7260
atcatctccc tatcttcaaa caacgtaagg gtgaggacaa tgtcctcaag aatgtcctcg   7320
ttctcctcat tgtccaggaa gtccttgtct ttaatgattt tcaggagatc gtgatacgtt   7380
cccagggatg cgttgaagcg atcctccact ccgctgattt caacagagtc gaaacattca   7440
atctttttga aatagtcttc tttgagctgt ttcacggtaa ctttccggtt cgtcttgaag   7500
aggaggtcca cgatagcttt cttctgctct ccagacagga atgctggctt tctcatccct   7560
tctgtgacgt atttgacctt ggtgagctcg ttataaactg tgaagtactc gtacagcaga   7620
gagtgtttag gaagcacctt ttcgttaggc agatttttat caaagttagt catccttcg    7680 atgaaggact gggcagaggc cccttatcc acgacttcct cgaagttcca gggagtgatg   7740
gtctcttctg atttgcgagt catccacgcg aatctggaat ttccccgggc gaggggcct    7800 acatagtagg gtatccgaaa tgtgaggatt ttctcaatct tttccctgtt atcttcaaa    7860 aaggggtaga atcctcttg ccgcctgagg atagcgtgca gttcgcccag gtgaatctgg     7920
tgggggatgc ttccattgtc gaaagtgcgc tgtttgcgca acagatcttc tctgttaagc   7980
tttaccagca gctcctcggt gccgtccatt ttttccaaga tgggcttaat aaatttgtaa   8040
aattcctcct ggcttgctcc gccgtcaatg tatccgcgt agccattttt agactgatcg    8100
aagaaaattt ccttgtactt ctcaggcagt tgctgtctga aagggccctt cagcaaagtc   8160
aagtcttggt ggtgctcatc atagcgcttg atcatactag cgctcagcgg agctttggtg   8220
atctccgtgt tcactcgcag aatatcactc agcagaatgg cgtctgacag gttctttgcc   8280
gccaaaaaaa ggtctgcgta ctggtcgccg atctgggcca gcagattgtc gagatcatca   8340
```

```
tcgtaggtgt ctttgctcag ttgaagcttg gcatcttcgg ccaggtcgaa gttagattta    8400
aagttggggg tcagcccgag tgacagggcg ataagattac caaacaggcc gttcttcttc    8460
tccccaggga gctgtgcgat gaggttttcg agccgccggg atttggacag cctagcgctc    8520
aggattgctt tggcgtcaac tccggatgcg ttgatcgggt tctcttcgaa aagctgattg    8580
taagtctgaa ccagttggat aaagagtttg tcgacatcgc tgttgtctgg gttcaggtcc    8640
ccctcgatga ggaagtgtcc ccgaaatttg atcatatgcg ccagcgcgag atagatcaac    8700
cgcaagtcag ccttatcagt actgtctaca agcttcttcc tcagatgata tatggttggg    8760
tacttttcat ggtacgccac ctcgtccacg atattgccaa agattgggtg gcgctcgtgc    8820 ttttatcct cctccaccaa aaaggactcc tccagcctat ggaagaaaga gtcatccacc    8880
ttagccatct cattactaaa gatctcctgc aggtagcaga tccgattctt tctgcgggta    8940
tatctgcgcc gtgctgttct tttgagccgc gtggcttcgg ccgtctcccc ggagtcgaac    9000
aggagggcgc caatgaggtt cttctttatg ctgtggcgat cggtattgcc cagaactttg    9060 aatttttgc tcggcacctt gtactcgtcc gtaatgacgg cccagccgac gctgtttgtg    9120
ccgatatcga gcccaatgga gtacttcttg tccatggcga aaatccgggt cgaaagttac    9180
ggttatcgcg cactctactt tccacaaatc ctcacccaaa aaccaagcac agtttattca    9240
actgaagtat tcgcgatact tctttatcta ataataatgt acatgtaact aaactcgctt    9300
ttgggttaaa atcgtgacgc agaggcaaaa aaaatcgtat gtcccttaga caacttgaaa    9360
caactgcgaa gcgtacggca attccaggaa ttttgtggta aagctacgcg ccaactaacg    9420
gttcttgctt agaggtggaa taatgtagtt ttccagcgat aataaatata tcgatatttt    9480
tagtaaaatt gaaaaggtaa acttaatttt agaaaataat ttataagaaa tttaatagta    9540
tgcaaaataa ttttttacttg ctaagaatat gtgccactaa ttaaaagctg acaccgcgc    9600 aatggaaaat agtactacaa cacagcaaca aagcctgagt tatcaacaaa aaaatacgaa    9660
aacatctccc aaaactaagc acccacacgc gccactcgcc gtcacaacac aatcactgca    9720
caccaccatt cgaatttcgc gcactgtgac aacatcacat gatatcggcg cggcaacatc    9780
ggattaccga caaaacgaac tatcgcacga gccaccgccg gcgaagagcg ctcgttttgc    9840
aacaccggcg cgcgctgaac gaagagaaca gctgactgct tgatacgtgc gtgtttcgcg    9900
gcaggaatta cataaagttt agagcctctg acgccagacc ccccgaacat tcgctccgat    9960
caaactacct gcgaacggtc acctaatccc caccatgcat ggtaggttac ctctgatccc   10020
ggtcatcact ggcgttcgct cacatccgtc cttacatgtg catatttcga ggttaaaacg   10080
gtcgaagctt ggatccgcta gcgttgttgg ttggcacacc acaaatatac tgttgccgag   10140
cacaattgat cggctaaatg gtatggcaag aaaaggtatg caatataata atctttattt   10200
gggtatgcaa cgaaaatttg tttcgtcaac gtatgcaata ttctttatta aagagggta   10260 tgcaatgtat tttattaaaa acgggtatgc aatataataa tcttttattg ggtatgcaac   10320
gaaaatttgt ttcgtcaaag tatgcaatat ttttattaa aagagggtat gcaatgtatt   10380
ttattaaaaa cgggtatgca ataaaaaatt atttggtttc tctaaaaagt atgcagcact   10440 tatttttga taaggtatgc aacaaatttt tactttgccg aaaatatgca atgttttgc   10500 gaataaattc aacgcacact tattacgtgg ccaactagcc tagttccagt gaaatccaag   10560
cacttgaggt ccgacccgat gaattctttt ttgctcacct gtgattgctc ctactccaat   10620
acaaaaacat caaattttct gtcaataaag catatttatt tatatttatt ttacaggaaa   10680
```

```
gaattccttt taaagtgtat tttaacctat aatgaaaaac gattaaaaaa aatacataaa   10740
ataattcgaa aattttgaa tagcccaggt tgataaaaat tcatttcata cgttttataa    10800
cttatgcccc taagtatttt ttgaccatag tgtttcaatt ctacattaat tttacagagt   10860
agaatgaaac gccacctact cagccaagag gcgaaaaggt tagctcgcca agcagagagg   10920
gcgccagtgc tcactacttt ttataattct caacttcttt ttccagactc agttcgtata   10980
tatagaccta ttttcaattt aacgtcgctg cagcgatgcc attccagttt cagagctatg   11040
ctggaaacag catagcaagt tgaaataagg ctagtccgtt atcaacttga aaaagtggca   11100
ccgagtcggt gcttttttgc ctacctggag cctgagagtt gttcaataaa ataaaaatgt   11160
ttcgtttttt tgctttcgcc agtatttatt attttcatc aatatgtatt caatttggta    11220
tgtatttagt aattgtaata tatagacaat ggttttccgt tgacgtacat acatctgacg   11280
tgtgtttatt tagacataat agttatgttt tcacatcttt ttaatgttcg cttaatgcgt   11340
atgcattcta gattttcaac gtcctcgata gtatagtggt tagtatcccc gcctgtcacg   11400
cgggagaccg gggttcaatt ccccgtcggg gagaatctgt gattcttttt ttttttcttt   11460
tactttgtta tataaacaat ttttgttta attgaatcta atttgccatt gcttttagga    11520
atctcaggca tccagcaagc gtttgtccgc cgaatcgccc atcagtgaag aagatcctgt   11580
ggcggctacg aaaatctccc cggccatgtc ggcctccacc tccagcgaaa aacccatcag   11640
cgagctggcc acctctgtgc tgacccaccg ctttccagac tccacctcct cacccggcga   11700
acatggcctt ggacgaatgc agttgtcgat ccgctacagc gcccagcgtc aaaaactaga   11760
cgtgaccata cacaaaatcc agaagatacc acttcgcgat cccagcaata tccccgatcc   11820
gtatgttaag ctgtatctgt tgcctggacg caccaaggag tcgaaacgca agacgagcgt   11880
gatcaaggac aactgcaacc ccgtctacga tgcatccttt gagtacctga tttccattgc   11940
cgaactcagg cagacggaac tggaggtgac ggtgtgcacc caaaagggat tcctatccgg   12000
cggtagtccc atcattggca tggtaggtac ccgaaagcaa ccccttagtt acagacacag   12060
cgcgtacgtc cttcgcatcc ttatgattcc caagtacata ttctgcaaga gtacagtata   12120
tataggaaag atatccgggt gaacttcgca ggacaacgcc cttggcgagt tcagagcta    12180 tgctggaaac agcatagcaa gttgaaataa ggctagtccg ttatcaactt gaaaaagtgg   12240
caccgagtcg gtgctttttt gcctacctgg agcctgagag ttgttcaatc tagacaattg   12300
tgctcggcaa cagtatattt gtggtgtgcc aaccaacaac ctgcaggagc tccagctttt   12360 gttccctta gtgagggtta attttttttg ctcacctgtg attgctccta ctcaaataca    12420
aaaacatcaa atttctgtc aataaagcat atttatttat atttattta caggaaagaa     12480 ttccttttaa agtgtatttt aacctataat gaaaacgat taaaaaaat acataaaata     12540 attcgaaaat ttttgaatag cccaggttga taaaaattca tttcatacgt tttataactt   12600
atgcccctaa gtattttttg accatagtgt tcaattcta cattaatttt acagagtaga    12660
atgaaacgcc acctactcag ccaagaggcg aaaaggttag ctcgccaagc agagagggcg   12720
ccagtgctca ctacttttta taattctcaa cttcttttc cagactcagt tcgtatatat    12780
agacctattt tcaatttaac gtcgcaacat tgtactgtgc cgcggtttca gagctatgct   12840
ggaaacagca tagcaagttg aaataaggct agtccgttat caacttgaaa agtggcacc    12900 gagtcggtgc ttttttgcct acctggagcc tgagagttgt tcaataaaat aaaaatgttt   12960 cgttttttg ctttcgccag tatttattat ttttcatcaa tatgtattca atttggtatg    13020
tatttagtaa ttgtaatata tagacaatgg ttttccgttg acgtacatac atctgacgtg   13080
```

```
tgtttattta gacataatag ttatgttttc acatctttt  aatgttcgct taatgcgtat  13140
gcattctaga ttttcaacgt cctcgatagt atagtggtta gtatcccgc  ctgtcacgcg  13200 ggagaccggg gttcaattcc ccgtcgggga gaatctgtga ttcttttttt ttttctttta  13260
ctttgttata taaacaattt ttgttttaat tgaatctaat ttgccattgc tttaggaat   13320 ctcaggcatc cagcaagcgt ttgtccgccg aatcgcccat cagtgaagaa gatcctgtgg  13380
cggctacgaa aatctccccg gccatgtcgg cctccacctc cagcgaaaaa cccatcagcg  13440
agctggccac ctctgtgctg acccaccgct ttccagactc cacctcctca cccggcgaac  13500
atggccttgg acgaatgcag ttgtcgatcc gctacagcgc ccagcgtcaa aaactagacg  13560
tgaccataca caaatccag  aagataccac ttcgcgatcc cagcaatatc cccgatccgt  13620
atgttaagct gtatctgttg cctggacgca ccaaggagtc gaaacgcaag acgagcgtga  13680
tcaaggacaa ctgcaacccc gtctacgatg catcctttga gtacctgatt tccattgccg  13740
aactcaggca gacggaactg gaggtgacgg tgtgcaccca aaagggattc ctatccggcg  13800
gtagtcccat cattggcatg gtaggtaccc gaaagcaacc ccttagttac agacacagcg  13860
cgtacgtcct tcgcatcctt atgattccca agtacatatt ctgcaagagt acagtatata  13920
taggaaagat atccgggtga acttcgcacc agcacgcact ttcgatgttt cagagctatg  13980
ctggaaacag catagcaagt tgaaataagg ctagtccgtt atcaacttga aaaagtggca  14040
ccgagtcggt gcttttttgc ctacctggag cctgagagtt gttcaatcta gacaattgtg  14100
ctcggcaaca gtatatttgt ggtgtgccgt accgggccaa ttcgagct                14148
```